US009068920B2

(12) United States Patent
Churilla

(10) Patent No.: US 9,068,920 B2
(45) Date of Patent: Jun. 30, 2015

(54) SYSTEM AND METHOD FOR SCANNING AND PROCESSING PRINTED MEDIA

(76) Inventor: John Eric Churilla, Austin, TX (US)

(*) Notice: Subject to any disclaimer, the term of this patent is extended or adjusted under 35 U.S.C. 154(b) by 1059 days.

(21) Appl. No.: 12/687,057

(22) Filed: Jan. 13, 2010

(65) Prior Publication Data

US 2010/0322373 A1 Dec. 23, 2010

Related U.S. Application Data

(60) Provisional application No. 61/144,729, filed on Jan. 14, 2009.

(51) Int. Cl.
| G01N 23/04 | (2006.01) |
| G01N 23/083 | (2006.01) |
| G01N 23/087 | (2006.01) |
| H04N 1/00 | (2006.01) |
| H04N 1/04 | (2006.01) |
| H04N 1/12 | (2006.01) |

(52) U.S. Cl.
CPC ............. *G01N 23/046* (2013.01); *G01N 23/04* (2013.01); *G01N 23/087* (2013.01); *G01N 23/083* (2013.01); *H04N 1/00127* (2013.01); *H04N 1/00795* (2013.01); *H04N 1/00827* (2013.01); *H04N 1/04* (2013.01); *H04N 1/12* (2013.01); *H04N 2201/0081* (2013.01); *H04N 2201/0434* (2013.01)

(58) Field of Classification Search
CPC ... G01N 23/04; G01N 23/046; G01N 23/083; G01N 23/087; G01N 23/10
USPC .................................................. 378/57, 198
See application file for complete search history.

(56) References Cited

U.S. PATENT DOCUMENTS

| 4,181,347 | A | * | 1/1980 | Clark ............................ 378/199 |
| 5,097,497 | A | * | 3/1992 | Deucher et al. ............... 378/204 |
| 5,182,764 | A | * | 1/1993 | Peschmann et al. ........... 378/57 |
| 5,229,934 | A | * | 7/1993 | Mattson et al. ............... 600/425 |
| 5,367,552 | A | * | 11/1994 | Peschmann ..................... 378/57 |
| 6,430,255 | B2 | * | 8/2002 | Fenkart et al. .................. 378/57 |
| 6,437,344 | B1 | * | 8/2002 | Strawson ................ 250/455.11 |
| 6,481,887 | B1 | * | 11/2002 | Mirabella ..................... 378/198 |
| 6,672,760 | B2 | * | 1/2004 | Ishii et al. ..................... 378/198 |
| 6,928,143 | B2 | * | 8/2005 | Menear et al. .................. 378/69 |
| 6,990,434 | B2 | * | 1/2006 | Minogue et al. .............. 702/188 |
| 7,016,459 | B2 | * | 3/2006 | Ellenbogen et al. ........... 378/19 |
| 7,039,154 | B1 | * | 5/2006 | Ellenbogen et al. ........... 378/19 |
| 7,062,011 | B1 | * | 6/2006 | Tybinkowski et al. ......... 378/57 |
| 7,072,434 | B1 | * | 7/2006 | Tybinkowski et al. ........... 378/4 |
| 7,151,817 | B1 | * | 12/2006 | Abraham et al. ............... 378/57 |
| 7,272,207 | B1 | * | 9/2007 | Aufrichtig et al. ............ 378/116 |
| 7,319,733 | B2 | * | 1/2008 | Price et al. ........................ 378/5 |
| 7,378,660 | B2 | * | 5/2008 | Case et al. ............... 250/363.01 |

(Continued)

*Primary Examiner* — Allen C. Ho
(74) *Attorney, Agent, or Firm* — J. Eric Churilla

(57) ABSTRACT

A mobile scanner is disclosed and may include a frame. A front axle and a rear axle may be attached to the frame. The front axle may include a first tire/wheel assembly mounted thereon and a second tire/wheel assembly mounted thereon. Further, the rear axle may include a first tire/wheel assembly mounted thereon and a second tire/wheel assembly mounted thereon. Moreover, a cab may be mounted on the frame and a body may be mounted on the frame adjacent to the cab. A volumetric document scanner may be disposed within the body. The volumetric document scanner may be configured to use x-ray computed tomography in order to scan documents and create a three-dimensional data set representing the documents.

18 Claims, 81 Drawing Sheets

(56) References Cited

U.S. PATENT DOCUMENTS

| | | | |
|---|---|---|---|
| 7,384,194 B2* | 6/2008 | Gatten | 378/208 |
| 7,415,094 B2* | 8/2008 | Johnson et al. | 378/57 |
| 8,038,347 B2* | 10/2011 | Manak et al. | 378/189 |
| 8,164,802 B2* | 4/2012 | Pedley et al. | 358/474 |
| 8,243,876 B2* | 8/2012 | Morton | 378/19 |
| 2004/0051913 A1* | 3/2004 | Pedley et al. | 358/474 |
| 2010/0033772 A1* | 2/2010 | Borison et al. | 358/474 |

* cited by examiner

SYSTEM AND METHOD FOR SCANNING AND PROCESSING PRINTED MEDIA

RELATED APPLICATIONS

The present application claims priority to U.S. Provisional Patent Application Ser. No. 61/144,729, entitled SYSTEM AND METHOD FOR SCANNING AND PROCESSING PRINTED MEDIA, filed on Jan. 14, 2009.

FIELD

The present disclosure relates generally to scanning paper media. More specifically, the present disclosure relates to volumetrically scanning printed media and processing the data derived from the volumetric scan of printed media.

DESCRIPTION OF THE RELATED ART

Worldwide, many, many pages of printed media exists. This printed media includes books, magazines, newspapers, maps, blue prints, etc. Further, this printed media includes paper generated in multiple business settings, e.g., medical records, financial forms, loan applications, etc. Typically, businesses maintain archives or libraries in which the paper generated by the business is stored for record keeping purposes.

In recent years, businesses, hospitals, schools, etc., have begun to digitize their paper content. In other words, these institutions have begun the slow process of scanning their analog content, i.e., paper, in order to create digital content, i.e., electronic representations thereof. Unfortunately, present scanners are relatively slow and the process of digitizing paper content may be very laborious.

Accordingly, there exists a need for an improved system and method for scanning and processing printed media.

DETAILED DESCRIPTION

The word "exemplary" is used herein to mean "serving as an example, instance, or illustration." Any aspect described herein as "exemplary" is not necessarily to be construed as preferred or advantageous over other aspects.

Volumetric scanning is a means of performing non-destructive penetrating scans of an object without having to deconstruct, take apart, open or dissect the scanned object. Volumetric scans output a three-dimensional rendering of the scanned object, and may be used to discern the structure, components, and other internal details within an object that would otherwise be unobservable to the naked eye. In rendering a three-dimensional dataset, volumetric scanning may be carried out using a great variety of means, including without limitation: Nuclear Magnetic Resonance scans (NMR), Computed Tomography using X-Rays (X-Ray CT), Computed Tomography using Terahertz Rays (T-Ray CT), CAT scans, PET scans, Ultrasound Scans, Supersonic Scans, Laser 3D scans, and any other means well known in the art that may yield a three-dimensional dataset of a scanned object. For any of the aforementioned means of performing a volumetric scan, such means may be utilized either alone or in combination. By way of a non-limiting example, a volumetric scan as described herein may be performed on an object using X-Ray CT alone, or a volumetric scan may be performed on an object using a combination of X-Ray CT and T-Ray CT.

Figure 20:
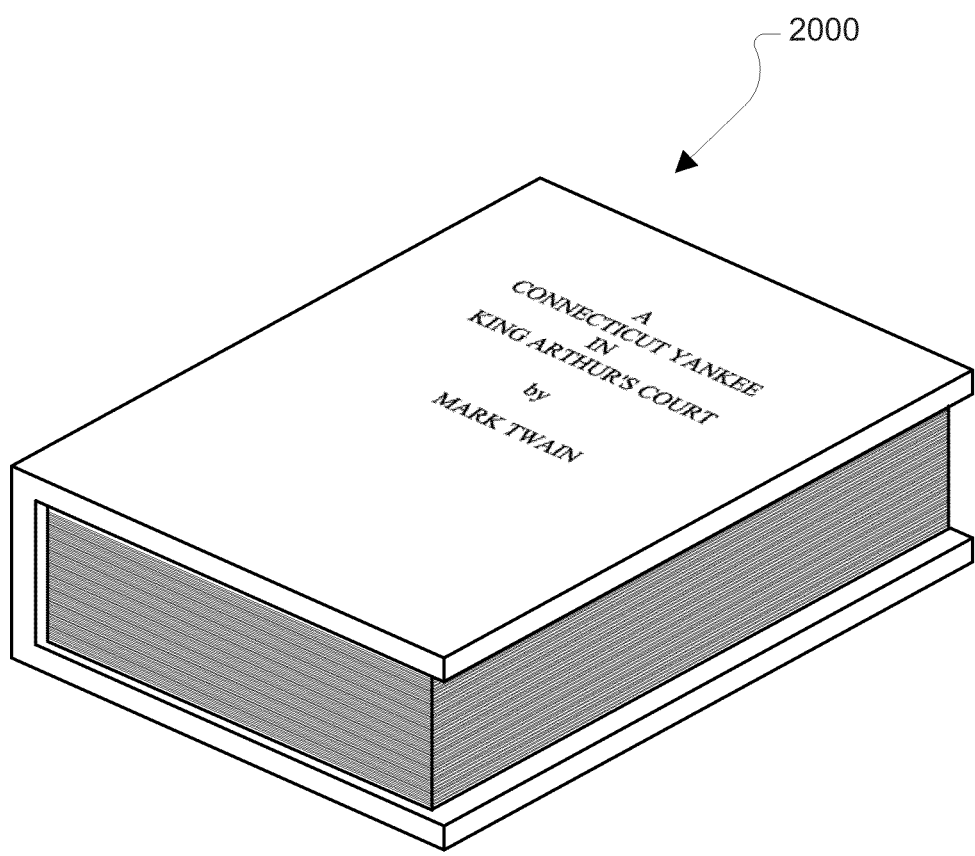
FIG. 20 is a view of a book.
Figure 21:
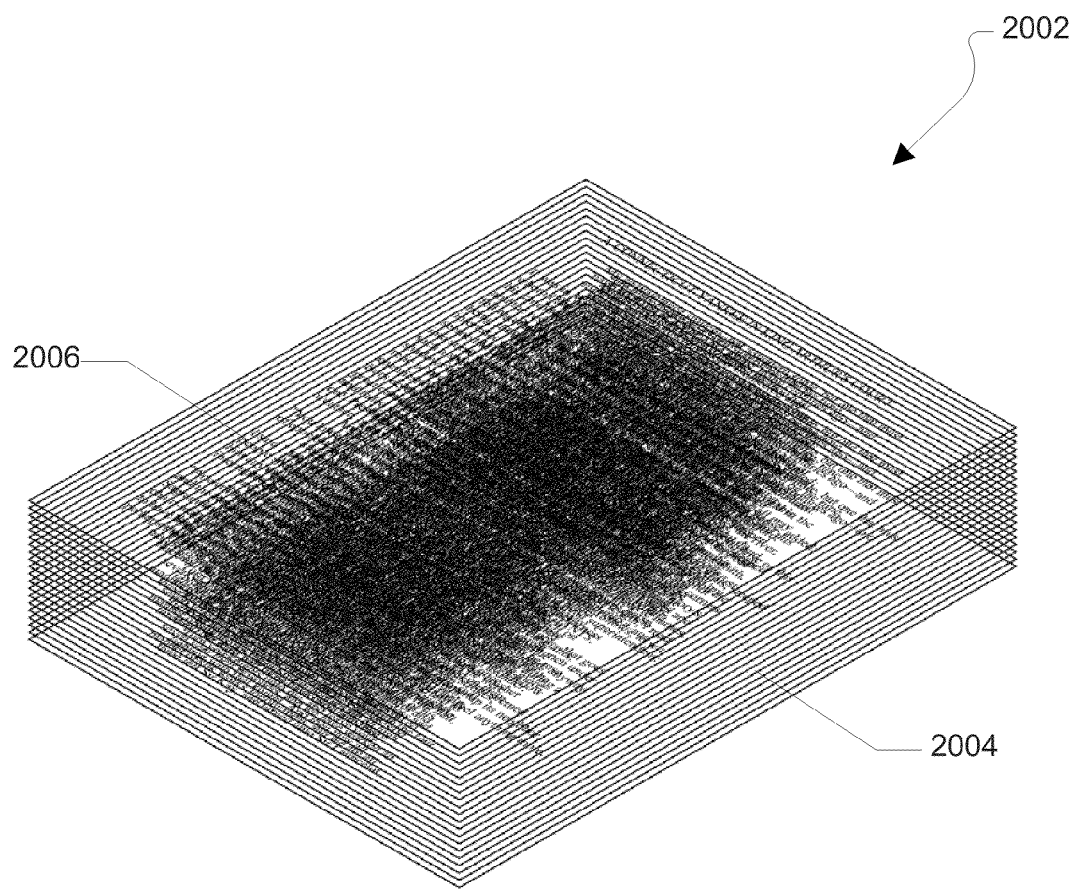
FIG. 21 is a view of ink and paper data.
Figure 22:
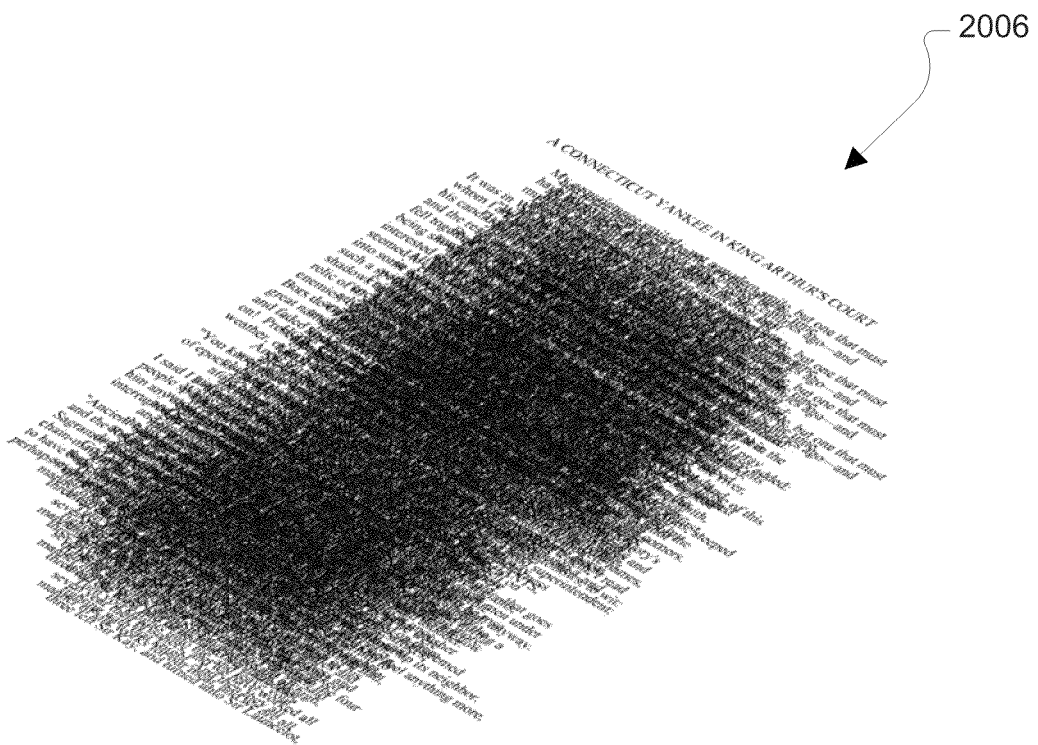
FIG. 22 is a view of ink data.

Using NMR/MRI, X-Ray, X-Ray CT, T-Ray, T-Ray CT, or any combination thereof slices of an object may be generated. These slices may then be assembled, or otherwise rendered, to generate a 3 dimensional dataset representing an object, e.g., printed media. The content of the printed media may then be derived from 3D dataset by processing the 3 dataset as described herein. FIG. 20 through FIG. 22 illustrate a book, a 3D dataset representing a book, and ink content derived from the 3D dataset. It is to be understood that the 3D dataset includes a plurality of voxels. Each voxel is a volume element that includes a portion of data derived from the volumetric scan of the book. The voxels may be processed in many ways, as described herein, to yield various results.

Figure 1:
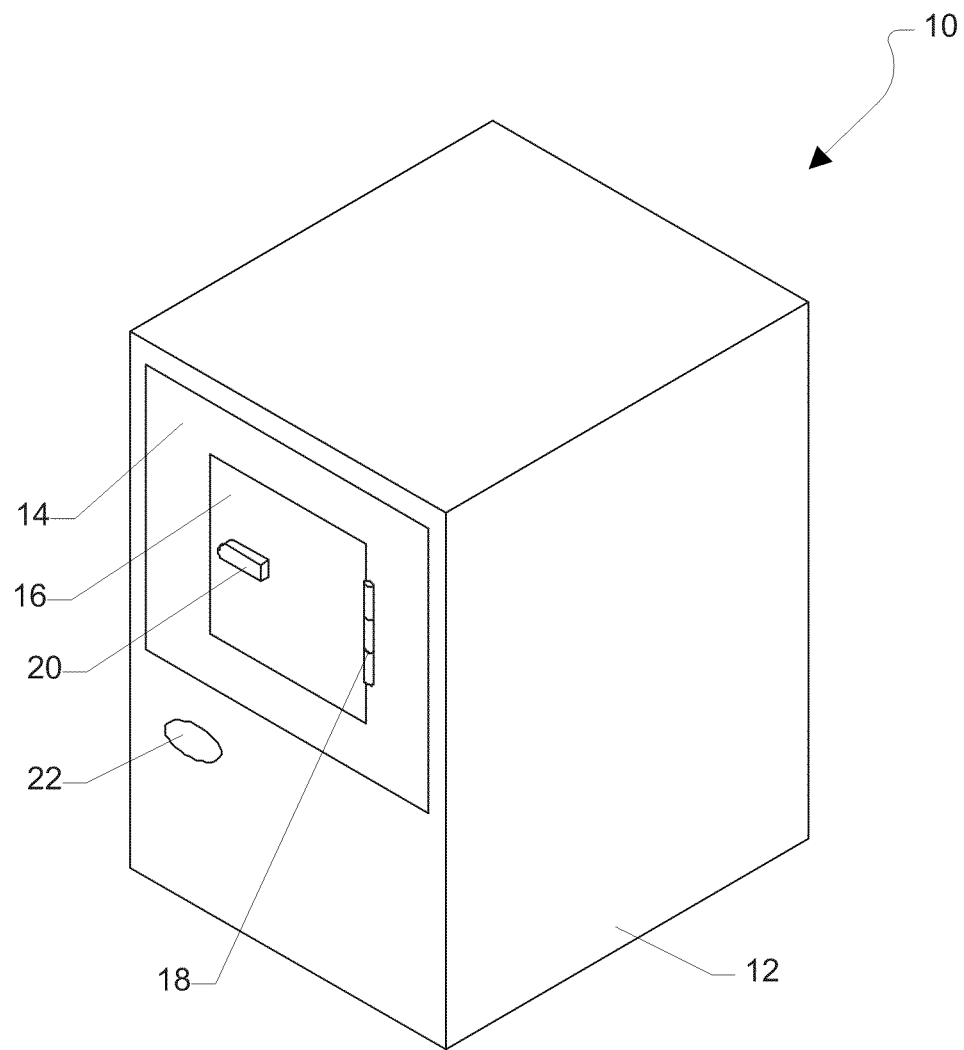
FIG. 1 is a front plan view of an exemplary NMR/MRI scanner.

By means of a non-limiting example, volumetric scanning may be carried out by using Nuclear Magnetic Resonance scans (NMR) and/or Magnetic Resonance Imaging (MRI) to output a three-dimensional dataset of an object. As used herein, the use of the terms of "NMR" and "MRI" are interchangeable and refer generally to any use of a magnet to resonate isotopes having non-zero spins for various elements in order to generate an image or images therefrom. Referring initially to FIG. 1, an exemplary, non-limiting aspect of a nuclear magnetic resonance/magnetic resonance imaging (NMR/MRI) volumetric scanner is shown and is generally designated 10. FIG. 1 shows that the volumetric scanner 10 includes a housing 12 having a removable front panel 14. A door 16 may be incorporated into the front panel 14. Preferably, the door 16 is attached to the front panel 14 by a hinge 18 and it rotates about the hinge 18 when it is opened and closed. The door 16 includes a handle 20 that may be used to latch and unlatch the door 16. As shown in FIG. 1, a scan button 22 may be incorporated into the front of the housing 12, but scan button 22 may be incorporated separate from housing 12 and be located in a remote location. It is to be understood that the scan button 22 may be toggled in order to begin the scan process, described in detail below.

Figure 2:
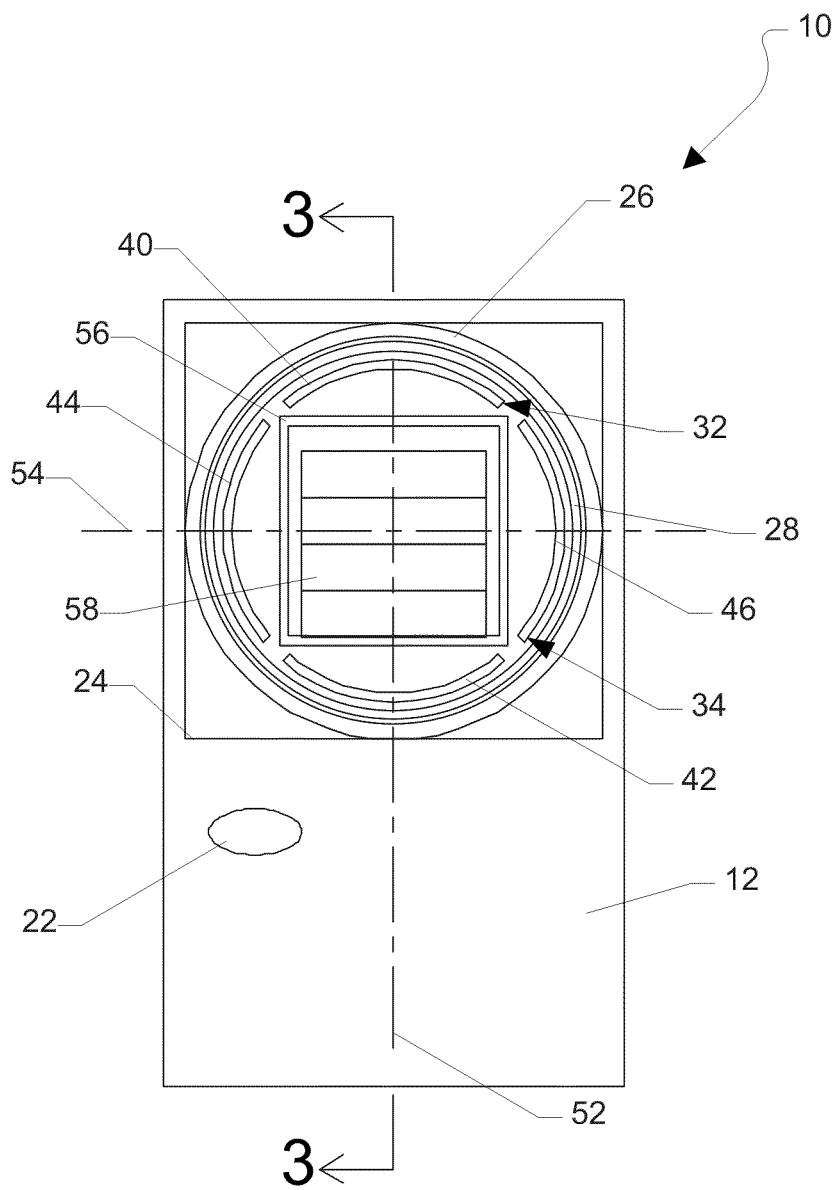
FIG. 2 is a front plan view of the NMR/MRI scanner with a front panel removed.
Figure 3:
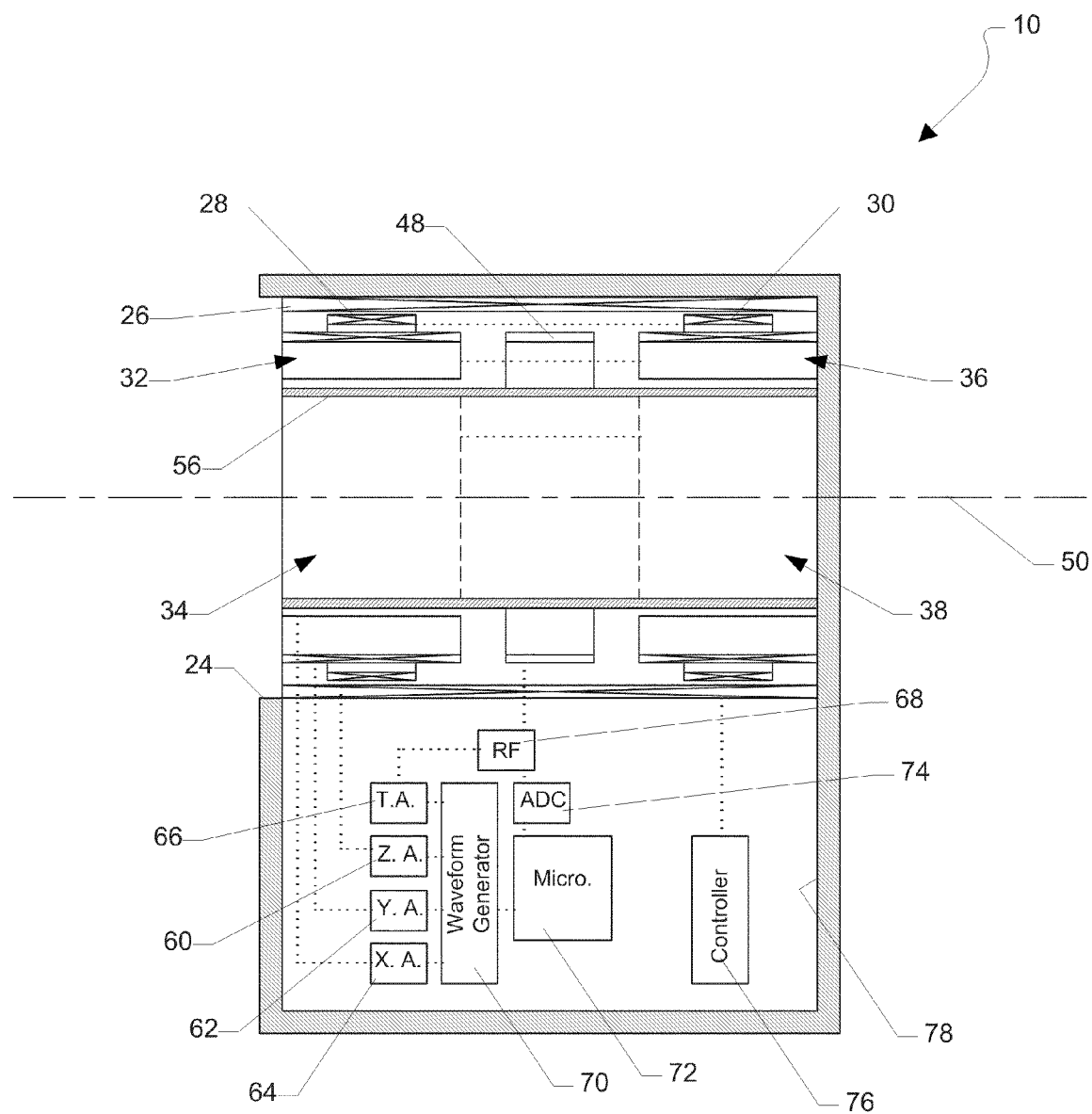
FIG. 3 is a cross-section view of the NMR/MRI scanner taken along line 3-3 in FIG. 2.

Referring now to FIG. 2 and FIG. 3, details concerning the internal components of the volumetric scanner 10 are shown. As shown, the housing 12 includes an opening 24 in which the front panel 14 (FIG. 1) fits. A generally cylindrical main coil assembly 26 is disposed within the housing 12. A generally cylindrical first Z-coil assembly 28 and a generally cylindrical second Z-coil assembly 30 are disposed within the main coil 26 near respective ends thereof. Moreover, a first Y coil assembly 32 and a first X coil assembly 34 are disposed within the first Z-coil assembly 28. A second Y coil assembly 36 and a second X coil assembly 38 are disposed within the second Z-coil assembly 30.

Each Y coil assembly 32, 36 includes a first saddle-shaped coil 40 and a second saddle-shaped coil 42 placed within respective Z-coil assemblies 28, 30 opposite each other. Also, each X coil assembly 34, 38 includes a first saddle-shaped coil 44 and a second saddle-shaped coil 46 placed within the respective Z-coil assemblies 28, 30 opposite each other. FIG. 3 further shows a transceiver coil assembly 48 that is disposed within the main coil assembly 26 between the first coil assemblies 28, 32, 34 and the second coil assemblies 30, 36, 38.

It is to be understood that the main coil assembly 26 may be used to create a magnetic field along a Z axis 50 defined by the volumetric scanner 10 from the front of the volumetric scanner 10 to the back of the scanner 10. The Z-coil assemblies 28, 30 may be used to vary the magnetic field along the Z axis 50. The Y-coil assemblies 32, 36 may be used to vary the magnetic field along a Y axis 52 defined by the volumetric scanner 10 perpendicular to the Z axis 50 from the top of the volumetric scanner 10 to the bottom of the scanner 10. Also, the X-coil assemblies 34, 38 may be used to vary the magnetic field along an X axis 54 defined by the volumetric scanner 10. The X axis 54 is perpendicular to the Z axis 50 and the Y axis 52 and is established from side to side. The transceiver coil assembly 48 is used to send and receive radio frequency signals.

As shown in FIG. 2 and FIG. 3, all of the coil assemblies 26, 28, 30, 32, 34, 36, 38 are centered on the Z axis 50. Moreover, the saddle-shaped coils 40, 42, 44, 46 comprising each Y coil assembly 32, 36 and each X coil assembly 34, 38 are alternating and equally spaced around the Z axis 50 within the Z coil assemblies 28, 30. FIG. 2 also shows a paper media support tray 56 in which paper media 58 that is to be scanned may be placed. In a particular aspect, the paper media 58 may be comprised of any configuration, orientation and combination of printed media, as the volumetric scan and resultant three-dimensional rendering may accommodate and process paper media 58 that is bound or unbound, paper media 58 that has text and/or images on a single side of the paper media 58, the paper media 58 that has text and/or images on both sides of the paper media 58, paper media 58 that is contained in an envelope, paper media 58 that is contained in a folder, paper media 58 that is folded or unfolded, paper media 58 that is contained in an opened or unopened box, paper media 58 that is stacked vertically, horizontally, or a combination thereof, paper media 58 that is stapled or paper clipped together, paper media 58 that isn't of uniform size or shape (e.g. letter sized paper and legal sized paper may be scanned simultaneously), paper media 58 that may be oriented in different x,y,z axis, and/or paper media 58 that may be found in any combination of the foregoing.

Referring to FIG. 3, a Z coil amplifier 60 is connected to the Z coil assemblies 28, 30. A Y coil amplifier 62 is connected to the Y coil assemblies 32, 36. Moreover, an X coil amplifier 64 is connected to the X coil assemblies 34, 38. Moreover, a transceiver amplifier 66 is connected to the transceiver coil assembly 48 through appropriate radio frequency (RF) electronics 68. A waveform generator 70 is connected to the amplifiers 60, 62, 64, 66. FIG. 3 shows that a microprocessor 72 is connected to the waveform generator 70 and to the RF electronics 68 through an analog-to-digital converter 74. As shown in FIG. 3, a controller 76 is connected to the main coil assembly 26. FIG. 3 also shows that a magnetic field shielding layer 78 may be disposed on the interior of the housing 12.

When implementing NMR/MRI to volumetrically scan paper media transposed with text and/or images, it may be advantageous to differentiate the text and images from the underlying paper substrate when outputting a three-dimensional rendering of the paper media and text and/or images. As recognized herein, almost every element in the periodic table has an isotope with a non-zero nuclear spin. A nuclear magnetic resonance (NMR)/MRI volumetric scan may only be performed on isotopes whose natural abundance is high enough to be detected. Carbon-13 is an isotope of carbon that has a non-zero nuclear spin and may be detected using a NMR/MRI volumetric scan. Naturally occurring carbon includes approximately one and one-tenth percent (1.1%) of carbon-13. Black printing ink includes approximately fifteen percent to twenty percent (15%-20%) of carbon black which, in turn, includes approximately ninety-seven percent to ninety-nine percent (97-99%) of naturally occurring carbon. Black toner includes approximately ten percent (10%) carbon black. Accordingly, black printing ink and black toner contains enough carbon-13 that it may be detected using a NMR/MRI volumetric scan. On average, paper contains approximately thirty-eight percent (38%) of carbon and may also be detected using a NMR/MRI volumetric scan.

As such, the exemplary scanner 10, described above may be configured to detect the carbon-13 in the paper media, the carbon-13 in any text transposed on the paper media (including text on both sides of the same sheet of paper), and the carbon-13 in any images transposed on the paper media (including images on both sides of the same sheet of paper). Because of the presence of Carbon-13, a NMR/MRI volumetric scan of a stack of papers, a closed and unopened book, a box of documents, or any other printed media may output a three-dimensional (3-D) dataset representing the carbon-13 configuration of each individual page of a book or each individual page in a box of documents, and as well as the carbon-13 configuration of any text and/or images transposed therein. This three-dimensional dataset may be processed as described in detail below in order to generate an electronic representation of the paper media, i.e., identifying and differentiating the paper and the ink.

Figure 4:
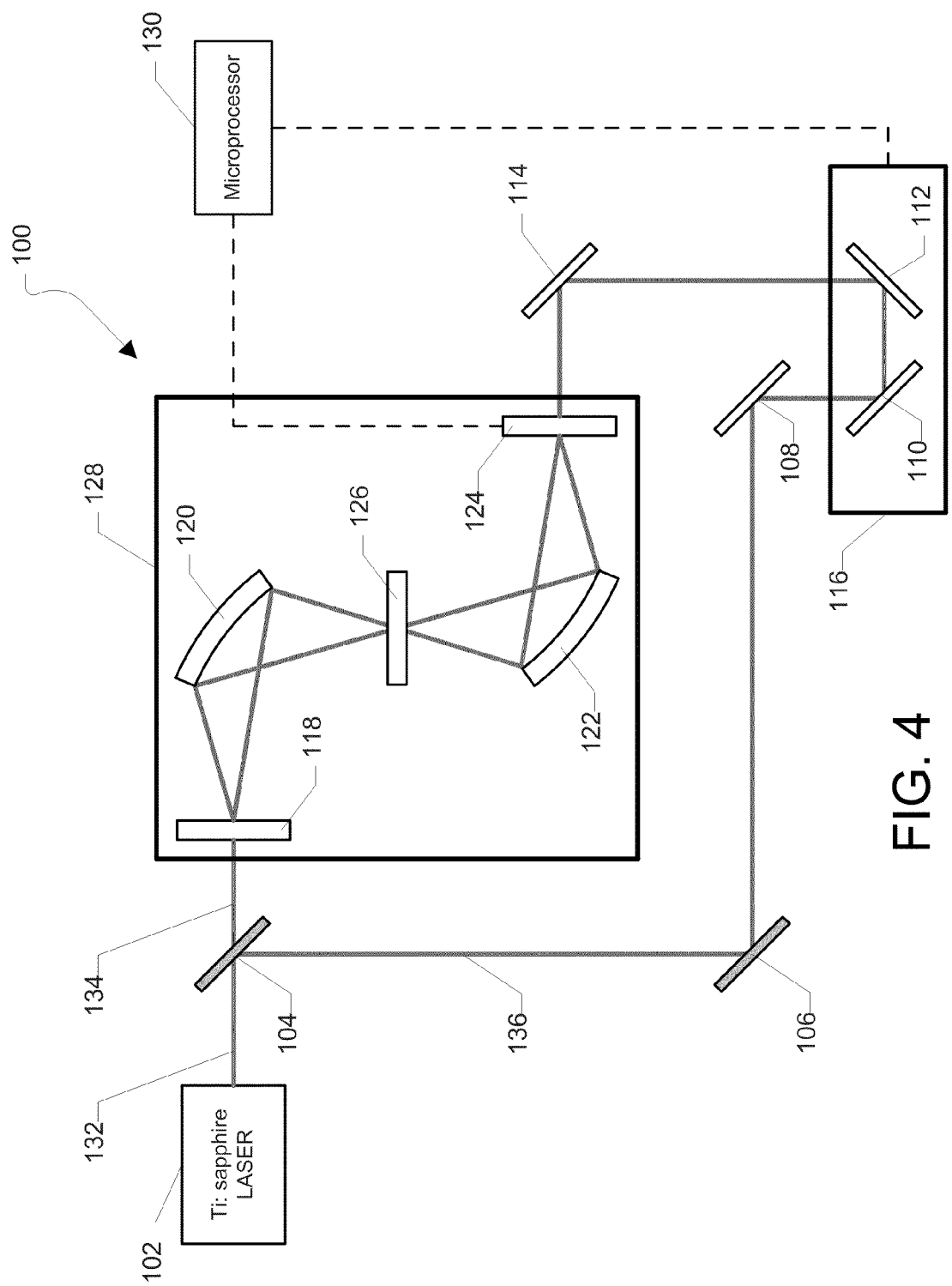
FIG. 4 is a block diagram of an exemplary aspect of a T-Ray scanner.

In addition to utilizing NMR/MRI to scan paper based media, volumetric scanning of paper based media may be performed by means of using Terahertz Rays (THz Rays). Referring now to FIG. 4, an exemplary, non-limiting aspect of a Terahertz Ray volumetric scanner is shown and is generally designated 100. As shown, the volumetric scanner 100 may include a laser 102. The laser 102 may be a pulsed laser, e.g., a titanium sapphire laser. As illustrated, the volumetric scanner 100 may include a beam splitter 104, a first reflector 106, a second reflector 108, a third reflector 110, a fourth reflector 112, and a fifth reflector 114. The third reflector 110 and the fourth reflector 112 may be part of an optical delay 116.

As depicted in FIG. 4, the volumetric scanner 100 may also include an emitter 118, a first paraboloidal mirror 120, a second paraboloidal mirror 122, and a detector 124. The emitter 118 may be a dipole-type, photoconductive antenna that may emit TeraHertz Ray wave pulses, as described herein. The detector 124 may also be a dipole-type, photoconductive antenna that is gated with time-delayed probe pulses that are divided from pump pulses, as described herein. A sample 126 may be placed between the first paraboloidal mirror 120 and the second paraboloidal mirror 122. In a particular aspect, the sample 126 may be any sort of printed media, and may be comprised of any configuration, orientation and combination of printed media, as the volumetric scan and resultant three-dimensional rendering may accommodate and process printed media that is bound or unbound, printed media that has text and/or images on a single side of the printed media, the printed media that has text and/or images on both sides of the printed media, printed media that is contained in an envelope, printed media that is contained in a folder, printed media that is folded or unfolded, printed media that is contained in an opened or unopened box, printed media that is stacked vertically, horizontally, or a combination thereof, printed media that is stapled or paper clipped together, printed media that isn't of uniform size or shape (e.g. letter sized paper and legal sized paper may be scanned simultaneously), printed media that may be oriented in different x,y,z axis, and/or printed media that may be found in any combination of the foregoing.

Further, in a particular aspect, the emitter 118, the first paraboloidal mirror 120, the second paraboloidal mirror 122, the detector 124, and the sample 126 may be located within a sample chamber 128. The sample chamber 128 may be a vacuum chamber, tilled with a gas, or purged with a gas. FIG. 4 indicates that the volumetric scanner 100 may further include a microprocessor 130 that may be electrically connected to the optical delay 116 and to the detector 124. The microprocessor 130 may act as a reconstruction/rendering apparatus that may be used to render a 3D voxel set from the data received from the volumetric scanner 100.

As illustrated in FIG. 4, during operation, the laser 102 may emit a pulsed laser beam 132 directed at the beam splitter 104. The laser pulses may have a pulse duration of approximately one hundred femtoseconds (100 fs). Further, the laser pulses may have a wavelength of approximately eight hundred nanometers (800 nm). The beam splitter 104 may split the pulsed laser beam 132 into a pump pulse beam 134 and a probe pulse beam 136.

The pump pulse beam 134 may be directed at, and illuminate, the emitter 118. As a result, the emitter 118 may emit THz wave pulses. The THz wave pulses from the emitter 118 may be collimated and focused by the first paraboloidal mirror 120 onto the sample 126 at approximately normal incidence. The probe pulse beam 136 may be reflected by the reflectors 106, 108, 110, 112, 114 through the optical delay 116 and onto the detector 124. The probe pulse beam 136 may be a collimated and focused by the second paraboloidal mirror 122 onto the sample 126 at approximately normal incidence. Detection may be achieved by varying the difference between the optical path lengths of the pump pulses and probe pulses in order to measure the waveform of the THz wave, which is measured in the time domain. The sample 126 may be placed on a sample tray (not shown) that may be moved along X-Y axes by a pair of linear motor stages (not shown) in order to acquiring images in two dimensions. The sample tray (not shown) may also be moved along a Z axis in order to acquire data in a third dimension relative to the first two dimensions. Conversely, it is also possible that the aforementioned components of volumetric scanner 100 may move around sample 126, so long as sample 126 remains in a stationary position relative to the moving components of volumetric scanner 100.

In a particular aspect, the sample tray may include, or be formed with, at least one plate formed with metallic plasmonic crystals (MPC) that may be placed above the sample, below the sample, or a combination thereof. The MPC may act as a THz surface plasmon resonance (SPR) sensing imaging plate at normal incidence. Further, the MPC may be a metallic plate formed with an array of circular holes. The use of the MPC may allow the sensor to obtain high sensitivity and large-area detection of samples. When the MPC is illuminated with terahertz (THz) waves, as described herein, the surface plasmon polariton (SPP) may be excited in the vicinity of the metal surface provided by the MPC as a result of the interference of scattered light from the aperture array, i.e., the array of circular holes in the MPC.

In a particular aspect, the excitation of the SPP may occur at certain resonant frequencies that are determined by the geometrical structure of the MPC. Accordingly, a resonant narrow band-pass characteristic may appear in the transmission spectrum. This resonant narrow band-pass characteristic depends on the dielectric distribution near the surface of the MPC due to the strong localization of the electric field of SPPs near the surface of the MPC.

When implementing THz rays to volumetrically scan paper media transposed with text and/or images, it may be advantageous to differentiate the text and images from the underlying paper substrate when outputting a three-dimensional rendering of the paper media and text and/or images. During a scan of printed media, the ink and the paper will reflect and absorb T-Rays differently. The differing frequencies of the reflected T-rays may then be used to create a 3D representation of the scanned object, e.g., printed media. Alternatively, special "fingerprints" within the TeraHertz range may be identified offering an ability to combine spectral identification with imaging, or any other methods know for TeraHertz time domain spectroscopy. As such, a T-Ray scan may be used to determine the chemical compositions of inks, paper, or a combination thereof.

Figure 5:
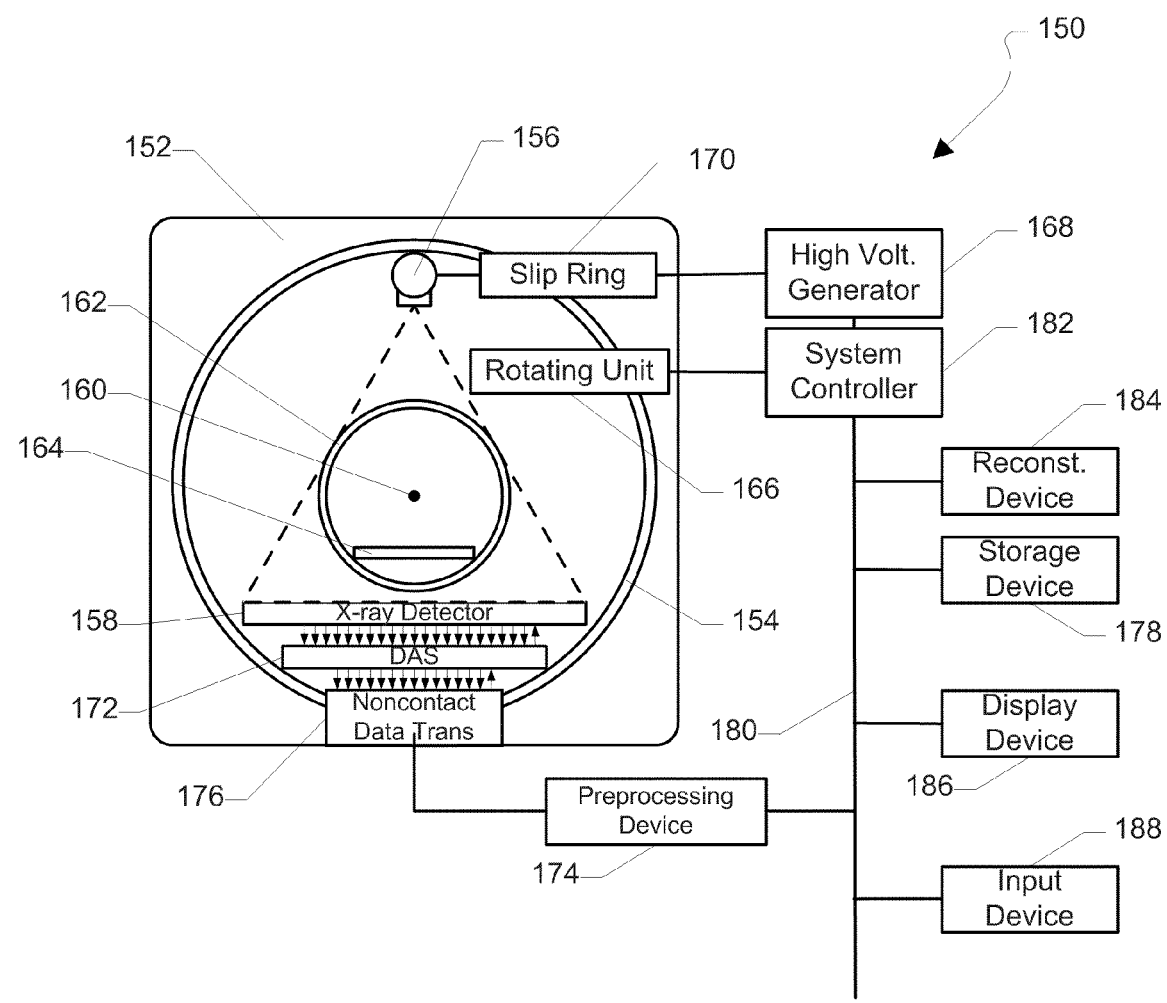
FIG. 5 is a diagram of an exemplary aspect of an X-Ray CT scanner.

In addition to utilizing a NMR/MRI volumetric scan or a TeraHertz volumetric scan to scan paper based media, a volumetric scan of paper based media may be performed by means of using X-Rays. Referring now to FIG. 5, an exemplary, non-limiting aspect of an X-ray computed tomography (CT) volumetric scanner is shown and is generally designated 150. As shown in FIG. 5, the volumetric scanner 150 may include a gantry 152 in which a generally cylindrical frame 154 is installed. An X-ray tube 156 and an X-ray detector 158 may be installed, or otherwise mounted, on the frame 154. In an exemplary, non-limiting aspect, the X-ray detector 158 may be a multi-row detector. In a given aspect, the X-ray detector 158 may be a two-dimensional array type detector or flat panel detector or any other type of detector well known in the art. Further, the X-ray detector 158 may include, for example, sixty-four (64) rows, two hundred and fifty-six (256) rows, three-hundred and twenty (320) rows, or any other number of rows well known in the art. Additionally, in another aspect, the X-ray detector 158 may be an X-ray detector having any other shape well known in the art.

In a particular aspect, the frame 154, the X-ray tube 156, and the X-ray detector 158 may rotate around an axis of rotation 160. In another aspect (not shown), there may be multiple X-ray tube 156, and not just one X-ray tube 156. In a given aspect, X-ray tube 156 may be dual source or have any number of x-ray sources greater than one. As illustrated in FIG. 5, a generally cylindrical sample chamber 162 may be located within the gantry 152. Specifically, the sample chamber 162 my be located within the frame 154 and the sample chamber 162 may be concentric with the frame 154. The sample chamber 162 may further include a generally flat sample tray 164 that may be configured to receive paper media. In a particular aspect, flat sample tray 164 may be configured to receive any sort of paper media, and may be comprised to receive any configuration, orientation and combination of paper media, as the volumetric scan and resultant three-dimensional rendering may accommodate and process paper media that is bound or unbound, paper media that has text and/or images on a single side of the paper media, the paper media that has text and/or images on both sides of the paper, paper media that is contained in an envelope, paper media that is contained in a folder, paper media that is folded or unfolded, paper media that is contained in an opened or unopened box, paper media that is stacked vertically, horizontally, or a combination thereof, paper media that is stapled or paper clipped together, paper media that isn't of uniform size or shape (e.g. letter sized paper and legal sized paper may be scanned simultaneously), paper media that may be oriented in different x,y,z axis, and/or paper media that may be found any combination of the foregoing.

As illustrated in FIG. 5, the X-ray tube 156 and the X-ray detector 158 may be mounted on the frame 154 so that the X-ray detector 158 faces the X-ray tube 156. The volumetric scanner 150 may also include a rotating unit 166 that can, during operation of the volumetric scanner 150, rotate the frame 154 at a high angular speed, e.g., less than 1.0 seconds per full rotation.

The volumetric scanner 150 shown in FIG. 5 may also include a high voltage generator 168 that may apply a tube voltage to the X-ray tube 156 through a slip ring 170 and that may supply a filament current to the X-ray tube 156. As such, the X-ray tube 156 may generate X-rays that may pass through a sample that is placed in the sample chamber 162. The X-ray detector 158 may detect the X-rays that are transmitted through the sample within the sample chamber 162.

As depicted, the volumetric scanner 150 may also include a data acquisition circuit 172, aka, a data acquisition system (DAS). A preprocessing device 174 may be connected to the data acquisition circuit 172 via a non-contact data transmitter 176. The preprocessing device 174 may be housed in a console (not shown) located outside the gantry 152. In a particular aspect, the data acquisition circuit 172 is configured to convert a signal output from the X-ray detector 158 for each channel into a voltage signal, amplify the voltage signal, and convert the voltage signal into a digital signal. The data acquisition circuit 172 may transmit raw data, i.e., the digital signal, to the preprocessing device 174 through the non-contact data transmitter 176. The preprocessing device 174 may perform correction processing such as sensitivity correction for the raw data. A storage device 178 may be coupled to the preprocessing device 174 via a data/control bus 180. The preprocessing device 174 may transmit the resultant data to the storage device 178 and the storage device 178 may store the resultant data as projection data at a stage immediately before reconstruction processing.

FIG. 5 further indicates that the volumetric scanner 150 may include a system controller 182 that may be connected to the storage device 178 via the bus 180. Further, a reconstruction device 184, a display device 186, and an input device 188 may be connected to the system controller 182 and other components via the bus 180.

It may be appreciated that there are a plurality of scan conditions associated with the scanner that are relevant to the item to be scanned. For example, these scan conditions may include many setting items such as a scan mode which discriminates the type of scan, a tube voltage, a tube current, the diameter (S-FOV) of an imaging field, the diameter (D-FOV) of a reconstruction field, an imaging slice thickness, a reconstruction slice thickness, a helical pitch, the number of slices, a start time representing an elapsed time from the start time point of a scan, a wait time representing the time interval between adjacent scan elements, and a pause time representing the intervals of X-ray generation within a scan element in S & S or the like. The scan modes typically include scanography, a dynamic scan, a 4D dynamic scan, an S & S scan, and a helical scan.

In a particular aspect, in order to reconstruct one-slice tomographic image data, projection data corresponding to one rotation, i.e., approximately three hundred sixty degrees (360°), around a sample may be used. For a half scan, approximately one hundred eighty degrees (180°) of projection data may be used. Several techniques are well known for converting incident X-rays into electric charges. For example, an indirect conversion technique that converts X-rays into light through a phosphor such as a scintillator and converts the light into electric charges through photoelectric conversion elements such as photodiodes may be used. Also, a direct conversion type that uses generation of electron-hole pairs in a semiconductor by X-rays and migration of the electron-hole pairs to an electrode, i.e., a photoconductive phenomenon, may be used.

When implementing X-ray computed tomography (CT) volumetric scanning to scan paper media transposed with text and/or images, it may be advantageous to differentiate the text and images from the underlying paper substrate when outputting a three-dimensional rendering of the paper media and text and/or images. During a scan of printed media, the ink and the paper may absorb X-Rays differently. The differing absorption of the X-rays may then be used to create a 3D representation of the scanned object, e.g., printed media.

In addition to the use of MRI, CT, and Terahertz, volumetric scans of paper media may also be carried out using any other type of non-destructive scan that renders a three-dimensional dataset of the sample. They may include, without limitation, CAT scans, PET scans, Ultrasound Scans, Supersonic Scans, Laser 3D scans, or a combination thereof.

Figure 6:
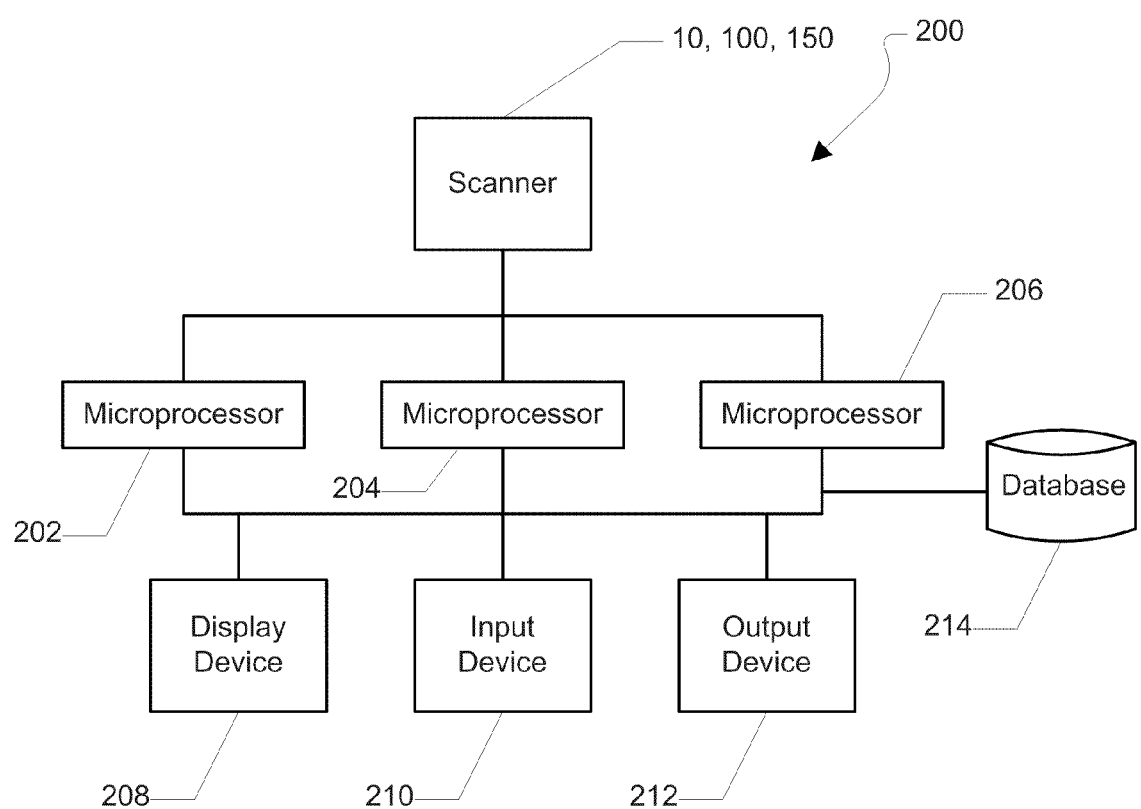
FIG. 6 is a block diagram of a scanning system.

Referring now to FIG. 6, a system for scanning paper media is shown and is generally designated 200. In a particular aspect, the system 200 may include a non-invasive scanner, e.g., the NMR/MRI volumetric scanner 10, the TeraHertz Ray volumetric scanner 100, the X-ray CT volumetric scanner 150, or a combination thereof. Alternatively, the system 200 may utilize any other non-invasive scanner that is configured to scan and recognize paper and ink and discern a difference there between and render a three-dimensional dataset of the volumetrically scanned paper and ink.

FIG. 6 shows that system 200 may include a first microprocessor 202, a second microprocessor 204, and a third microprocessor 206 that may be connected to the volumetric scanner 10, 100, 150. In alternate aspects, any number of microprocessors may be included in system 200. Further, the system 200 may include a display device 208, e.g., a monitor, connected to the microprocessors 202, 204, 206. An input device 210, e.g., a keyboard, a mouse, a light pen, etc., may be connected to the microprocessors 202, 204, 206. Also, an output device 212, e.g., a printer, may be connected to the microprocessors 202, 204, 206. Moreover, a database 214, e.g., random access memory (RAM), a RAID array, etc, may be connected to the microprocessors 202, 204, 206.

Each microprocessor 202, 204, 206 may include a series of computer-executable instructions, as described below, that may process a three-dimensional dataset representing paper media received from the volumetric scanner 10, 100, 150. The instructions may be contained in the database 214 or on a data storage device with a computer readable medium, such as a computer diskette. Or, the computer-executable instructions may be stored on a magnetic tape, conventional hard disk drive, electronic read-only memory (ROM), optical storage device, or other appropriate data storage device or transmitting device thereby making a computer program product, i.e., an article of manufacture according to the disclosure. In an illustrative aspect, the computer-executable instructions may be written, e.g., using C++, but may be written in any type of software language known in the art.

The flow charts herein illustrate the structure of the logic of the present methods as embodied in computer program software. Those skilled in the art will appreciate that the flow charts illustrate the structures of computer program code elements including logic circuits on an integrated circuit that function according to this disclosure. Manifestly, the method(s) disclosure herein may be practiced by a machine component that renders the program elements in a form that instructs a digital processing apparatus (that is, a computer) to perform a sequence of function steps corresponding to those shown.

Figure 7:
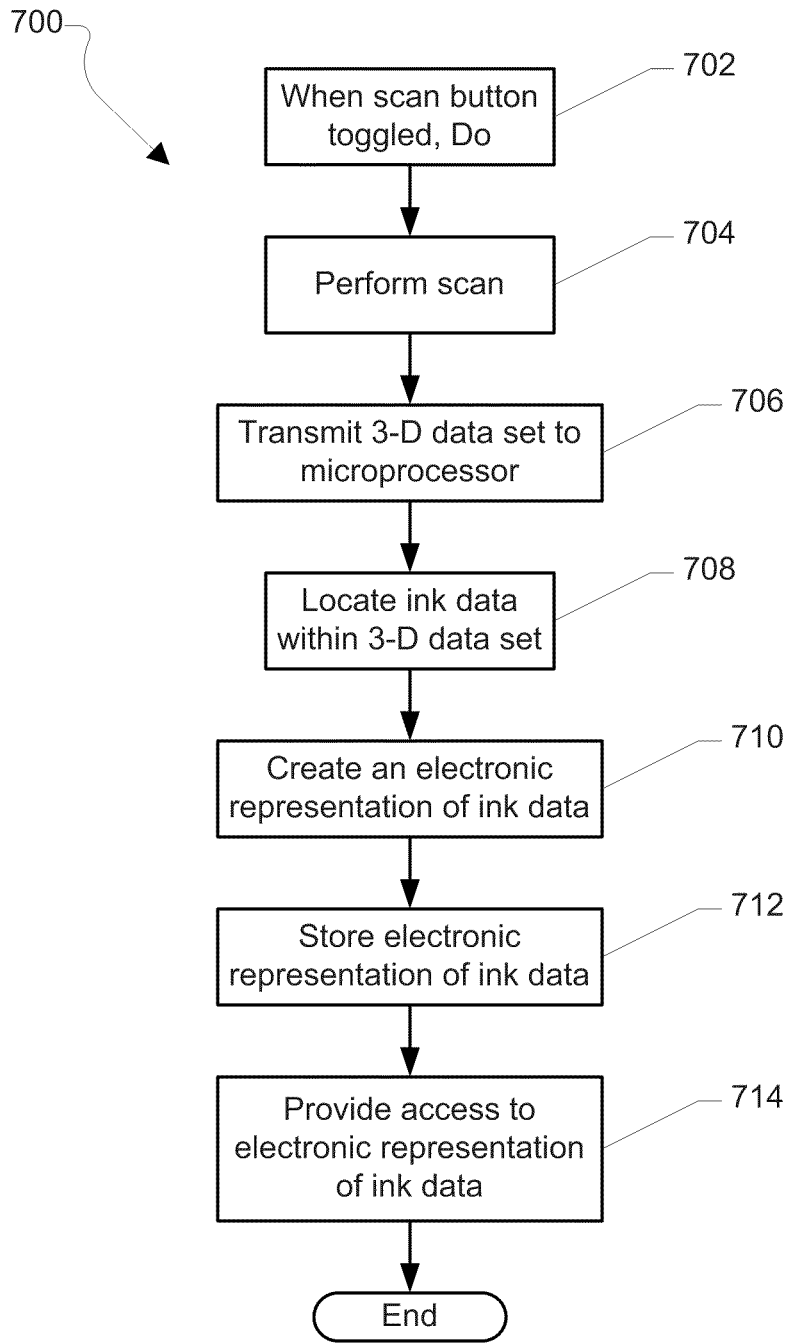
FIG. 7 is a flow chart representing a first aspect of a method of scanning paper media.

Referring to FIG. 7, a method of scanning paper media is shown and is generally designated 700. The method 700 commences at block 702 with a do loop wherein when a scan button, e.g., the scan button 22 (FIG. 1), is toggled, the following steps are performed. At block 704, paper media placed with a volumetric scanner may be scanned using non-invasive scanning means. For example, the paper media may be scanned using NMR/MRI means, TeraHertz ray means, x-ray computed tomography means, Terahertz ray computed tomography means, or any combination thereof. Depending on which volumetric scanning means utilized, it may be advantageous to remove all staples and paperclips from the paper media, but may not be possible or necessary. At block 706, a 3-D dataset representing printed media is transmitted to one or more of the microprocessors. Moving to block 708, ink data within the 3-D dataset is located within the 3-D dataset.

At block 710, an electronic representation of the ink data is created. In a particular aspect, this electronic representation is created by "reading" the ink data with typical OCR that is well known in the art. Alternatively, the electronic representation may be created by "reading" the ink data using volumetric character recognition (VCR) described herein. Alternatively, the electronic representation may be created by "reading" the ink data by mapping the location of the ink data in reference to the three-dimensional dataset in which it resides. Continuing to block 712, the electronic representation of the ink data is stored in a database, e.g., the database 214 (FIG. 6). Then, at block 714, access to the electronic representation of the ink data may be provided. For example, a user may simply read the electronic representation on a lap top computer, desk top computer, hand held computer, wireless telephone, portable data assistant, or any other similar device well known in the art. Also, a user may search the electronic representation of the ink data using a key word search, Boolean search, semantic search, or any other search means known in the art. By way of non-limiting examples, the electronic representation of the ink data may be uploaded to a web server and made available via the Internet or the electronic representation of the ink data may be appended with metatags, database attributes, and/or other search classification formats and integrated into any number of electronic content management (ECM) systems known in the art And, all or portions of the electronic representation of the ink data may be printed or outputted at an output device, e.g., the output device 212 (FIG. 6). It may be appreciated that once the electronic representation of the ink data is created a range of pages may be easily located and printed, uploaded, searched, or otherwise manipulated. From block 714, the method may end.

Figure 8:
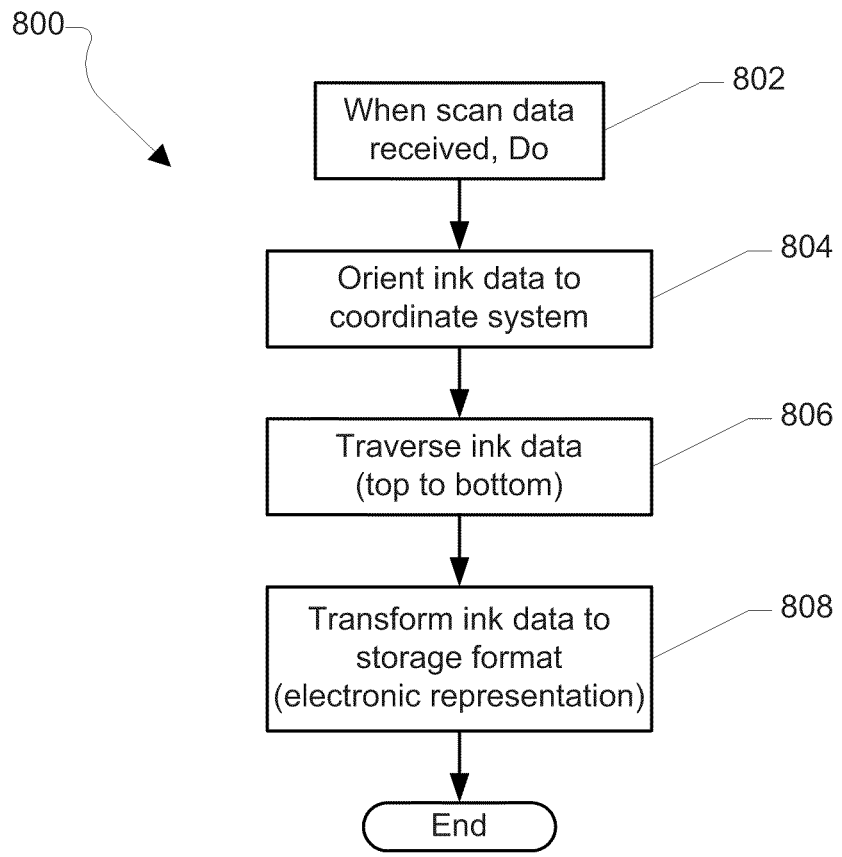
FIG. 8 is a flow chart representing a method of processing paper/ink data.
Figure 9:
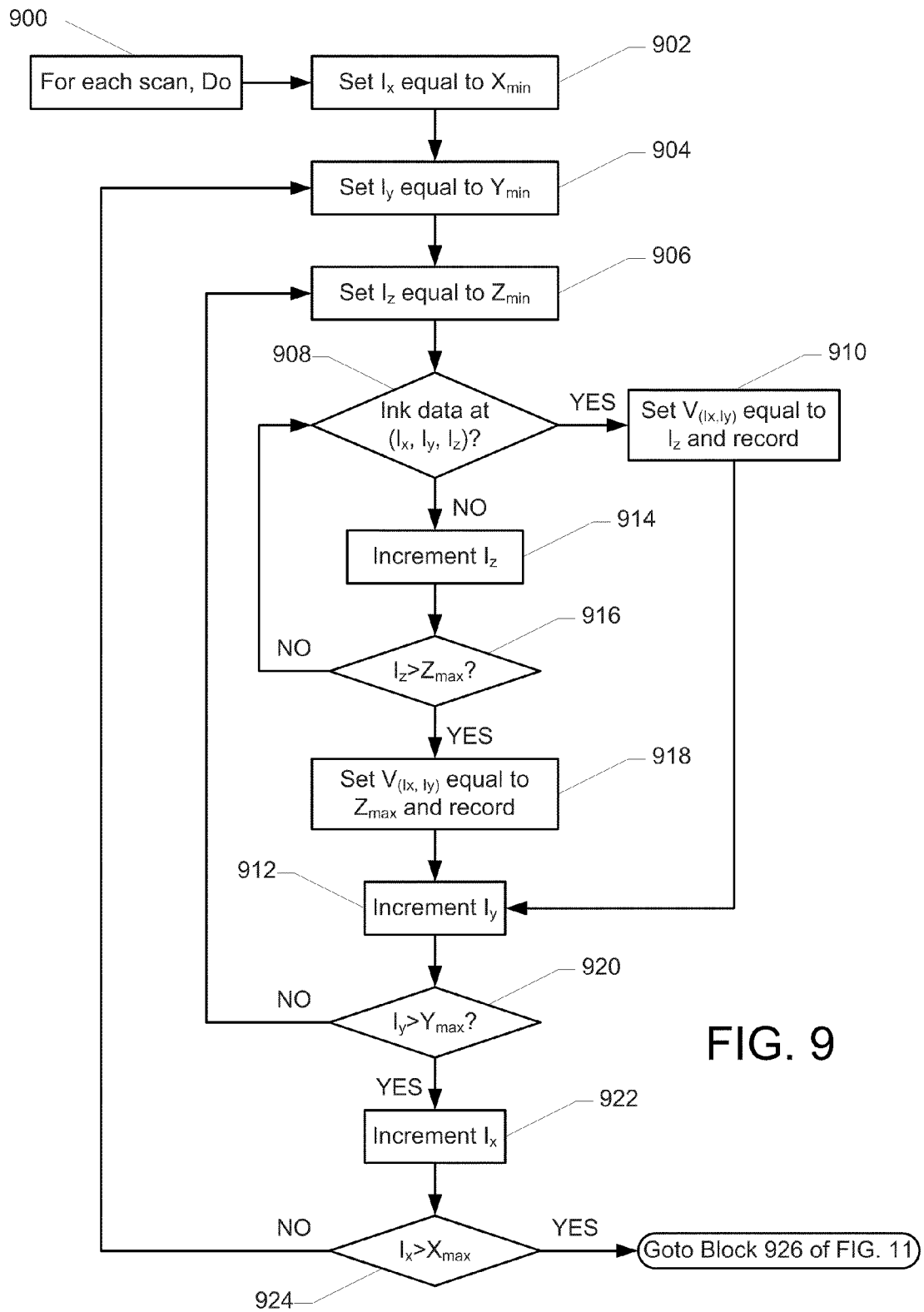
FIG. 9 is a flow chart representing a first portion of a method of orienting paper and ink data.

Referring now to FIG. 8, a method of processing paper/ink data is shown and commences at block 802 with a do loop wherein when volumetric scan data is received, the following steps are performed. At block 804, the ink data is oriented to a predetermined coordinate system well known in the art, such as without limitation, a rectangular (a.k.a Cartesian) coordinate system, a polar coordinate system, etc. Next, at block 806, the ink data is traversed top to bottom in order to "read" the ink data. Alternatively, the ink data may be traversed from bottom to top, side to side, front to back, back to front, along the z-axis in any direction, or any combination thereof. Moving to block 808, the data is transformed to any storage format known in the art, such as without limitation order to create an electronic representation of the paper media scanned by the volumetric scanner 10, 100, 150. The method may then end.

FIG. 9 through FIG. 14 illustrate a method of orienting paper and ink data. Beginning at block 900 of FIG. 9, a do loop is entered wherein the steps shown in FIG. 9 through FIG. 14 are performed. At block 902, a variable Ix is set equal to $X_{min}$, where $X_{min}$ is the minimum data point of the 9-D dataset along the X axis of a rectangular coordinate system. At block 904, a variable $I_y$ is set equal to $Y_{min}$, where $Y_{min}$ is the minimum data point along the Y axis. Further, at block 906, another variable $I_z$ is set equal to $Z_{min}$, i.e., the minimum data point along the Z axis of the rectangular coordinate system.

Moving to decision diamond 908, it is determined whether the data found at ($I_x$, $I_y$, $I_z$) is ink data. If so, the logic proceeds to block 910 and a variable, $V_{(Ix, Iy)}$, is set equal to $I_z$. In other words, during the first loop, if at a particular location, e.g., ($I_x$, $I_y$, $I_z$) equal to (0, 0, 5) ink data is found, the variable $V_{(0,0)}$ is set equal to five (5) and recorded. Thus, the system knows that there is ink at location (0, 0, 5). The logic then proceeds to block 912 and $I_y$ is incremented, e.g., by one integer.

Returning to decision diamond 908, if there is not any ink data at ($I_x$, $I_y$, $I_z$), the logic continues to block 914 and $I_z$ is incremented, e.g., by one integer. Next, at decision diamond 916, it is determined whether $I_z$ is greater than $Z_{max}$, i.e., the maximum data point along the Z axis. If not, the logic returns to decision diamond 908 and continues as described above. If $I_z$ is greater than $Z_{max}$, the logic moves to block 918 where $V_{(Ix, Iy)}$ is set equal to $Z_{max}$ and recorded. Next, at block 912, $I_y$ is incremented by one predefined increment.

Proceeding to decision diamond 920, it is determined whether $I_y$ is less than $Y_{max}$, i.e., the maximum data point along the Y axis of the 9-D dataset. If not, the logic returns to block 906 and continues as described above. Otherwise, if $I_y$ is greater than $Y_{max}$, the logic moves to block 922 where Ix is incremented, e.g., by one predefined increment. Moving to decision diamond 924, it is determined whether Ix is greater than $X_{max}$, where $X_{max}$ is the maximum data point along the X axis. If not, the logic returns to block 904 and continues as described above. On the other hand, if Ix is indeed greater than $X_{max}$ the logic continues to FIG. 10. It is to be understood that the portion of the orientation logic shown in FIG. 9 may be used to determine which points in the three-dimensional dataset obtained during a scan represent ink. Those points that represent ink data are recorded as described above.

Figure 10:
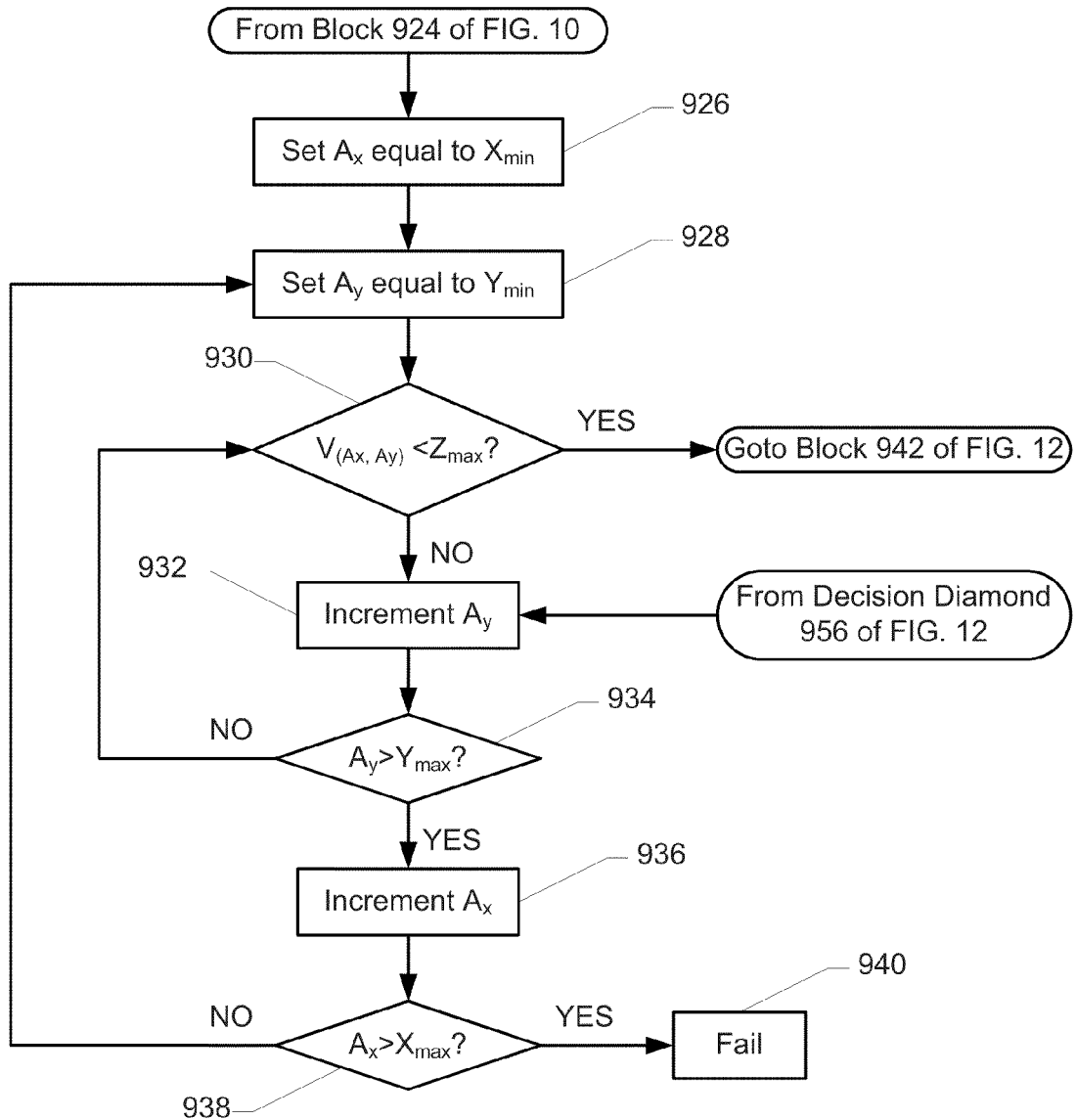
FIG. 10 is a flow chart representing a second portion of a method of orienting paper and ink data.

Moving to block 926 of FIG. 10, a variable, $A_x$, is set equal to $X_{min}$. Next, at block 928, a variable, $A_y$, is set equal to $Y_{min}$. Moving to decision diamond 930 it is determined if $V_{(Ax,Ay)}$ is less than $Z_{max}$. If not, the logic moves to block 932 and $A_y$ is incremented by one predetermined increment. If $V_{(Ax,Ay)}$ is less than $Z_{max}$, the logic moves to FIG. 11 and continues as described below. Proceeding to decision diamond 934, it is determined if $A_y$ is greater than $Y_{max}$. If not, the logic returns to decision diamond 930 and continues as described above. Otherwise, the logic moves to block 936 and $A_x$ is incremented by one predefined increment. Continuing to decision diamond 938, it is determined whether $A_x$ is greater than $X_{max}$. If so, a "Fail" signal is presented at block 940 and the logic ends. Conversely, if $A_x$ is less than or equal to $X_{max}$, the logic returns to block 928 and continues as described above.

Figure 11:
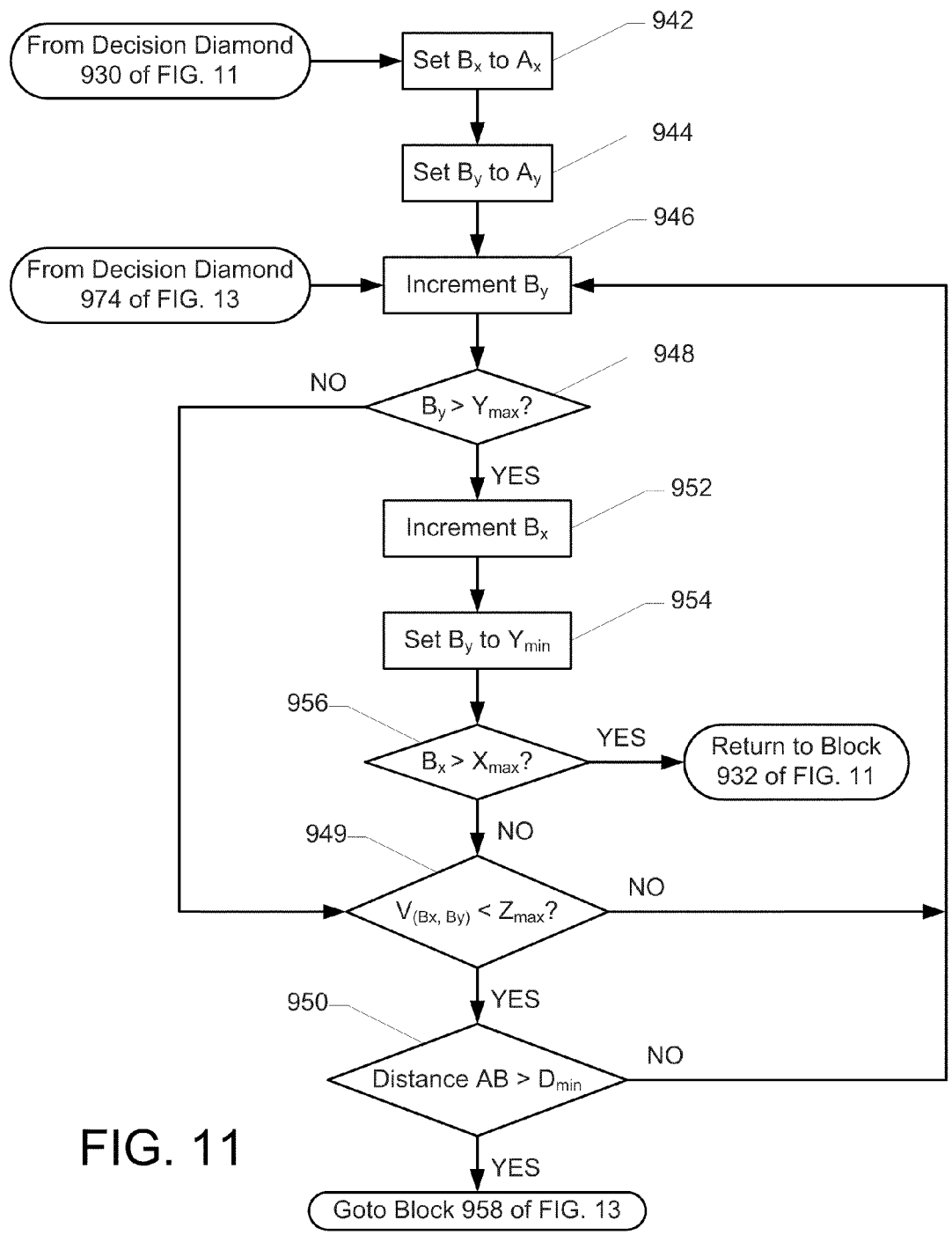
FIG. 11 is a flow chart representing a third portion of a method of orienting paper and ink data.

As described above at decision diamond 930, if $V_{(Ax,Ay)}$ is less that $Z_{max}$, the logic proceeds to block 942 of FIG. 11. At block 942, $B_x$ is set equal, to $A_x$. At block 944, $B_y$ is set equal to $A_y$. Moving to block 946, $B_y$ is incremented by one predetermined increment. Next, at decision diamond 948, it is determined whether $B_y$ is greater than Y. If not, the logic moves to decision diamond 949 where it is determined whether $V_{(Bx,By)}$ is less than $Z_{max}$. If $V_{(Bx,By)}$ is greater than or equal to $Z_{max}$, the logic returns to block 946 and continues as described above. If $V_{(Bx,By)}$ is less than $Z_{max}$, the logic moves to decision diamond 950 and it is determined whether the distance between $A_{(Ax,Ay)}$ and $B_{(Bx,By)}$ is greater than a predetermined minimum threshold, $D_{min}$. If so, the logic moves to FIG. 12. Otherwise, the logic returns to block 946 and $B_y$ is incremented by one predetermined increment.

Returning to decision diamond 948, if $B_y$ is indeed greater than $Y_{max}$, the logic moves to block 952 where $B_x$ is incremented by one predefined increment. Then, at block 954, $B_y$ is set equal to $Y_{min}$. Moving to decision diamond 956 it is determined whether $B_x$ is greater than $X_{max}$. If so, the logic returns to block 932 of FIG. 10. If $B_x$ is less than or equal to $X_{max}$, the logic moves to decision diamond 950 and continues as described above.

Figure 12:
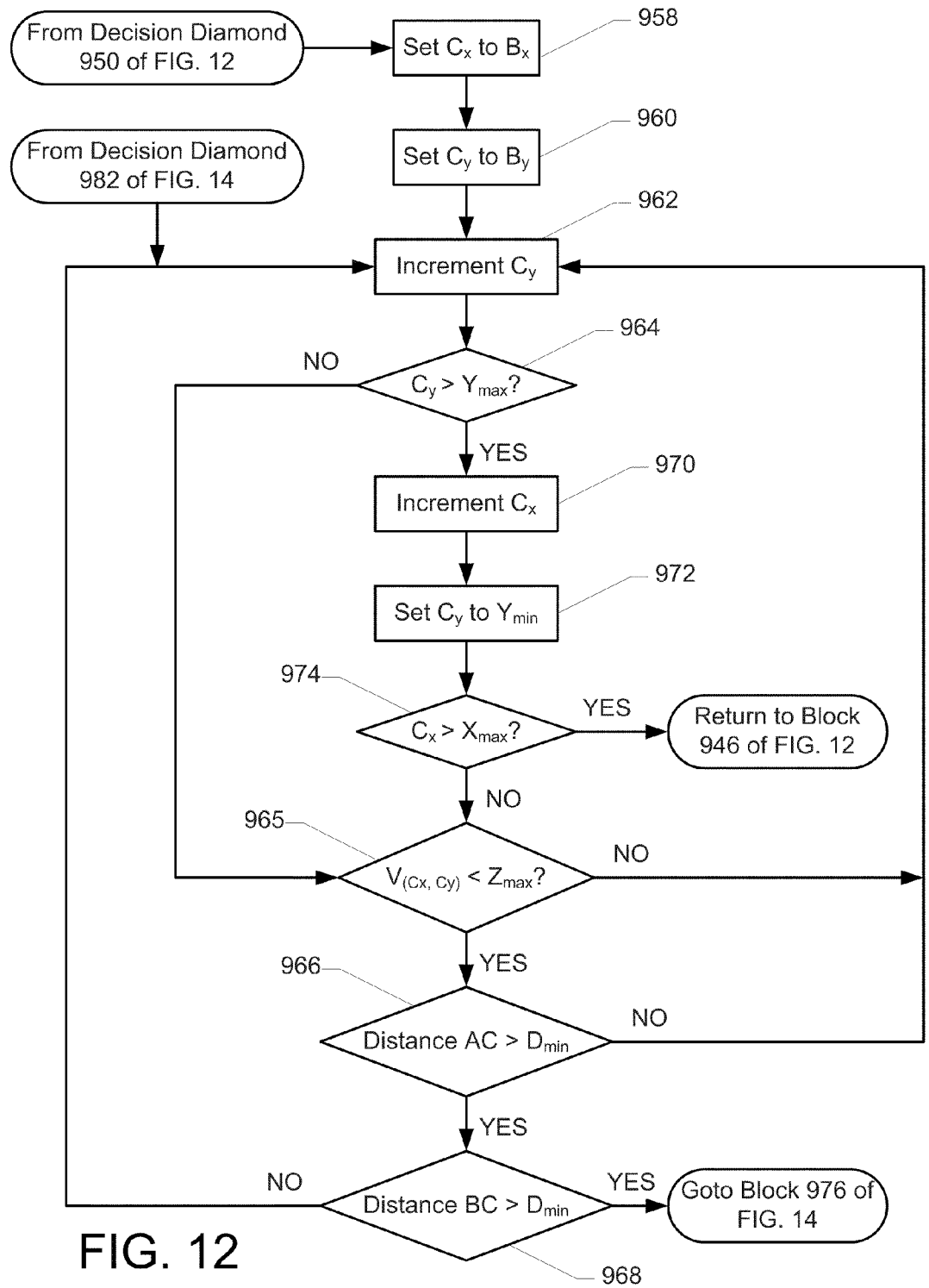
FIG. 12 is a flow chart representing a fourth portion of a method of orienting paper and ink data.

As described above, if the distance from $A_{(Ax,Ay)}$ to $B_{(Bx,By)}$ is greater than $D_{min}$, the logic moves to FIG. 12, i.e., block 958 of FIG. 12. At block 958, $C_x$ is set equal to $B_x$. Also, at block 960 $C_y$ is set equal to $B_y$. Continuing to block 962, $C_y$ is incremented by one predetermined increment. Next, at decision diamond 964, it is determined whether $C_y$ is greater than $Y_{max}$. If not, the logic moves to decision diamond 965 where it is determined whether $V_{(Cx,Cy)}$ is less than $Z_{max}$. If $V_{(Cx,Cy)}$ is greater than or equal to $Z_{max}$, the logic returns to block 962 and continues as described above. If $V_{(Cx,Cy)}$ is less than $Z_{max}$, the logic moves to decision diamond 966 where it is determined whether the distance between $A_{(Ax,Ay)}$ and $C_{(Cx,Cy)}$ is greater than the predetermined minimum threshold, $D_{min}$. If not, the logic returns to block 962 and continues as described above. If the distance between $A_{(Ax,Ay)}$ and $C_{(Cx,Cy)}$ is indeed greater $D_{min}$, the logic moves to decision diamond 968, where it is determined whether the distance between $B_{(Bx,By)}$ and $C_{(Cx,Cy)}$ is greater than $D_{min}$. If so, the logic continues to FIG. 13. Otherwise, the logic returns to block 962 and continues as described above.

Returning to decision diamond 964, if $C_y$ is greater than $Y_{max}$, the logic moves to block 970 where $C_x$ is incremented by one predefined increment. Then, at block 972, $C_y$ is set equal to $Y_{min}$. Moving to decision diamond 974 it is determined whether $C_x$ is greater than $X_{max}$. If so, the logic returns to block 946 of FIG. 11. If $C_x$ is less than or equal to $X_{max}$, the logic moves to decision diamond 966 and continues as described above.

Figure 13:
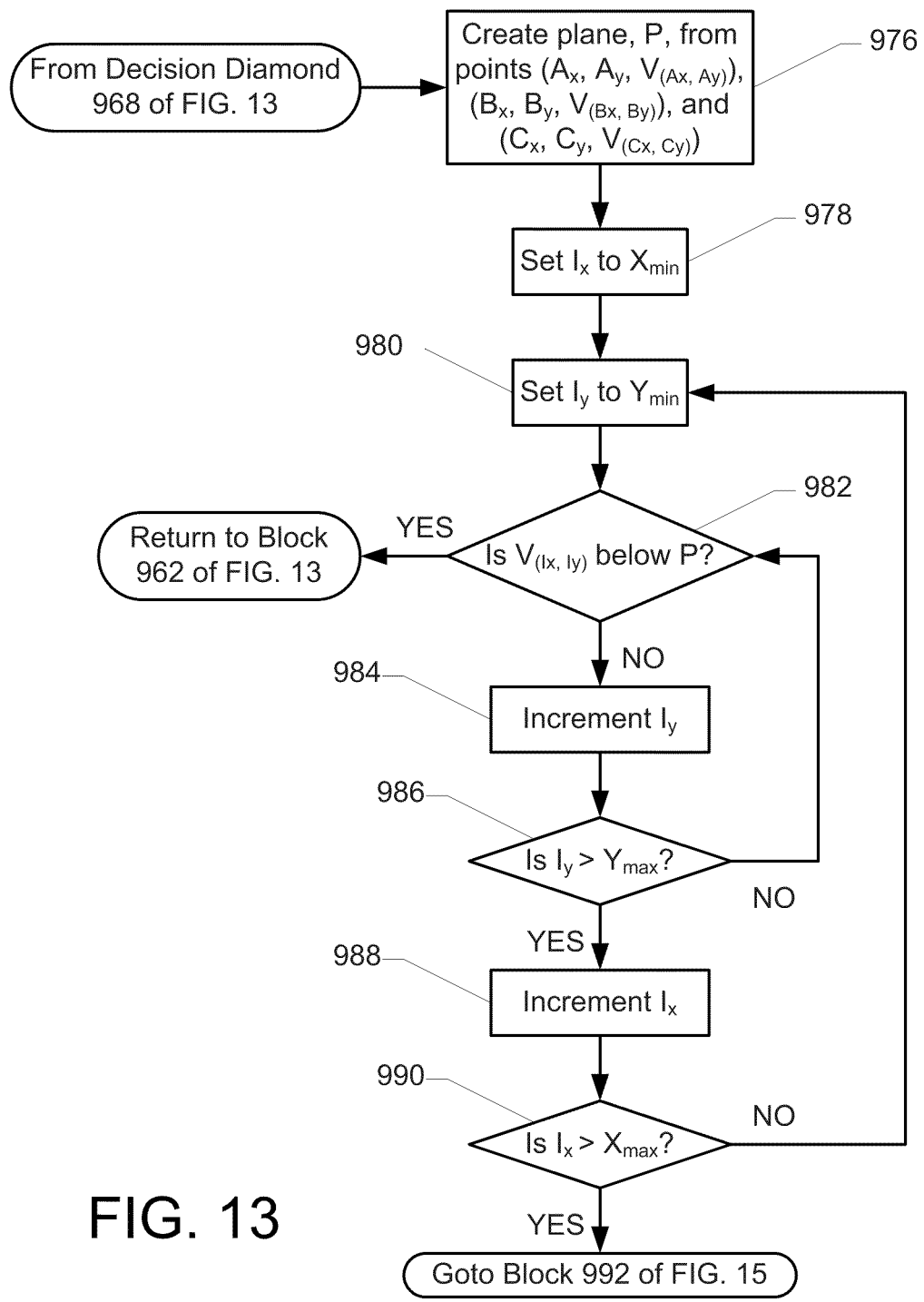
FIG. 13 is a flow chart representing a fifth portion of a method of orienting paper and ink data.

As stated above, at decision diamonds 966 and 968, if the distanced between $A_{(Ax,Ay)}$ and $C_{(Cx,Cy)}$ is greater $D_{min}$, and the distance between $B_{(Bx,By)}$ and $C_{(Cx, Cy)}$ is also greater than $D_{min}$, the logic moves to block 976 of FIG. 13. At block 976, a plane, P, is created using ($A_x$, $A_y$, $V_{(Ax,Ay)}$), ($B_x$, $B_y$, $V_{(Bx,By)}$), and ($C_x$, $C_y$, $V_{(Cx,Cy)}$). Then, at block 978, $I_x$ is set equal to $X_{min}$. At block 980, $I_y$ is set equal to $Y_{min}$. Proceeding to decision diamond 982, it is determined whether $V_{(Ix,Iy)}$ is below the plane, P. If so, the logic returns to block 962 of FIG. 12. If $V_{(Ix, Iy)}$ is not below P, the logic continues to block 984 and $I_y$ is incremented by one predefined increment.

Thereafter, at decision diamond 986, it is determined whether $I_y$ is greater than Y. If not, the logic returns to decision diamond 982 and continues as described above. If $I_y$ is greater than $Y_{max}$, the logic moves to block 988 where $I_x$ is incremented by one predefined increment. Moving to decision diamond 990, it is determined whether $I_x$ is greater than $X_{max}$. If not, the logic returns to block 980 and continues as described above. Otherwise, if $I_x$ is greater than $X_{max}$, the logic continues to block 992 of FIG. 14.

Figure 14:
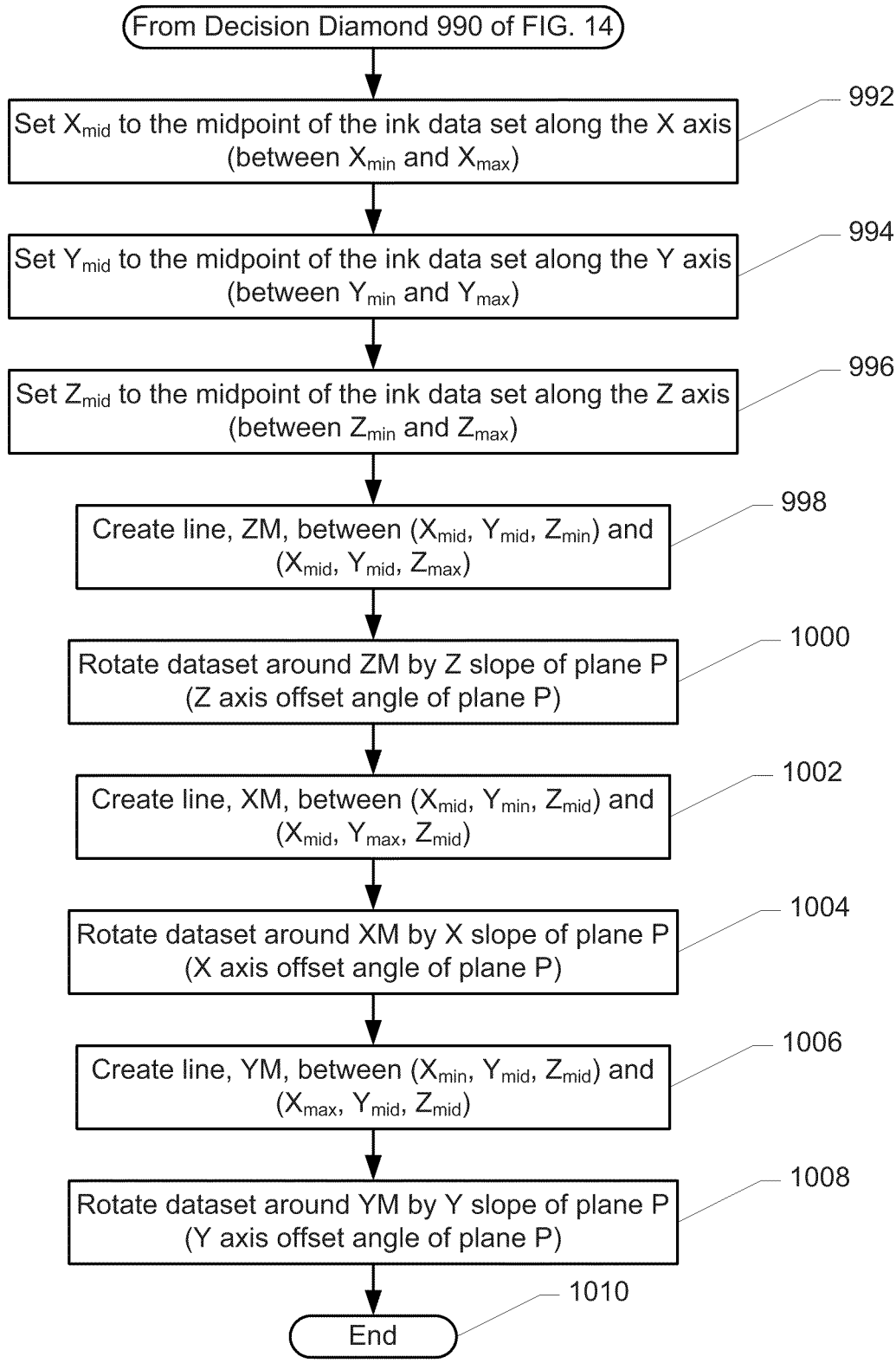
FIG. 14 is a flow chart representing a sixth another portion of a method of orienting paper and ink data.

At block 992 of FIG. 14, a variable $X_{mid}$ is set to the midpoint of the dataset along the X axis of the between $X_{min}$ and $X_{max}$. At block 994, a variable $Y_{mid}$ is set to the midpoint of the dataset along the Y axis between $Y_{min}$ and $Y_{max}$. Moreover, at block 996, a variable $Z_{mid}$ is set to the midpoint of the dataset along the Z axis between $Z_{min}$ and $Z_{max}$. Continuing to block 998, a line, ZM, is created between ($X_{mid}$, $Y_{mid}$, $Z_{min}$) and ($X_{mid}$, $Y_{mid}$, $Z_{max}$). Then, at block 1000, the entire dataset is rotated around ZM by the Z slope of the plane, P, in order to eliminate any offset angle of the plane P with respect to the Z axis.

Moving to block 1002, a line, XM, is created between ($X_{mid}$, $Y_{min}$, $Z_{mid}$) and ($X_{mid}$, $Y_{max}$, $Z_{mid}$). Then, at block 1004, the dataset is rotated about XM by the X slope of the plane P in order to eliminate any offset angle of the plane P with respect to the X axis. At block 1006, a line, YM, is created between ($X_{min}$, $Y_{mid}$, $Z_{mid}$) and ($X_{max}$, $Y_{mid}$, $Z_{mid}$). Then, at block 1008, the entire dataset is rotated around YM by the Y slope of the plane, P, in order to eliminate any offset angle of the plane P with respect to the Y axis. The logic then ends at state 1010. Accordingly, the ink data has been found and aligned with the rectangular coordinate system.

Figure 15:
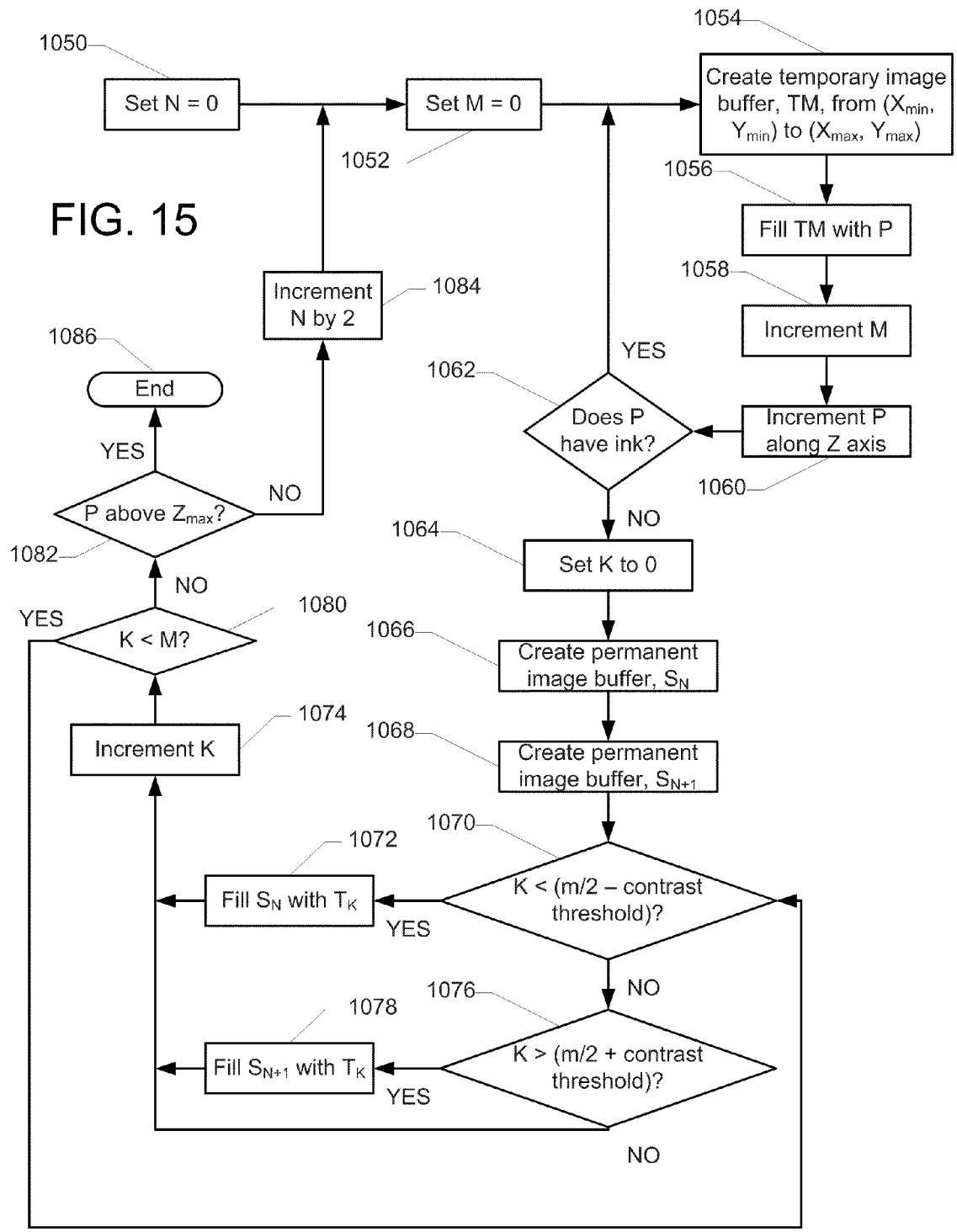
FIG. 15 is a flow chart representing a method of traversing paper and ink data.

Referring now to FIG. 15, a method of traversing paper and ink data is shown and commences at block 1050 wherein a variable N is set equal to zero (0). At block 1052, another variable M is also set equal to zero (0). Proceeding to block 1054, a temporary image buffer, TM, is created from ($X_{min}$, $Y_{min}$) to ($X_{max}$, $Y_{max}$). Then, at block 1056 TM is filled with data from plane P, which is the lowest plane of ink found as described above. Continuing to block 1058, M is increased by a predefined increment. Moreover, P is incremented along the Z axis by one predefined increment at block 1060.

Moving to decision diamond 1062, it is determined whether P includes ink data. If so, the logic returns to block 1054 and continues as described above. On the other hand, if P does not have ink, the logic moves to block 1064 where a variable K is set equal to zero (0). Then, at block 1066 a permanent image buffer $S_N$ is created. At block 1068, another permanent image buffer $S_{N+1}$ is created.

Proceeding to decision diamond 1070, it is determined whether K is less than one-half M minus a predetermined contrast threshold (M/2−CT). It is to be understood that the contrast threshold is no larger than the number of layers of ink between two facing pages that may be detected using a scanner, e.g., one of the scanners described above. If K is less than one-half M minus the contrast threshold the logic moves to block 1072 where $S_N$ is filled with the ink data in $T_K$. It is to be understood that the ink data is added to any ink data previously in $S_N$. The logic then moves to block 1074 where K is increased by a predetermined increment.

On the other hand, if K is greater than one-half M minus the contrast threshold, the logic proceeds to decision diamond 1076 where it is determined whether K is greater than one-half M plus the contrast threshold (M/2+CT). If so, $S_{N+1}$ is filled with the data within $T_K$ at block 1078. Then, the logic continues to block 1074 where K is increased by the predetermined increment. If K is less than or equal to one-half M plus the contrast threshold, the logic moves directly to block 1074 and K is increased by a predetermined increment, as described above.

Moving to decision diamond 1080, it is determined whether K is less than M. If so, the logic returns to decision diamond 1070 and continues as described above. If K is greater than or equal to M, the logic continues to decision diamond 1082 where it is determined whether the plane, P, is above $Z_{max}$. If not, the logic moves to block 1084 where N is incremented by two (2) predetermined increments. The logic then returns to block 1052 and continues as described above. On the other hand, if P is above $Z_{max}$ at decision diamond 1082, the logic ends at state 1086.

Figure 16:
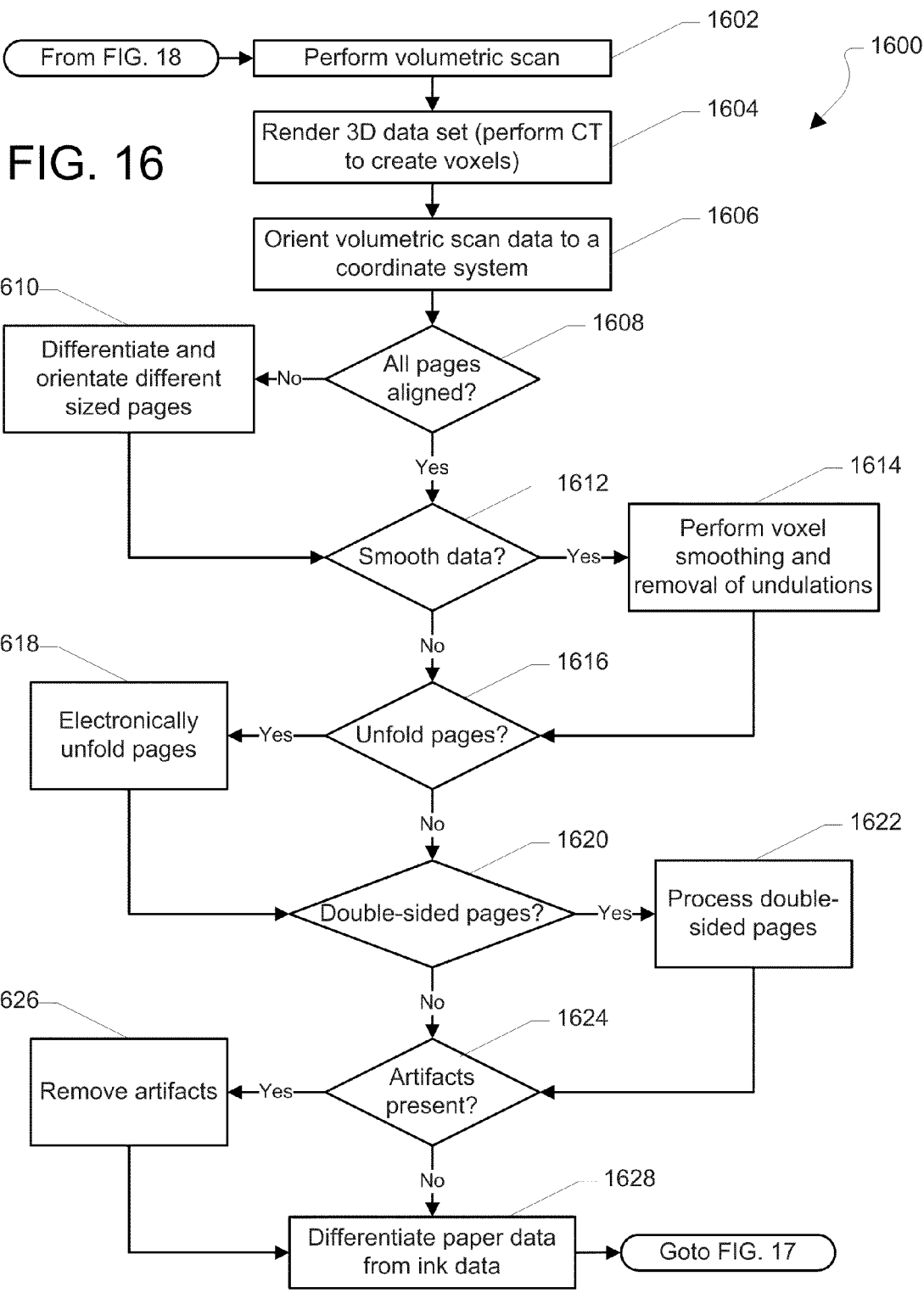
FIG. 16 is a flow chart representing a first portion of a second aspect of a method of scanning paper media.

FIG. 16 depicts another aspect of a method of scanning paper media that is generally designated 1600. Beginning at block 1602, a volumetric scan may be performed, e.g., using MRI, X-ray, T-ray, or a combination thereof. At block 1604, a processor may render a 3D dataset, i.e., CT may be performed to create multiple layers, or slices, of voxels. Moving to block 1606, the volumetric scan data, i.e., the voxels, may be oriented to a coordinate system, e.g., a Cartesian coordinate system, a polar coordinate system, another coordinate system, or a combination thereof.

At decision 1608, the processor may determine whether all pages are in the aligned. If not, the method 1600 may proceed to block 1610 and the processor may differentiate and orient different sized pages. Then, the method 1600 may proceed to decision 1612. Returning to decision 1608, if all of the pages are not in the same plane, the method 1600 may proceed directly to decision 1612.

Moving to decision 1612, the processor may determine whether to smooth the 3D data. If so, the method 1600 may move to block 1614 and the processor may perform voxel smoothing and may remove any undulations. Thereafter, the method 1600 may move to decision 1616. Returning to decision 1612, if the data does not need smoothing, the method 1600 may move directly to decision 1616.

At decision 1616, the processor may determine whether any pages need to be unfolded. If any pages need to be unfolded, the method 1600 may proceed to block 1618 and the processor may electronically unfold pages. Thereafter, the method 1600 may proceed to decision 1620. Returning to decision 1616, if no pages need to be unfolded, the method 1600 may proceed directly to decision 1620 and the processor may determine whether there are any double-sided pages. If so, the method 1600 may proceed to block 1622 and the processor may process the double-sided pages as described herein. Then, the method 1600 may move to decision 1624. Returning to decision 1620, if there are not any double-sided pages, the method 1600 may proceed directly to decision 1624.

At decision 1624, the processor may determine whether there are any artifacts present. Artifacts may include voxels of data within the 3D dataset that do not represent ink data, paper data, or a combination thereof. For example, artifacts may be caused by stapes, paperclips, thumbtacks, other metallic objects, other objects, or a combination thereof. If there are any artifacts present in the 3D dataset, the method 1600 may proceed to block 1626 and the artifacts may be removed. The method 1600 may then move to block 1628 and continue as described herein.

Returning to decision 1624, if there are not any artifacts present within the 3D dataset, the method 1600 may proceed directly to block 1628. At block 1628, the processor may differentiate paper data from ink data. Next, the method 1600 may continue to block, 1702 of FIG. 17.

Figure 17:
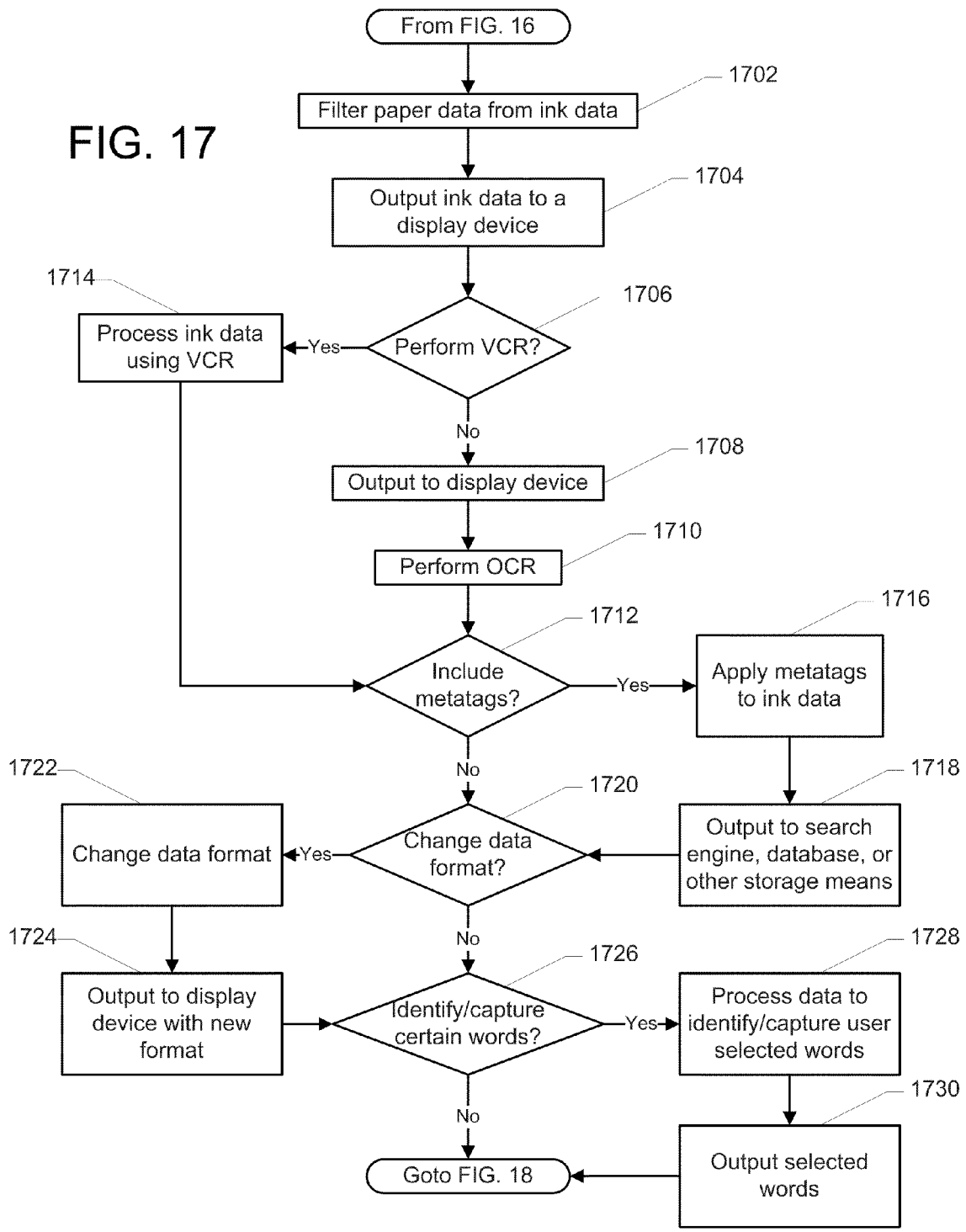
FIG. 17 is a flow chart representing a second portion of the second aspect of a method of scanning paper media.

Referring to FIG. 17, at block 1702, the processor may filter paper data from ink data. At block 1704, the processor may output ink data to a display device. Moving to decision 1706, the processor may determine whether to perform voxel character recognition (VCR). If not, the method 1600 may proceed to block 1708 and the processor may output the ink data to a display device. Next, at block 1710, the processor may perform optical character recognition (OCR) on the ink data. Thereafter, the method 1600 may move to decision 1712 and continue as described herein.

Returning to decision 1706, if the processor determines to perform VCR on the ink data, the method 1600 may proceed to block 1714 and the processor may process the ink data using VCR as described herein. Then, the method 1600 may proceed to decision 1712 and the processor may determine whether to include metatags in the data processed using VCR or OCR. This determination may be based on a user preference, the data processed, a predetermined preference, or a combination thereof. If the processor determines to include metatags, the method 1600 may proceed to block 1716 and the processor may apply metatags to the processed ink data. Then, the method 1600 may proceed to block 1718 and the processor may output the processed ink data with metatags to a search engine, a database, another storage means, or a combination thereof. The method 1600 may continue to decision 1720 and continue as described herein.

Returning to decision 1712, if the processor determines not to include metatags, the method 1600 may move directly to decision 1720 and the processor may determine whether to change the data format, e.g., from one storage format to another storage format. If so, the method 1600 may move to block 1722 and the processor may change data format as specified by a user, a programmer, a program, a predetermined selection, or a combination thereof. Then, the method 1600 may move to block 1724 and the processor may output the processed ink data to display device with the new format. Next, the method 1600 may move to decision 1726 and continue as described herein.

Returning to decision 1720, if the processor determines to not change the data format, the method 1600 may move directly to decision 1726. At decision 1726, the processor may determine whether to identify/capture certain words, e.g., user selected words, program selected words, other predetermined words, or a combination thereof. If the processor determines to identify/capture certain words, the method 1600 may continue to block 1728 and the processor may process the data to identify/capture the selected words. Thereafter, at block 1730, the processor may output the selected words. The method may then proceed to decision 1802 of FIG. 18. Returning to decision 1726, if the processor determines not to identify/capture certain words, the method 1600 may move directly to decision 1802 of FIG. 18.

Figure 18:
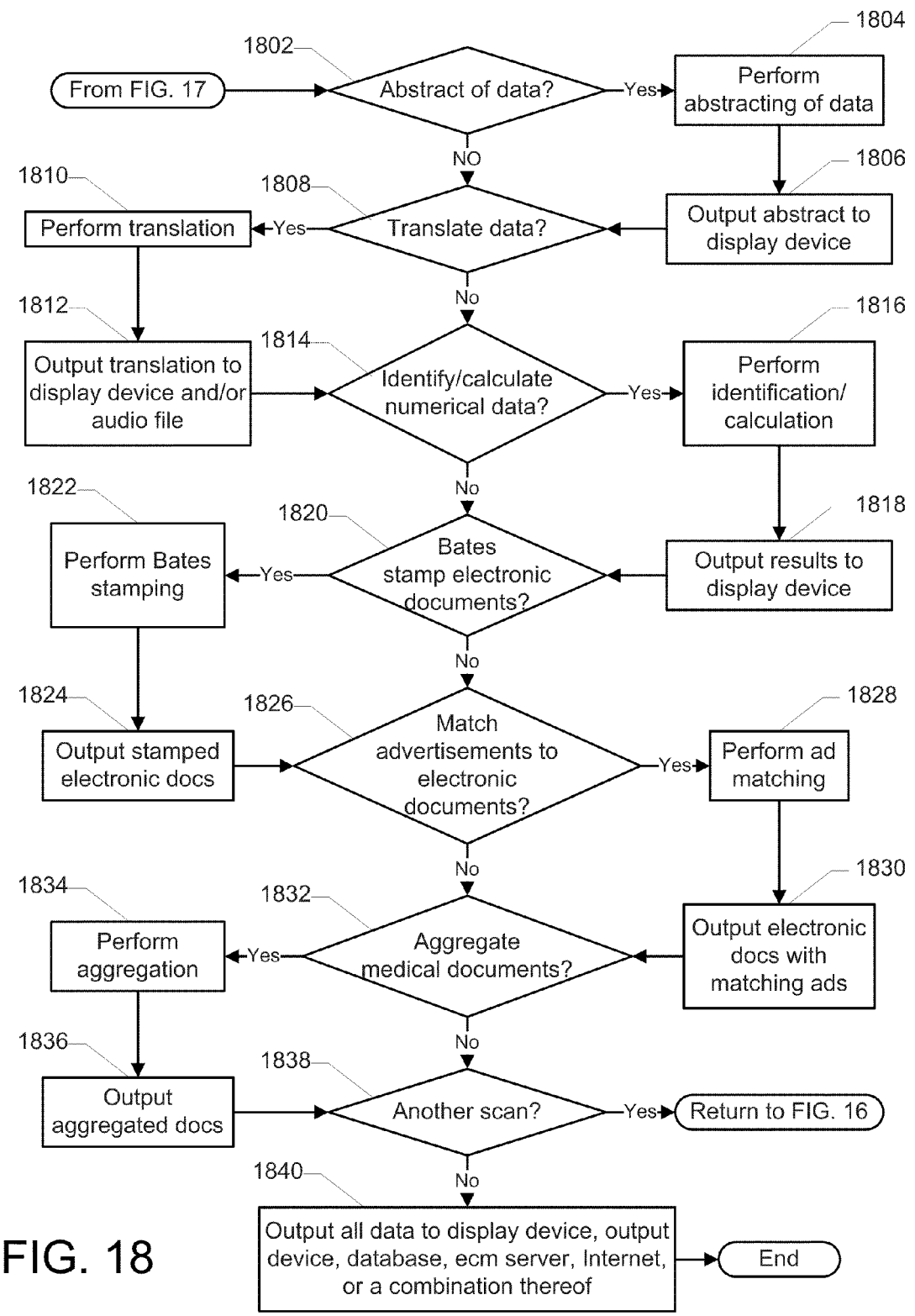
FIG. 18 is a flow chart representing a third portion of the third aspect of a method of scanning paper media.

At decision 1802 of FIG. 18, the processor may determine whether an abstract of the data is required, e.g., by a user, another program, or a combination thereof. If so, the method 1600 may proceed to block 1804 and the processor perform abstracting of the data as described herein. At block 1806, the processor may output abstract to display device. The method 1600 may then move to decision 1808.

Returning to decision 1802, if the processor determines to not abstract the data, the method 1600 may move directly to decision 1808 and the processor may determine whether to translate the data, i.e., from a first language to a second language. For example, the data may be translated from English to Spanish, Spanish to English, English to Japanese, Japanese to English, English to Mandarin, etc. The processor may determine whether to translate the data based on a user selection, a predetermined selection, etc. If the processor determines to translate the data, the method 1600 may proceed to block 1810 and the processor may perform the translation. Then, the method 1600 may continue to block 1812 and the processor may output the translation to a display device, an audio file, or a combination thereof. From block 1812, the method 1600 may move to decision 1814 and continue as described herein.

Returning to decision 1808, if the processor determines not to translate the data, the method 1600 may proceed directly to decision 1814. At decision 1814, the processor may determine whether to identify/calculate numerical data. If so, the method 1600 may move to block 1816 and the processor perform the identification/calculation. At block 1818, the processor may output the results to a display device, a storage device, or a combination thereof. The method 1600 may then continue to decision 1820 and continue as described herein.

Returning to decision 1814, if the processor determines to not identify/calculate the numerical data, the method 1600 may move directly to decision 1820 and the processor may determine whether to Bates stamp electronic documents. If so, the method may move to block 1822, and the processor may perform the Bates stamping and Bates stamp each page of the electronic documents. Then, the method 1600 may move to block 1824, and the processor may output the Bates stamped electronic documents to a display device, a storage device, or a combination thereof. From block 1824, the method 1600 may move to decision 1826.

Returning to decision 1820, if the processor determines not to Bates stamp the electronic documents, the method 1600 may proceed directly to decision 1826 and the processor may determine whether to match any advertisements to the electronic documents. If so, the method 1600 may continue to block 1828 and the processor may perform an advertising matching process in order to match advertisements to the electronic documents based on the content of the electronic documents, based on user selections, based on predetermined criteria, or a combination thereof. Then, the method 1600 may proceed to block 1830 and the processor may output the electronic docs with the matching advertisements to a display device, a storage device, or a combination thereof. Then, the method 1600 may move to decision 1832 and continue as describe herein.

Returning to decision 1826, if the processor determines to not match advertisements to the electronic documents, the method 1600 may move directly to decision 1832. At decision 1832, the processor may determine whether to aggregate the documents. The documents may be aggregated based on content, a source of the documents, a type of documents, key words, or a combination thereof. In the case of medical documents, the medical documents may be aggregated based on a patient name, symptoms, a doctor's name, a particular diagnosis, a particular medication, or a combination thereof. If the processor determines to aggregate the documents, method 1600 may continue to block 1834 and the processor may perform the aggregation. Next, the processor may output the aggregated documents, e.g., to a display device, a storage device, a printer, or a combination thereof. The method may continue to decision 1838 and proceed as described herein.

Returning to decision 1832, if the processor determines not to aggregate the documents, the method 1600 may proceed directly to decision 1838 and the processor may determine whether to perform another scan. If so, the method 1600 may return to block 1602 of FIG. 16. Otherwise, the method 1600 may proceed to block 1840 and the processor may output all data to a display device, an output device, a database, an enterprise content management (ECM) server, the Internet, another network, or a combination thereof. Then, the method 1600 may end.

Figure 19:
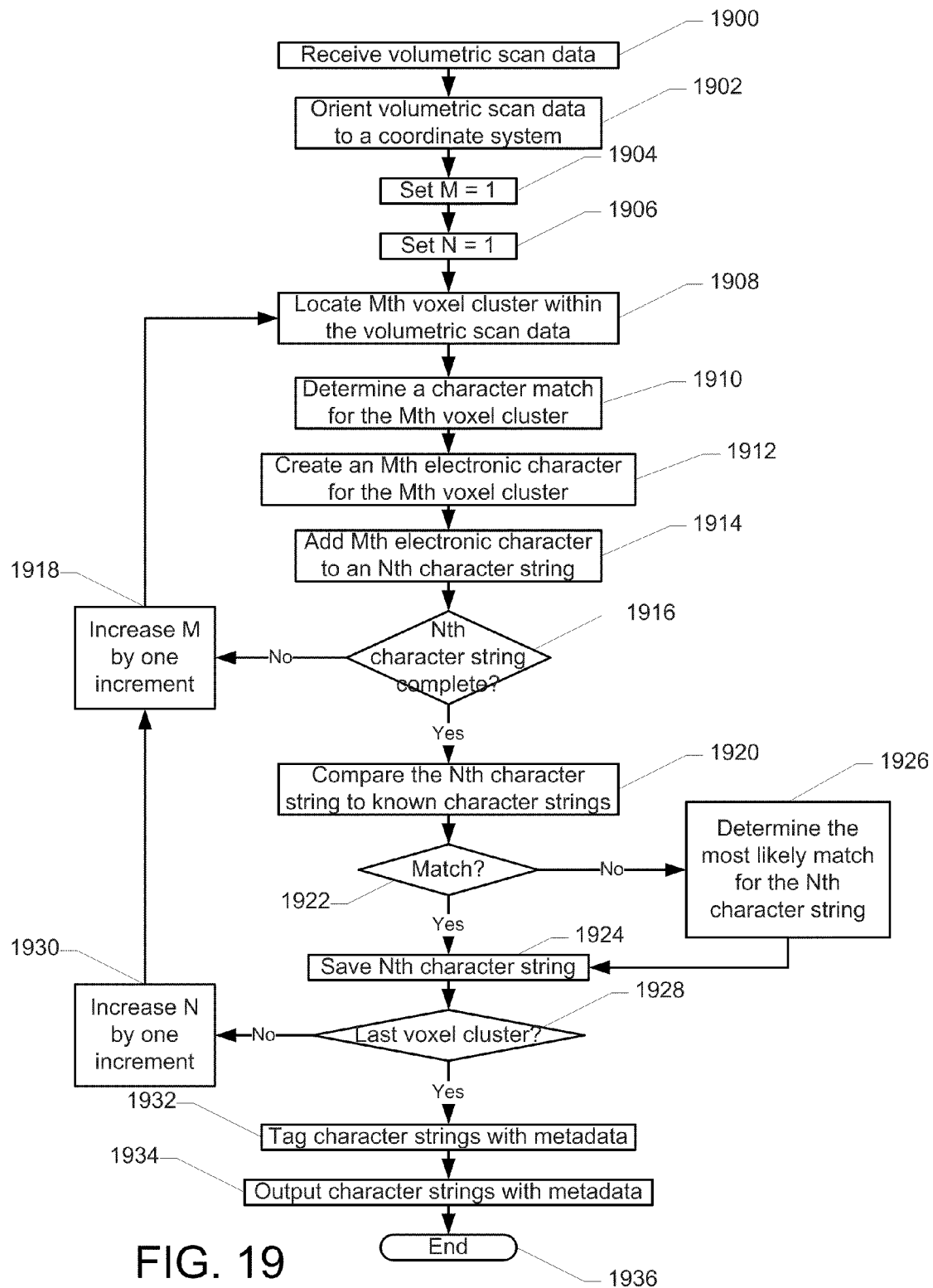
FIG. 19 is a flow chart representing a method of recognizing characters in volumetric ink data.

Referring now to FIG. 19, a method of recognizing alphanumeric characters in volumetric data is shown and commences at block 1900. The method set forth in FIG. 19, et. seq. differs from Optical Character Recognition (OCR), which is a well known method in the art for recognizing characters transposed in two-dimensional static photographic images. The method set forth in FIG. 19 et. seq. recognizes characters in three-dimensional dynamic datasets. At block 1900, volumetric scan data is received via any one of the non-penetrating volumetric scan modalities set forth previously and herein. The volumetric scan data may include at least paper data and ink data. Conversely, the volumetric scan data may include ink data. In either case, the volumetric scan data may also include various artifacts due to staples, paperclips, and other paper fasteners. Further, the volumetric scan data may include artifacts due to repeated copying of particular documents. Also, the volumetric scan data may include artifacts due to faxing of particular documents.

Moving to block 1902, the volumetric scan data may be oriented to a coordinate system, e.g., a Cartesian coordinate system, a polar coordinate system, a curvilinear coordinate system, or any other well known coordinate system. At block 1904, a first counter, M, is set equal to one (M=1). At block 1906, a second counter, N, is set equal to one (N=1). Thereafter, at block 1908, the Mth voxel cluster within the volumetric scan data may be received. As used in the context of FIG. 19, a voxel cluster may be considered a group of voxels that contain ink data. A voxel cluster may, or may not, be surrounded by voxels that contain paper data. Further, a voxel cluster may, or may not, include voxels that contain paper data interspersed with voxels that contain ink data.

Proceeding to block 1910, the ASCII character represented by the Mth voxel cluster may be determined. For example, the ASCII character represented by the Mth voxel cluster may be determined using matrix matching. In other words, the ASCII character represented by Mth voxel cluster may be determined by comparing the Mth voxel cluster to a library of character matrices or templates. When the Mth voxel cluster matches one of the prescribed clusters of data within a given level of similarity, e.g., ninety percent (90%) or greater, the Mth voxel cluster may be marked, tagged, or otherwise indicated, as the matching ASCII character.

Alternatively, the ASCII character represented by the Mth voxel cluster may be determined using feature extraction. In other words, general features, e.g., open areas, closed shapes, diagonal lines, line intersections, etc., of the Mth voxel cluster may be determined and these general features may be used to determine the ASCII character that matches the Mth voxel cluster within a given level of similarity, e.g., ninety percent (90%) or greater. Once a matching ASCII character is determined for the Mth voxel cluster, the Mth voxel cluster may be marked, tagged, or otherwise indicated, as the matching ASCII character.

Moving to block 1912, an Mth electronic character is created that represents the Mth voxel cluster. Then, at block 1914, the Mth electronic character may be added to an Nth character string. At decision step 1916, it may be determined whether the Nth character string is complete. If not, the method may proceed to block 1918 and M may be increased by one (1) increment. Thereafter, the method may return to block 1908 and continue as described herein. At decision step 1916, if the Nth character string is complete, the method may continue to block 1920 and the Nth character string may be compared to a library, or libraries, of known character strings, i.e., words.

Proceeding to decision step 1922, it may be determined whether a match for the Nth character string is found. If a match is found, the Nth character string may be saved in a memory or database. If a match is not found, the method may move to block 1926 and a most likely match for the Nth character string may be determined. Thereafter, the method may proceed to block 1924 and proceed as described herein. From block 1924, the method may move to decision step 1928. At decision step 1928, it may be determined if the last voxel cluster has been "read". If not, the method may move to block 1930 and N may be increase by one (1) increment. Thereafter, the method may proceed to block 1918 and continue as described herein.

Returning to decision step 1928, if the last voxel cluster is read, the method may move to block 1932 and the group of character strings, i.e., an electronic version of the scanned document, may be tagged with metadata. The metadata may include keywords in the group of character strings that may be used to facilitate searching the group of character strings. Also, the metadata may include phrases that may be used to abstract the group of character strings. At block 1934, the group of character strings may be output to an electronic file with the metadata and stored. Thereafter, the method may end at state 1926.

FIG. 20 illustrates a book, designated 2000. The book 2000 may be scanned using one of the non-invasive volume scanning means described herein. After the book is scanned, a volumetric, or three-dimensional dataset, may be created, as set forth herein. FIG. 21 illustrates a volumetric dataset, designated 2002 that may be created from the book 2000 shown in FIG. 20. The volumetric dataset 2002 may include paper data 2004, i.e., data that represents each page of the book 2000 (FIG. 20), and ink data 2006, data that represents the printing on each page of the book 2000 (FIG. 20). The volumetric dataset 2002 may also include other data such as the cover of the book, staples, clips, bindings, etc. Certain things such as staples may appear as artifacts. However, in many cases, those artifacts may appear in what would be a margin of the volumetric dataset 2002 and may easily be removed, or filtered, from the volumetric dataset 2002 without obscuring the data in the volumetric dataset 2002. In a particular aspect, the volumetric dataset 2002 may be processed, as described herein, to yield the ink data 2006, shown in FIG. 22. The ink data 2006 may be "read" using OCR or using volumetric character recognition (VCR), as described herein, in order to create an electronic version of the ink data 2006.

Figure 23:
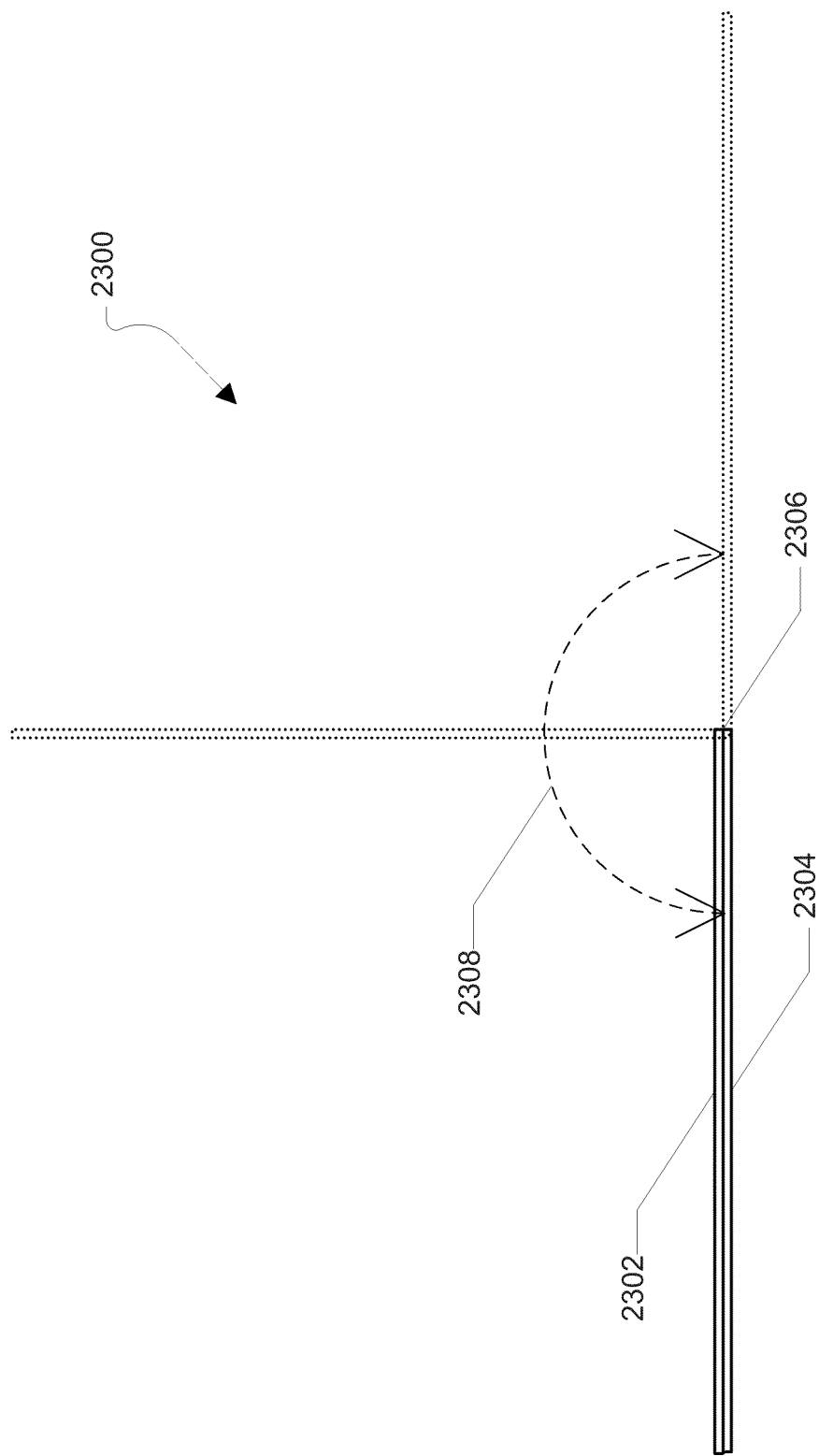
FIG. 23 is a view of a bi-folded document, i.e., a C-fold document, with the unfolded document shown in dashed lines.

FIG. 23 illustrates a first document, designated 2300. The first document 2300 may include a single sheet of paper, or multiple sheets of paper. Further, the first document 2300 may have ink printed on one side or both sides of each sheet of paper within the document 2300. The first document 2300 may include a first portion 2302 and a second portion 2304. The first portion 2302 may be rotated relative to the second portion 2304 around a hinge 2306 created by a folding process, as indicated by arc 2308. As shown, the first portion 2302 may be folded onto the second portion 2304 and the first document 2300 may be moved from a flat position to a folded position. It is to be understood that folding the first document 2300 in half as depicted in FIG. 23 results in a bi-fold.

When the first document 2300 is in the folded position, indicated by the solid lines, and scanned according to one or more of the systems, devices, or methods described herein, the resulting ink data and paper data may also be considered folded. The resulting ink data and paper data may be unfolded, as described herein, in order to more easily process the ink data, the paper data, or a combination thereof in order to extract the contents of the data and create an electronic representation of the first document 2300 in the unfolded position. The folded data, e.g., ink data, paper data, or a combination of ink and paper data, may be unfolded around a data hinge that corresponds to the hinge 2306 depicted in FIG. 23.

Figure 24:
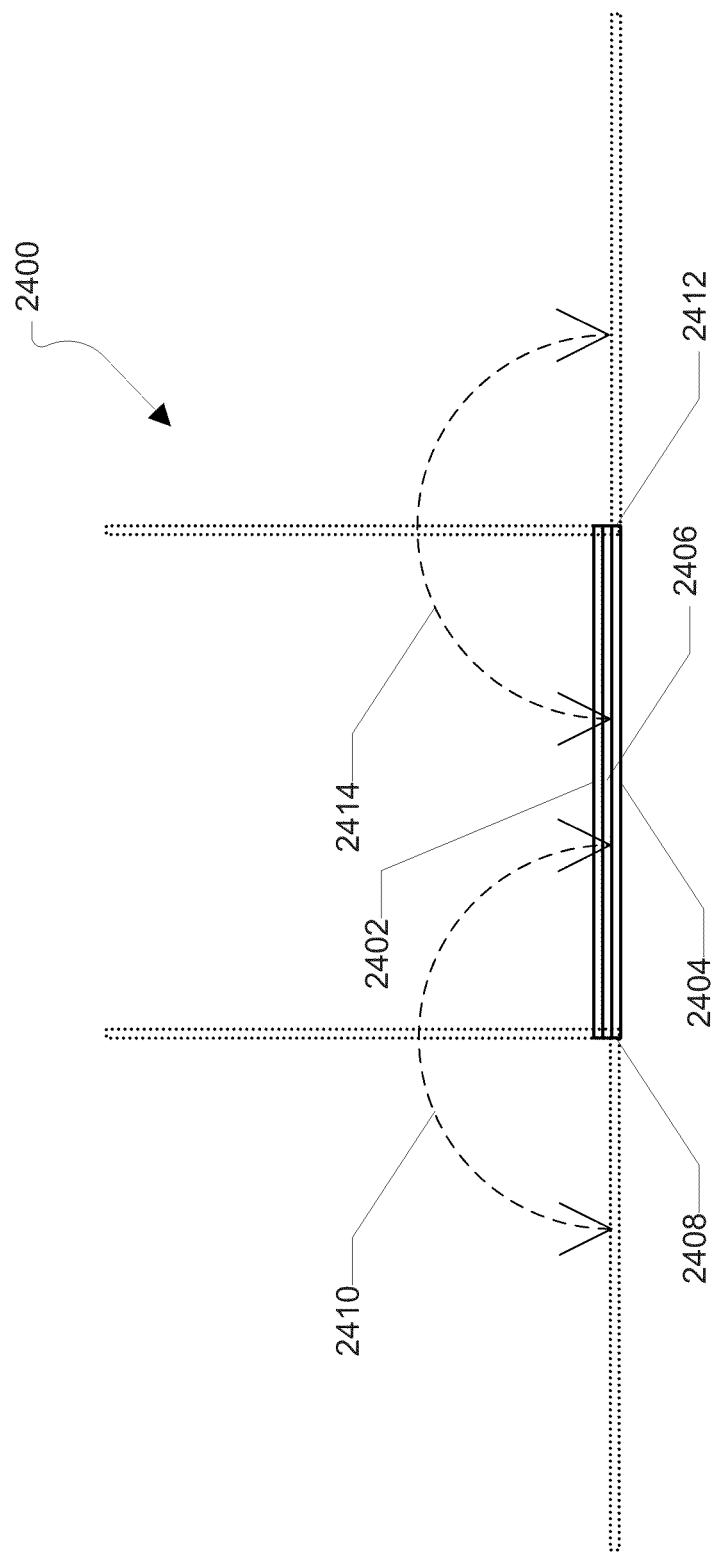
FIG. 24 is a view of a first aspect of a tri-folded document, i.e., a Z-fold document, with the unfolded document shown in dashed lines.

FIG. 24 illustrates a second document, designated 2400. The document 2400 may include a single sheet of paper, or multiple sheets of paper. Further, the document 2400 may have ink printed on one side or both sides of each sheet of paper within the document 2400. The document 2400 may include a first portion 2402, a second portion 2404, and a third portion 2406. The first portion 2402 may be rotated clockwise relative to the second portion 2404 around a first hinge 2408 created by a first folding process, as indicated by arc 2410. The third portion 2406 may be rotated counterclockwise relative to the second portion 2404 around a second hinge 2412 created by a second folding process, as indicated by arc 2414. As shown, the first portion 2402 and the third portion 2406 may be folded onto the second portion 2404 and the document 2400 may be moved from a flat position to a folded position. It is to be understood that folding the document 2400 in thirds as depicted in FIG. 24 results in a C-fold.

When the document 2400 is in the folded position, indicated by the solid lines, and scanned according to one or more of the systems, devices, or methods described herein, the resulting ink data and paper data may also be considered folded. The resulting ink data and paper data may be unfolded, as described herein, in order to more easily process the ink data, the paper data, or a combination thereof in order to extract the contents of the data and create an electronic representation of the document 2400 in the unfolded position. The folded data, e.g., ink data, paper data, or a combination of ink and paper data, may be unfolded around a first data hinge and a second data hinge that correspond to the hinges 2408, 2412 depicted in FIG. 24.

Figure 25:
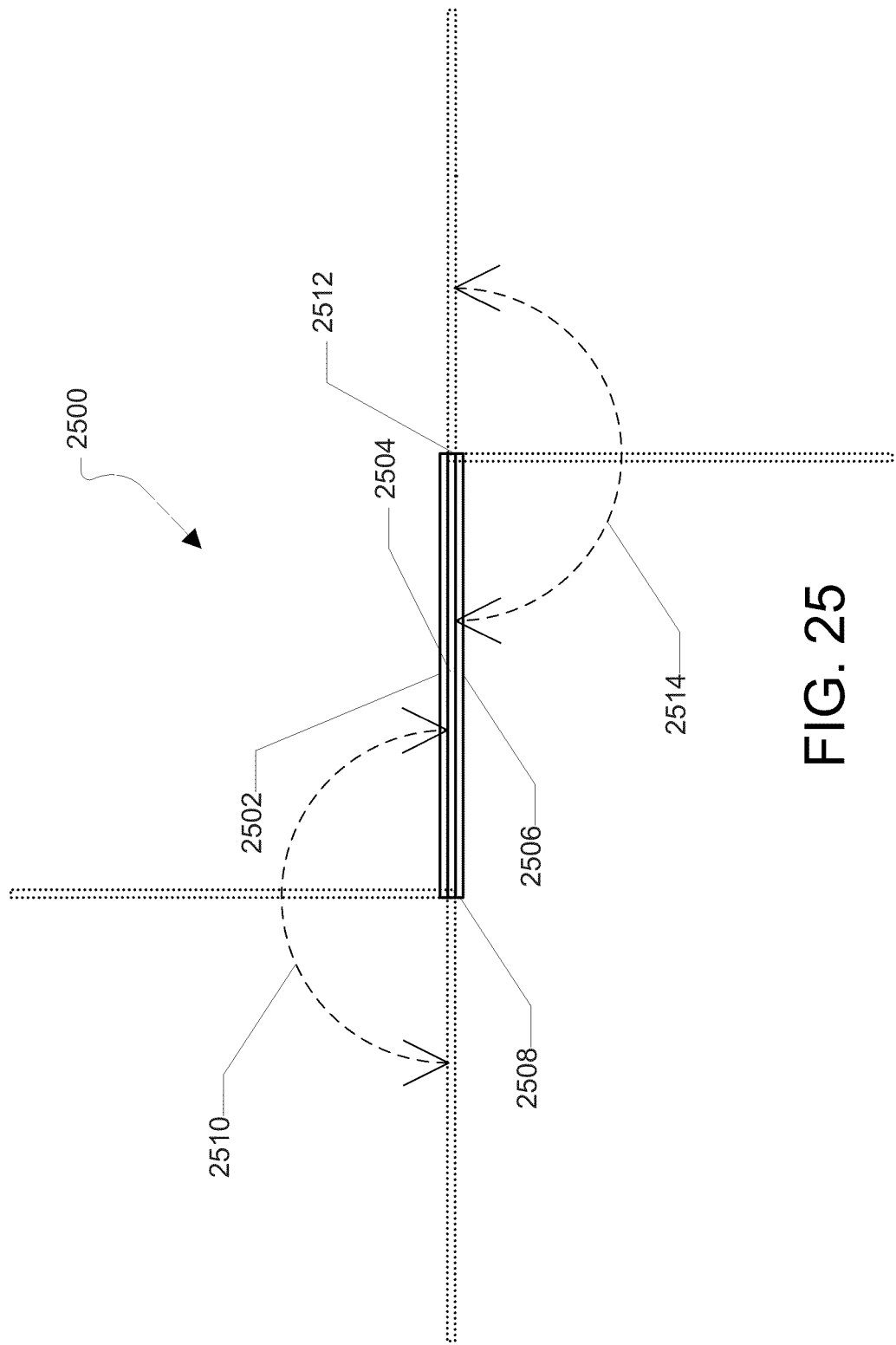
FIG. 25 is a view of a second aspect of a tri-folded document, i.e., a Z-fold document, with the unfolded document shown in dashed lines.

FIG. 25 illustrates a second document, designated 2500. The document 2500 may include a single sheet of paper, or multiple sheets of paper. Further, the document 2500 may have ink printed on one side or both sides of each sheet of paper within the document 2500. The document 2500 may include a first portion 2502, a second portion 2504, and a third portion 2506. The first portion 2502 may be rotated clockwise relative to the second portion 2504 around a first hinge 2508 created by a first folding process, as indicated by arc 2510. The third portion 2506 may also be rotated clockwise relative to the second portion 2504 around a second hinge 2512 created by a second folding process, as indicated by arc 2514. As shown, the first portion 2502 and the third portion 2506 may be folded onto the second portion 2504 and the document 2500 may be moved from a flat position to a folded position. It is to be understood that folding the document 2500 in thirds as depicted in FIG. 25 results in a Z-fold.

When the document 2500 is in the folded position, indicated by the solid lines, and scanned according to one or more of the systems, devices, or methods described herein, the resulting ink data and paper data may also be considered folded. The resulting ink data and paper data may be unfolded, as described herein, in order to more easily process the ink data, the paper data, or a combination thereof in order to extract the contents of the data and create an electronic representation of the document 2500 in the unfolded position. The folded data, e.g., ink data, paper data, or a combination of ink and paper data, may be unfolded around a first data hinge and a second data hinge that correspond to the hinges 2508, 2512 depicted in FIG. 25.

Figure 26:
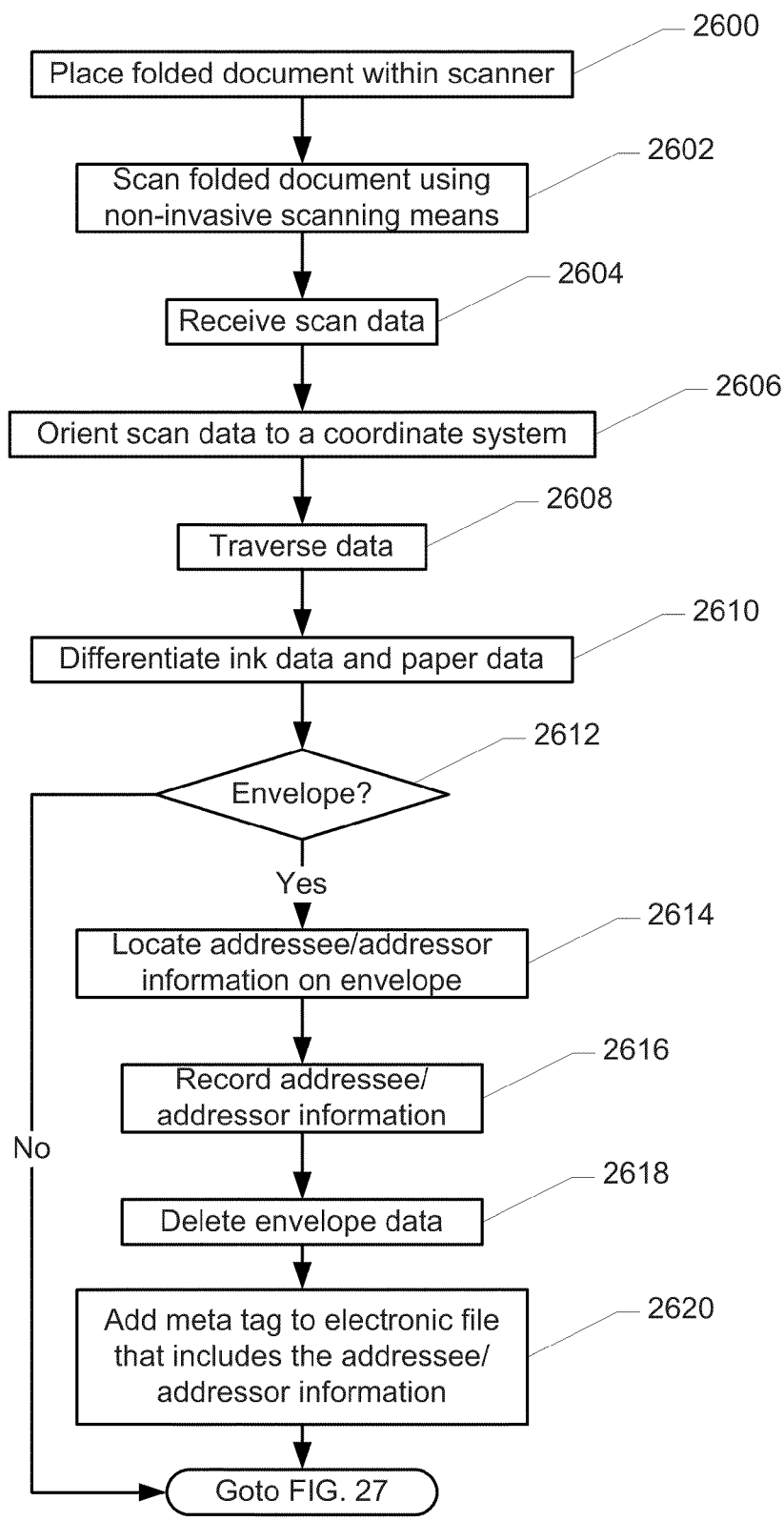
FIG. 26 is a flowchart representing a first portion of a first aspect of a method of electronically unfolding data obtained from a volumetric scan of a folded document.

Referring now to FIG. 26, a first method of unfolding data is illustrated and commences at block 2600. At block 2600, at least one folded document may be placed within a volumetric document scanner, e.g., a scanner configured as described herein or any other scanner that utilizes non-invasive means in order create a three-dimensional dataset representing documents placed therein. At block 2602, the at least one folded document may be scanned using non-invasive scanning means, e.g., MRI, NMR, T-ray, X-ray, X-ray CT, T-ray CT, or any combination thereof. Further, at block 2604, the scan data may be received. The scan data may be received by a processor within, or without, the scanner in which the scanning takes place.

Moving to block 2606, the scan data may be oriented to a coordinate system, e.g., a Cartesian coordinate system, a polar coordinate system, a curvilinear coordinate system, or any other well known coordinate system. Thereafter, at block 2608, the scan data may be traversed, e.g., from top-to-bottom, from bottom-to-top, from side-to-side, or any combination thereof. At block 2610, ink data and paper data may be differentiated from each other. Continuing to decision step 2612, it may be determined whether the folded document is contained within an envelope. If not, the method may proceed directly to 2622 of FIG. 27. On the other hand, if the folded document is contained within an envelope, the method may proceed to block 2614 and the addressee/addressor information on the envelope may be located. At block 2616, the addressee/addressor information may be recorded, e.g., in a database or other memory. Thereafter, at block 2618, the envelope data, i.e., the scan data that represents the physical envelope, may be deleted. At block 2620, a metatag may be added to an electronic file associated with the folded document. The metatag may include the addressee/addressor information.

Figure 27:
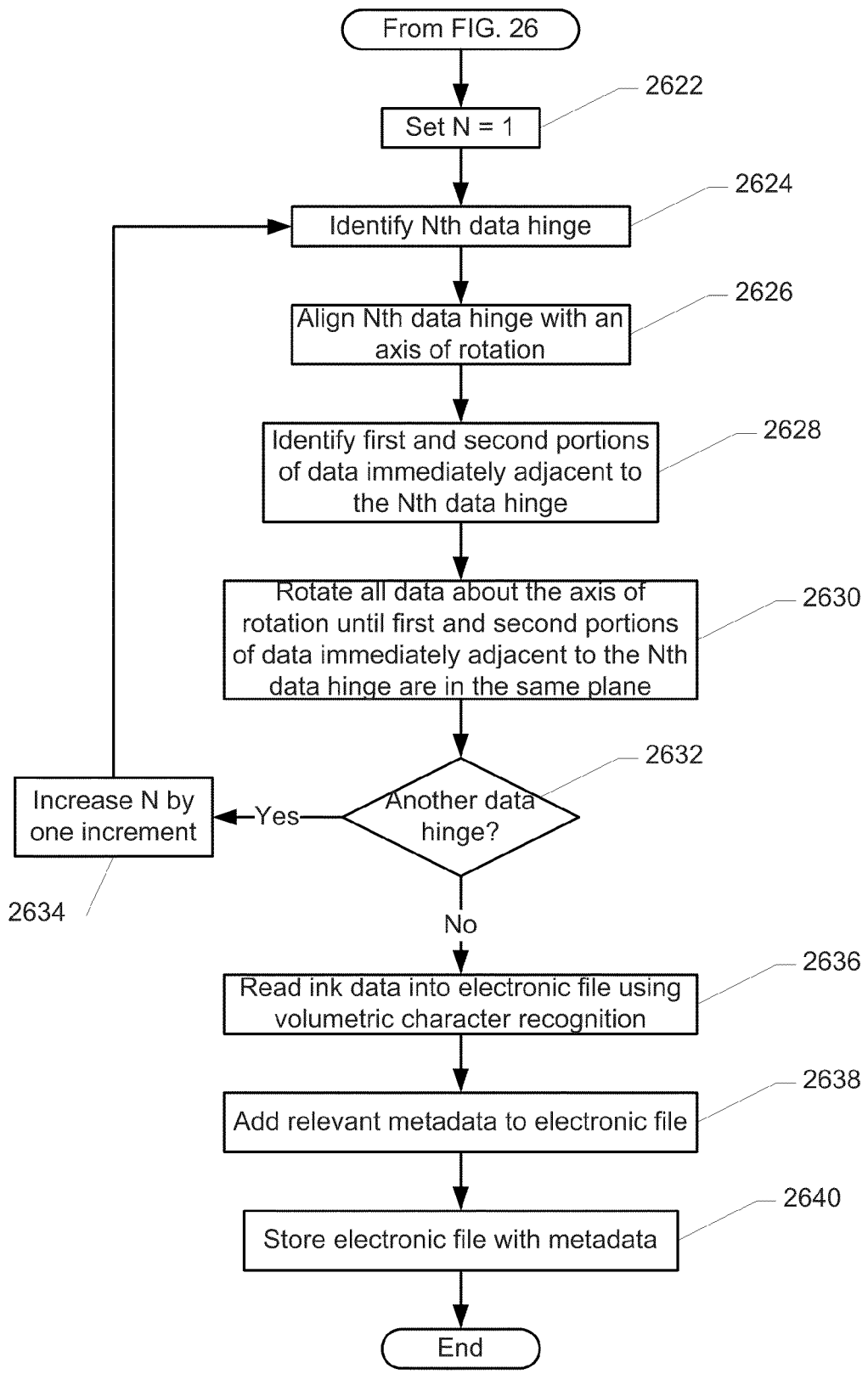
FIG. 27 is a flowchart representing a second portion of the first aspect of a method of electronically unfolding data obtained from a volumetric scan of a folded document.

Continuing to block 2622 of FIG. 27, a counter, N, may be set equal to one (1). At block 2624, the Nth data hinge may be identified. Further, at block 2626, the Nth data hinge may be aligned with an axis of rotation. At block 2628, a first and second portion of data immediately adjacent to, i.e., on either side of, the Nth data hinge may be identified. Then, at block 2630, all data may be rotated about the axis of rotation until the first and second portions of data immediately adjacent to the Nth data are in the same plane, i.e., co-planar.

At decision step 2632, it may be determine whether the scan data includes another data hinge. If so, the method may proceed to block 2634 and N may be increased by one (1) increment. Thereafter, the method may return to block 2624 and continue as described herein. If the scan data does include another data hinge, the method may move to block 2636 and the ink data within the scan data may be read into an electronic file using volumetric character recognition, as described herein. At block 2638, any relevant metadata may be added to the electronic file associated with the folded document. The metadata may include keywords from the folded document that may be used to facilitate searching the electronic file that represents the folded document. Also, the metadata may include phrases that may be used to abstract the information contained in the folded document. At block 2640, the electronic file and the metadata may be stored, e.g., in a database, a memory, or some other storage medium well known in the art. The method may then end.

Figure 28:
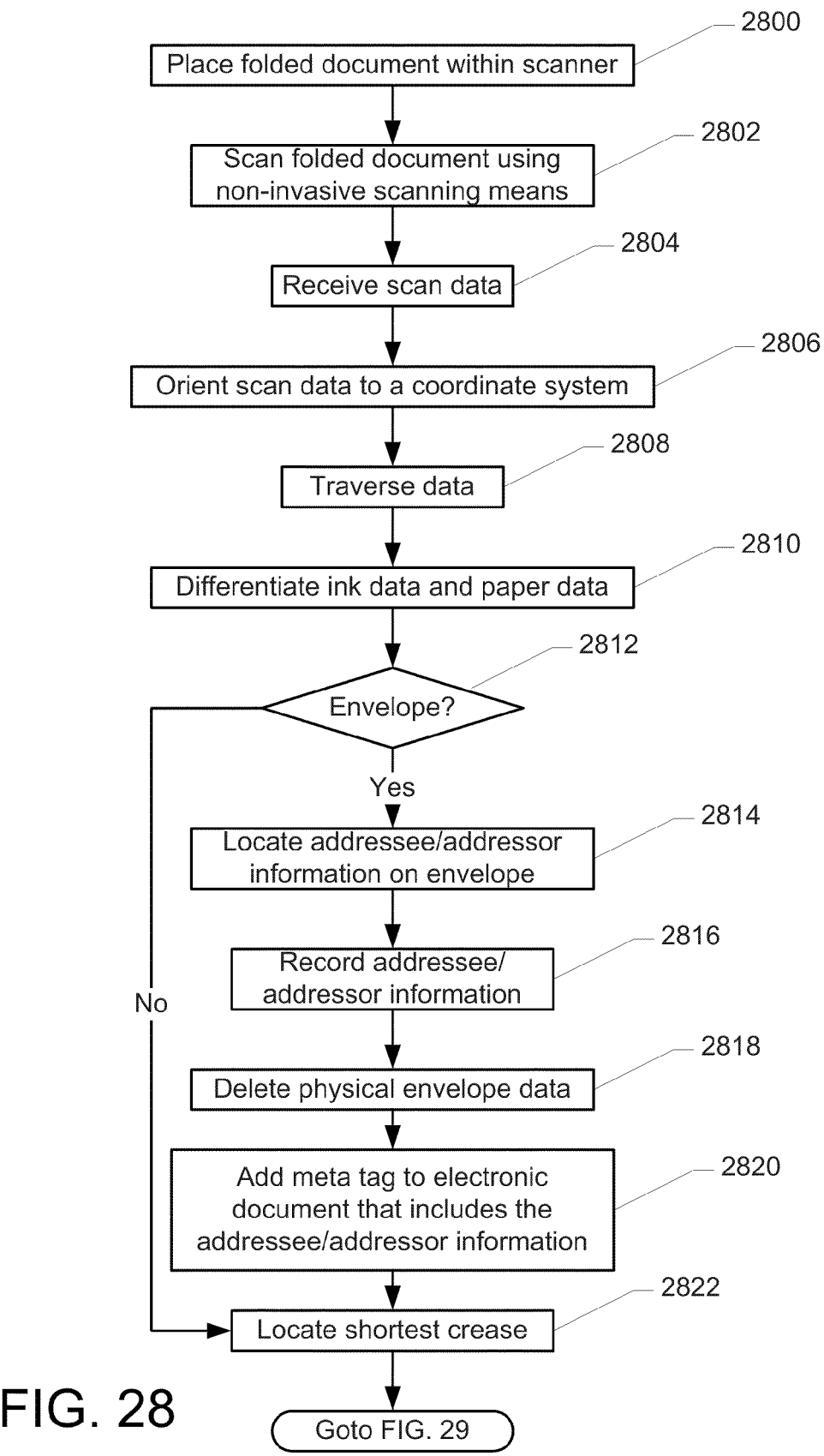
FIG. 28 is a flowchart representing a first portion of a second aspect of a method of electronically unfolding data obtained from a volumetric scan of a folded document.

FIG. 28 illustrates a second method of unfolding data. Beginning at block 2800, at least one folded document may be placed within a volumetric document scanner, e.g., a scanner configured as described herein or any other scanner that utilizes non-invasive means in order create a three-dimensional dataset representing documents placed therein. At block 2802, the at least one folded document may be scanned using non-invasive scanning means, e.g., MRI, NMR, T-ray, X-ray, X-ray CT, T-ray CT, or any combination thereof. Further, at block 2804, the scan data may be received. The scan data may be received by a processor within, or without, the scanner in which the scanning takes place.

Moving to block 2806, the scan data may be oriented to a coordinate system, e.g., a Cartesian coordinate system, a polar coordinate system, a curvilinear coordinate system, or any other well known coordinate system. Thereafter, at block 2808, the scan data may be traversed, e.g., from top-to-bottom, from bottom-to-top, from side-to-side, or any combination thereof. At block 2810, ink data and paper data may be differentiated from each other. Continuing to decision step 2812, it may be determined whether the folded document is contained within an envelope. If the folded document is contained within an envelope, the method may proceed to block 2814 and the addressee/addressor information on the envelope may be located. At block 2816, the addressee/addressor information may be recorded, e.g., in a database or other memory. Thereafter, at block 2818, the envelope data, i.e., the scan data that represents the physical envelope, may be deleted. At block 2820, a metatag may be added to an electronic file associated with the folded document. The metatag may include the addressee/addressor information.

From block 2820, the method may move to block 2822 and the shortest crease, or fold, in the folded document may be located. Then, the method may proceed to block 2824 of FIG. 29. Returning to decision step 2812, if the folded document is not contained within an envelope, the method may move directly to block 2822 and continue as described herein.

Figure 29:
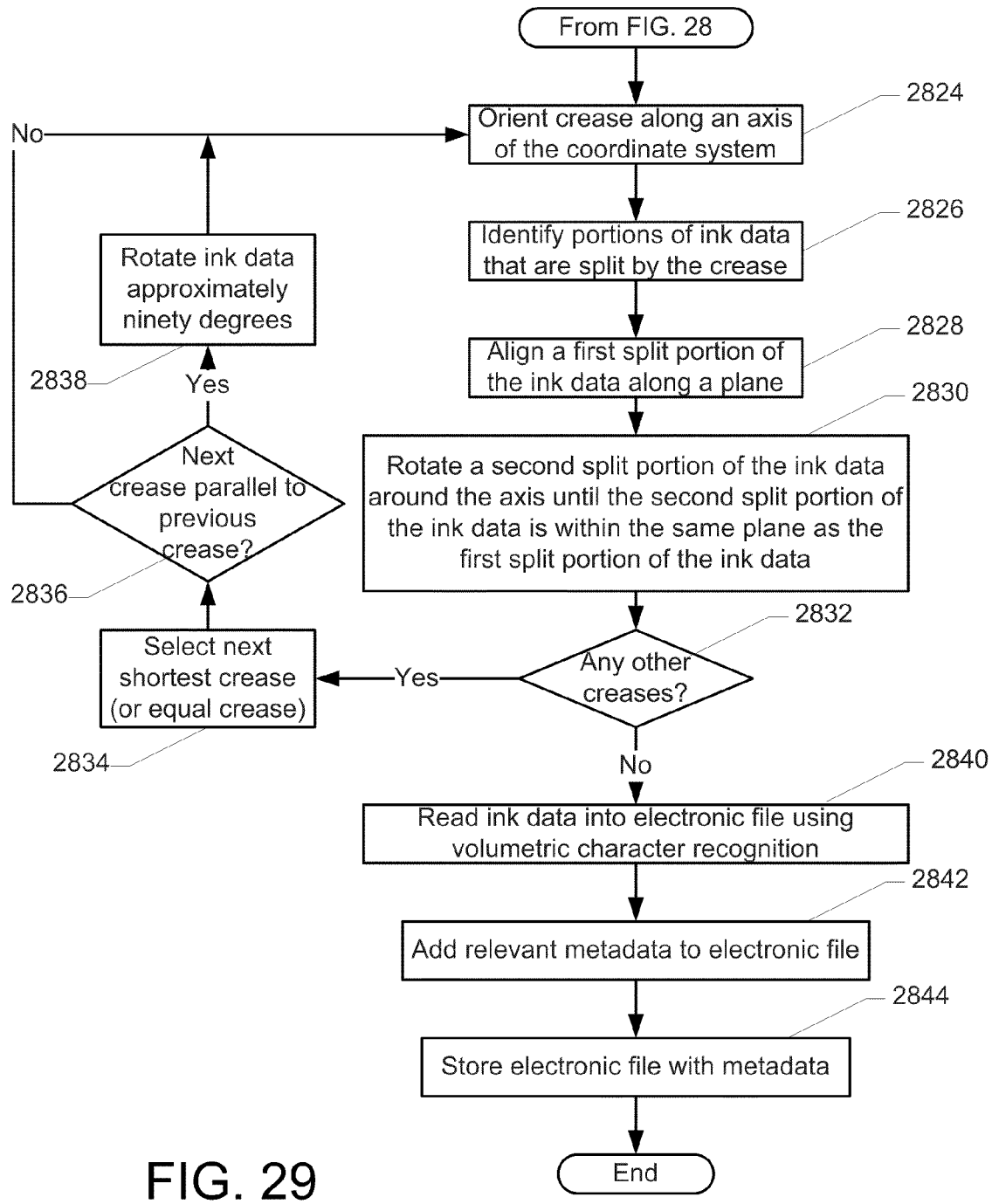
FIG. 29 is a flowchart representing a second portion of the second aspect of a method of electronically unfolding data obtained from a volumetric scan of a folded document.

Moving to block 2824 of FIG. 29, the crease may be oriented along an axis of the coordinate system. At block 2826, the portions of ink data that are split by the crease may be identified. The ink data may include ink data only or the ink data may ink data may include ink data and paper data. At block 2828, a first split portion of the ink data may be aligned along a plane. Further, at block 2830, a second split portion of the ink data may be rotated around the axis until the second split portion of the ink data is within the same plane as the first split portion of the ink data, i.e., until the second split portion is coplanar with the first split portion.

Proceeding to decision step 2832, it may be determine whether the scan data from the folded document includes any other creases. If so, the method may move to block 2834 and the next shortest crease, or an equal length crease, may be selected. Then, at decision step 2836, it may be determined whether the next crease is parallel to the previous crease. If not, the method may move directly to block 2824 and continue as described herein. Conversely, the method may move to block 2838 and the ink data may be rotated approximately ninety degrees. Thereafter, the method may return to block 2824 and continue as described herein.

Returning to decision step 2832, if the scan data does include any other creases, or folds, the method may move to block 2840 and the ink data within the scan data may be read into an electronic file using volumetric character recognition, as described herein. At block 2842, any relevant metadata may be added to the electronic file associated with the folded document. The metadata may include keywords from the folded document that may be used to facilitate searching the electronic file that represents the folded document. Also, the metadata may include phrases that may be used to abstract the information contained in the folded document. At block 2844, the electronic file and the metadata may be stored, e.g., in a database, a memory, or some other storage medium well known in the art. The method may then end.

Figure 30:
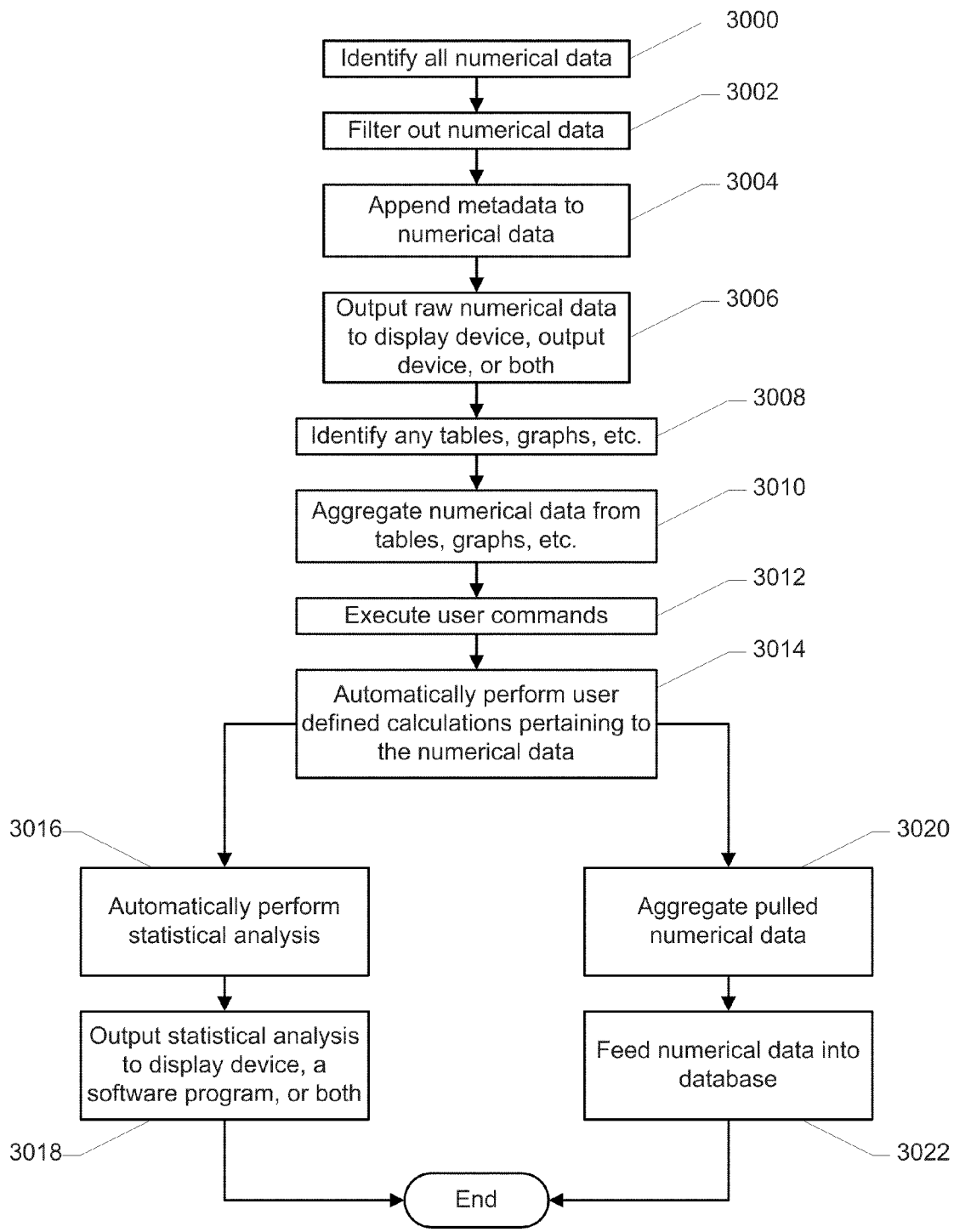
FIG. 30 is a flowchart representing a method of manipulating and calculating numerical data derived from a volumetric scan of one or more documents.

Referring to FIG. 30 a method of manipulating and calculating numerical data derived from a volumetric scan of one or more documents is shown and commences at block 3000. At block 3000, a processor may identify all numerical data within a 3D dataset of ink data, paper data, or a combination thereof. At block 3002, the processor may filter out numerical data from the 3D dataset.

Moving to block 3004, the processor may append metadata to the numerical data. At block 3006, the processor may output raw numerical data to a display device, an output device, or a combination thereof. Continuing to block 3008, the processor may identify any tables, graphs, etc. within 3D dataset. At block 3010, the processor may aggregate numerical data from the tables, graphs, etc. Further, at block 3012, the processor may execute one or more user commands. For example, the user commands may be any number of mathematical commands: add, subtract, divide, multiply, sum, etc.

Proceeding to block 3014, the processor may automatically perform one or more user defined calculations pertaining to the numerical data. From block 3014, the method may move to block 3016 and block 3020. At block 3016, the processor may automatically perform a statistical analysis on the numerical data. At block 3018, the processor may output the statistical analysis to a display device, a software program, or a combination thereof. At block 3020, the processor may aggregate the numerical data. Moreover, at block 3022, the processor may feed the numerical data into a database. From block 3018 and block 3022, the method may end.

Figure 31:
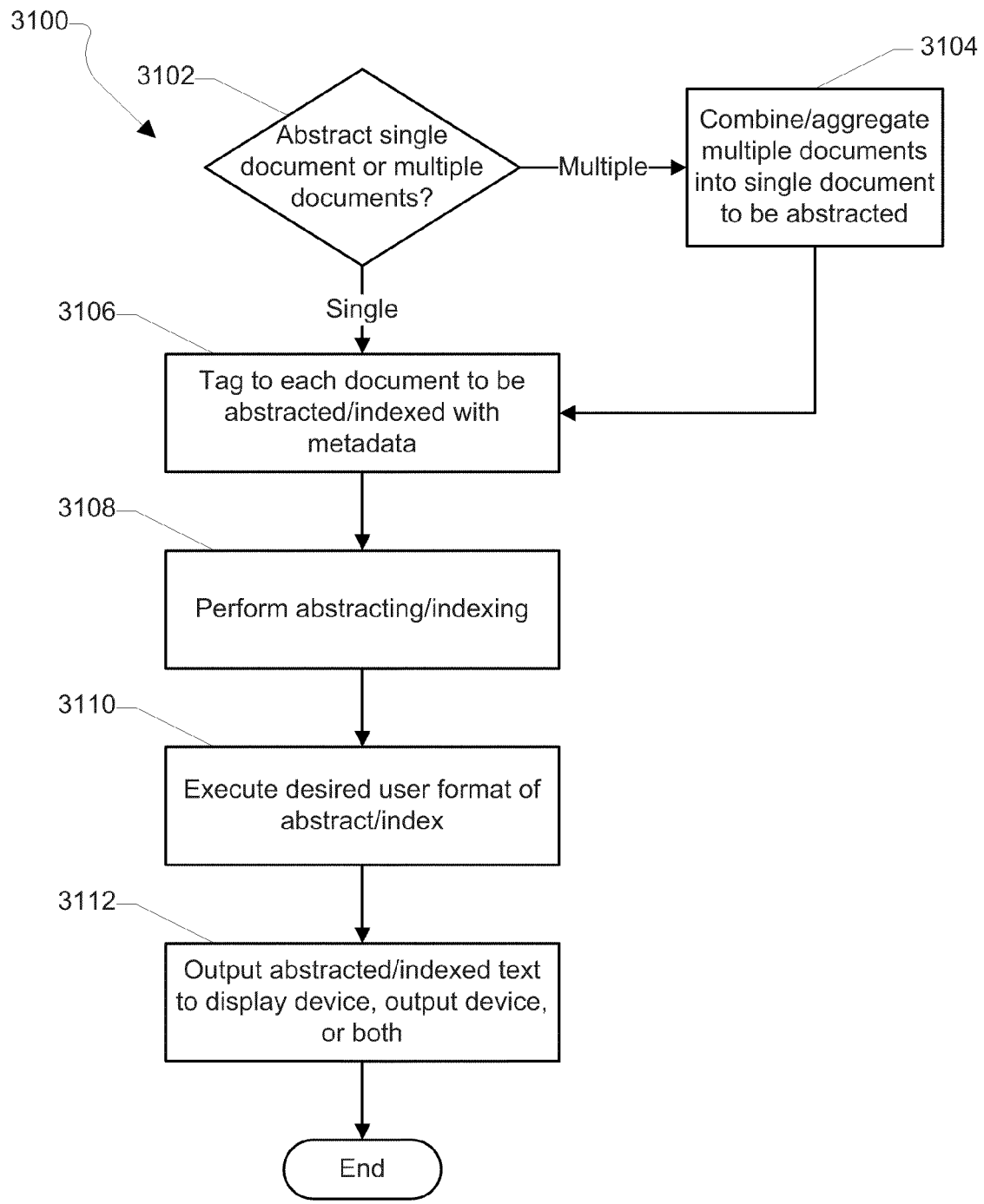
FIG. 31 is a flowchart representing a first aspect of a method of abstracting data derived from a volumetric scan of one or more documents.

FIG. 31 depicts a first aspect of a method of abstracting data derived from a volumetric scan of one or more documents. The method is generally designated 3100 and may commence at decision 3102. At decision 3102, a processor may determine whether to abstract a single document or multiple documents. If multiple documents are to be abstracted, the method 3100 may proceed to block 3104 and the processor may combine, or otherwise aggregate, multiple documents into a single document to be abstracted. From block 3104, the method 3100 may move to block 3106. Returning to decision 3102, if a single document is to be abstracted, the method 3100 may also proceed to block 3106.

At block 3106, the processor may tag each document to be abstracted, or indexed, with metadata. Next, at block 3108, the processor may perform an abstracting, or indexing, procedure on each document. At block 3110, the processor may execute a desired user format of the abstract or index. Thereafter, at block 3112, the processor may output the abstracted, or indexed, text to a display device, an output device, or a combination thereof. The method 3100 may then end.

Figure 32:
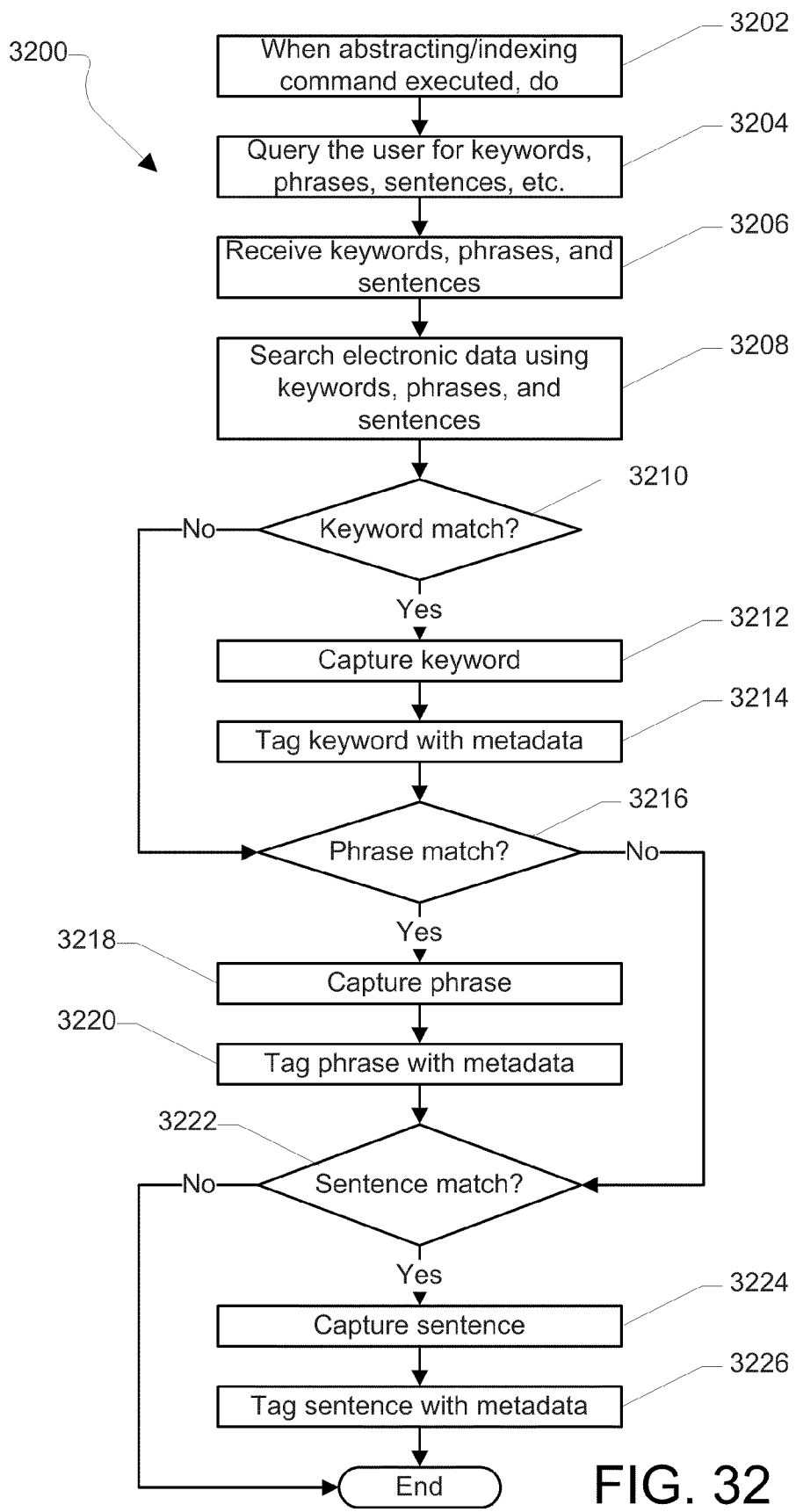
FIG. 32 is a flowchart representing a second aspect of a method of abstracting data derived from a volumetric scan of one or more documents.

FIG. 32 shows a second aspect of a method of abstracting data derived from a volumetric scan of one or more documents. The method is generally designated 3200. Beginning at block 3202, when abstracting/indexing command is executed, or otherwise selected, the following steps may be performed. At block 3204, a processor may query a user for keywords, phrases, sentences, etc. Next, at block 3206, the processor may receive the keywords, phrases, and sentences from the user.

Moving to block 3208, the processor may search the electronic data using the keywords, phrases, and sentences. Thereafter, at decision 3210, the processor may determine whether there is a keyword match. If so, the method 3200 may move to block 3212, and the processor capture the matching keyword. At block 3214, the processor may tag the matching keyword with metadata. Then, the method 3200 may move to decision 3216 and continue as described herein.

Returning to decision 3210, if there is not a keyword match, the method 3200 may proceed directly to decision 3216 and the processor may determine whether there is a phrase match. If a phrase match exists, the method 3200 may move to block 3218 and the processor may capture the matching phrase. At block 3220, the processor may tag the matching phrase with metadata. Next, the method 3200 may proceed to decision 3222 and continue as described herein.

Returning to decision 3216, if there is not a phrase match, the method 3200 may move directly to decision 3222 and the processor may determine whether there is a sentence match. If there is a sentence match, the method 3200 may continue to block 3224 and the processor may capture the matching sentence. Then, the processor may tag the matching sentence with metadata. Thereafter, the method 3200 may end. Returning to decision 3222, if there is not a matching sentence, the method 3200 may end.

Figure 33:
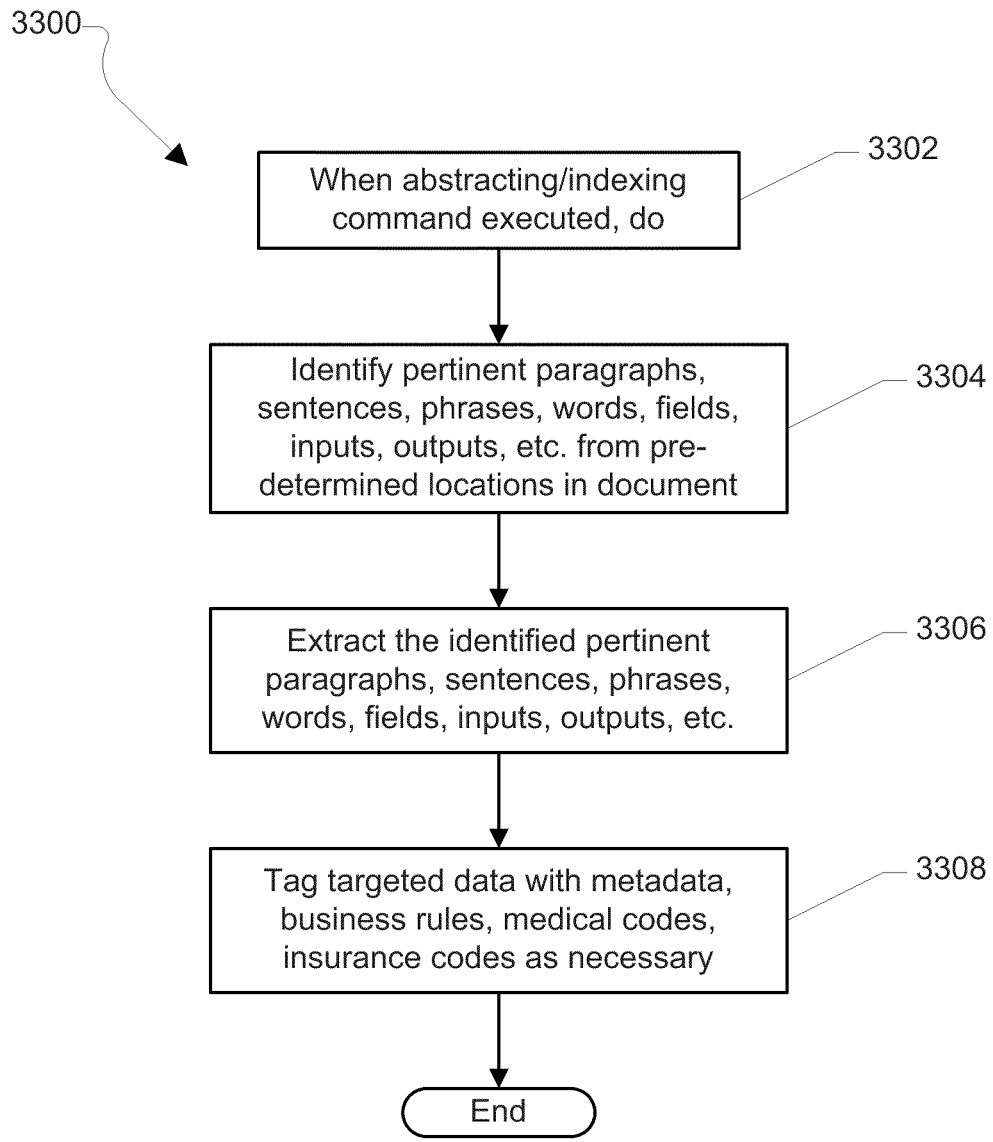
FIG. 33 is a flowchart representing a third aspect of a method of abstracting data derived from a volumetric scan of one or more documents.

FIG. 33 depicts a third aspect of a method of abstracting data derived from a volumetric scan of one or more documents that is generally designated 3300. Commencing at block 3302, when an abstracting/indexing command is executed, or otherwise selected, the following steps may be performed. At block 3304, the processor may identify pertinent paragraphs, sentences, phrases, words, fields, inputs, outputs, etc. from pre-determined locations in document. Further, at block 3306, the processor may extract the identified pertinent paragraphs, sentences, phrases, words, fields, inputs, outputs, etc. Then, at block 3308, the processor may tag the targeted data with metadata, business rules, medical codes, insurance codes, etc. as necessary. The method 3300 may then end.

Figure 34:
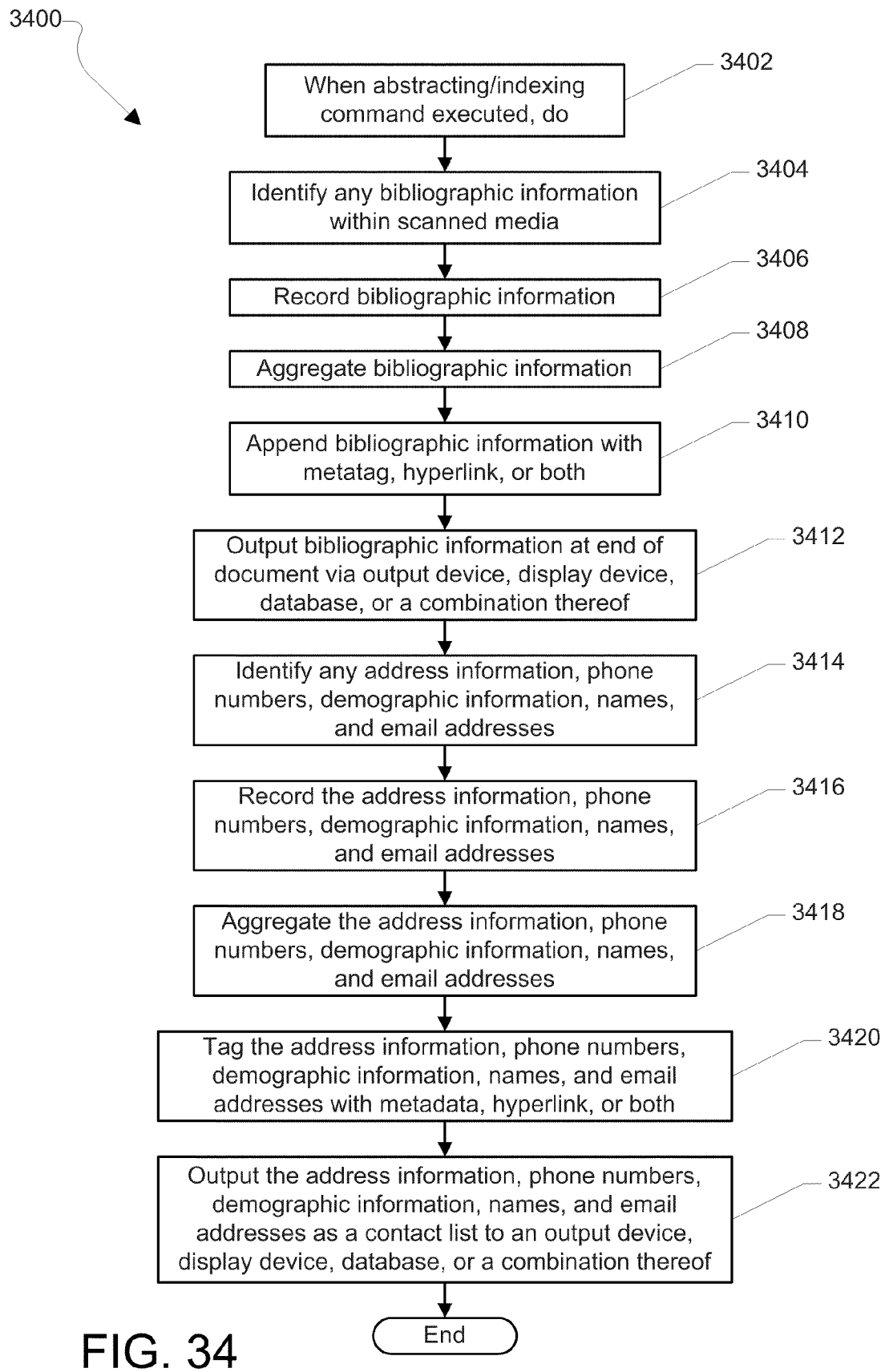
FIG. 34 is a flowchart representing a fourth aspect of a method of abstracting data derived from a volumetric scan of one or more documents.

Referring now to FIG. 34, a fourth aspect of a method of abstracting data derived from a volumetric scan of one or more documents is illustrated and is generally designated 3400. Beginning at block 3402, when an abstracting/indexing command executed, or otherwise selected, the following steps may be performed. At block 3404, a processor may identify any bibliographic information within scanned media. At block 3406, the processor may record the bibliographic information. Further, at block 3408, the processor may aggregate the bibliographic information.

Moving to block 3410, the processor may append the bibliographic information with metatags, metadata, hyperlinks, or a combination thereof. At block 3412, the processor may output, or otherwise append, the bibliographic information to an end of the document via an output device, a display device, a database, or a combination thereof.

Proceeding to block 3414, the processor may identify any address information, phone numbers, demographic information, names, and email addresses. At block 3416, the processor may record the address information, phone numbers, demographic information, names, and email addresses. Moreover, at block 3418, the processor may aggregate the address information, phone numbers, demographic information, names, and email addresses. Additionally, at block 3420, the processor may tag the address information, phone numbers, demographic information, names, and email addresses with metatags, metadata, hyperlinks, or a combination thereof. At block 3422, the processor may output the address information, phone numbers, demographic information, names, and email addresses as a contact list to an output device, display device, database, or a combination thereof. Then, the method 3400 may end.

Figure 35:
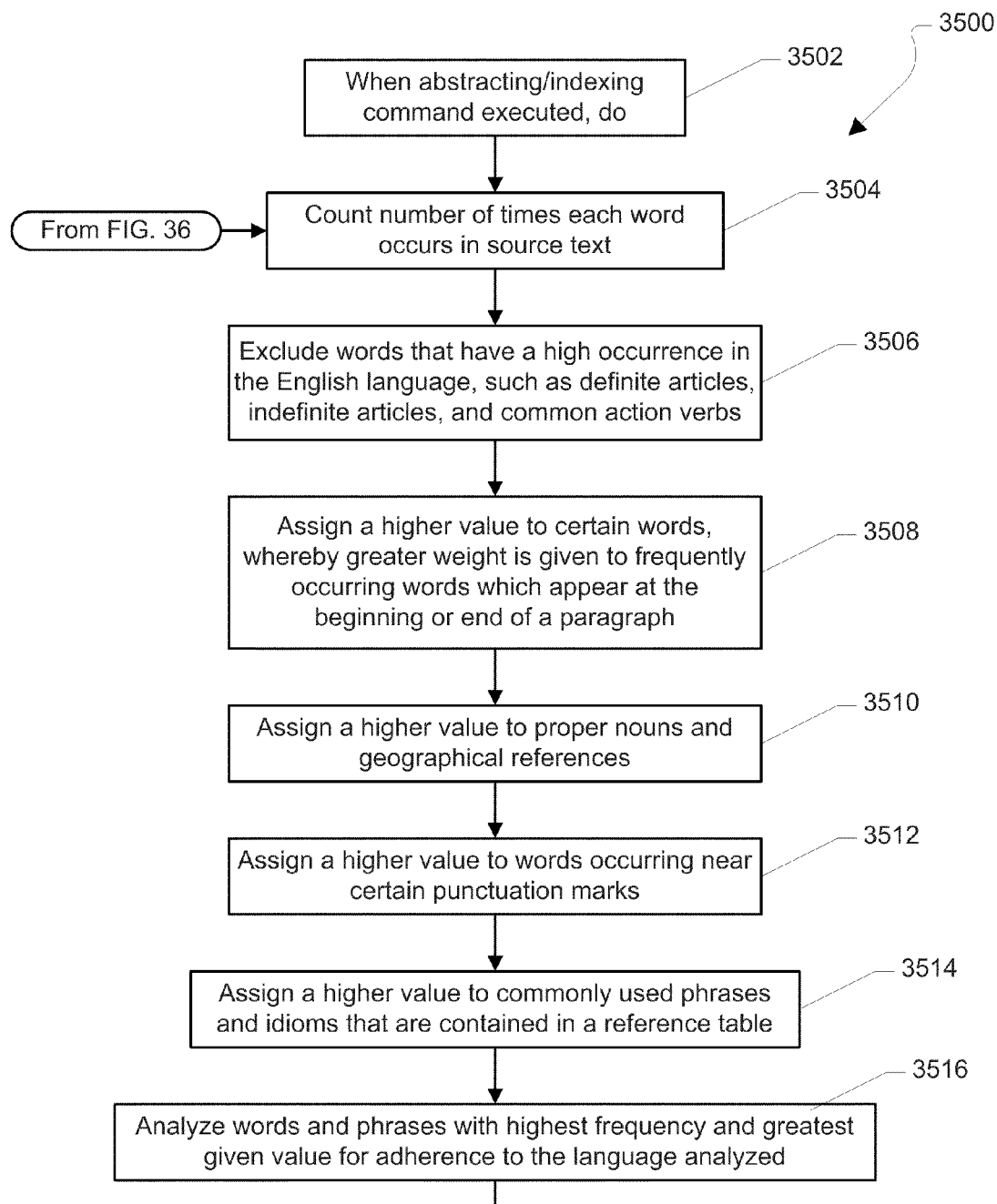
FIG. 35 is a flowchart representing a first portion of a fifth aspect of a method of abstracting data derived from a volumetric scan of one or more documents.
Figure 36:
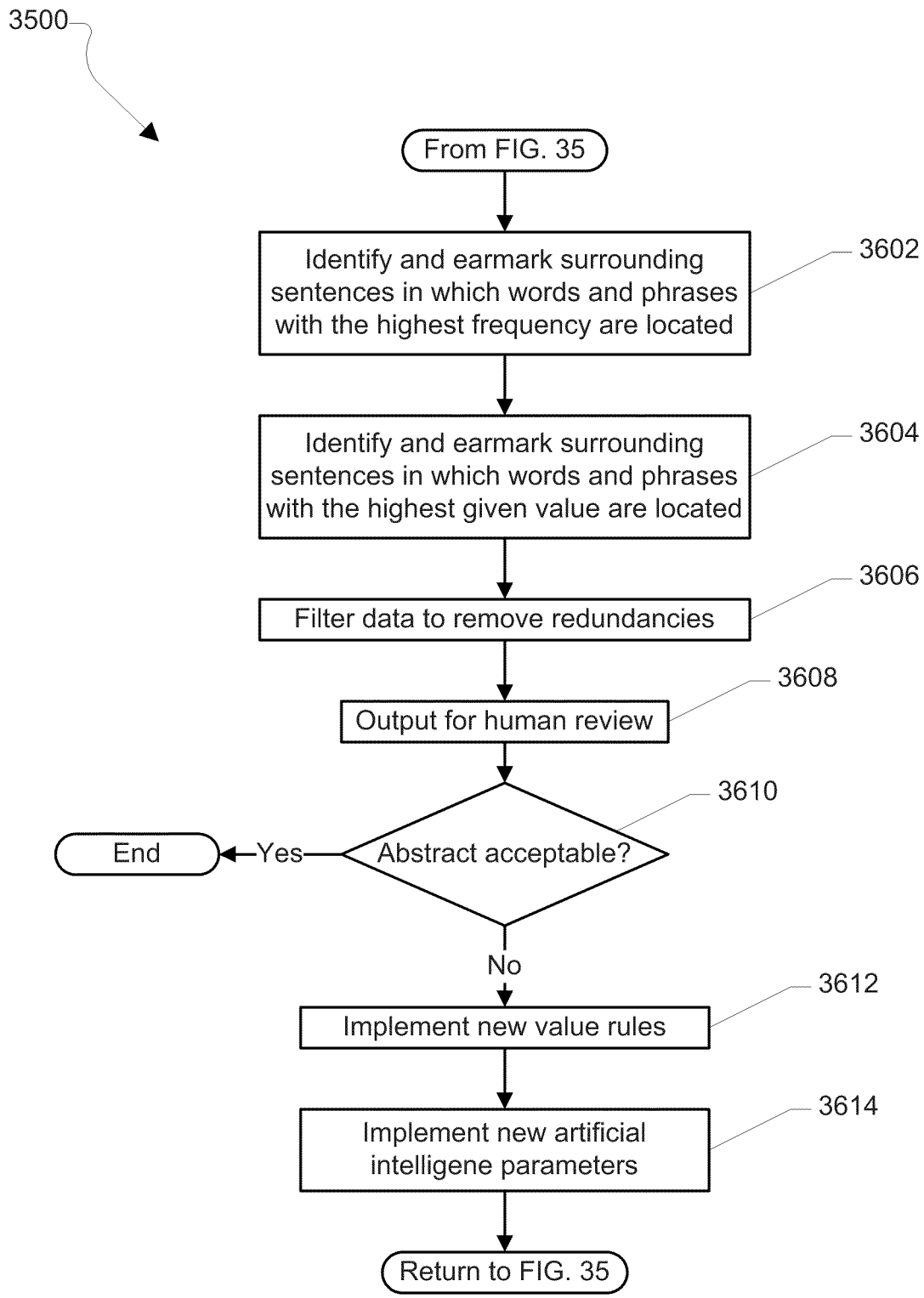
FIG. 36 is a flowchart representing a second portion of the fifth aspect of a method of abstracting data derived from a volumetric scan of one or more documents.

FIG. 35 and FIG. 36 depict a fifth aspect of a method of abstracting data derived from a volumetric scan of one or more documents. The method is generally designated 3500. Beginning at block 3502, when an abstracting/indexing command executed, or otherwise selected, the following steps may be performed. At block 3504, the processor may count a number of times each word occurs in source text. At block 3506, the processor may exclude words that have a high occurrence in the English language, such as definite articles, indefinite articles, and common action verbs.

Moving to block 3508, the processor may assign a higher value to certain words, whereby greater weight is given to frequently occurring words which appear at the beginning or end of a paragraph. At block 3510, the processor may assign a higher value to proper nouns and geographical references. Further, at block 3512, the processor may assign a higher value to words occurring near certain punctuation marks. At block 3514, the processor may assign a higher value to commonly used phrases and idioms that are contained in a reference table. Moreover, at block 3516, the processor may analyze words and phrases with highest frequency and greatest given value for adherence to the language analyzed. Then, the method 3500 may continue to block 3602 of FIG. 36.

At block 3602 of FIG. 36, the processor may identify and earmark surrounding sentences in which words and phrases with the highest frequency are located. Next, at block 3604, the processor may identify and earmark surrounding sentences in which words and phrases with the highest given value are located. At block 3606, the processor may filter the data to remove redundancies.

Proceeding to block 3608, the processor may output the abstract for human review, e.g., to a printer, a display device, or a combination thereof. At decision 3610, the processor may receive an indication from a user of whether or not the abstract is acceptable. If the abstract is acceptable, the method 3500 may end. Otherwise, if the abstract is not acceptable method 3500 may proceed to block 3612 and the processor may implement new rule values. The new rule values may be received from a user. At block 3614, the processor may implement new artificial intelligence parameters. The new artificial intelligence parameters may be received from a user. From block 3614 of FIG. 36, the method 3500 may return to block 3504 of FIG. 35. Thereafter, the method 3500 may continue as described herein.

Figure 37:
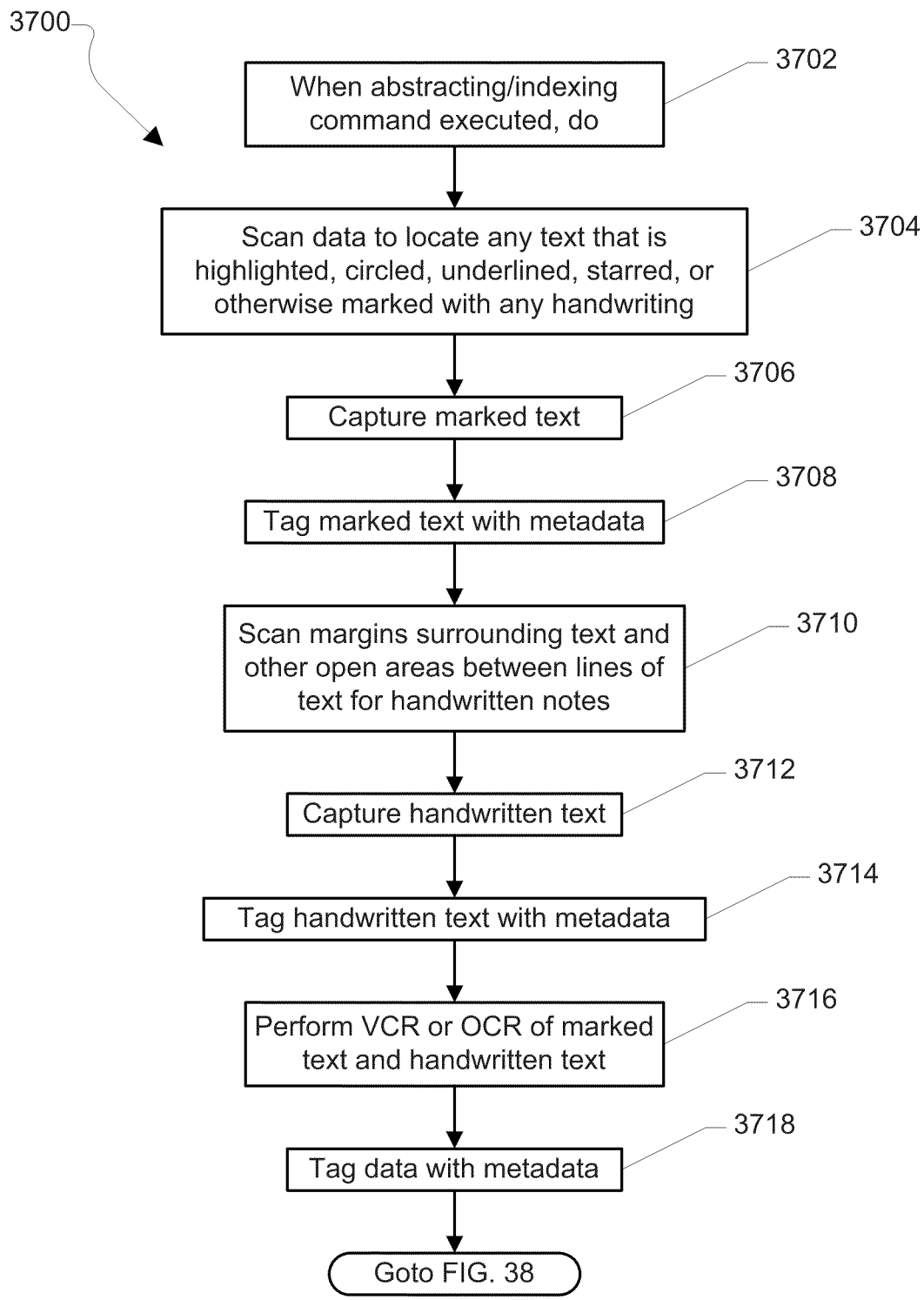
FIG. 37 is a flowchart representing a first portion of a sixth aspect of a method of abstracting data derived from a volumetric scan of one or more documents.

Referring now to FIG. 37, a sixth aspect of a method of abstracting data derived from a volumetric scan of one or more documents is shown and is designated 3700. At block 3702, when an abstracting/indexing command executed, or otherwise selected, the following steps may be performed. At block 3704, a processor may scan data to locate any text that is highlighted, circled, underlined, starred, or otherwise marked with any handwriting. At block 3706, the processor may capture the marked text. Further, at block 3708, the processor may tag the marked text, e.g., with metadata.

Moving to block 3710, the processor may scan the margins surrounding the text and other open areas between lines of text for handwritten notes. At block 3712 the processor may capture any handwritten text. Further, at block 3714, the processor may tag any handwritten text with metadata. At block 3716, the processor may perform VCR or OCR of the marked text and the handwritten text. Moreover, at block 3718, processor may tag the data obtained from the VCR or OCR processor, e.g., with metadata, metatags, or a combination thereof. Thereafter, the method 3700 may proceed to decision 3802 of FIG. 38.

Figure 38:
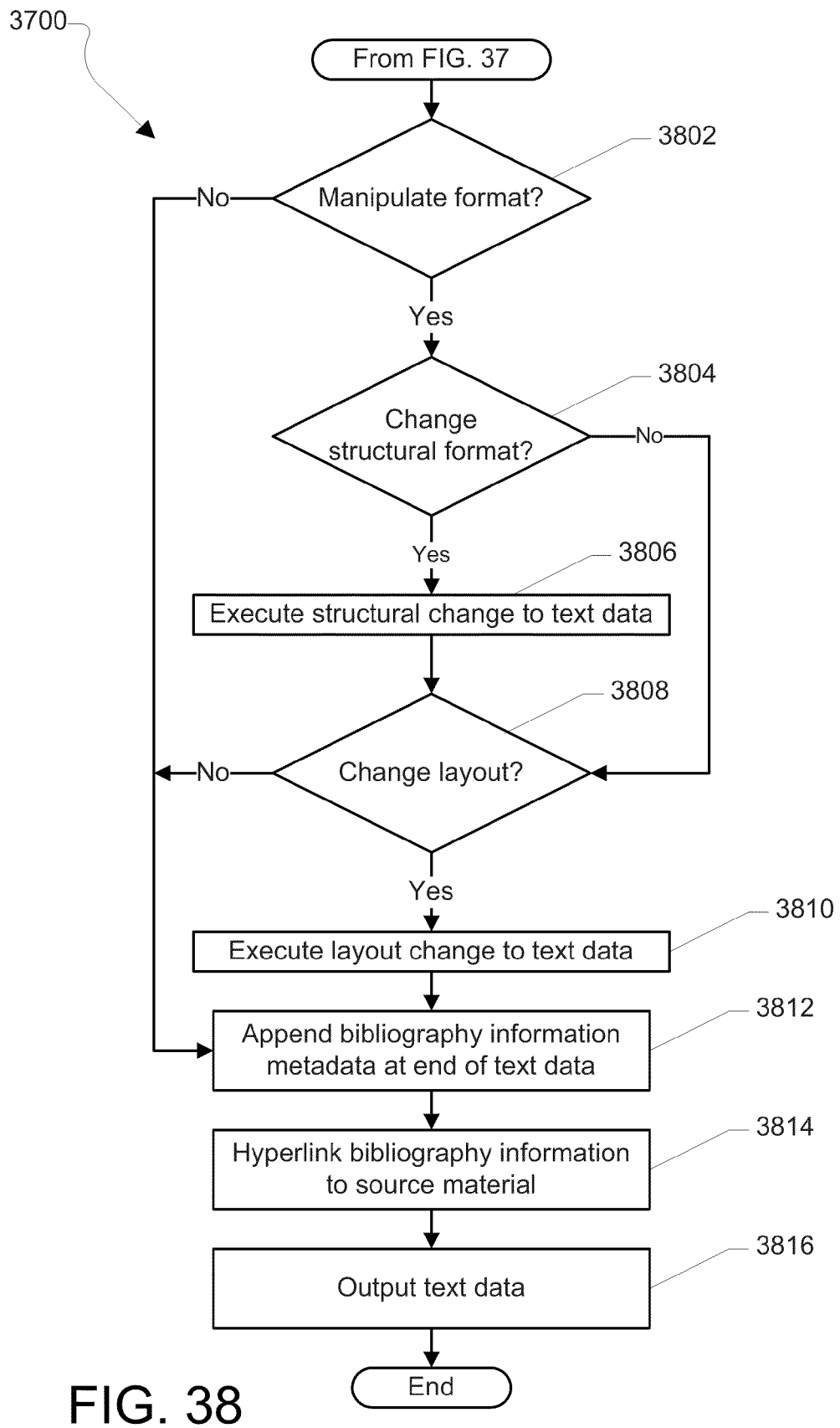
FIG. 38 is a flowchart representing a second portion of the sixth aspect of a method of abstracting data derived from a volumetric scan of one or more documents.

At decision 3802 of FIG. 38, the processor may determine whether to manipulate the format of the data, e.g., based on a user selection or preference. If so, the method 3700 may move to decision 3804 and the processor may determine whether to change the structural format of the data, e.g., based on a use selection, a user preference, a file requirement, a storage requirement, or a combination thereof. If so, the method 3700 may continue to block 3806 and the processor may execute selected structural changes to the text data. Then, the method 3700 may move to decision 3808 and the method 3700 may continue as described herein.

Returning to decision 3804, if the processor determines to not change the structural format of the data, the method 3700 may continue directly to decision 3808. At decision 3808, the processor may determine whether to change the layout of the data, e.g., based on a user selection, a user preference, a file requirement, a storage requirement, or a combination thereof. If so, the method 3700 may move to block 3810 and the processor may execute the layout change to text data. Next, the method 3700 may move to block 3812 and continue as described herein.

Returning to decision 3802, if the processor determines to not manipulate the format of the data, the method 3700 may continue directly to block 3812. At block 3812, the processor may append any bibliography information metadata at an end of the text data. Further, at block 3814, the processor may hyperlink the bibliography information to the source material. Then, at block 3816, the processor may output the text data to a display device, an output device, a storage device, a network, an ECM server, or a combination thereof. Thereafter, the method 3700 may end.

Figure 39:
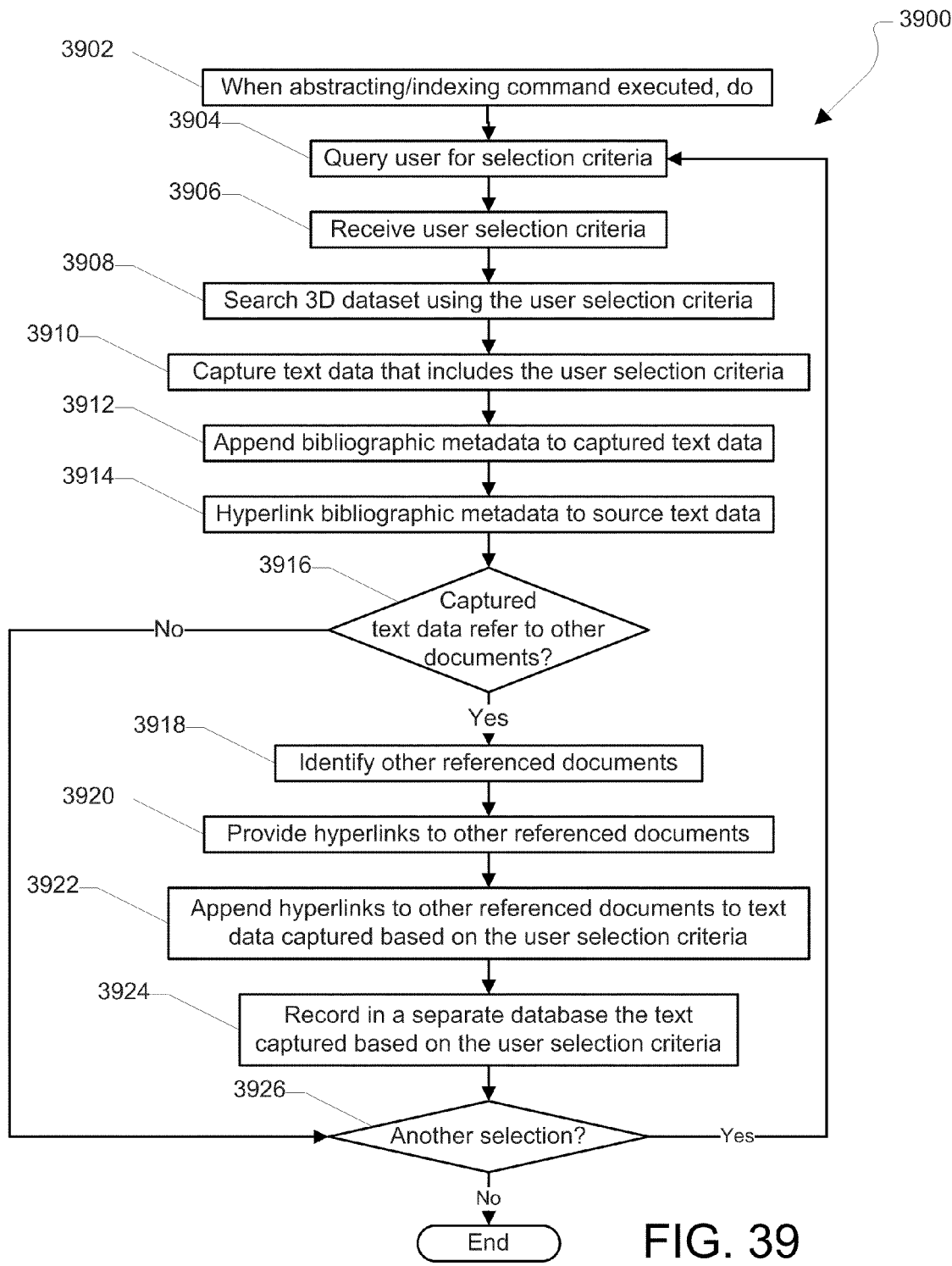
FIG. 39 is a flowchart representing a seventh aspect of a method of abstracting data derived from a volumetric scan of one or more documents.

FIG. 39 illustrates a seventh aspect of a method of abstracting data derived from a volumetric scan of one or more documents. The method is generally designated 3900. Beginning at block 3902, when an abstracting/indexing command is executed, or otherwise selected, the following steps may be performed. At block 3904, the processor may query user for one or more selection criteria. At block 3906, the processor may receive the user selection criteria. Thereafter, at block 3908, the processor may search a 3D dataset using the user selection criteria.

Moving to block 3910, the processor may capture any text data that includes the user selection criteria. At block 3912, the processor may append bibliographic metadata to the captured text data. Further, at block 3914, the processor may hyperlink the bibliographic metadata to the source text data.

At decision 3916, the processor may determine whether the captured text data refers to any other documents. If the captured text data refers to any other documents, the method 3900 may move to block 3918 and the processor may identify the other referenced documents. At block 3920, the processor may provide hyperlinks to the other referenced documents. Additionally, at block 3922, the processor may append hyperlinks to the other referenced documents to the text data captured based on the user selection criteria. At block 3924, the processor may record in a separate database the text captured based on the user selection criteria. From block 3924, the method 3900 may proceed to decision 3926 and continue as described.

Returning to decision 3916, if the capture text data does not refer to any other documents, the method 3900 may proceed directly to decision 3926. At decision 3926, the processor may determine whether the user wishes to search using another selection, e.g., based on a user query. If there is another selection, the method 3900 may return to block 3904 and the method 3900 may continue as described herein. Otherwise, if another selection is not made, the method 3900 may end.

Figure 40:
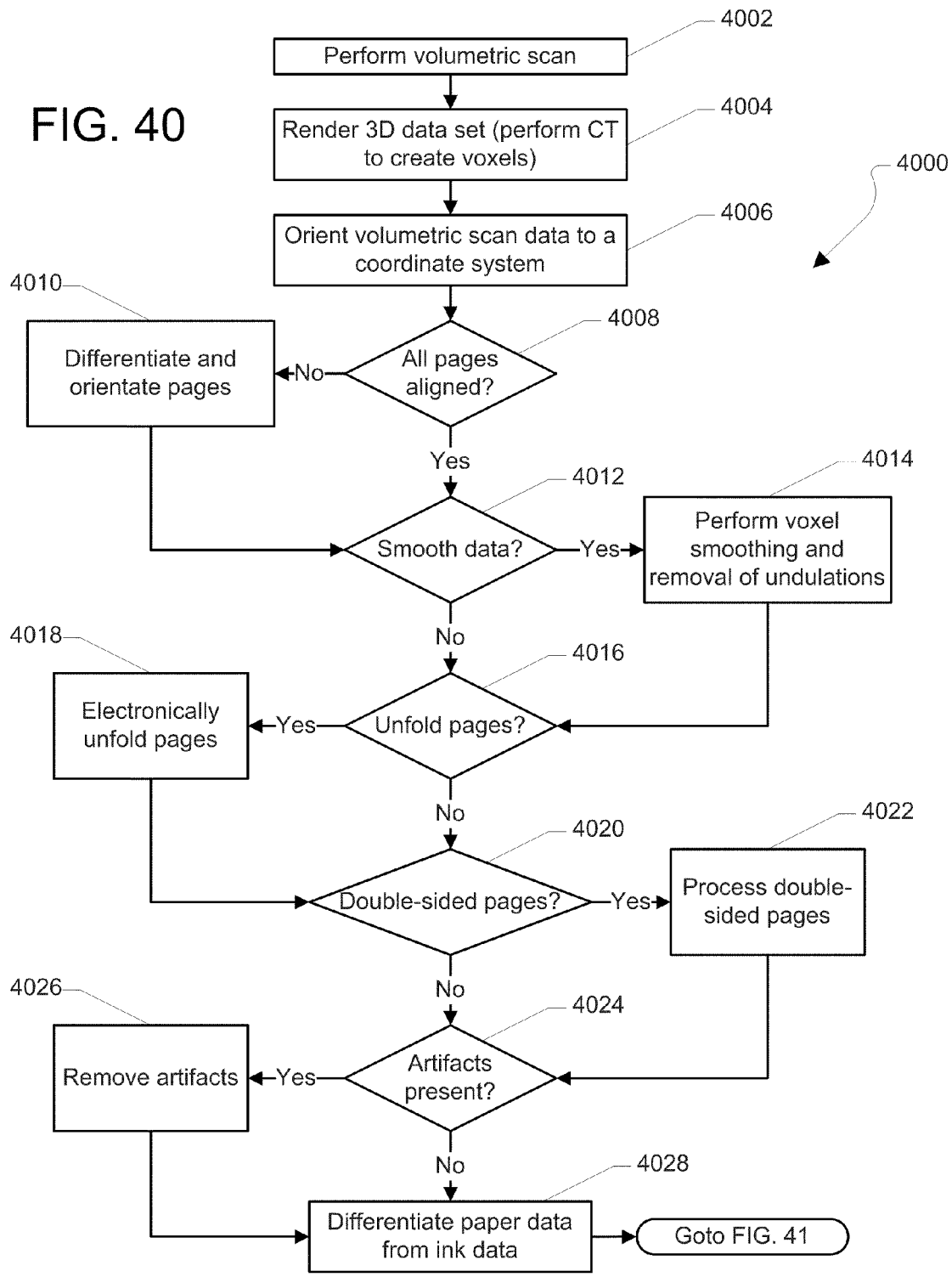
FIG. 40 is a flowchart representing a first portion of an eighth aspect of a method of abstracting data derived from a volumetric scan of one or more documents.
Figure 41:
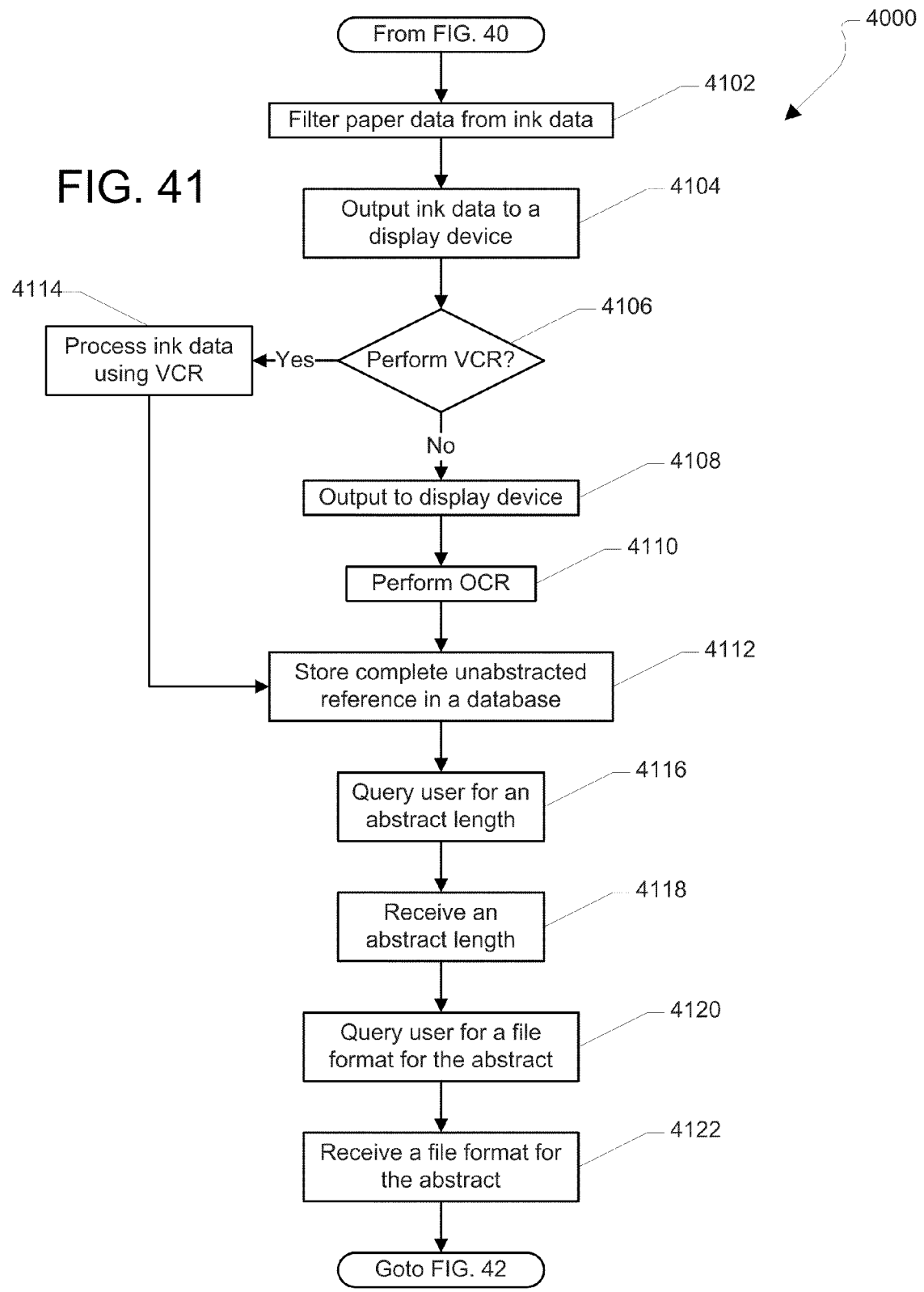
FIG. 41 is a flowchart representing a second portion of the eight aspect of a method of abstracting data derived from a volumetric scan of one or more documents.
Figure 42:
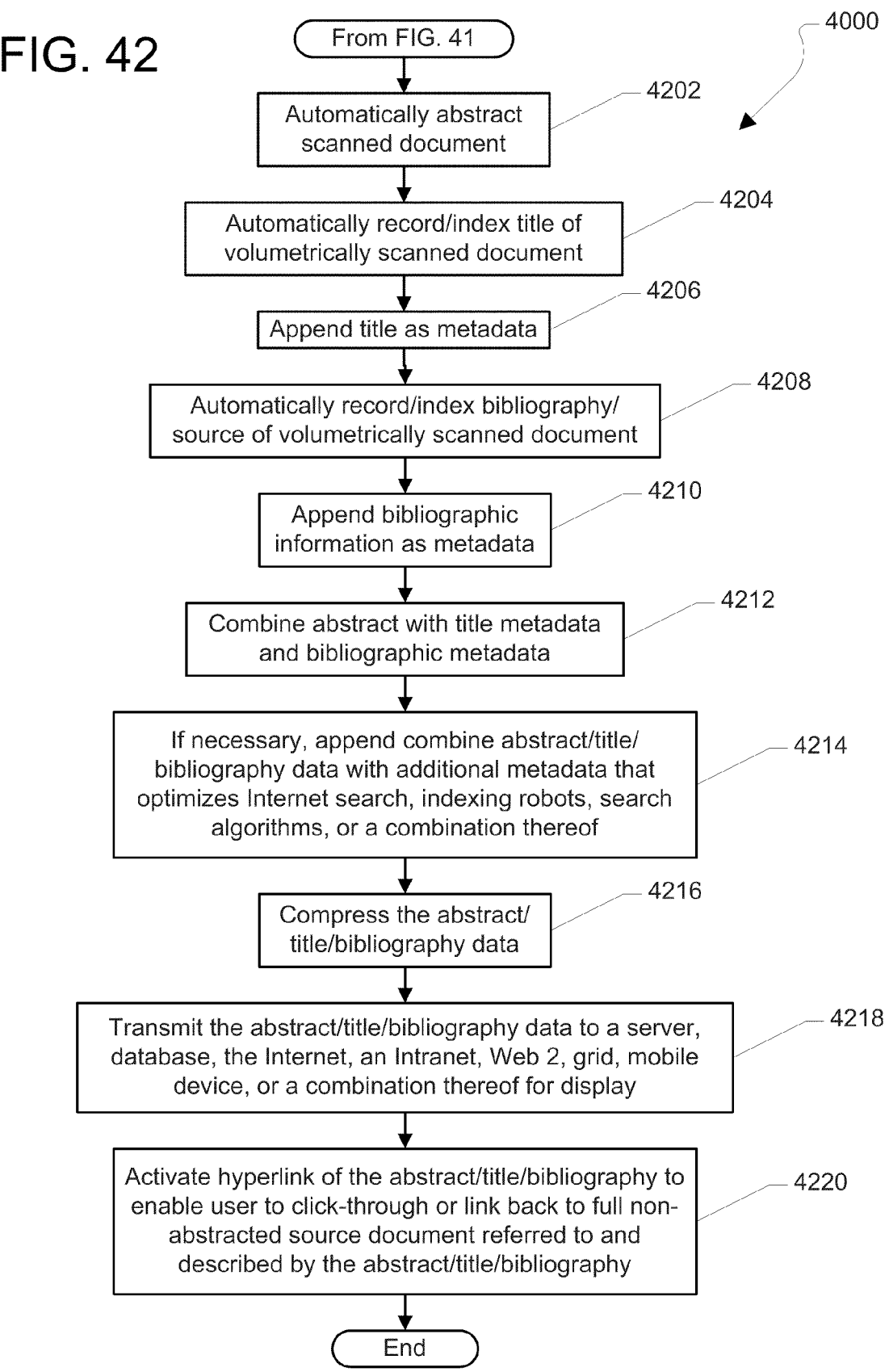
FIG. 42 is a flowchart representing a third portion of the eight aspect of a method of abstracting data derived from a volumetric scan of one or more documents.

Referring now to FIG. 40 through FIG. 42, an eighth aspect of a method of abstracting data derived from a volumetric scan of one or more documents is depicted and is generally designated 4000. Beginning at block 4002, a volumetric scan may be performed. At block 4004, a processor may render 3D dataset, e.g., the processor may perform computed tomography (CT) to create voxels arranged in slices or layers. Moving to block 4006, the processor may orient volumetric scan data to a coordinate system.

At decision 4008, the processor may determine whether all pages are the aligned. If not, the method 4000 may move to block 4010 and the processor may differentiate and orientate, or otherwise align, the pages. Different sized pages may be grouped together. In a particular aspect, like sized pages may be grouped together. From block 4010, the method 4000 may move to decision 4012 and continue as described herein.

Returning to decision 4008, if all the pages are the same size, the method 4000 may move to decision 4012. At decision 4012, the processor may determine whether the data needs to be smoothed. In other words, the processor may determine whether the data has any undulations or is otherwise warped and if so, smoothing the data may remove the undulations or warping. If the processor determines to smooth the data, the method 4000 may proceed to block 4014 and the processor may perform voxel smoothing and removal of undulations. Next, the method 4000 may proceed to decision 4016 and continue as described.

Returning to decision 4012, if the processor determines to not smooth the data, the method 4000 may proceed directly to decision 4016 and the processor may determine whether it is necessary to unfold any pages. If so, the method may move to block 4018 and the processor may electronically unfold any folded pages. Thereafter, the method 4000 may move to decision 4020.

Returning to decision 4016, if the processor determines not to unfold any pages, the method 4000 may move directly to decision 4020 and the processor may determine whether the data includes any double-side pages. If so, the method 4000 may move to block 4022 and the processor may process the double-side pages, as described herein: Next, the method 4000 may proceed to decision 4024 and proceed as described.

Returning to decision 4020, if the data does not include any double-sided pages, the method 4000 may continue to decision 4024 and the processor may determine whether any artifacts are present in the data. If the 3D data includes any artifacts, e.g., any non-ink data or non-paper data, the method 4000 may move to block 4026 and the processor may remove the artifacts. Thereafter, the method 4000 may move to block 4028.

Returning to decision 4024, if there are not any artifacts present in the 3D dataset, the method 4000 may move directly to block 4028 and the processor may differentiate paper data from ink data. Then, the method 4000 may move to block 4102 of FIG. 41.

Moving to FIG. 41, at block 4102, the processor may filter paper data from ink data. At block 4104, the processor may output ink data to a display device, a storage device, a printer, or a combination thereof. Further, at decision 4106, the processor may determine whether to perform VCR. If not, method 4000 may move to block 4108 and the processor may output the data to a display device or other device. Thereafter, at block 4110, the processor may perform OCR on the data. The method may then move to block 4112 and continue as described herein.

Returning to decision 4006, if the processor determines to perform VCR, the method 4000 may move to block 4114 and the processor may process the ink data using VCR as described herein. Next, the method 4000 may move to block 4112. At block 4112, the processor may store the complete unabstracted reference in a database. At block 4116, the processor may query a user for an abstract length. At block 4118, the processor may receive an abstract length. Moreover, at block 4120, the processor may query user for a file format for the abstract. Then, at block 4122, the processor may receive a file format for the abstract. The method 4000 may then proceed to block 4202 of FIG. 42.

Referring now to FIG. 42, at block 4202, the processor may automatically abstract the scanned document. At block 4204, the processor may automatically record/index the title of volumetrically scanned document. At block 4206, the processor may append the title of the volumetrically scanned document as metadata. Also, at block 4208, the processor may automatically record/index bibliography/source of volumetrically scanned document.

Moving to block 4210, the processor may append the bibliographic information as metadata. At block 4212, the processor may combine the abstract with the title metadata and the bibliographic metadata. Further, at block 4214, if necessary, the processor may append, or otherwise combine, the abstract/title/bibliography data with additional metadata that optimizes an Internet search, indexing robots, search algorithms, or a combination thereof.

At block 4216, the processor may compress the abstract/title/bibliography data. Moreover, at block 4218, the processor may transmit the abstract/title/bibliography data to a server, database, the Internet, an Intranet, Web 41, grid, mobile device, or a combination thereof for display. At block 4220, the processor may activate hyperlink of the abstract/ title/bibliography to enable user to click-through or link back to full non-abstracted source document referred to and described by the abstract/title/bibliography. Then, the method 4000 may end.

Figure 43:
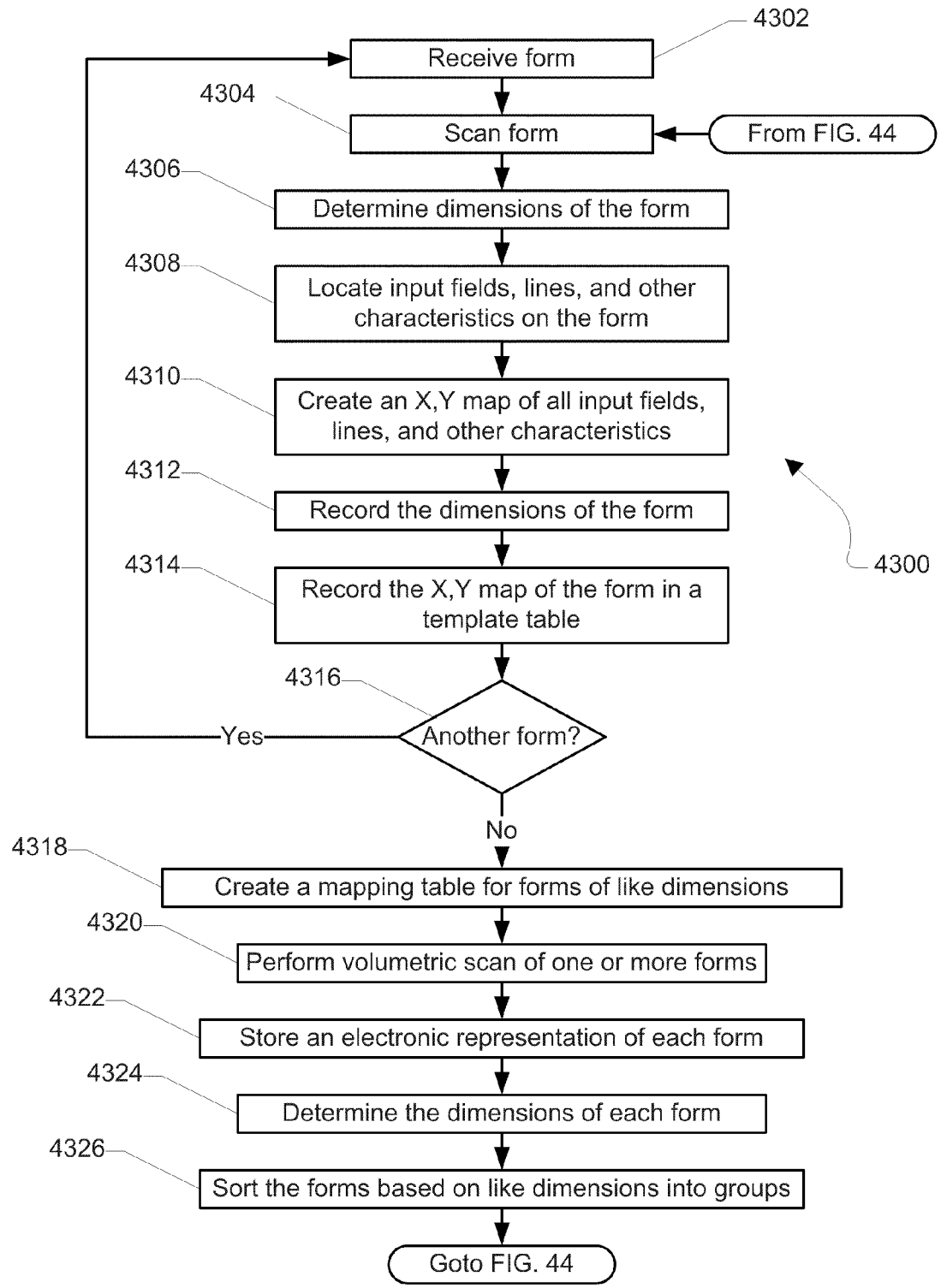
FIG. 43 is a flowchart representing a first portion of a method of volumetrically scanning paper forms.
Figure 44:
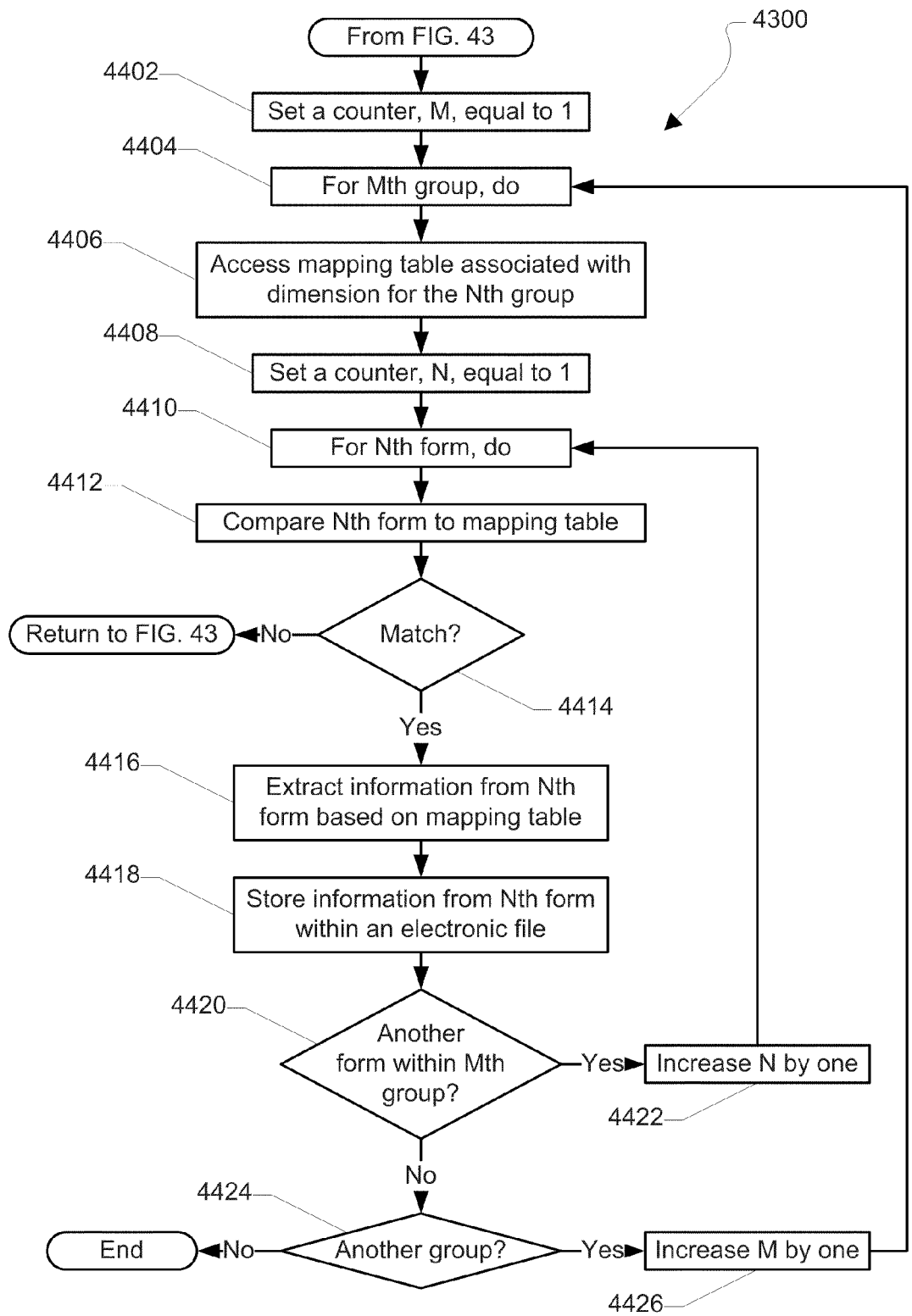
FIG. 44 is a flowchart representing a second portion of a method of volumetrically scanning paper forms.
Figure 45:
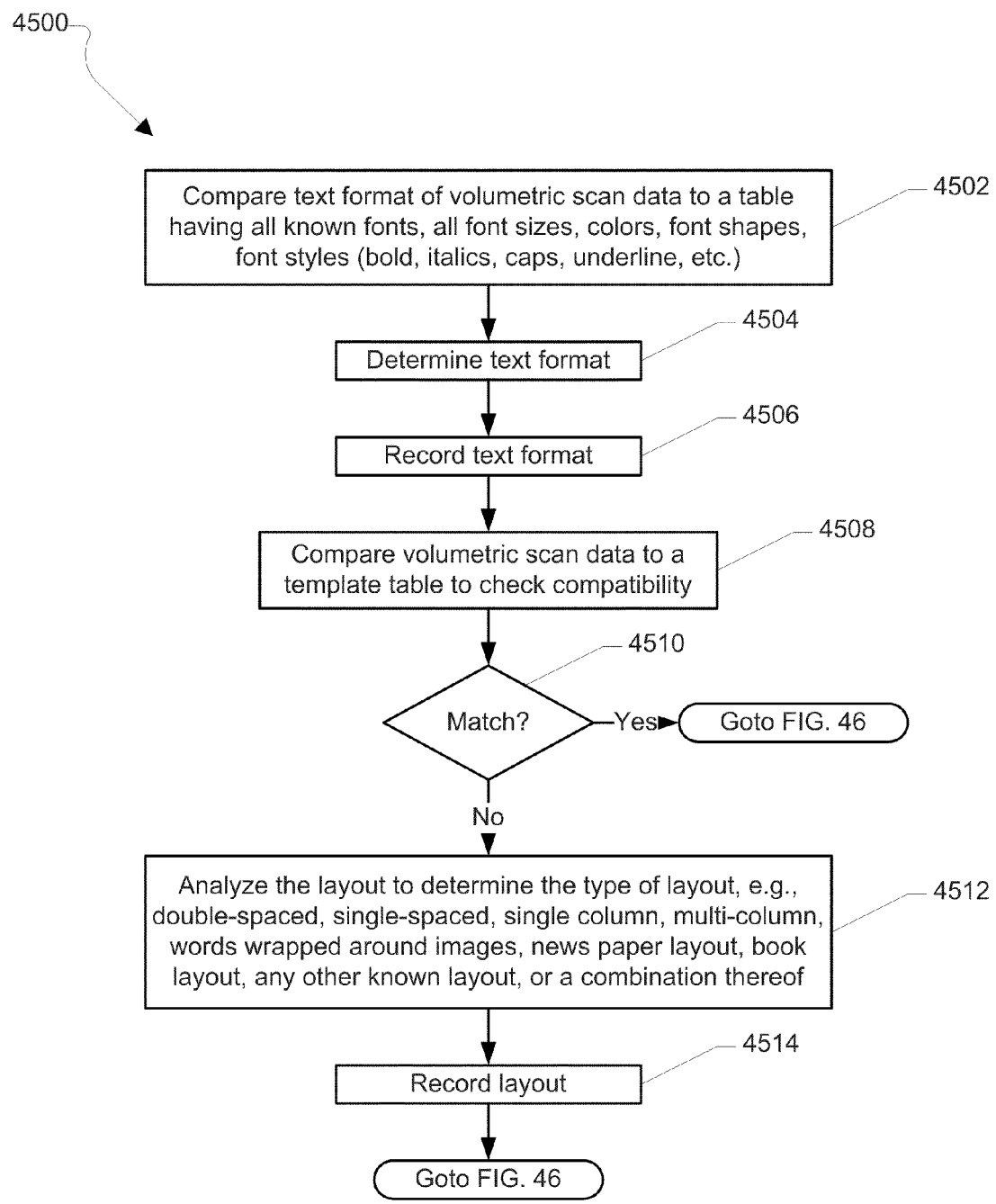
FIG. 45 is a flowchart representing a first portion of a method of recognizing and manipulating volumetric data formats.

FIG. 43 and FIG. 44 show a method of volumetrically scanning paper forms, generally designated 4300. Beginning at block 4302, a form may be received. At block 4304, the form may be scanned. At block 4306, a processor may determine dimensions of the form. Next, at block 4308, the processor may locate input fields, lines, and other characteristics on the form.

Moving to block 4310, the processor may create an X,Y map of all input fields, lines, and other characteristics. Further, at block 4312, the processor may record the dimensions of the form. At block 4314, the processor may record the X,Y map of the form in a template table. At decision 4316, the processor may determine whether another form is available. If so, the method 4300 may return to block 4302 and the method 4300 may continue as described herein.

If there is not another form, the method 4300 may proceed to block 4318 and the processor may create a mapping table for forms of like dimensions. At block 4320, a volumetric scan of one or more forms may be performed. Then, at block 4322, the processor may store an electronic representation of each form. At block 4324, the processor may determine the dimensions of each form. At block 4326, the processor may sort the forms based on like dimensions into groups. Then, the method may continue to block 4402 of FIG. 44.

Moving to block 4402 of FIG. 44, the processor may set a counter, M, equal to one (1). Then, at block 4404, a do loop may be entered in which for an Mth group of forms, the following nested steps may be performed. At block 4406, the processor may access a mapping table associated with dimension for the Mth group. Next, at block 4408, the processor may set a counter, N, equal to one (1). At block 4410, another do loop may entered in which for an Nth form, the following nested steps may be performed. At block 4412, the processor may compare the Nth form to a mapping table.

At decision 4414, the processor may determine whether the Nth form matches any entry within the mapping table. If not, the method 4300 may return to block 4304 of FIG. 43. Otherwise, if the Nth form matches an entry within the mapping table, the method 4300 may continue to block 4416 and the processor may extract information from Nth form based on the mapping table. At block 4418, the processor may store information from Nth form within an electronic file.

Moving to decision 4420, the processor may determine whether there is another form within the Mth group. If so, the method 4300 may continue to block 4422 and the processor may increase N by one. Thereafter, the method 4300 may return to block 4410 and the method 4300 may continue as described.

At decision 4420, if there is not another form within the Mth group, the method 4300 may continue to decision 4424 and the processor may determine whether there is another group of forms. If not, the method 4300 may end. If there is another group of forms, the method 4300 may proceed to block 4426 and the processor may increase M by one. Then, the method 4300 may return to block 4404 and the method 4300 may continue as described herein.

FIG. 45 through FIG. 49 depict a method of recognizing and manipulating volumetric data formats. At block 4502, a processor may compare the text format of volumetric scan data to a table having all known fonts, all font sizes, colors, font shapes, font styles (bold, italics, caps, underline, etc.). At block 4504, the processor may determine the text format. Next, at block 4506, the processor may record the text format.

Moving to block 4508, the processor may compare volumetric scan data to a template table to check compatibility. At decision 4510, the processor may determine whether there is a match. If there is a match, the method 4500 may move directly to decision 4602 of FIG. 46. Otherwise, if there is not a match, the method 4500 may move to block 4512 and the processor may analyze the layout to determine the type of layout, e.g., double-spaced, single-spaced, single column, multi-column, words wrapped around images, news paper layout, book layout, any other known layout, or a combination thereof. At block 4514, the processor may record the layout. The method 4500 may then move to decision 4602 of FIG. 46.

Figure 46:
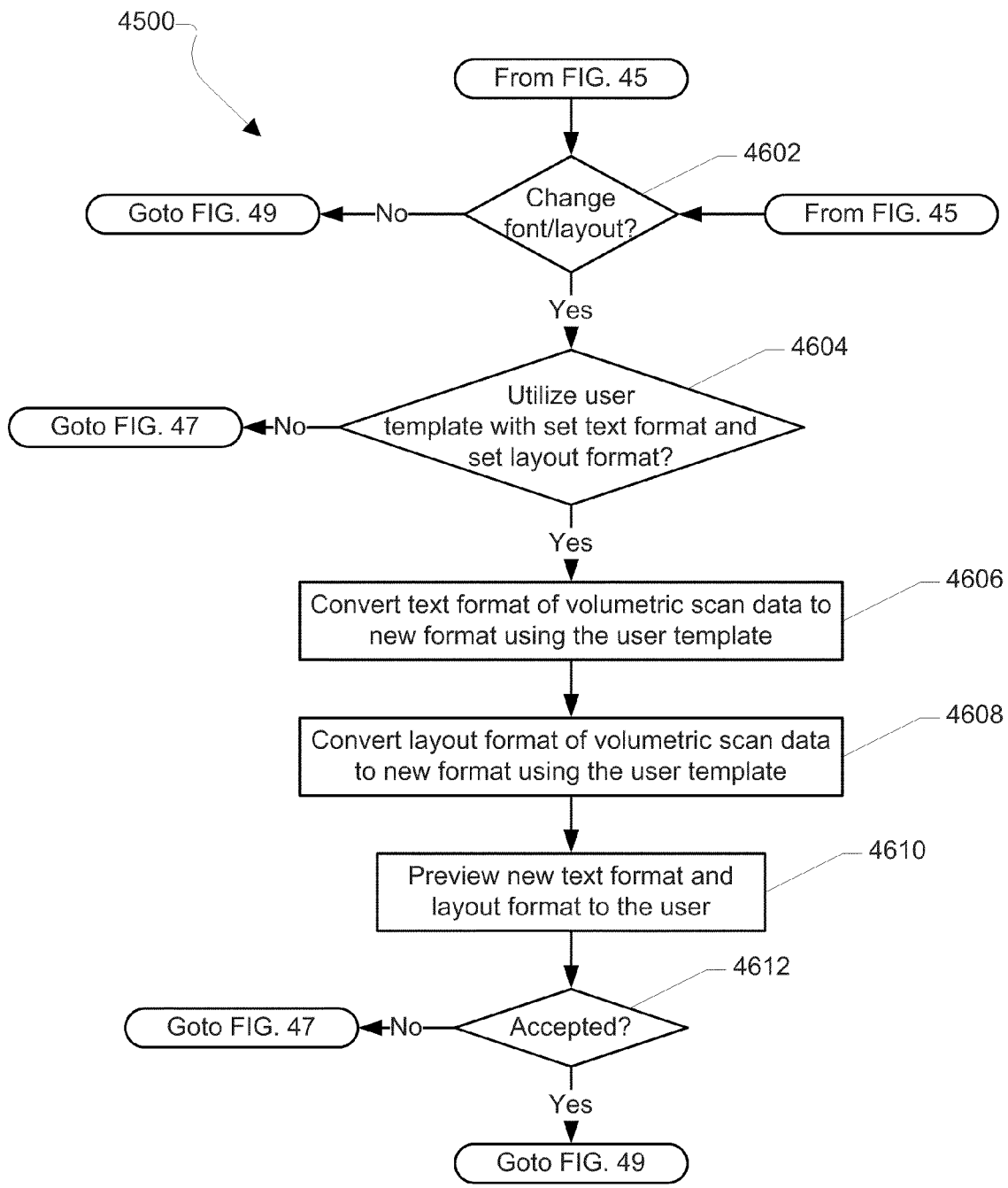
FIG. 46 is a flowchart representing a second portion of a method of recognizing and manipulating volumetric data formats.

At decision 4602 of FIG. 46, the processor may determine whether to change a font, a layout, or a combination thereof, e.g., by querying a user. If not, the method 4500 may move directly to block 4902 of FIG. 49. Otherwise, the method 4500 may move to decision 4604 and the processor may determine whether to utilize a user template with a set text form a and a set layout format. If not, the method 4500 may move directly to decision 4702 of FIG. 47. If so, the method 4500 may move to block 4606 and the processor may convert the text format of the volumetric scan data to a new format using the user template. At block 4608, the processor may convert the layout format of the volumetric scan data to a new format using the user template. Next, at block 4610, the processor may preview new text format and layout format to the user.

Moving to decision 4612, the processor may determine whether the new text format and layout format are accepted by the user. If not, the method 4500 may proceed to decision 4702 of FIG. 47. If so, the method 4500 may proceed to block 4902 of FIG. 49.

Figure 47:
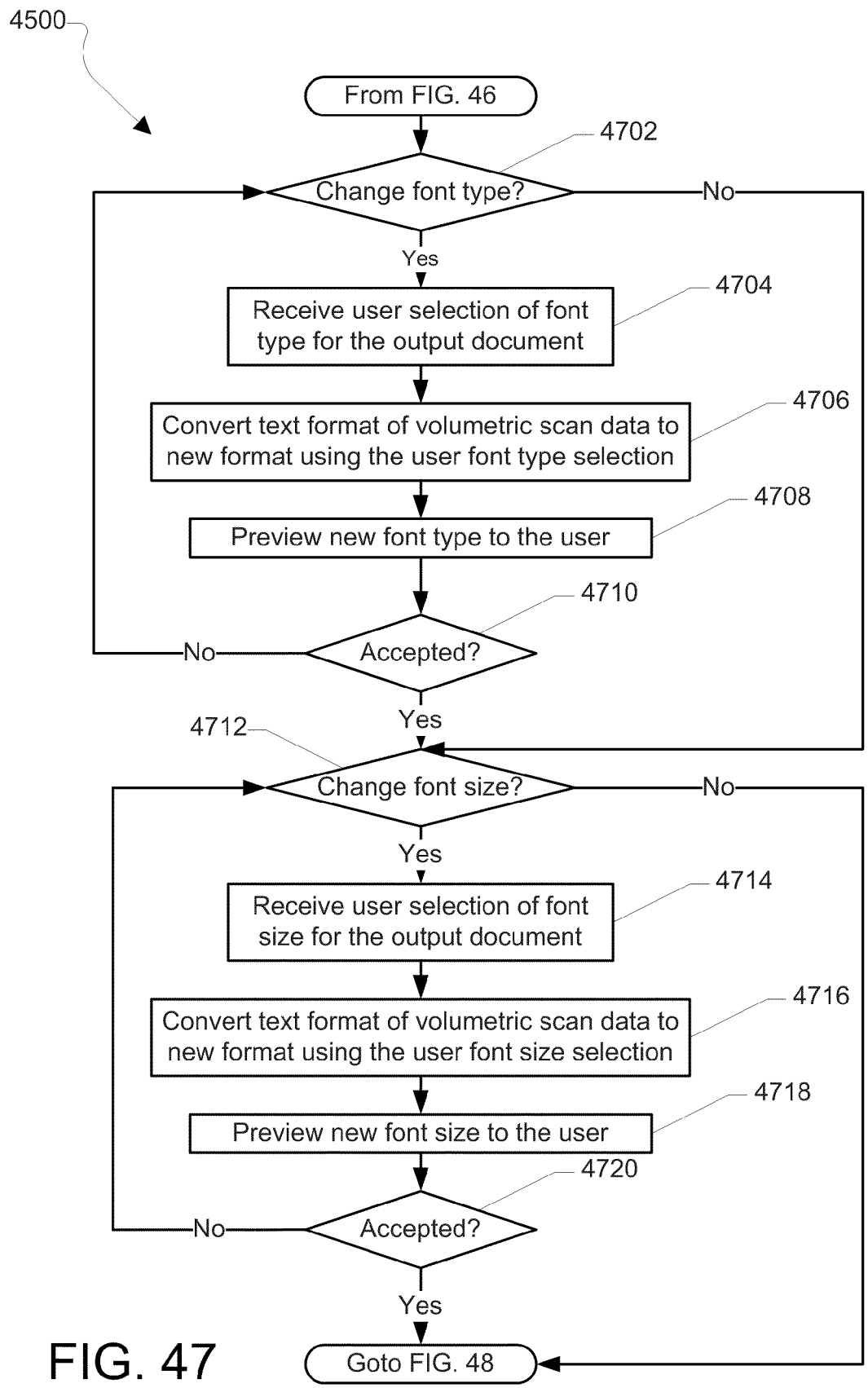
FIG. 47 is a flowchart representing a third portion of a method of recognizing and manipulating volumetric data formats.
Figure 48:
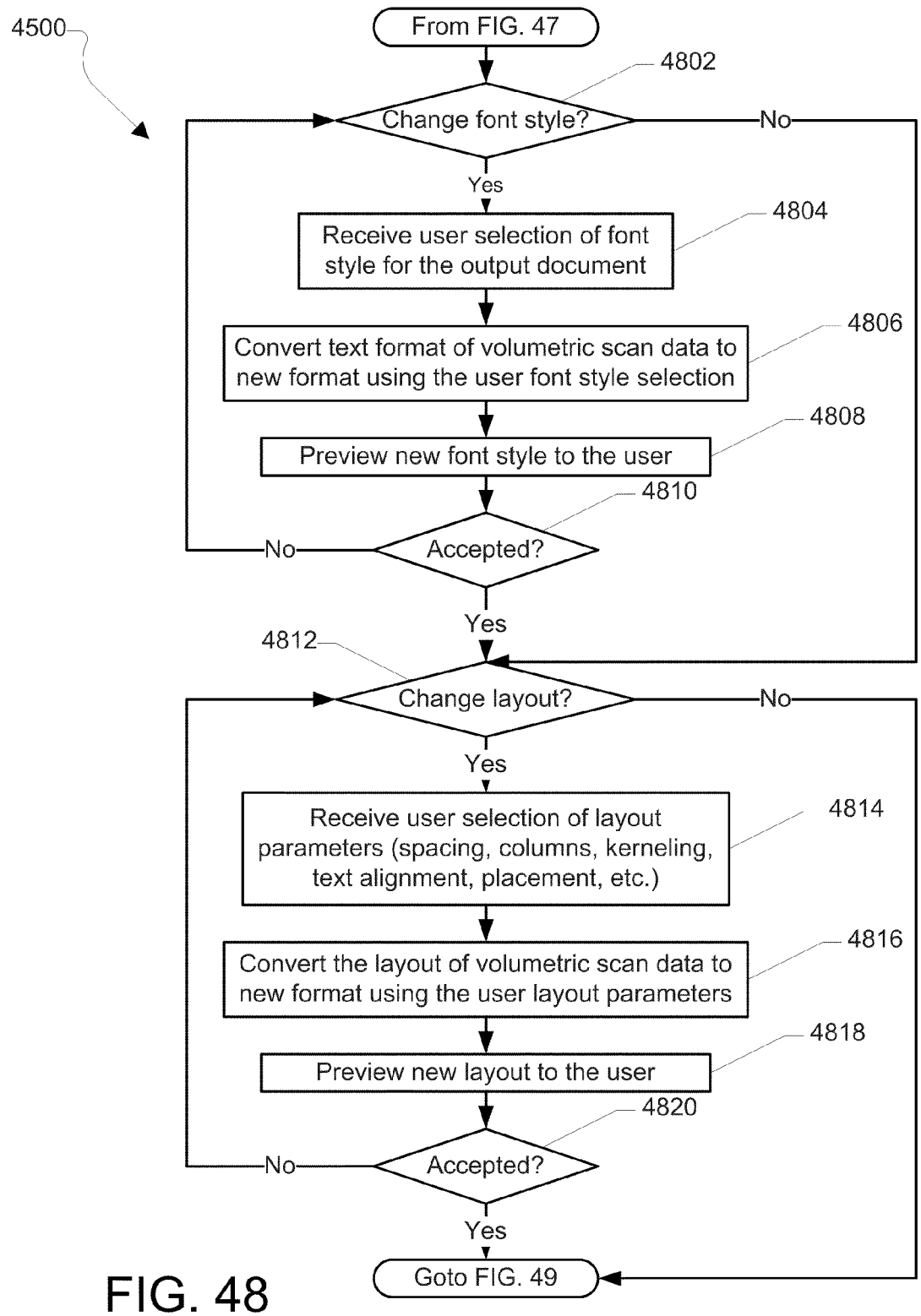
FIG. 48 is a flowchart representing a fourth portion of a method of recognizing and manipulating volumetric data formats.

Referring to FIG. 47, at decision 4702, the processor may query the user to change the font type. If the processor receives an indication to change the font type, the method may move to block 4704 and the processor may receive a user selection of a font type for the output document. At block 4706, the processor may convert the text format of the volumetric scan data to a new format using the user font type selection. At block 4708, the processor may preview the new font type to the user.

Moving to decision 4710, the processor may determine whether the new font type is accepted by the user. If not, the method 4500 may return to decision 4702 and continue as described herein. If so, the method 4500 may continue to decision 4712. Returning to decision 4702, if the user does not choose to change a font type, the method 4500 may move directly to decision 4712. At decision 4712, the processor may query the user to change the font size. If the user does not want to change the font size, the method 4500 may move directly to decision 4802 of FIG. 48. Conversely, if the processor receives an indication to change the font size, the method may move to block 4714 and the processor may receive a user selection of a font size for the output document. At block 4716, the processor may convert the text format of the volumetric scan data to a new format using the user font size selection. At block 4718, the processor may preview the new font type to the user.

Moving to decision 4720, the processor may determine whether the new font size is accepted by the user. If not, the method 4500 may return to decision 4712 and continue as described herein. If so, the method 4500 may continue to decision 4802 of FIG. 48.

At decision 4802, the processor may query the user to change the font style. If the processor receives an indication to change the font style, the method may move to block 4804 and the processor may receive a user selection of a font style for the output document. At block 4806, the processor may convert the text format of the volumetric scan data to a new format using the user font style selection. At block 4808, the processor may preview the new font style to the user.

Moving to decision 4810, the processor may determine whether the new font style is accepted by the user. If not, the method 4500 may return to decision 4802 and continue as described herein. If so, the method 4500 may continue to decision 4812. Returning to decision 4802, if the user does not choose to change a font style, the method 4500 may move directly to decision 4812. At decision 4812, the processor may query the user to change the document layout. If the user does not want to change the document layout, the method 4500 may move directly to block 4902 of FIG. 49. On the other hand, if the processor receives an indication to change the document layout, the method may move to block 4814 and the processor may receive a user selection of one or more layout parameters, e.g., spacing, columns, kerneling, text alignment, placement, etc. At block 4816, the processor may convert the layout of the volumetric scan data to a new format using the user layout parameters. At block 4818, the processor may preview the new layout to the user.

Moving to decision 4820, the processor may determine whether the new layout is accepted by the user. If not, the method 4500 may return to decision 4812 and continue as described herein. If so, the method 4500 may continue to block 4902 of FIG. 49.

Figure 49:
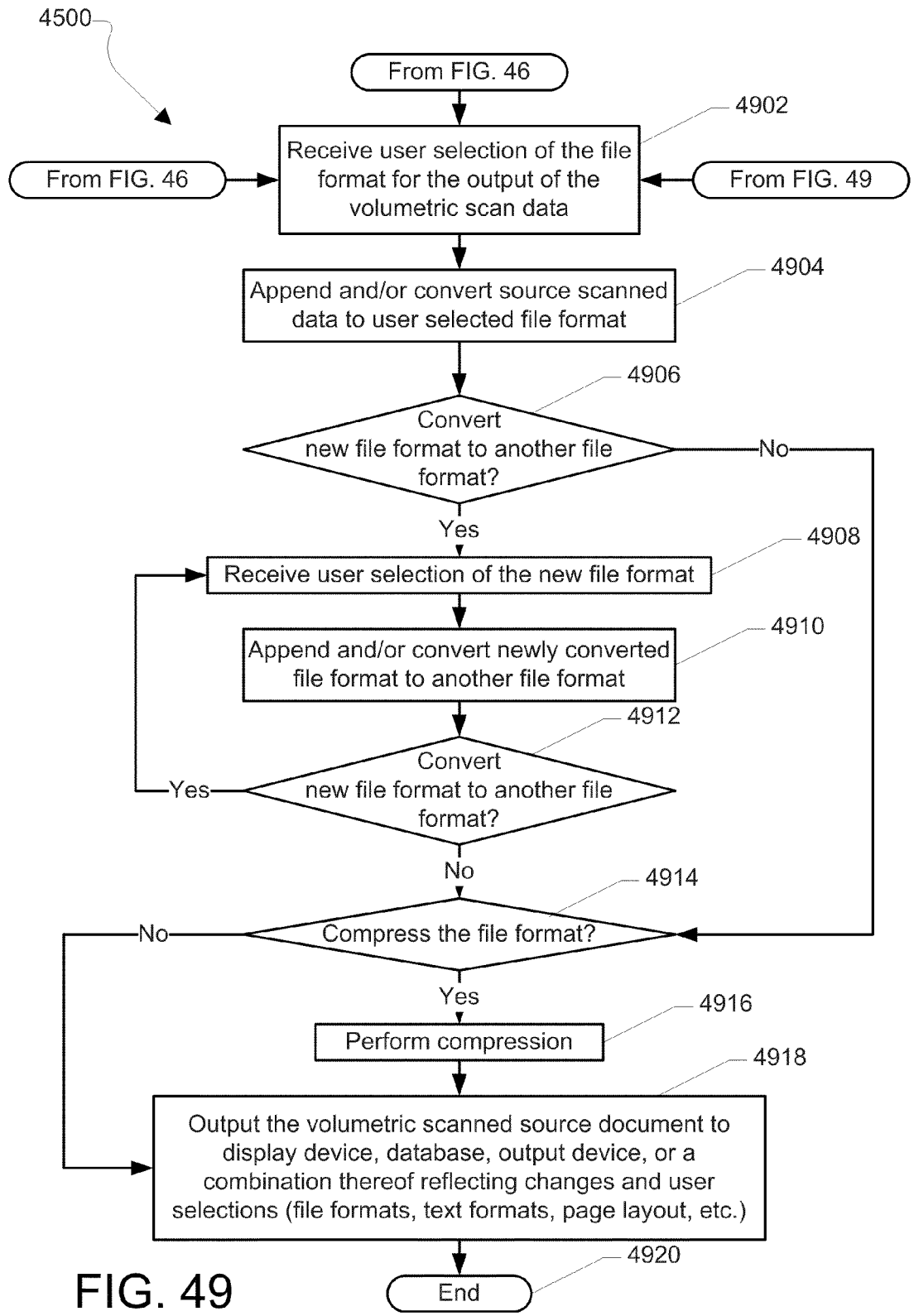
FIG. 49 is a flowchart representing a fifth portion of a method of recognizing and manipulating volumetric data formats.

At block 4902 of FIG. 49, the processor may receive a user selection of the file format for the output of the volumetric scan data. At block 4904, the processor may append and/or convert source scanned data to user selected file format. At decision 4906, the processor may query the user to convert the new file format to another file format. If the user chooses to convert the new file format to another file format, the method 4500 may proceed to block 4908 and the processor may receive a user selection of the new file format. At block 4910, the processor may append and/or convert the newly converted file format to another file format.

Moving to decision 4912, the processor, once again, may query the user to convert the new file format to another file format. If so, the method 4500 may return to block 4908 and continue as described herein. Otherwise, the method 4500 may continue to decision 4914 and the method 4500 may continue as described.

Returning to decision 4906, if the user does not choose to convert the new file format to another file format, the method 4500 may proceed directly to decision 4914. At decision 4914, the processor may determine whether to compress the file format. This determination may be based on a predetermined condition, e.g., file size, file type, or a combination thereof. This determination may also be based on a user query. If the processor determines to compress the file format, the method 4500 may proceed to block 4916 and the processor may perform the compression process on the data in order to compress the file size of the data. The method may then move to block 4918.

Returning to decision 4914, if the processor determines to not compress the file format, the method 4500 may move directly to block 4918 and the processor may output the volumetric scanned source document to a display device, a database, another output device, or a combination thereof reflecting any changes and user selections, e.g., file formats, text formats, page layout, etc. The method may then end.

Figure 50:
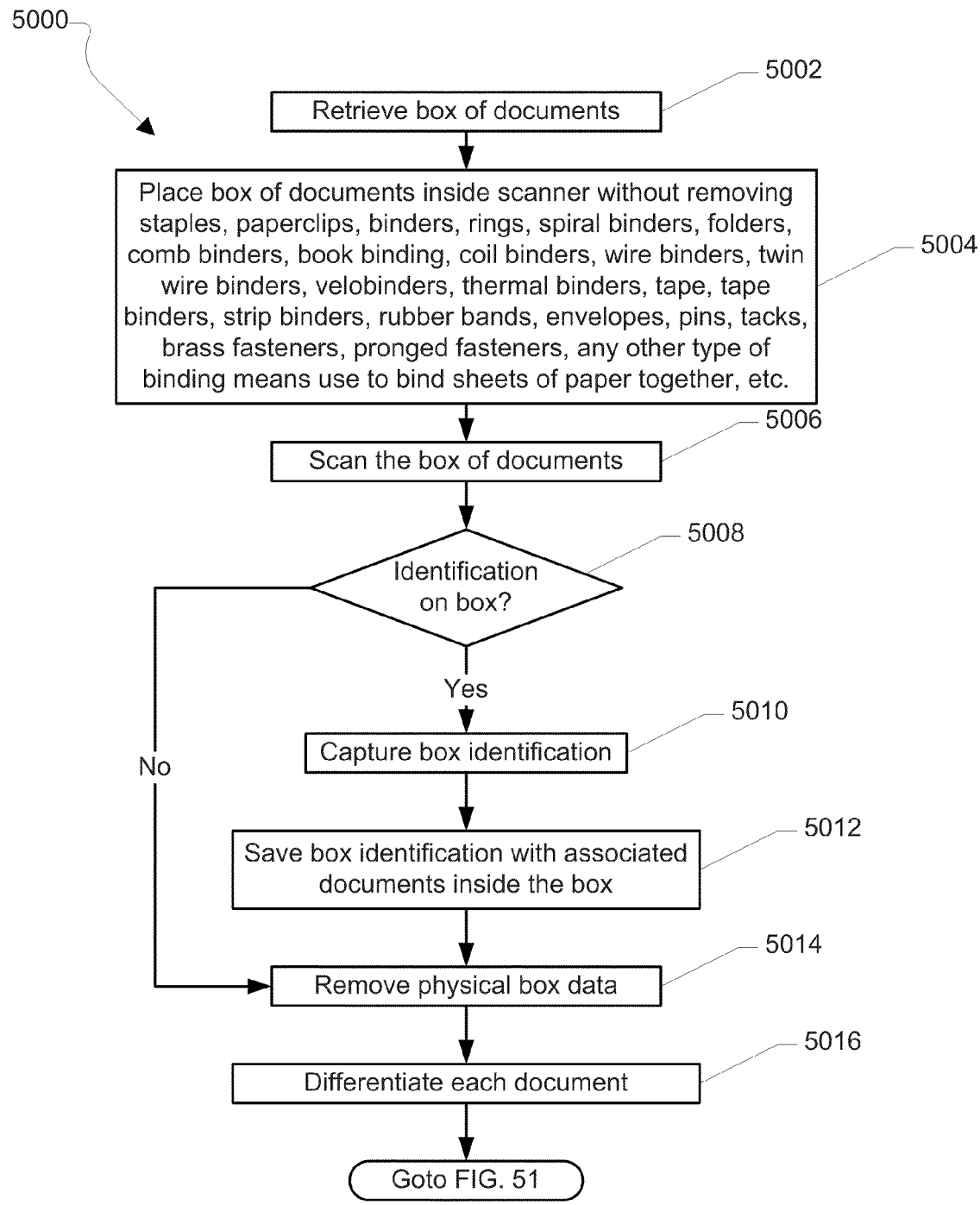
FIG. 50 is a flowchart representing a first portion of a first aspect of a method of volumetrically scanning boxed documents.
Figure 51:
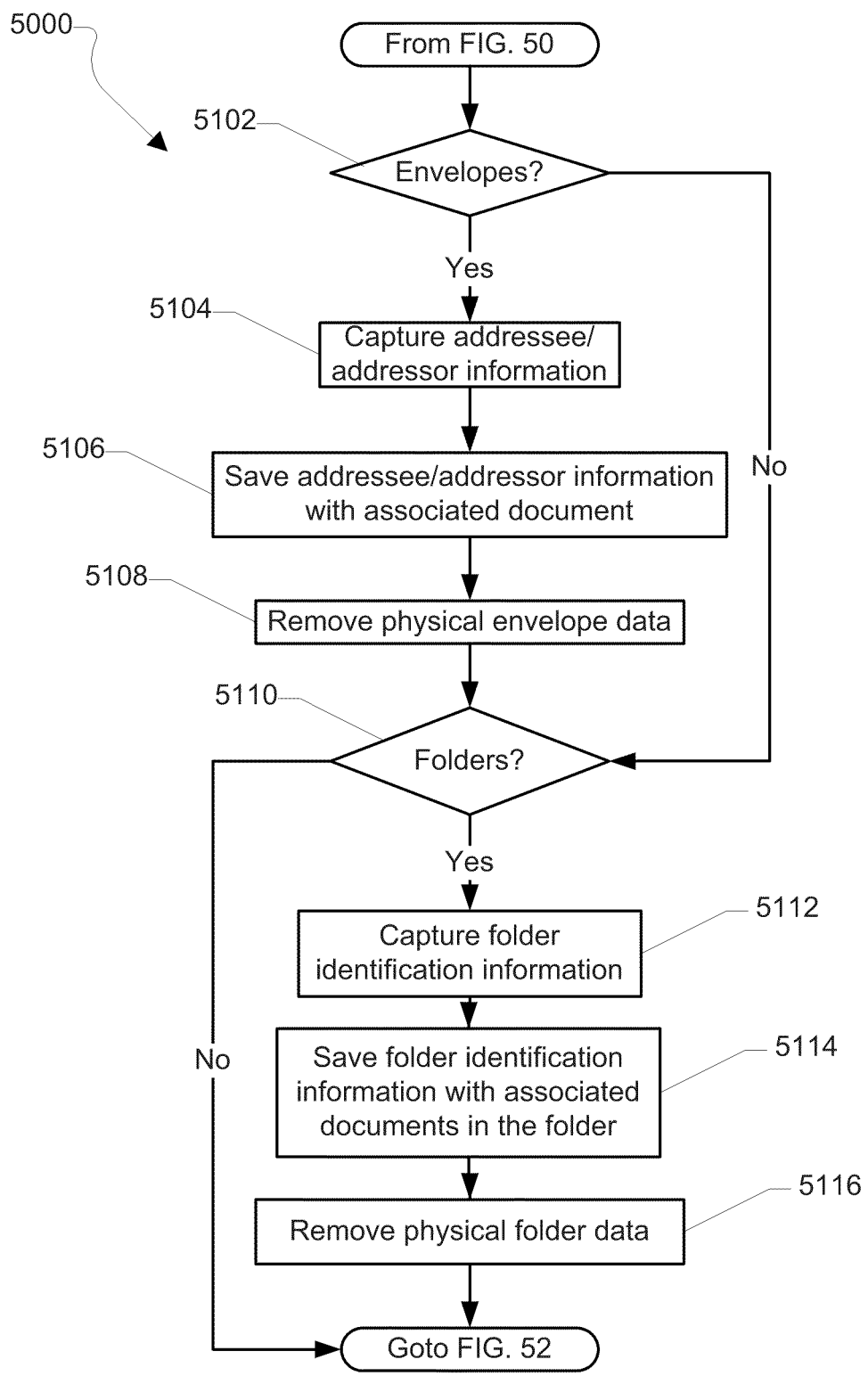
FIG. 51 is a flowchart representing a second portion of the first aspect of a method of volumetrically scanning boxed documents.

Referring now to FIG. 50 and FIG. 51, a first aspect of a method of volumetrically scanning boxed documents is shown and is generally designated 5000. Beginning at block 5002, a box of documents may be retrieved. At block 5004, the box of documents may be placed inside a scanner without removing staples, paperclips, binders, rings, spiral binders, folders, comb binders, book binding, coil binders, wire binders, twin wire binders, velobinders, thermal binders, tape, tape binders, strip binders, rubber bands, envelopes, pins, tacks, brass fasteners, pronged fasteners, any other type of binding means use to bind sheets of paper together, etc. The box of documents may be placed inside the scanner by a user. Alternatively, the box of documents may ride into the scanner on a conveyor belt.

Moving to block 5006, the box of documents may be scanned using MRI, X-Ray CT, T-Ray, or any combination thereof. At decision 5008, a processor may determine whether there is an identification on the box. If so, the method 5000 may proceed to block 5010 and the processor may capture the box identification. Then, at block 5012, the processor may save the box identification with the associated documents inside the box. The method 5000 may then proceed to block 5014 and continue as described.

Returning to decision 5008, if there is not an identification on the box, the method 5000 may move directly to block 5014 and the processor may remove the physical box data from the scan data. The physical box data is all data that represents the box in which the documents are stored. Moving to block 5016, the processor may differentiate each document within the box of documents. Next, the method 5000 may continue to decision 5102 of FIG. 51.

At decision 5102, the processor may determine whether the documents include any envelopes. If so, the method 5000 may continue to block 5104 and the processor may capture the addressee/addressor information. At block 5106, the processor may save the addressee/addressor information with the associated document. At block 5108, the processor may remove the physical envelope data. The physical envelope data is all data that represents the envelope in which the particular document is located. From block 5108, the method 5000 may move to decision 5110.

Returning to decision 5102, if the processor determines that the documents do not include any documents within envelopes, the method 5000 may move directly to decision 5110. At decision 5110, the processor may determine whether the documents include any folders. If so, the method 5000 may continue to block 5112 and the processor may capture the folder information. At block 5114, the processor may save the folder information with the associated document within the folder. At block 5116, the processor may remove the physical folder data. The physical folder data is all data that represents the folder in which the particular document is located. From block 5116, the method 5000 may move to block 5202 of FIG. 52.

Figure 52:
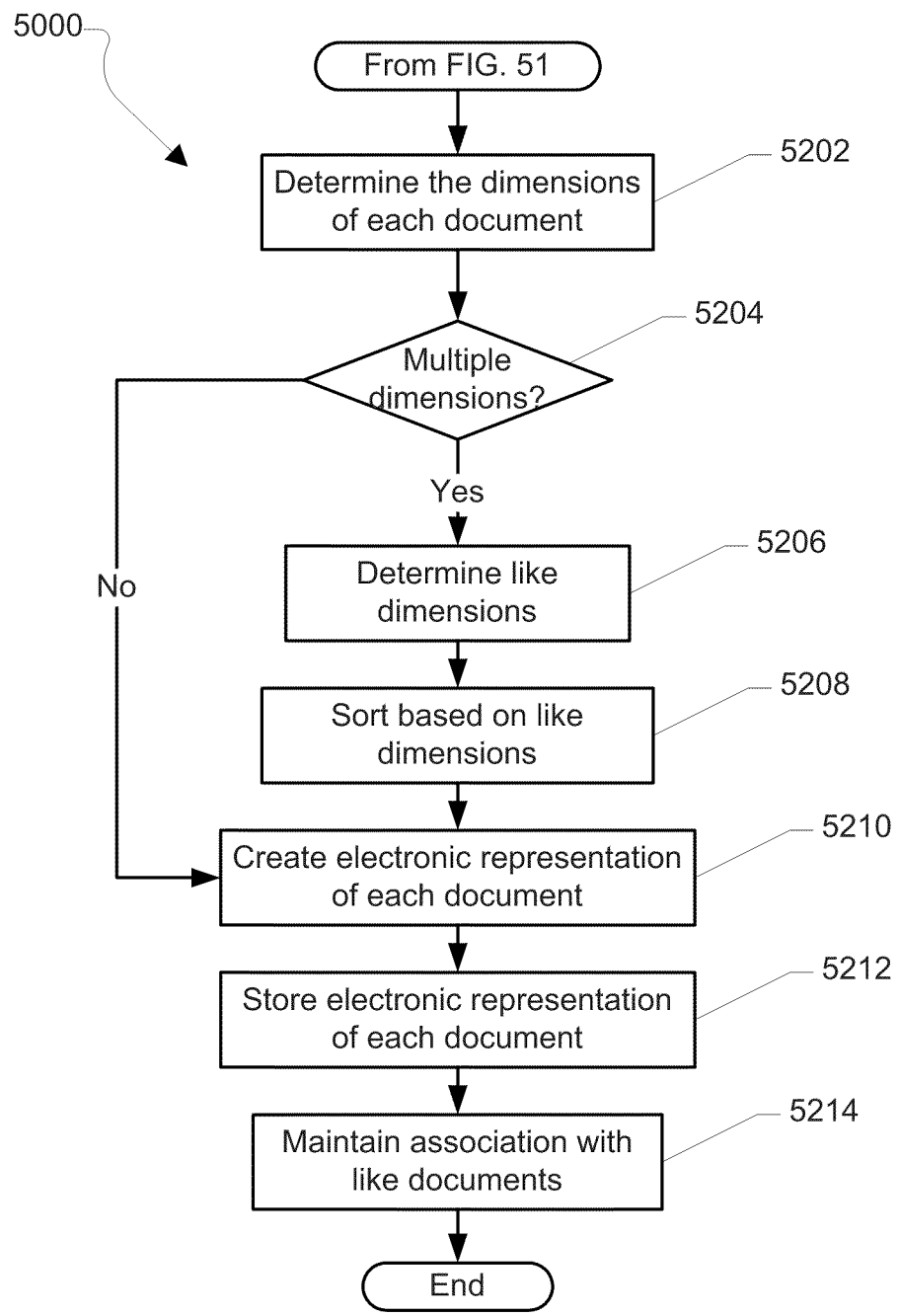
FIG. 52 is a flowchart representing a third portion of the first aspect of a method of volumetrically scanning boxed documents.

Returning to decision 5110, if the processor determines that the documents do not include any documents within folders, the method 5000 may move directly to block 5202 of FIG. 52.

At block 5202, the processor may determine the dimensions of each document. At decision 5204, the processor may determine whether the documents include documents of multiple dimensions, i.e., different sized documents. If so, the method 5000 may move to block 5206 and the processor may determine which documents have like dimensions. At block 5208, the processor may sort the documents based on the like dimensions. Thereafter, the method 5000 may move to block 5210 and continue as described herein.

Returning to decision 5204, if the processor determines that there are not documents of multiple dimensions, the method 5000 may move directly to block 5210 and the processor may create an electronic representation of each document. At block 5212, the processor may store an electronic representation of each document. Further, at block 5214, the processor may maintain the association with like documents based on sizes. Thereafter, the method may end.

Figure 53:
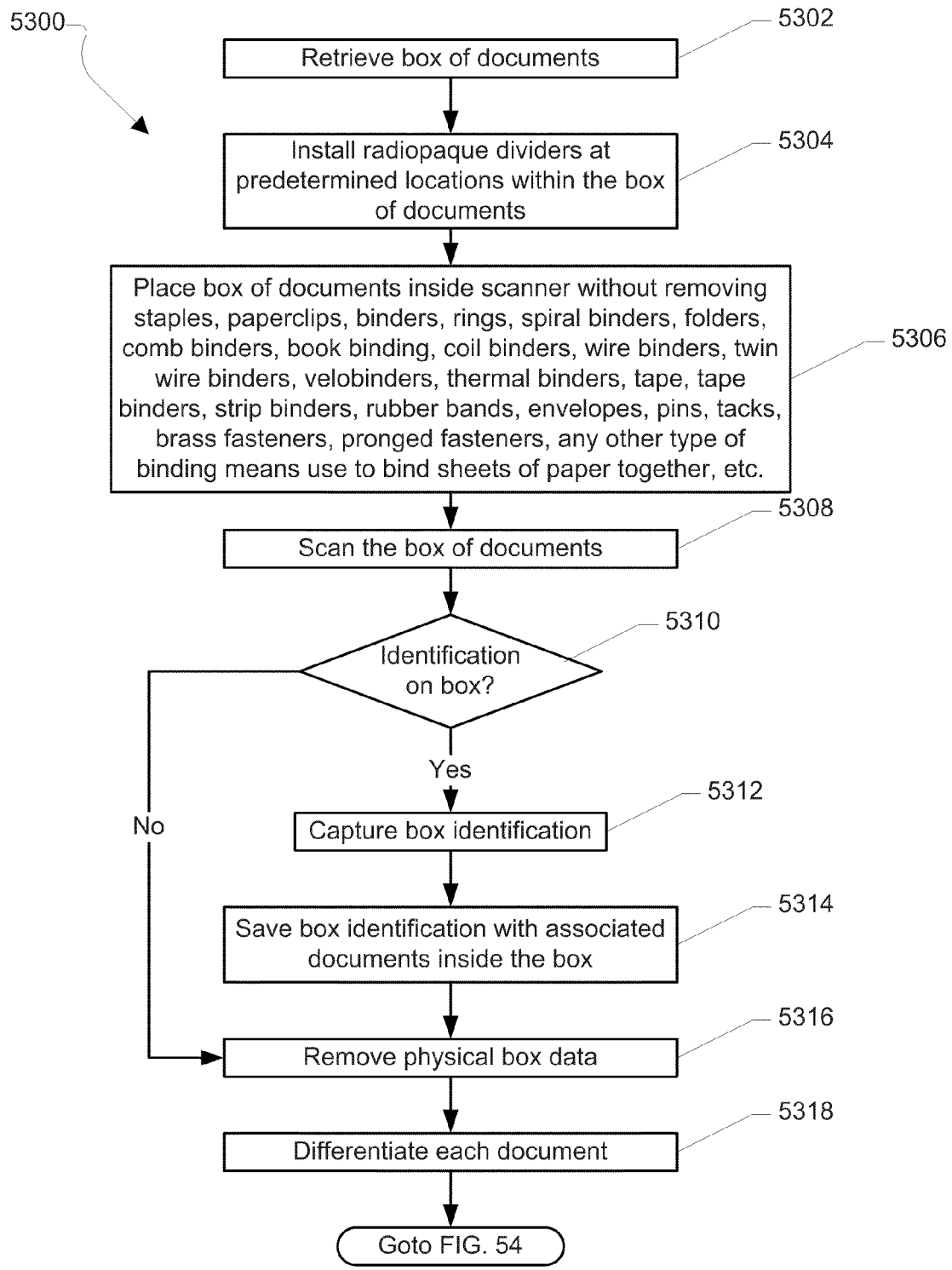
FIG. 53 is a flowchart representing a first portion of a second aspect of a method of volumetrically scanning boxed documents.
Figure 54:
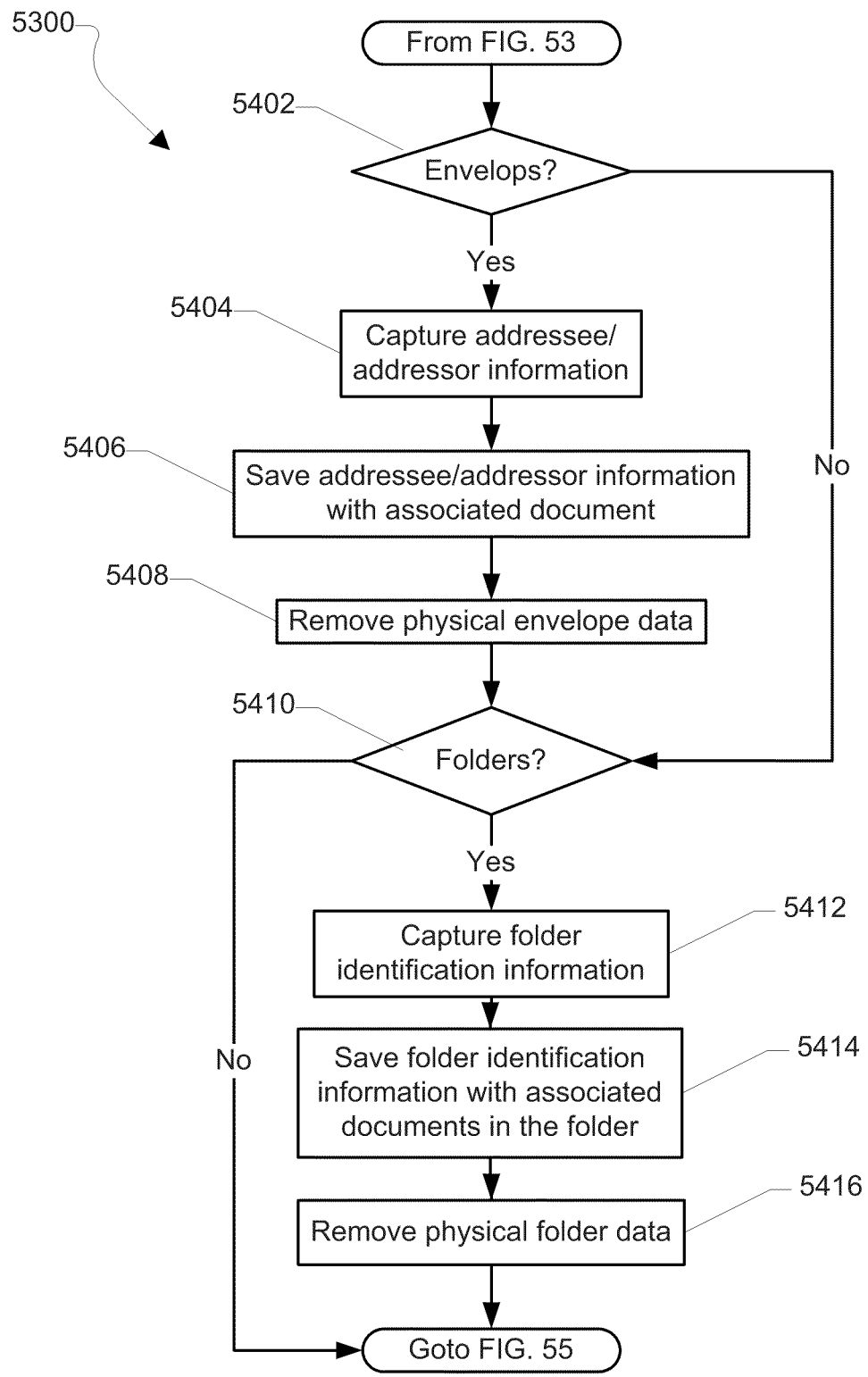
FIG. 54 is a flowchart representing a second portion of the second aspect of a method of volumetrically scanning boxed documents.

Referring to FIG. 53 and FIG. 54, a second aspect of a method of volumetrically scanning boxed documents is shown and is generally designated 5300. Beginning at block 5302, a box of documents may be retrieved. At block 5304, one or more radiopaque dividers may be installed within the box of documents at predetermined locations within the box of documents. At block 5306, the box of documents may be placed inside a scanner without removing staples, paperclips, binders, rings, spiral binders, folders, comb binders, book binding, coil binders, wire binders, twin wire binders, velobinders, thermal binders, tape, tape binders, strip binders, rubber bands, envelopes, pins, tacks, brass fasteners, pronged fasteners, any other type of binding means use to bind sheets of paper together, etc. The box of documents may be placed inside the scanner by a user. Alternatively, the box of documents may ride into the scanner on a conveyor belt.

Moving to block 5308, the box of documents may be scanned using MRI, X-Ray CT, T-Ray, or any combination thereof. At decision 5310, a processor may determine whether there is an identification on the box. If so, the method 5300 may proceed to block 5312 and the processor may capture the box identification. Then, at block 5314, the processor may save the box identification with the associated documents inside the box. The method 5300 may then proceed to block 5316 and continue as described.

Returning to decision 5310, if there is not an identification on the box, the method 5300 may move directly to block 5316 and the processor may remove the physical box data from the scan data. The physical box data is all data that represents the box in which the documents are stored. Moving to block 5318, the processor may differentiate each document within the box of documents. Next, the method 5300 may continue to decision 5402 of FIG. 54.

At decision 5402, the processor may determine whether the documents include any envelopes. If so, the method 5300 may continue to block 5404 and the processor may capture the addressee/addressor information. At block 5406, the processor may save the addressee/addressor information with the associated document. At block 5408, the processor may remove the physical envelope data. The physical envelope data is all data that represents the envelope in which the particular document is located. From block 5408, the method 5300 may move to decision 5410.

Returning to decision 5402, if the processor determines that the documents do not include any documents within envelopes, the method 5300 may move directly to decision 5410. At decision 5410, the processor may determine whether the documents include any folders. If so, the method 5300 may continue to block 5412 and the processor may capture the folder information. At block 5414, the processor may save the folder information with the associated document within the folder. At block 5416, the processor may remove the physical folder data. The physical folder data is all data that represents the folder in which the particular document is located. From block 5416, the method 5300 may move to block 5502 of FIG. 55.

Figure 55:
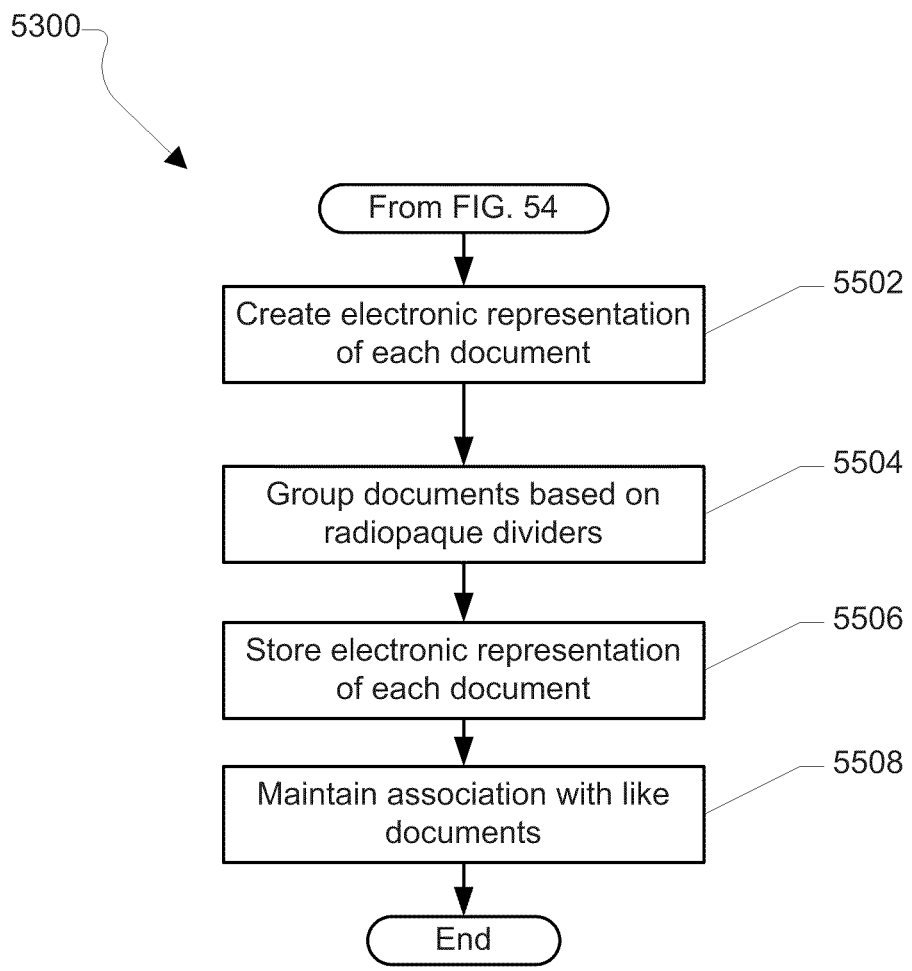
FIG. 55 is a flowchart representing a third portion of the second aspect of a method of volumetrically scanning boxed documents.

Returning to decision 5410, if the processor determines that the documents do not include any documents within folders, the method 5300 may move directly to block 5502 of FIG. 55.

At block 5502, the processor may create an electronic representation of each document. At block 5504, the processor may group, or otherwise sort, documents based on the radiopaque dividers, e.g., the locations of the radiopaque dividers. At block 5506, the processor may store an electronic representation of each document. Further, at block 5508, the processor may maintain the association with like documents based on the radiopaque divider groups. From block 5508, the method may end.

Figure 56:
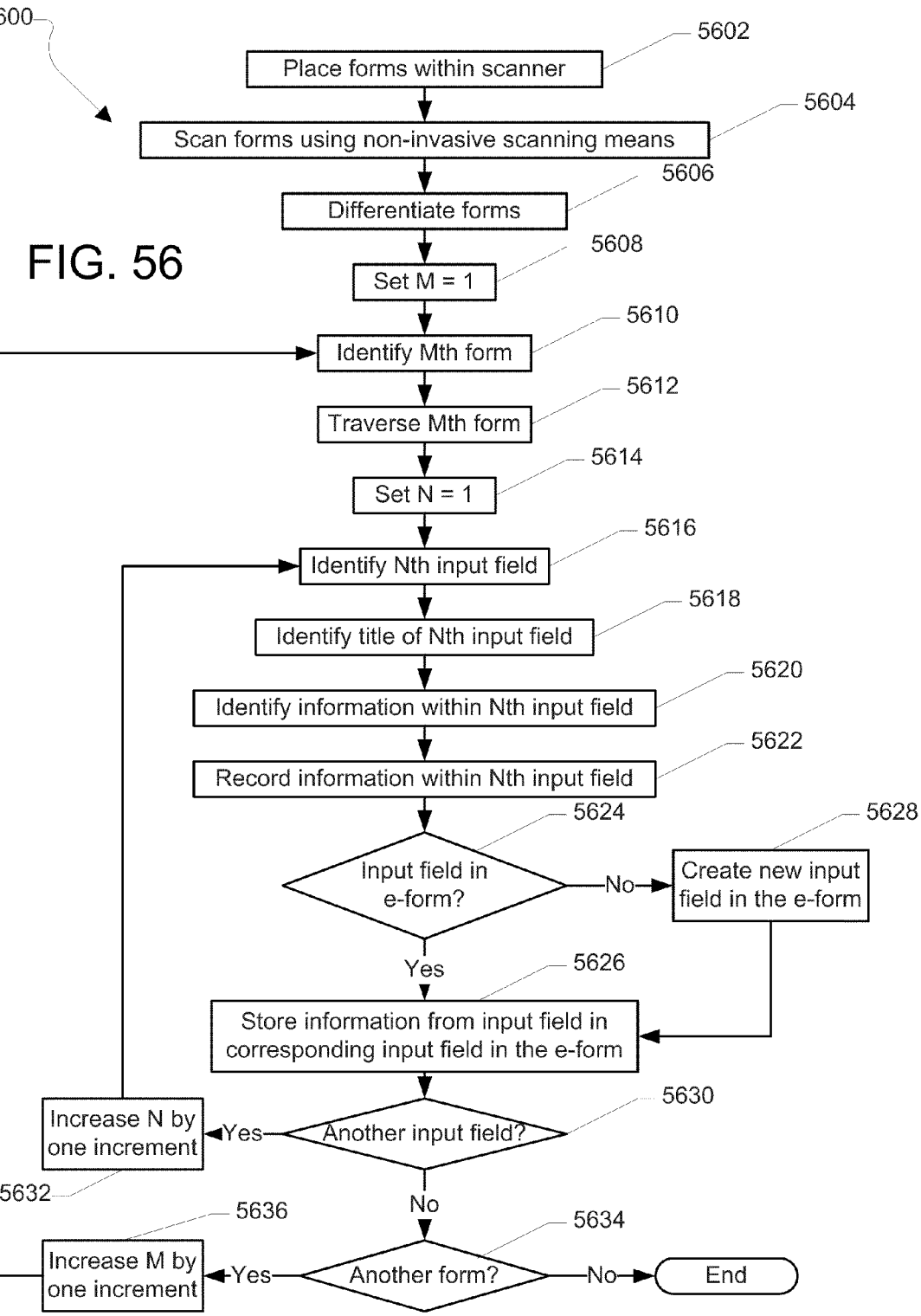
FIG. 56 is a flowchart representing a first aspect of a method of volumetrically scanning paper forms to e-forms.

FIG. 56 illustrates a first aspect of a method of volumetrically scanning paper forms to e-forms. The method is generally designated 5600 and begins at block 5602. At block 5602, one or more forms may be placed within a scanner. At block 5604, the forms may be scanned using a non-invasive scanning means, e.g., MRI, X-Ray CT, T-Ray, or a combination thereof.

Moving to block 5606, a processor may differentiate the forms. At block 5608, the processor may sent a counter, M, equal to one (1). At block 5610, the processor may identify the Mth form. Further, at block 5612, the processor may traverse the Mth form. At block 5614, the processor may set a counter, N, equal to one (1).

Proceeding to block 5616, the processor may identify an Nth input field. Then, at block 5618, the processor may identify a title of the Nth input field. At block 5620, the processor may identify the information within Nth input field. Moreover, at block 5622, the processor may record the information within Nth input field.

Moving to decision 5624, the processor may determine whether a corresponding input field exists in an electronic form (e-form). If so, the method 5600 may move to block 5626 and the processor may store the information from the input field in a corresponding input field in the e-form. Otherwise, at decision 5624, if a corresponding input field does not exist in the e-form, the method 5600 may proceed to block 5628 and the processor may create a new input field in the e-form. Then, at block 5626, the processor may store the information from the input field in the corresponding field in the e-form.

From block 5626, the method 5600 may move to decision 5630 and the processor may determine whether there is another input field within the Mth document. If so, the method 5600 may move to block 5632 and the processor may increase N by one (1) increment. Thereafter, the method 5600 may return to block 5616 and continue as described herein. At decision 5630, if there is not another input field, the method 5600 may proceed to decision 5634 and the processor may determine whether there is another form. If not, the method may end. Otherwise, if there is another form, the method may continue to block 5636 and the processor may increase M by one (1) increment. Thereafter, the method 5600 may return to block 5610 and the method 5600 may continue as described herein.

Figure 57:
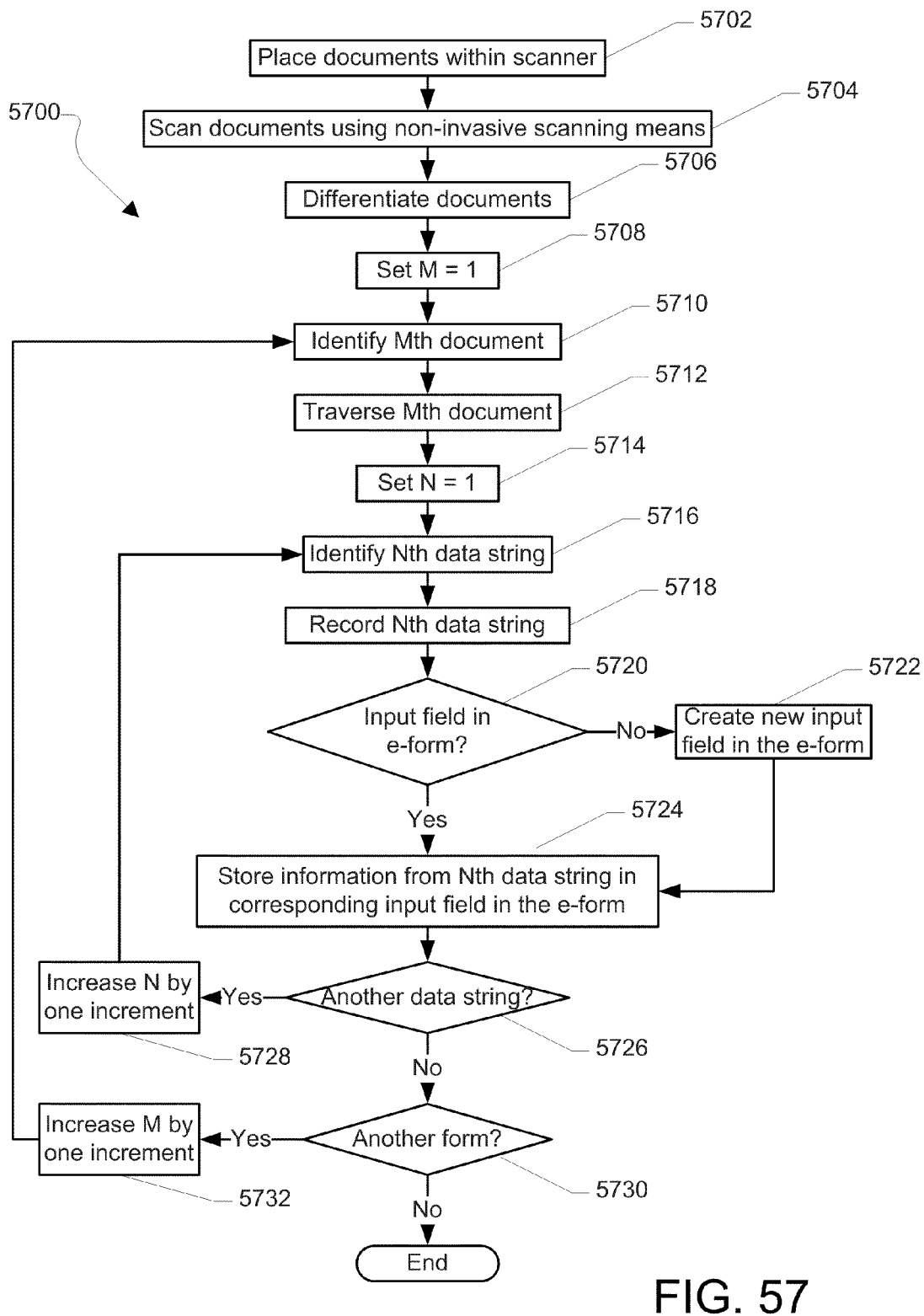
FIG. 57 is a flowchart representing a second aspect of a method of volumetrically scanning paper forms to e-forms.

FIG. 57 illustrates a second aspect of a method of volumetrically scanning paper forms to e-forms. The method is generally designated 5700. Commencing at block 5702, one or more forms may be placed within a scanner. At block 5704, the forms may be scanned using a non-invasive scanning means, e.g., MRI, X-Ray CT, T-Ray, or a combination thereof.

Moving to block 5706, a processor may differentiate the forms. At block 5708, the processor may sent a counter, M, equal to one (1). At block 5710, the processor may identify the Mth form. Further, at block 5712, the processor may traverse the Mth form. At block 5714, the processor may set a counter, N, equal to one (1).

Proceeding to block 5716, the processor may identify an Nth data string. Then, at block 5718, the processor may record the Nth data. At decision 5720, the processor may determine whether a corresponding input field exists in an e-form. If so, the method 5700 may move to block 5722 and the processor may store the information from the Nth data string in a corresponding input field in the e-form. Otherwise, at decision 5720, if a corresponding input field does not exist in the e-form, the method 5700 may proceed to block 5728 and the processor may create a new input field in the e-form. Then, at block 5722, the processor may store the information from the Nth data string in the corresponding field in the e-form.

From block 5722, the method 5700 may move to decision 5726 and the processor may determine whether there is another data string within the Mth document. If so, the method 5700 may move to block 5728 and the processor may increase N by one (1) increment. Thereafter, the method 5700 may return to block 5716 and continue as described herein. At decision 5726, if there is not another data string, the method 5700 may proceed to decision 5730 and the processor may determine whether there is another form. If not, the method may end. Otherwise, if there is another form, the method may continue to block 5732 and the processor may increase M by one (1) increment. Thereafter, the method 5700 may return to block 5710 and the method 5700 may continue as described herein.

Figure 58:
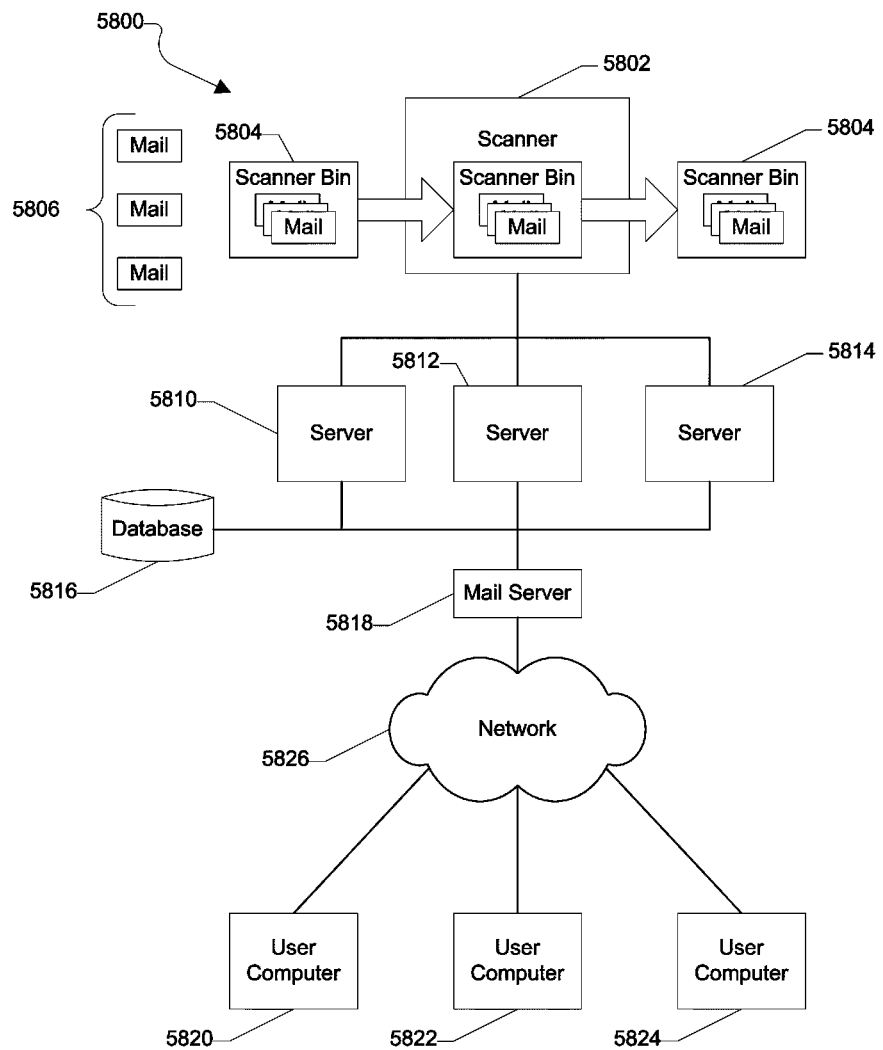
FIG. 58 is a block diagram representing a system of volumetrically scanning paper mail, converting the paper mail to electronic mail, and delivering the electronic mail.

FIG. 58 illustrates a system 5800 that may be used to volumetrically scanning paper mail, convert the paper mail to electronic mail, and deliver the electronic mail to one or more user computers. As shown, the system 5800 may include a volumetric scanner 5802, e.g., an MRI scanner, an X-ray CT scanner, a T-ray scanner, some other volumetric scanner, or a combination thereof. The scanner 5802 may include a scanner bin 5804 that may be placed within the scanner, e.g., manually or automatically. One or more pieces of mail 5806 may be placed within the scanner 5802 and volumetrically scanned as described herein.

FIG. 58 shows that the system 5800 may include a plurality of servers 5810, 5812, 5814 connected to the scanner 5802. The servers 5810, 5812, 5814 may be used to process 3D data received from the scanner 5802. The servers 5810, 5812, 5814 may execute one or more of the methods described herein to process the 3D data received from the scanner 5802. As shown, a database 5816 may be connected to the servers 5810, 5812, 5814.

As shown, a mail server 5818 may also be connected to the plurality of servers 5810, 5812, 5814. Once the servers 5810, 5812, 5814 have processed the 3D data received from the scanner 5802, the processed data may be delivered to the mail server 5818, e.g., in the format of electronic mail converted from paper mail. The mail server 5818 may deliver the electronic mail to one or more user computers 5820, 5822, 5824 via a network 5820.

Figure 59:
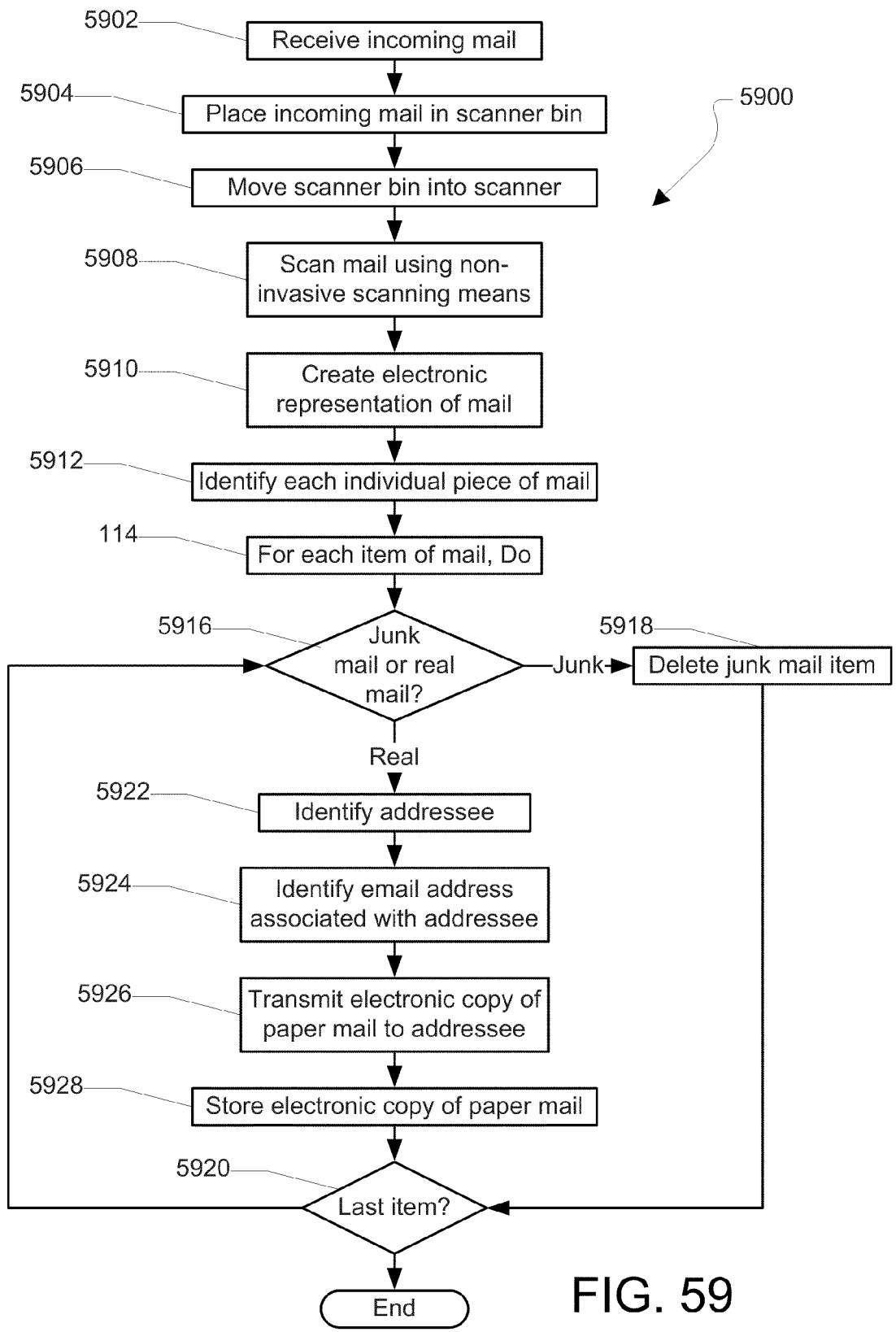
FIG. 59 is a flowchart representing a method of volumetrically scanning paper mail, converting the paper mail to electronic mail, and delivering the electronic mail.

Referring now to FIG. 59, a method of volumetrically scanning paper mail, converting the paper mail to electronic mail, and delivering the electronic mail is shown and is generally designated 5900. At block 5902, incoming mail may be received. At block 5904, the incoming mail may be placed in a scanner bin. Next, at block 5906, the scanner bin may be moved into a scanner, e.g., an MRI scanner, an X-ray CT scanner, a T-ray scanner, or a combination thereof. The scanner bin may be manually moved or automatically moved.

Moving to block 5908, the mail may be scanned using a non-invasive scanning means. At block 5910, a processor may create an electronic representation of each piece of the scanned mail. Then, at block 5912, the processor may identify each individual piece of mail.

At block 5914, a do loop may be entered in which for each item, or piece, of mail the following nested steps may be performed. At decision 5916, the processor may determine whether a current item of mail is junk mail or real mail. This determination may be made based on the return address, other markings on the envelope, keywords within the content of the item within the envelope, or a combination thereof.

If the current mail item is junk mail, the method 5900 may proceed to block 5918 and the data pertaining to the scanned junk mail item may be deleted. Then, the method 5900 may move to decision 5920 and the processor may determine whether the current item is a last item. If so, the method 5900 may end. Otherwise, the method 5900 may return to decision 5914 and the method 5900 may continue as described herein.

Returning to decision 5914, if the current mail item is determined to be real mail, the method 5900 may move to block 5922 and the processor may identify the addressee on the mail item. At block 5924, the processor may identify an email address associated with addressee. Next, at block 5926, the processor may transmit an electronic copy of the paper mail item to the addressee. At block 5928, the processor may store an electronic copy of the paper mail in a database or other storage device. Then, the method 5900 may proceed to decision 5920 and the method may continue as described herein.

Figure 60:
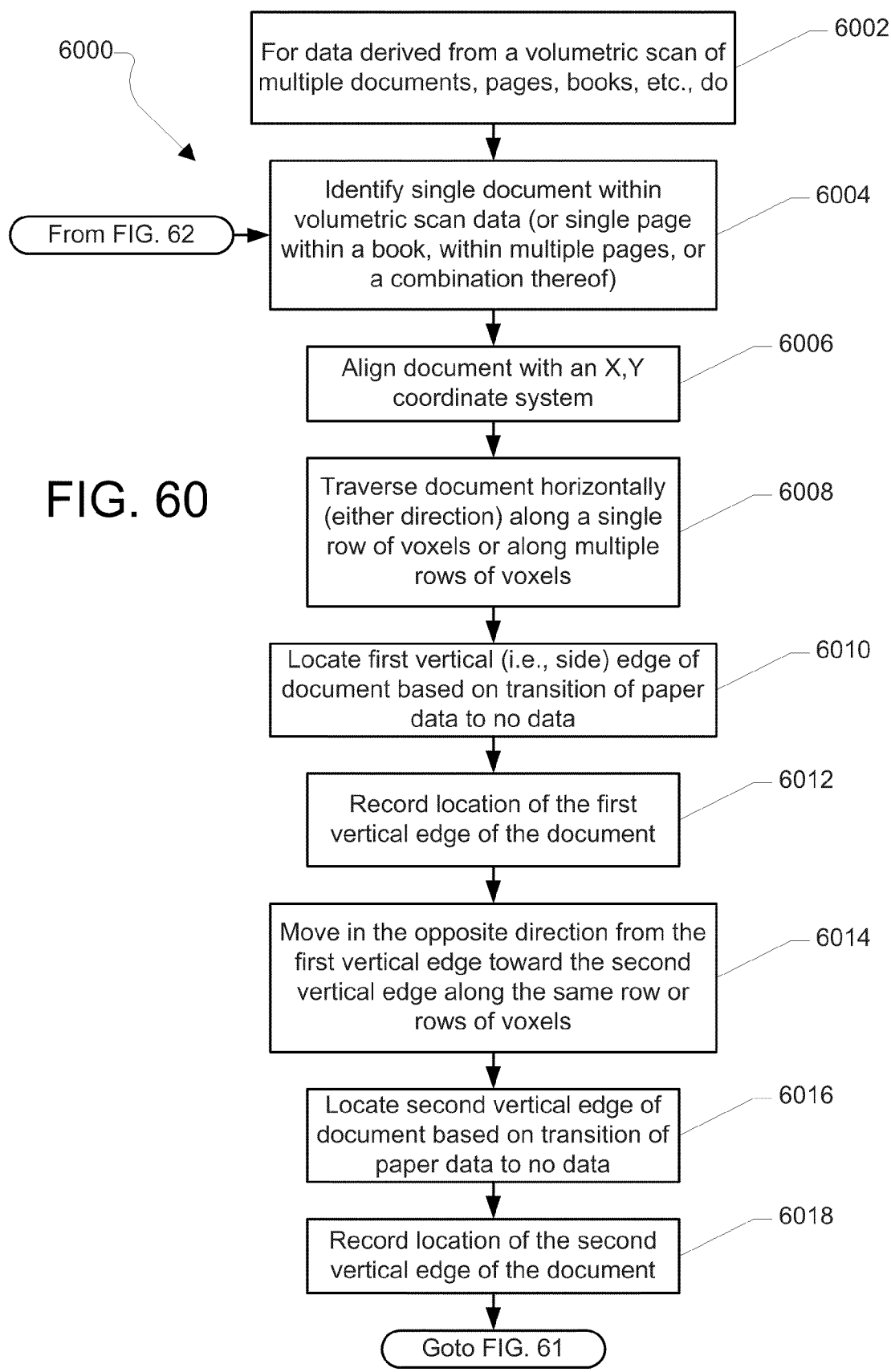
FIG. 60 is a flowchart representing a first portion of a method of determining dimensions of documents within data derived from a volumetric scan of the documents and sorting the documents based on the dimensions.
Figure 61:
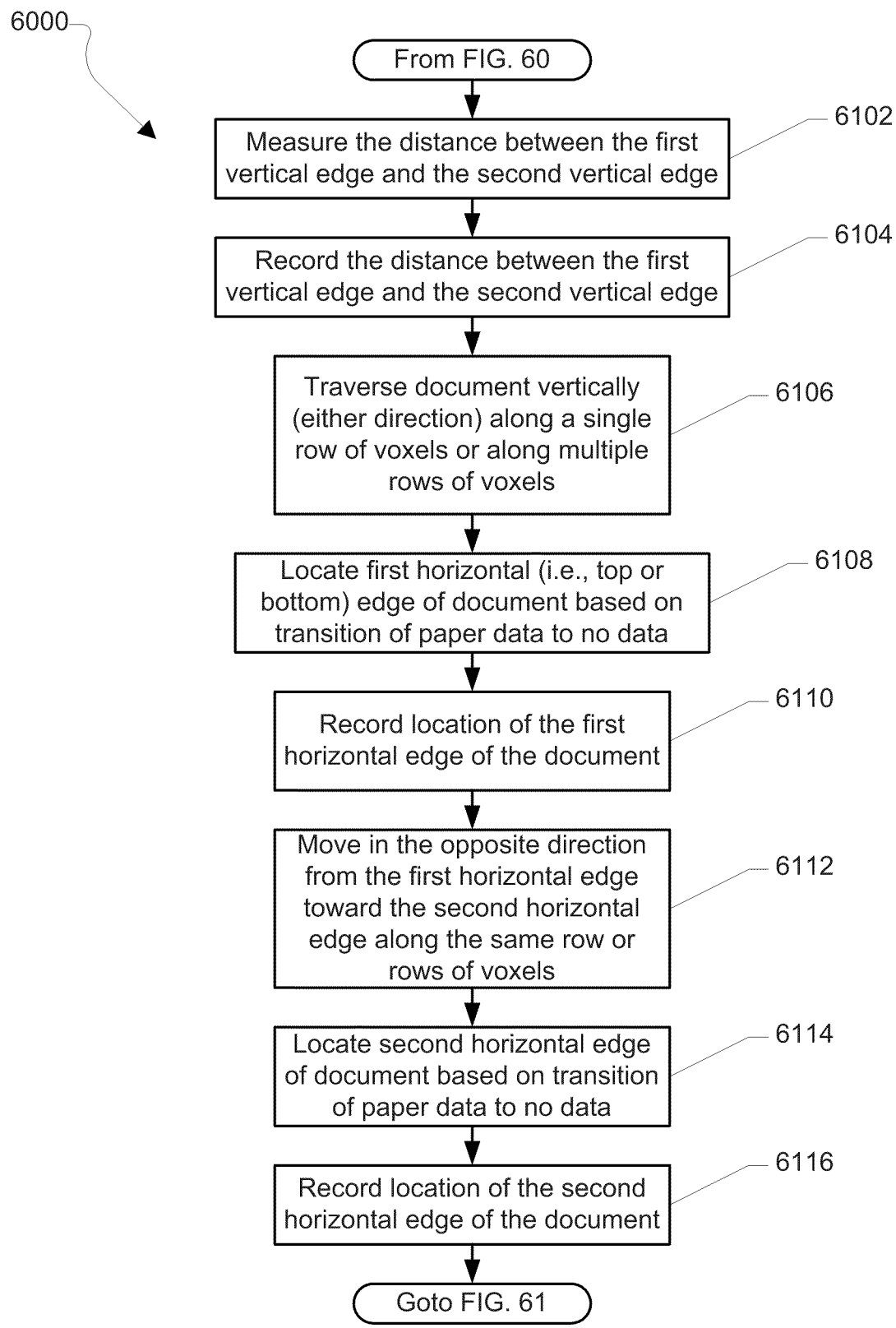
FIG. 61 is a flowchart representing a second portion of a method of determining dimensions of documents within data derived from a volumetric scan of the documents and sorting the documents based on the dimensions.
Figure 62:
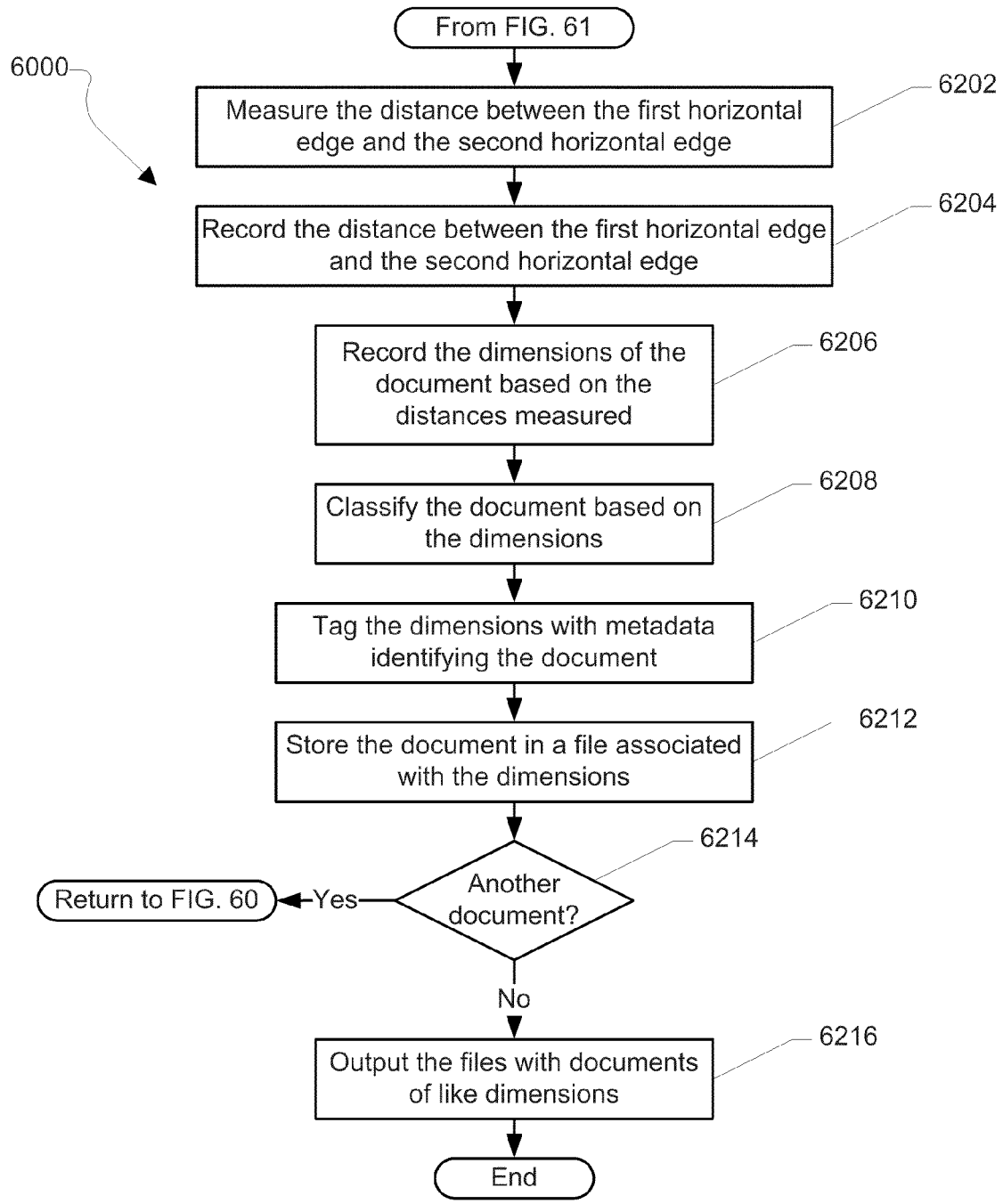
FIG. 62 is a flowchart representing yet a third portion of a method of determining dimensions of documents within data derived from a volumetric scan of the documents and sorting the documents based on the dimensions.

FIG. 60 through FIG. 62 illustrate a method of determining dimensions of documents within data derived from a volumetric scan of the documents and sorting the documents based on those dimensions. The method is generally designated 6000.

Beginning at block 6002, a do loop may be entered in which for data derived from a volumetric scan of multiple documents, pages, books, etc., the following steps may be performed. At block 6004, a processor may identify a single document within the volumetric scan data (or a single page within a book, within multiple pages, or a combination thereof). At block 6006, the processor may align a document with an X,Y coordinate system.

Moving to block 6008, the processor may traverse the document horizontally, in either direction, along a single row of voxels or along multiple rows of voxels. At block 6010, the processor may locate a first vertical, i.e., side, edge of document based on a transition of paper data to no data. At block 6012, the processor may record a location of the first vertical edge of the document.

Proceeding to block 6014, the processor may move in the opposite direction from the first vertical edge toward the second vertical edge along the same row or rows of voxels. At block 6016, the processor may locate a second vertical edge of the document based on a transition of paper data to no data. Next, at block 6018, the processor may record a location of the second vertical edge of the document. Thereafter, the method 6000 may proceed to block 6102 of FIG. 61.

At block 6102, the processor may measure the distance between the first vertical edge and the second vertical edge. Then, at block 6104, the processor may record the distance between the first vertical edge and the second vertical edge. Moving to block 6106, the processor may traverse the document vertically, in either direction, along a single row of voxels or along multiple rows of voxels. At block 6108, the processor may locate a first horizontal, i.e., top or bottom, edge of document based on a transition of paper data to no data. Further, at block 6110, the processor may record a location of the first horizontal edge of the document. Then, at block 6112, the processor may move in the opposite direction from the first horizontal edge toward the second horizontal edge along the same row or rows of voxels.

Continuing to block 6114, the processor may locate a second horizontal edge of the document based on a transition of paper data to no data. At block 6116, the processor may record a location of the second horizontal edge of the document. Thereafter, the method 6000 may proceed to block 6202 of FIG. 62.

At block 6202, the processor may measure the distance between the first horizontal edge and the second horizontal edge. Next, at block 6204, the processor may record the distance between the first horizontal edge and the second horizontal edge. At block 6206, the processor may record the dimensions of the document based on the distances measured herein.

Moving to block 6208, the processor may classify the document based on the dimensions determined herein. At block 6210, the processor may tag the dimensions with metadata identifying the document. Further, at block 6212, the processor may store the document in a file associated with the dimensions. Then, at decision 6214, the processor may determine whether there is another document. If so, the method 6000 may return to block 6004 of FIG. 60. Otherwise, if there is not another document, the method 6000 may proceed to block 6216 and the processor may output the files with documents of like dimensions. Then, the method 6000 may end.

Figure 64:
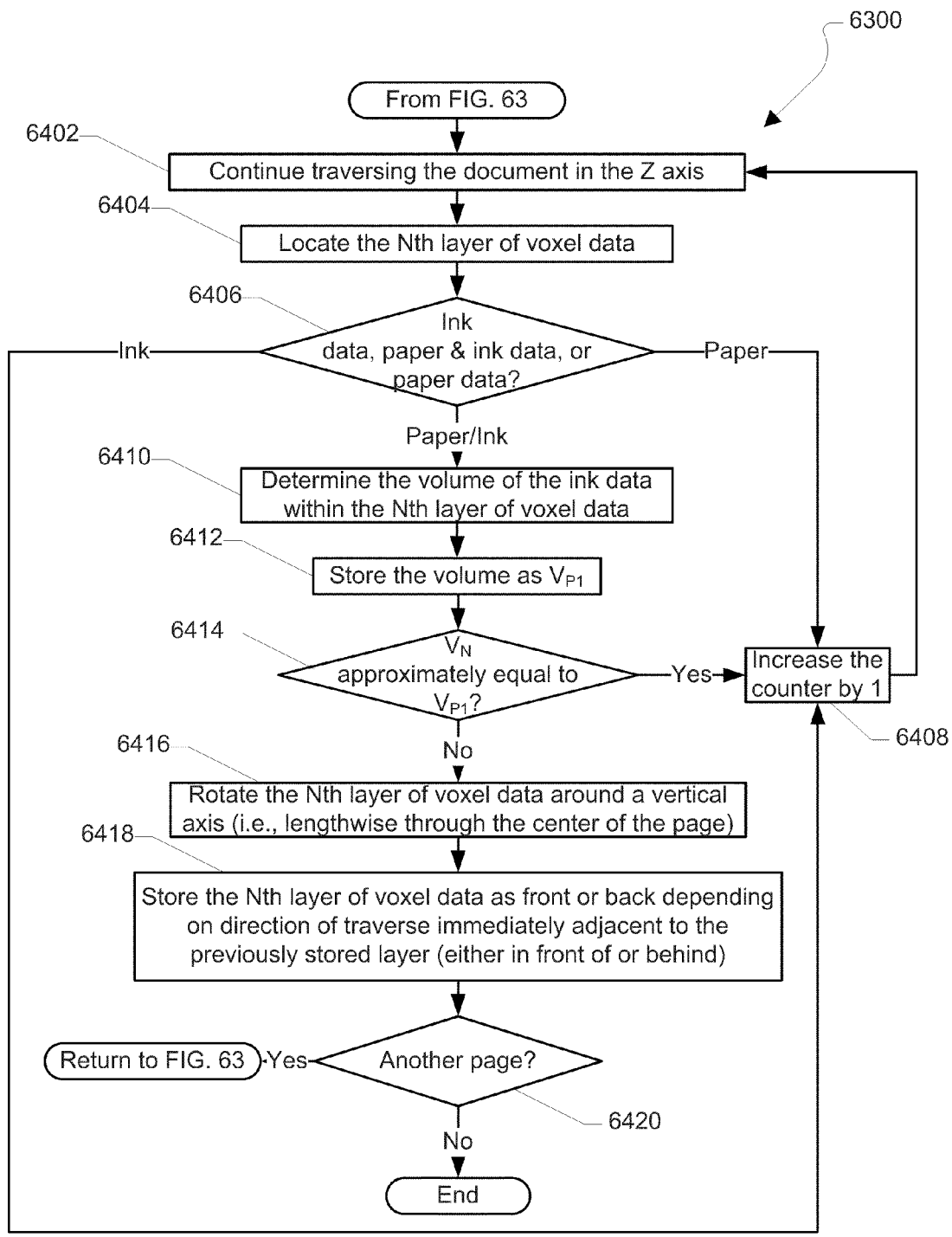
FIG. 64 is a flowchart representing a second portion of a method of processing double sided page data derived from a volumetric scan of one or more double sided pages.

Referring to FIG. 64, a method of processing double-sided page data derived from a volumetric scan of one or more double-sided pages is shown and is generally designated 6300. Beginning at block 6302, a do loop may be entered in which for volumetric scan data derived from a volumetric scan of multiple documents, pages, books, etc., the following steps may be performed.

At block 6304, a processor may align volumetric scan data with a coordinate system, e.g., an X,Y,Z system, such that the length and width of the voxel data is aligned with an X axis and a Y axis. At block 6306, the processor may identify a page within volumetric scan data, e.g., a first page. Then, at block 6308, the processor may traverse the document along a Z axis in either direction, i.e., from the top face to the bottom face or from the bottom face to the top face.

Moving to block 6310, the processor may set a counter, N, equal to one (1). At block 6312, the processor may locate the Nth layer of voxel data. Further, at decision 6314, the processor determine whether the Nth layer of voxel data includes ink data, paper and ink data, or paper data. If the Nth layer of voxel data includes ink data only, the method 6300 may move to block 6316 and the processor may store the Nth layer of voxel data as a front or back, depending on the direction of traverse. Thereafter, the method 6300 may move to block 6318 and the processor may increase the counter, N, by one (1). The method 6300 may then proceed to block 6402 of FIG. 64.

Returning to decision 6314, if the Nth layer of voxel data is paper and ink data, the method 6300 may move to block 6320 and the processor may determine the volume of the ink data within the Nth layer of voxel data. At block 6322, the processor may store the volume as $V_{P1}$. Thereafter, the method 6300 may proceed to block 6318 and continue as described herein. Returning to decision 6314, if the Nth layer of voxel data is paper data only, the method 6300 may move to block 6324 and the processor may store the Nth layer of voxel data as a blank page. The method 6300 may then proceed to block 6318 and continue as described.

From block 6318, the method 6300 may move to block 6402 of FIG. 64. At block 6402, the processor may continue traversing the document in the Z axis. At block 6404, the processor may locate the Nth layer of voxel data. Then, at decision 6406, the processor may determine whether the Nth layer of voxel data includes ink data, paper and ink data, or paper data. If the Nth layer of voxel data is ink data, the method 6300 may proceed to block 6408 and the processor may increase the counter, N, by one (1). The method 6300 may then return to block 6402 and continue as described herein.

Returning to decision 6406, if the Nth layer of voxel data is paper data, the method 6300 may proceed to block 6408 and the method 6300 may continue as described herein.

Again, returning to decision 6406 if the Nth layer of voxel data is ink and paper data, the method 6300 may continue to block 6410 and the processor may determine the volume of the ink data within the Nth layer of voxel data. At block 6412, the processor may store the volume as $V_N$. Moving to decision 6414, the processor may perform a comparison to determine whether $V_N$ is approximately equal to $V_{P1}$. If so, the method 6300 may continue to block 6408 and the method 6300 may continue as described herein. If not, the method 6300 may proceed to block 6416 and the processor may rotate the Nth layer of voxel data around a vertical axis, i.e., lengthwise through the center of the page so that all data on a particular pages faces a same direction. Then, at block 6418, the processor may store the Nth layer of voxel data as front or back depending on direction of traverse immediately adjacent to the previously stored layer, either in front of or behind.

Figure 63:
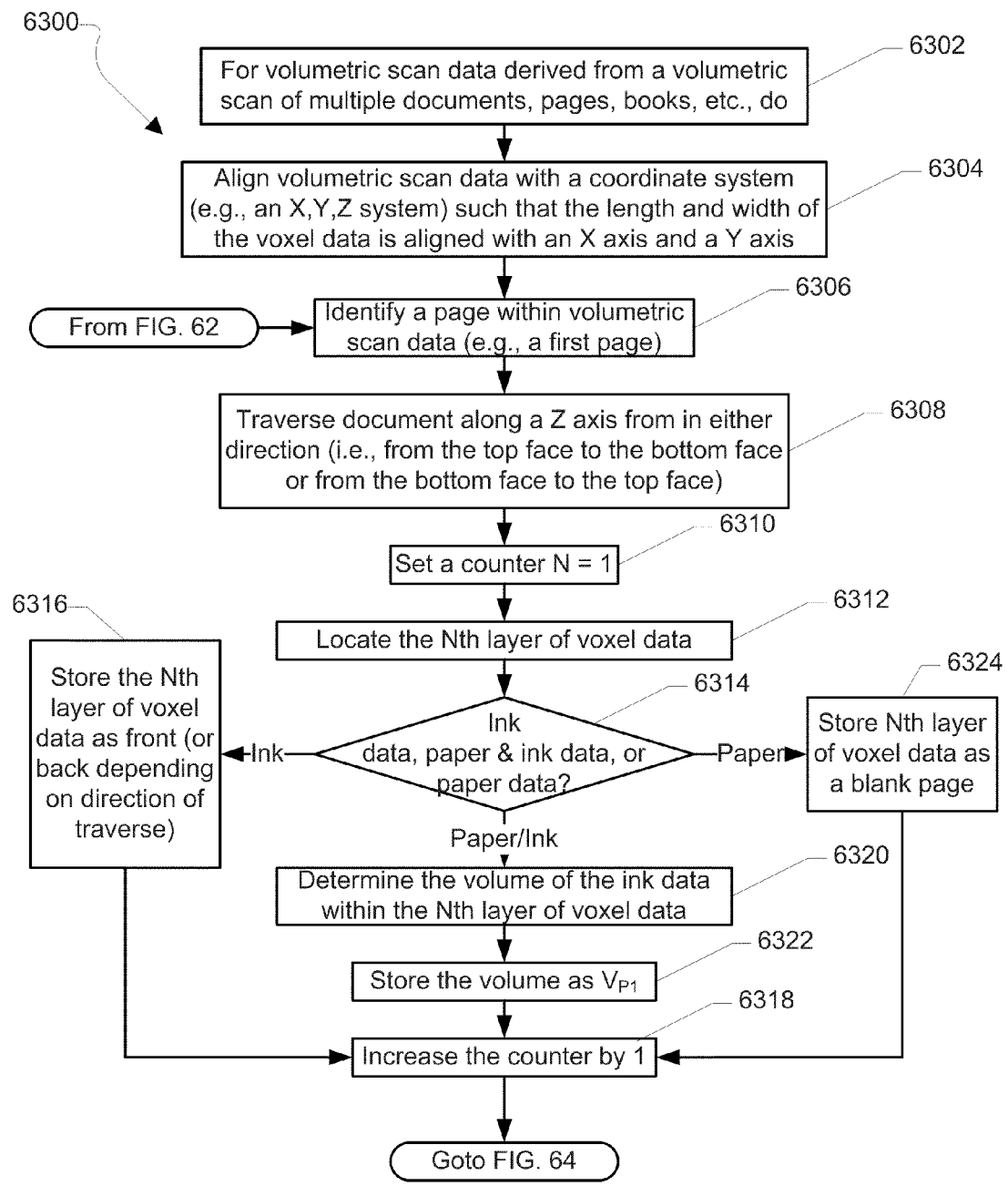
FIG. 63 is a flowchart representing a first portion of a method of processing double sided page data derived from a volumetric scan of one or more double sided pages.

Moving to decision 6420, the processor may determine whether there is another page. If so, the method may return, to block 6306 of FIG. 63 and the method 6300 may continue as described. Otherwise, the method 6300 may end.

Figure 65:
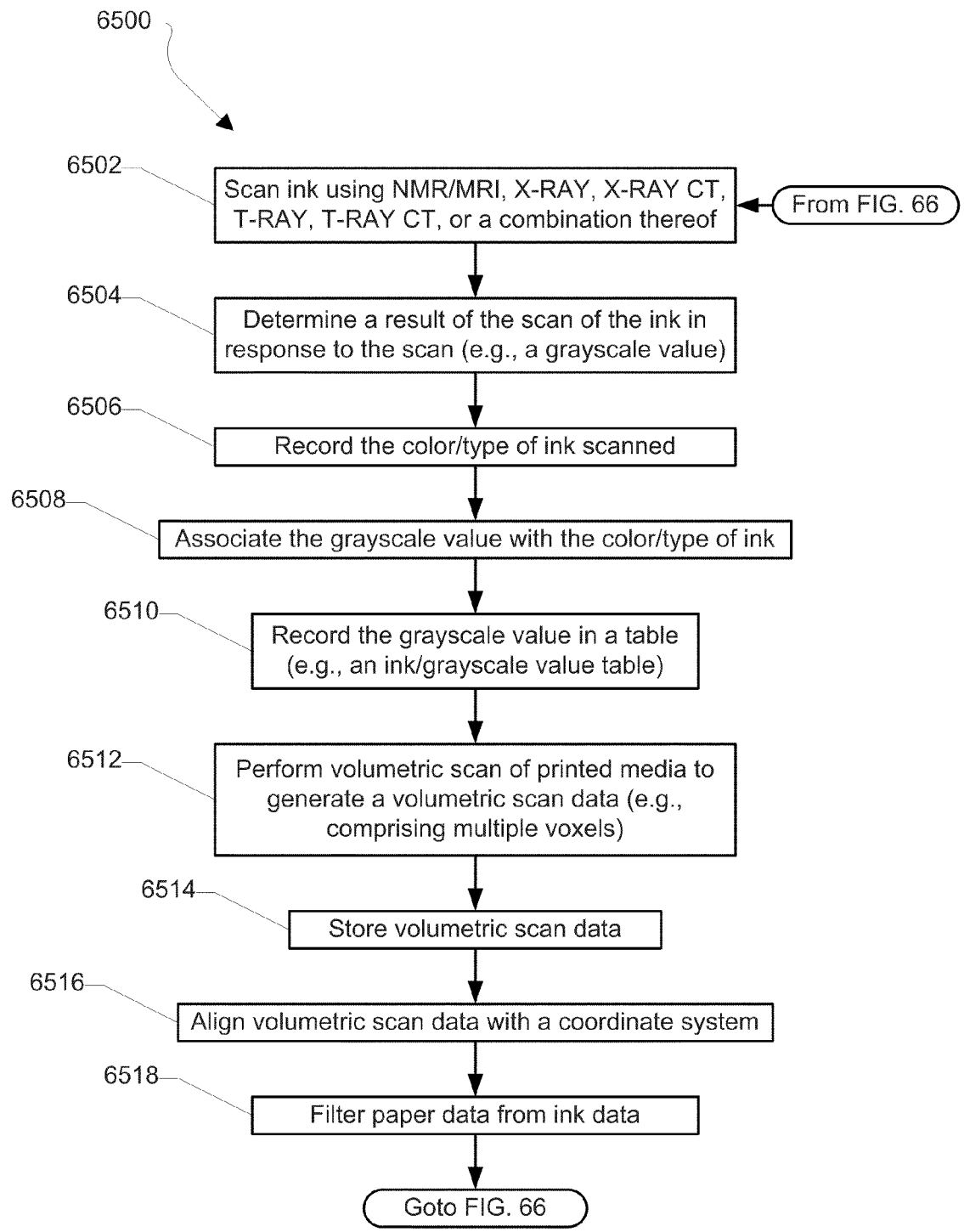
FIG. 65 is a flowchart representing a first portion of a method of processing color data derived from a volumetric scan of one or more documents having color images or color inks.
Figure 66:
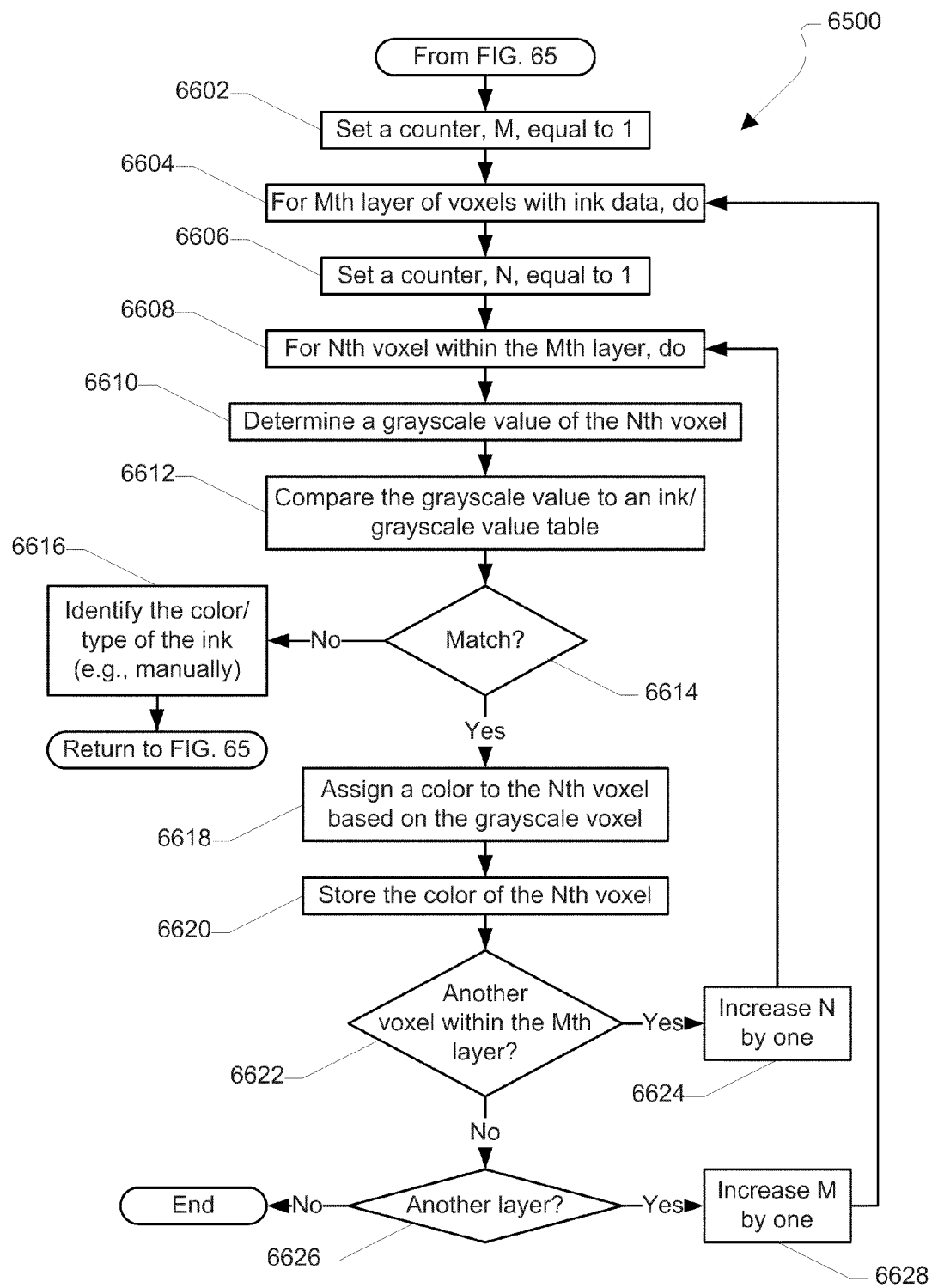
FIG. 66 is a flowchart representing a second portion of a method of processing color data derived from a volumetric scan of one or more documents having color images or color inks.
Figure 67:
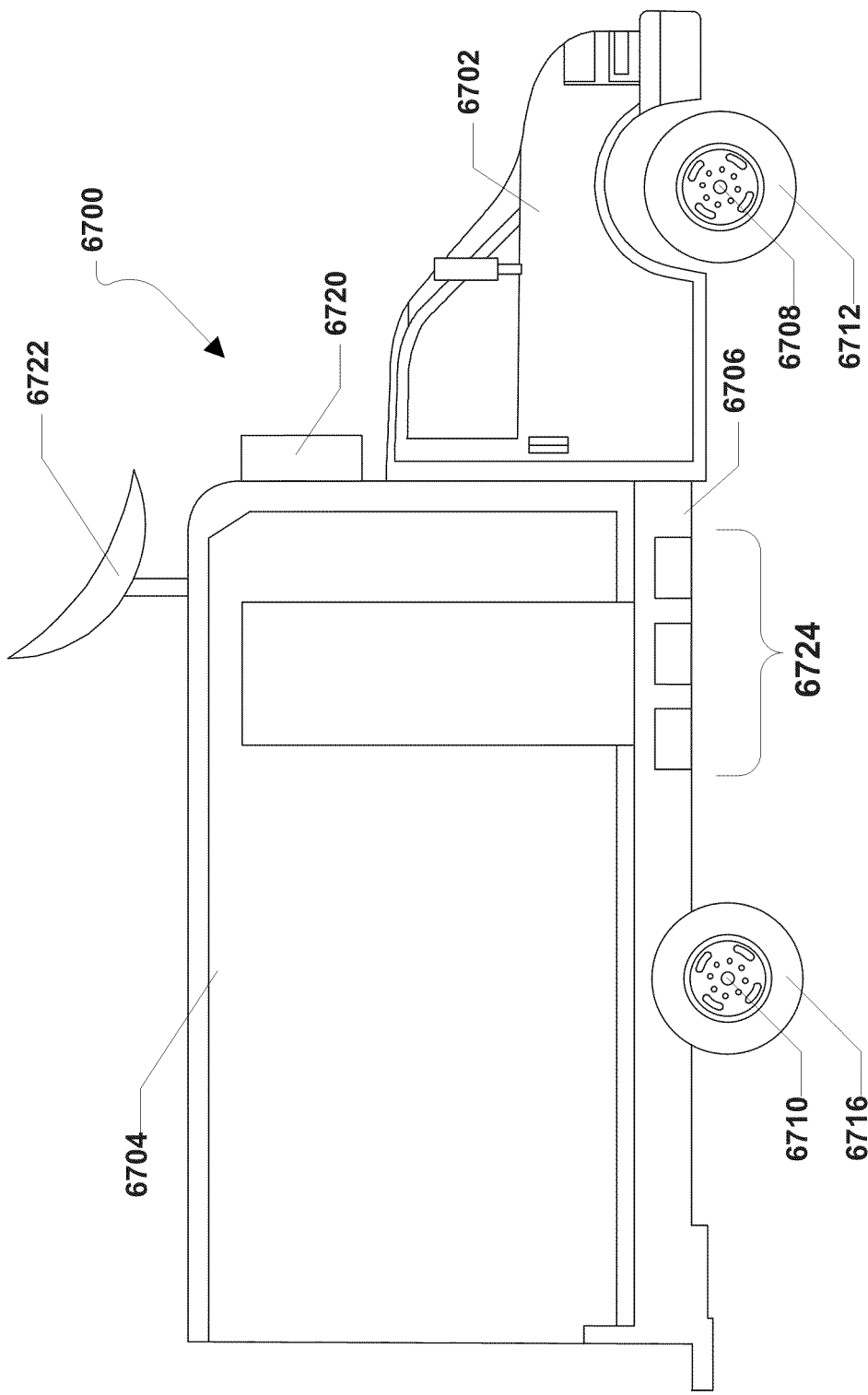
FIG. 67 is a first side plan view of a mobile scanner.
Figure 68:
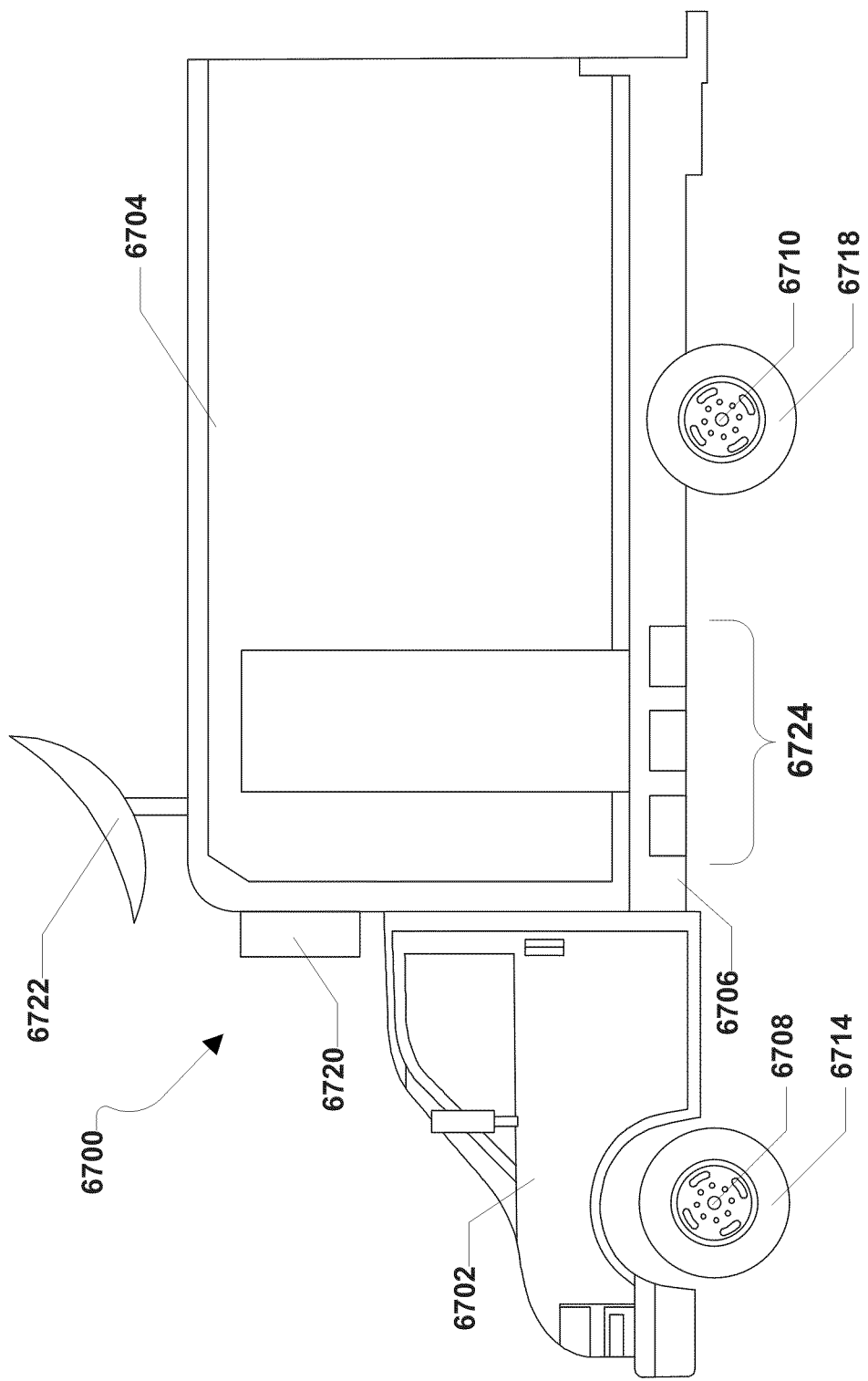
FIG. 68 is a second side plan view of a mobile scanner.
Figure 69:
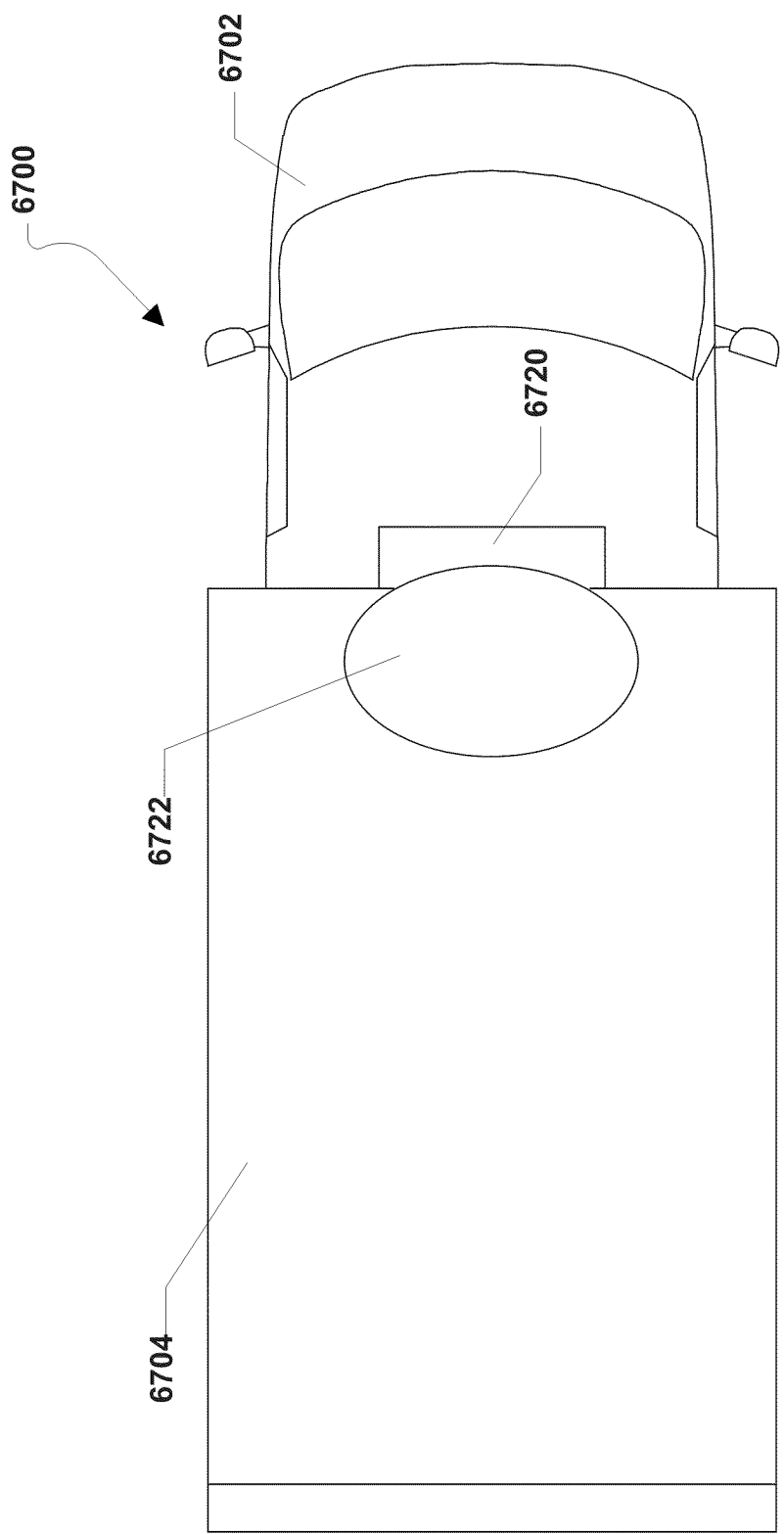
FIG. 69 is a first top plan view of a mobile scanner.

FIG. 65 and FIG. 66 illustrate a method of processing color data derived from a volumetric scan of one or more documents having color images or color inks. The method is generally designated 6500.

Beginning at block 6502 ink may be scanned using NMR/MRI, X-RAY, X-RAY CT, T-RAY, T-RAY CT, or a combination thereof. At block 6504, a processor may determine a result of the scan of the ink in response to the scan, e.g., a grayscale value. At block 6506, the processor may record the color/type of ink scanned. Further, at block 6508, the processor may associate the grayscale value with the color/type of ink. At block 6510, the processor may record the grayscale value in a table, e.g., an ink/grayscale value table.

Moving to block 6512, a volumetric scan of printed media may be performed in order to generate a volumetric scan data, e.g., comprising multiple voxels. At block 6514, the processor may store the volumetric scan data. At block 6516, the processor may align the volumetric scan data with a coordinate system. Then, at block 6518, the processor may filter paper data from ink data. From block 6518, the method 6500 may proceed to block 6602 of FIG. 66.

At block 6602, the processor may set a counter, M, equal to one. At block 6604, a do loop may be entered in which for an Mth layer of voxels with ink data the following steps may be performed. At block 6606, the processor may set a counter, N, equal to one (1). At block 6608, another do loop may be entered in which for an Nth voxel within the Mth layer, the following steps may be performed. At block 6610, the processor may determine a grayscale value of the Nth voxel. At block 6612, the processor may compare the grayscale value to an ink/grayscale value table.

Moving to decision 6614, the processor may determine whether the grayscale value matches an entry within the ink/grayscale value table. If not, the method may proceed to block 6616 and the color/type of ink may be identified. Thereafter, the method 6500 may return to block 6502 of FIG. 65 and continue as described herein.

If there is a match at decision 6614, the method 6500 may continue to block 6618 and the processor may assign a color to the Nth voxel based on the grayscale voxel. At block 6620, the processor may store the color of the Nth voxel within an electronic file associated with the current page of the document.

Proceeding to decision 6622, the processor may determine whether there is another voxel within the Mth layer. If so, the method may proceed to block 6624 and the processor may increase the counter, N, by one (I). The method 6500 may then return to block 6604 and the method 6500 may continue as described herein.

Returning to decision 6622, if there is not another voxel within the Mth layer, the method 6500 may move to decision 6626 and the processor may determine whether there is another layer. If there is another layer, the method 6500 may return to block 6604 and continue as described herein. Otherwise, if there is not another layer, the method 6500 may end. It may be appreciated that the method described in conjunction with FIG. 65 and FIG. 66 may be used to create a database of colored inks and their respective responses when scanned as described herein. Further, the method described in conjunction with FIG. 65 and FIG. 66 may also be used to create a database of various types of black inks and their respective responses when scanned as describe herein. Accordingly, there may be inks that are initially non-responsive to one or more of the scanning means described herein. However, after recalibration of a scanner, these inks may be responsive. Any response may be saved to a database with the associated scanner settings used to locate the inks within the paper media.

Referring now to FIG. 67 through FIG. 76, a mobile scanner is shown and is generally designated 6700. As shown, the mobile scanner 6700 includes cab 6702 and a body 6704 mounted on a frame 6706. Further, the frame 6706 may include a front axle 6708 and a rear axle 6710. The front axle 6708 may include a first front tire/wheel assembly 6712 and a second front tire/wheel assembly 6714 mounted thereon. The rear axle 6710 may include a first rear tire/wheel assembly 6716 and a second rear tire/wheel assembly 6718 mounted thereon.

As shown, the body 6704 of the mobile scanner 6700 may include a heating/cooling unit 6720 mounted thereon. The heating/cooling unit 6720 may provide a substantially constant temperature within the interior of the body 6704 of the mobile scanner 6700. The body 6704 of the mobile scanner 6700 may also include a satellite antenna 6722 mounted thereon. The satellite antenna 6722 may provide a data link for one or more computer devices within the body 6704 of the mobile scanner 6700. The satellite antenna 6722 may operate in conjunction with one or more microwave relays. Moreover, the satellite antenna 6722 may utilize any frequency known in the broadcast spectrum including the portion of the broadcast spectrum previously reserved for the broadcast of analog television signals.

In addition, the mobile scanner 6700 may include a battery array 6724 mounted underneath the body 6704 of the mobile scanner 6700, e.g., mounted on the frame 6706 of the mobile scanner 6700. The battery array 6724 may be used to store power generated by a generator 6730 and may be used to provide power to electrical equipment within the body 6704 of the mobile scanner 6700, e.g., when the generator 6722 is not in use.

Figure 70:
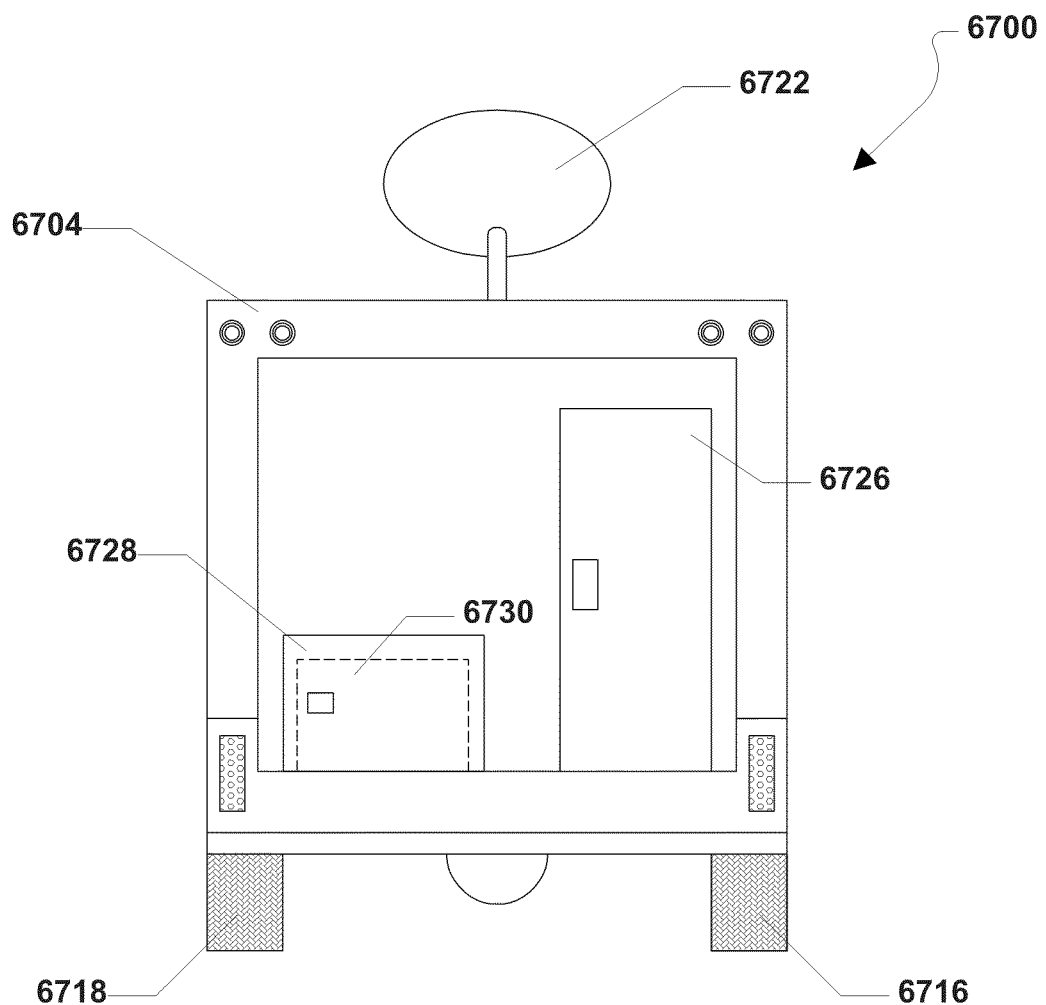
FIG. 70 is a first rear plan view of a mobile scanner.
Figure 71:
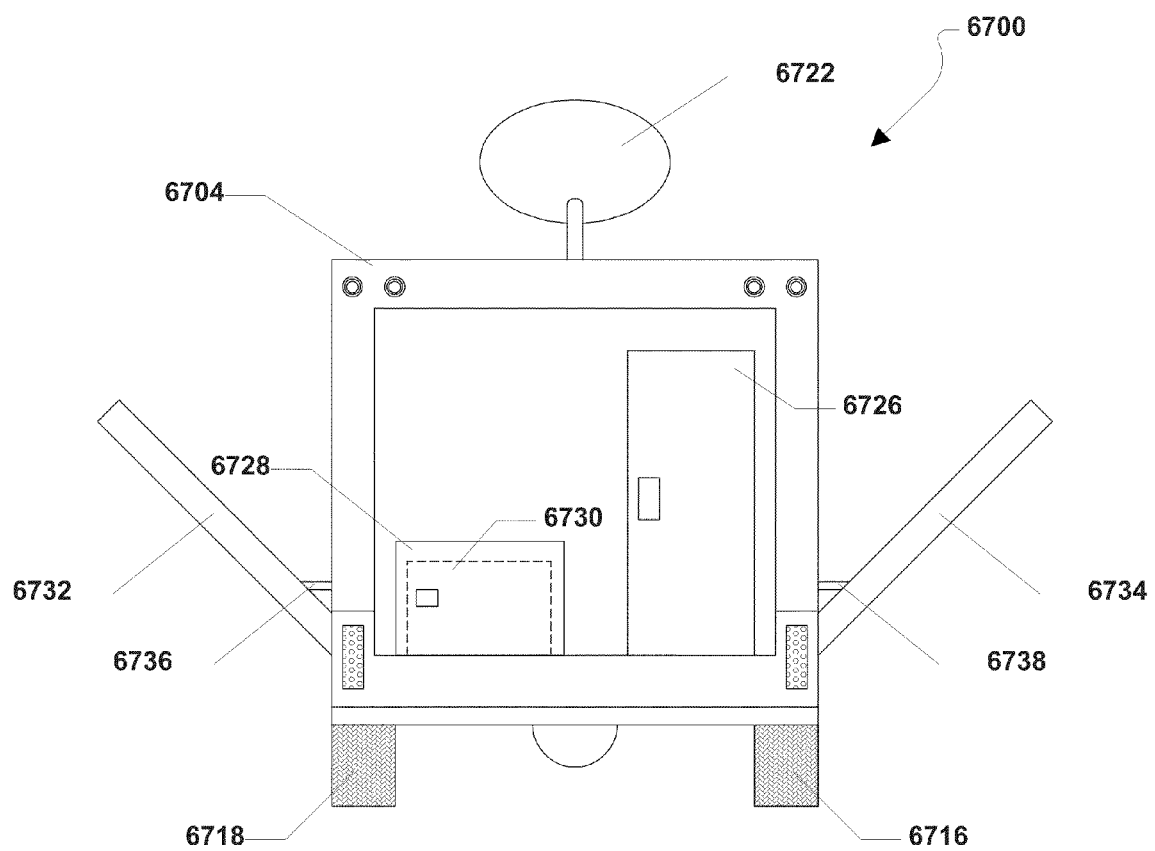
FIG. 71 is a second rear plan view of a mobile scanner.
Figure 72:
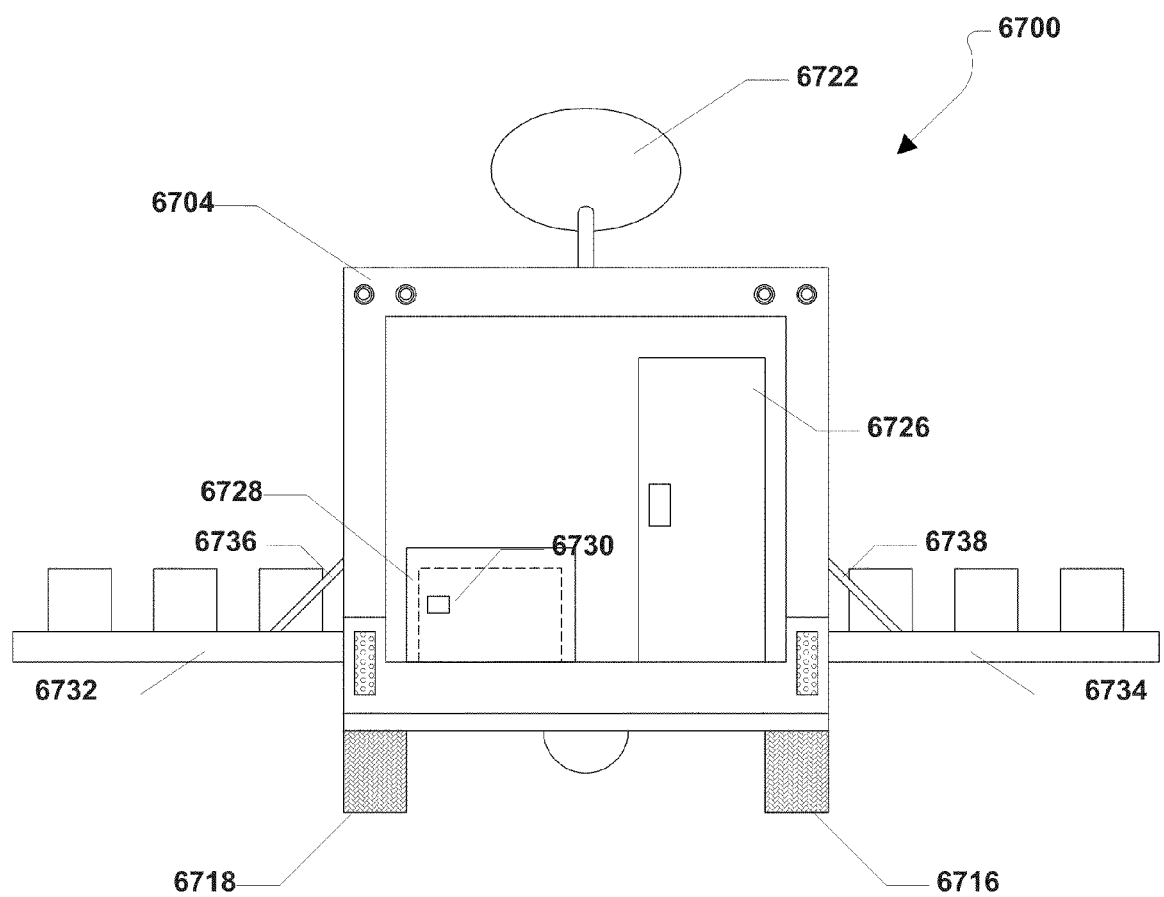
FIG. 72 is a third rear plan view of a mobile scanner.

FIG. 70 through FIG. 72 indicates that the body 6704 of the mobile scanner 6700 may include a rear door 6726. The rear door 6726 may provide access to an interior of the body 6704. FIG. 70 through FIG. 72 also show that the body 6704 of the mobile scanner 6700 may include a generator 6730 access door 6728 that provides access to a generator 6730 within the body 6704 of the mobile scanner 6700.

As shown in FIG. 71 and FIG. 72, the body 6704 of the mobile scanner 6700 may include a first external scanner access door 6732 and a second external scanner access door 6734. In a particular aspect, the first external scanner access door 6732 may be installed in, or otherwise incorporated into, the driver's side of the body 6704 of the mobile scanner 6700. Further, the second external scanner access door 6734 may be installed in, or otherwise incorporated into, the passenger's side of the body 6704 of the mobile scanner 6700.

The first external scanner access door 6732 may include a first actuation arm 6736. The second external scanner access door 6734 may include a second actuation arm 6738. The actuation arms 6736, 6738 may be electric, hydraulic, mechanical, or a combination thereof. The actuation arms 6736, 6738 may be used to raise and tower the external scanner access doors 6732, 6734 to provide access to a scanner, described below, that is located within the body 6704 of the mobile scanner 6700. Accordingly, the external scanner access doors 6732, 6734 may be configured to be moved between an open position, in which access is provided to the scanner, and a closed position, in which access is not provided to the scanner.

Figure 73:
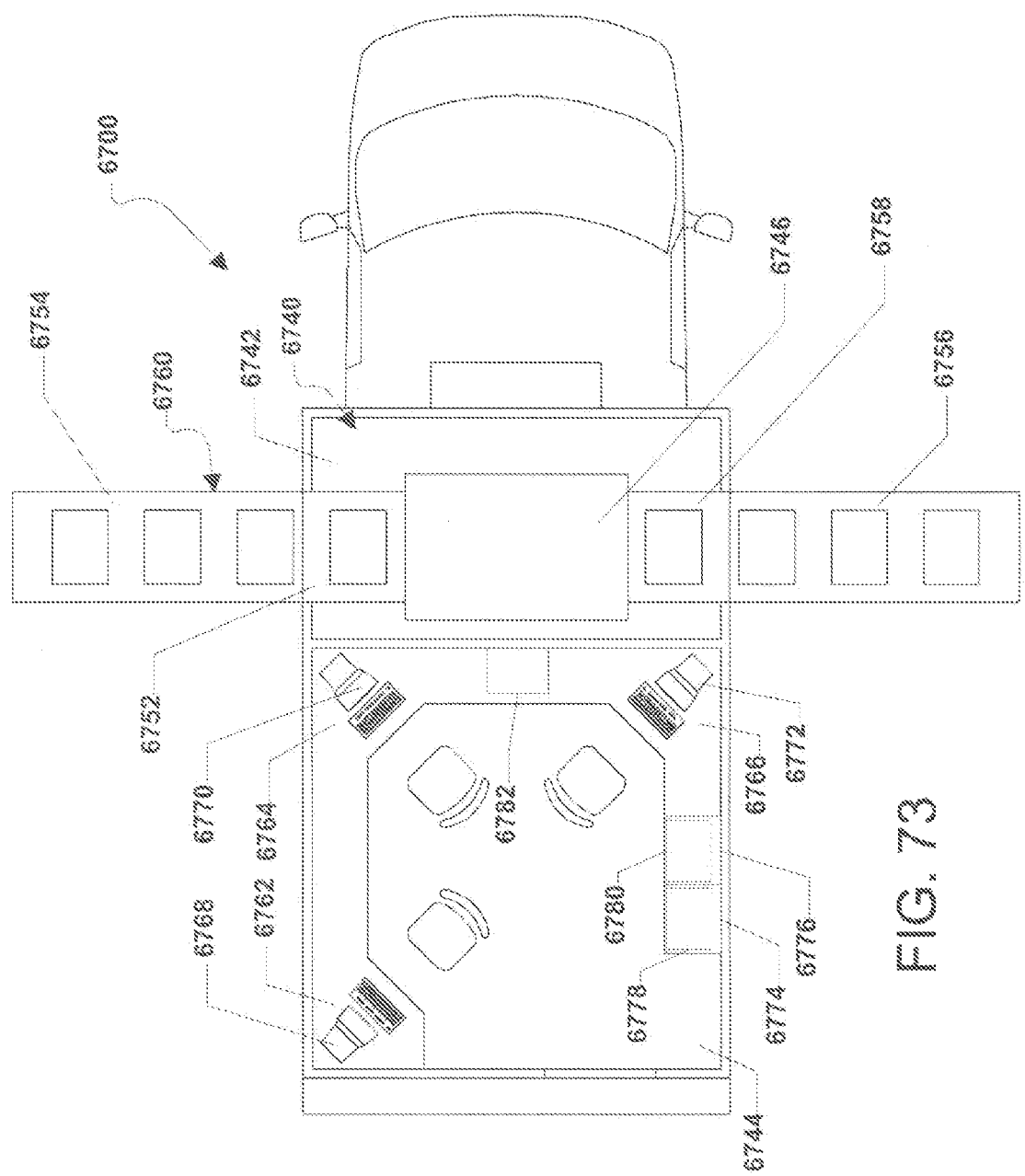
FIG. 73 is a second top view of a mobile scanner with portions cut away for clarity.

As shown in FIG. 73, the body 6704 of the mobile scanner 6700 may include an interior 6740. The interior 6740 may have a first portion 6742 and a second portion 6744. In a particular aspect, the first portion 6742 of the interior 6740 of the body 6704 may be in front of the second portion 6744 of the interior 6740 of the body 6704, i.e., relative to the driving direction of the mobile scanner 6700. The entire body 6704 of the mobile scanner 6700, i.e., the portion around the first portion 6742 of the interior 6740 and the portion around the second portion 6744 of the interior may be shielded. The shielding may be lead shielding or some other equivalent type of shielding to protect users within, or without, the body 6704 of the mobile scanner 6700 from harmful radiation, e.g., X-rays. Further, the shielding may be magnetic shielding in order to protect electrical equipment within, or without, the body 6704 of the mobile scanner 6700 from being harmed by magnetic fields emanating from a scanner, described below, installed within the body 6704 of the mobile scanner 6700. The magnetic shielding may also prevent loose magnetic items from being drawn toward the mobile scanner 6700 during operation of the mobile scanner 6700.

Figure 74:
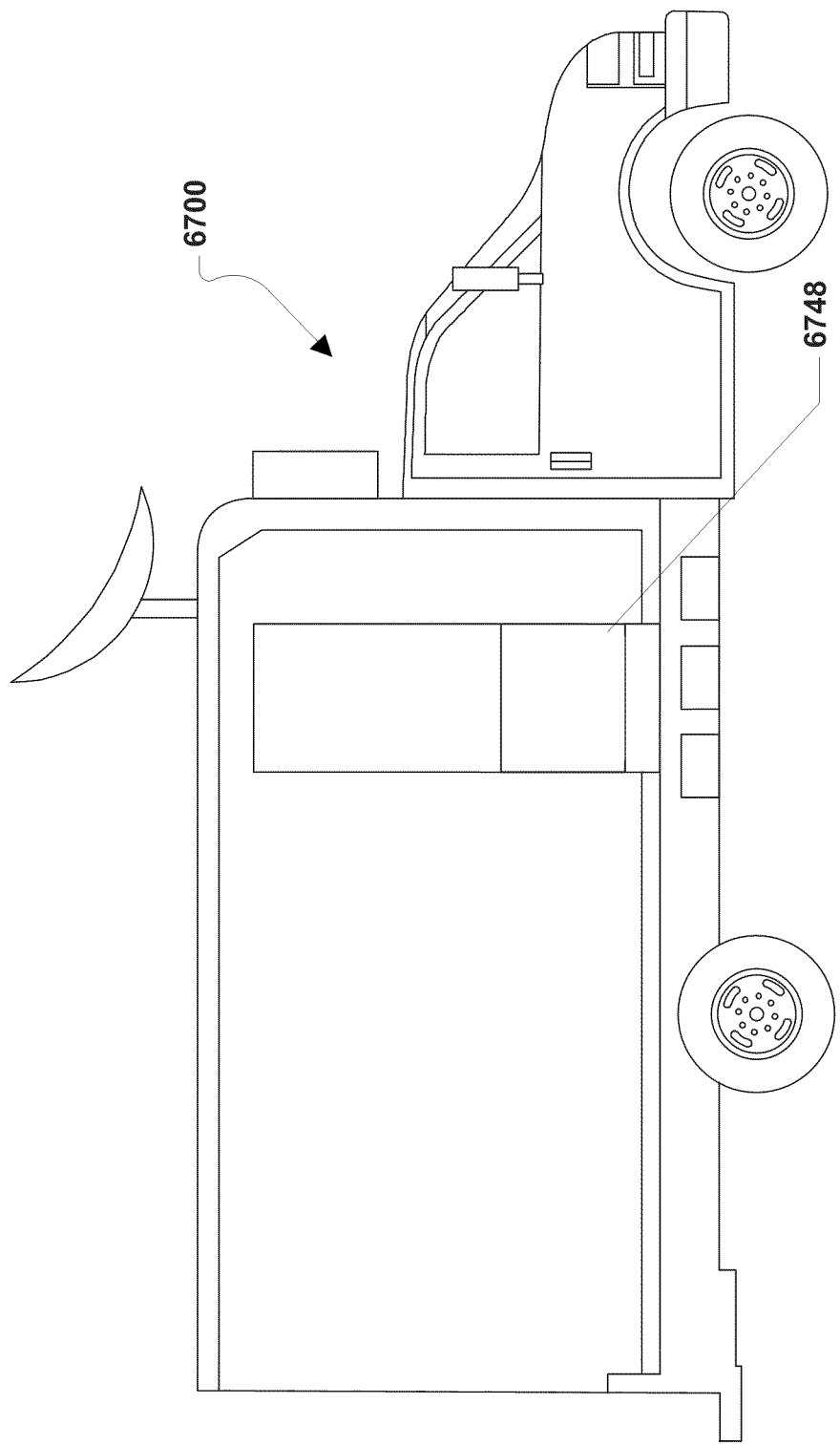
FIG. 74 is a third side plan view of a mobile scanner.
Figure 75:
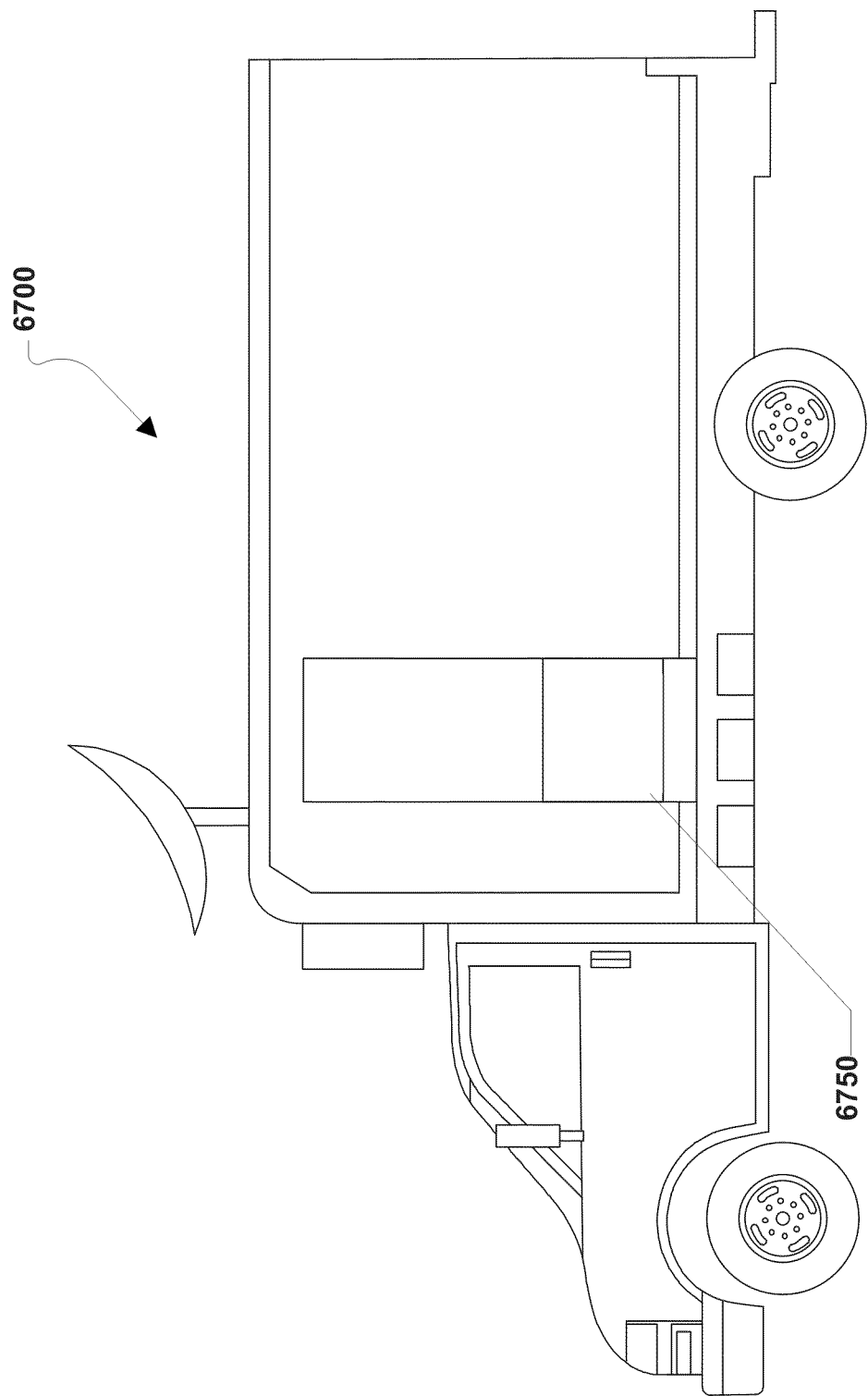
FIG. 75 is a fourth side plan view of a mobile scanner.
Figure 76:
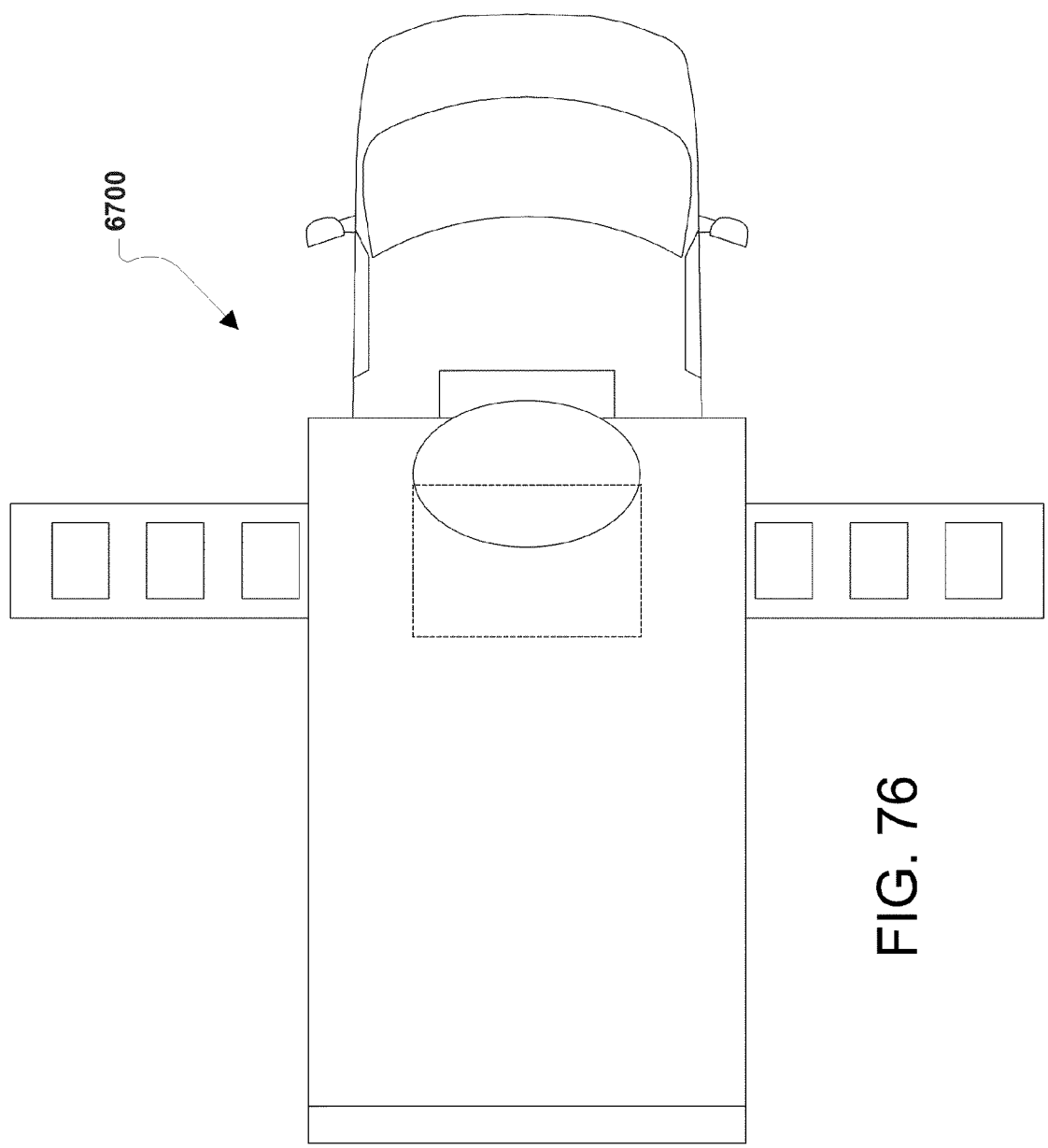
FIG. 76 is a third top plan view of a mobile scanner.

FIG. 73 shows that a scanner 6746 may be installed within the first portion 6742 of the interior 6740 of the body 6704 of the mobile scanner 6700. The scanner 6746 may be one of the scanners described herein and may utilize one or more of the non-invasive, volumetric scanning technologies described herein, e.g., MRI, CT, T-Ray, etc. FIG. 74 and FIG. 75 indicate that the scanner 6746 may include a first internal scanner access door 6748 and a second internal scanner access door 6750. The scanner 6746 may include an interior scanning cavity 6752 in which a document, group of documents, box of documents, etc. may be placed. Each internal scanner access door 6748, 6750 may be raised in order to provide access to the interior scanning cavity 6752. In other words, each internal scanner access door 6748, 6750 may be movable between a raised position, in which access to the interior scanning cavity 6752 is facilitated, and a lowered position, in which access to the interior scanning cavity 6752 is prevented, or otherwise prohibited. Further, each internal scanner access door 6748, 6750 may be shielded, e.g., with lead, to protect a user from radiation, e.g., X-rays, emanating from the scanner 6746. Further, the housing of the scanner 6746 may also be shielded to protect a user from radiation as well.

In another aspect, the internal scanner access doors 6748, 6750 may be shielded with magnetic shielding to prevent a magnetic field from emanating beyond the scanner 6746 and drawing loose magnetic materials around the scanner 6746 into the interior scanning cavity 6752 of the scanner 6746. Moreover, the housing of the scanner 6746 may be shielded with magnetic shielding as well.

As shown in FIG. 73, the first external scanner access door 6732 may include a first conveyor belt portion 6754. The second external scanner access door 6734 may include a second conveyor belt portion 6756. A third conveyor belt portion 6758 may installed between the first conveyor belt portion 6754 and the second conveyor belt portion 6756 within the first portion 6742 of the interior 6740 of the body 6704 of the mobile scanner 6700. The third conveyor belt portion 6758 may pass through the interior scanning cavity 6752 of the scanner 6746.

When the external scanner access doors 6732, 6734 are opened, a conveyor system 6760 may be established by the first conveyor belt portion 6754, the second conveyor belt portion 6756, and the third conveyor belt portion 6758. The conveyor system 6760 may pass through the interior scanning cavity 6752 of the scanner 6746. During operation, the conveyor system 6760 may be used to carry documents, boxed or otherwise, through the scanner 6746. The conveyor system 6760 may periodically stop when the documents are located within the interior scanning cavity 6752 of the scanner 6746 in order to scan the documents and obtain a three-dimensional, volumetric electronic representation of the documents.

Each time the conveyor system 6760 stops, the internal scanner access doors 6748, 6750 may be closed in order to protect a user, or worker, from radiation from the scanner 6746. The internal scanner access doors 6748, 6750 may also be closed to prevent loose magnetic items from being drawn into the interior scanning cavity 6752 of the scanner.

As depicted in FIG. 73, the second portion 6744 of the interior 6740 of the body 6704 of the mobile scanner 6700 may include a first work station 6762, a second work station 6764, and a third work station 6766. Each work station 6762, 6764, 6766 may include a computer 6768, 6770, 6772 that may be used to control the operation of the scanner 6746. Further, each computer 6768, 6770, 6772 may be used to process data received from the scanner 6746. Also, a first server rack 6774 and a second server rack 6776 may be installed within the second portion 6744 of the interior 6740 of the body 6704. Each server rack 6774, 6776 may include one or more removable servers 6778, 6780.

One or more removable memory systems 6782 may also be installed within the second portion 6744 of the interior 6740 of the body 6704. Each of the components within the body 6704 of the mobile scanner 6700, e.g., the computers 6768, 6770, 6772; the server racks 6774, 6776; the servers 6778, 6780; the memory system 6782; and the scanner 6746 may be interconnected by wired connections or wireless connections. Further, these components may be powered all, or in part, by the generator 6730 or the battery array 6724. Alternatively, these components may be powered by an external power source.

It may be appreciated that the mobile scanner 6700 may include any number of computers, server racks, servers, memory systems, and scanners and the numbers disclosed herein are exemplary and for illustrative purposes. Further, it may be appreciated that the mobile scanner 6700 may not actually be a vehicle, but it may be removably mounted within a vehicle and may be carried, or otherwise wheeled, into a facility in order to scan one or more documents within the facility. In such a case, the mobile scanner 6700 may include the electronic components described herein and it may include a conveyor system configured similar to that described herein.

Figure 77:
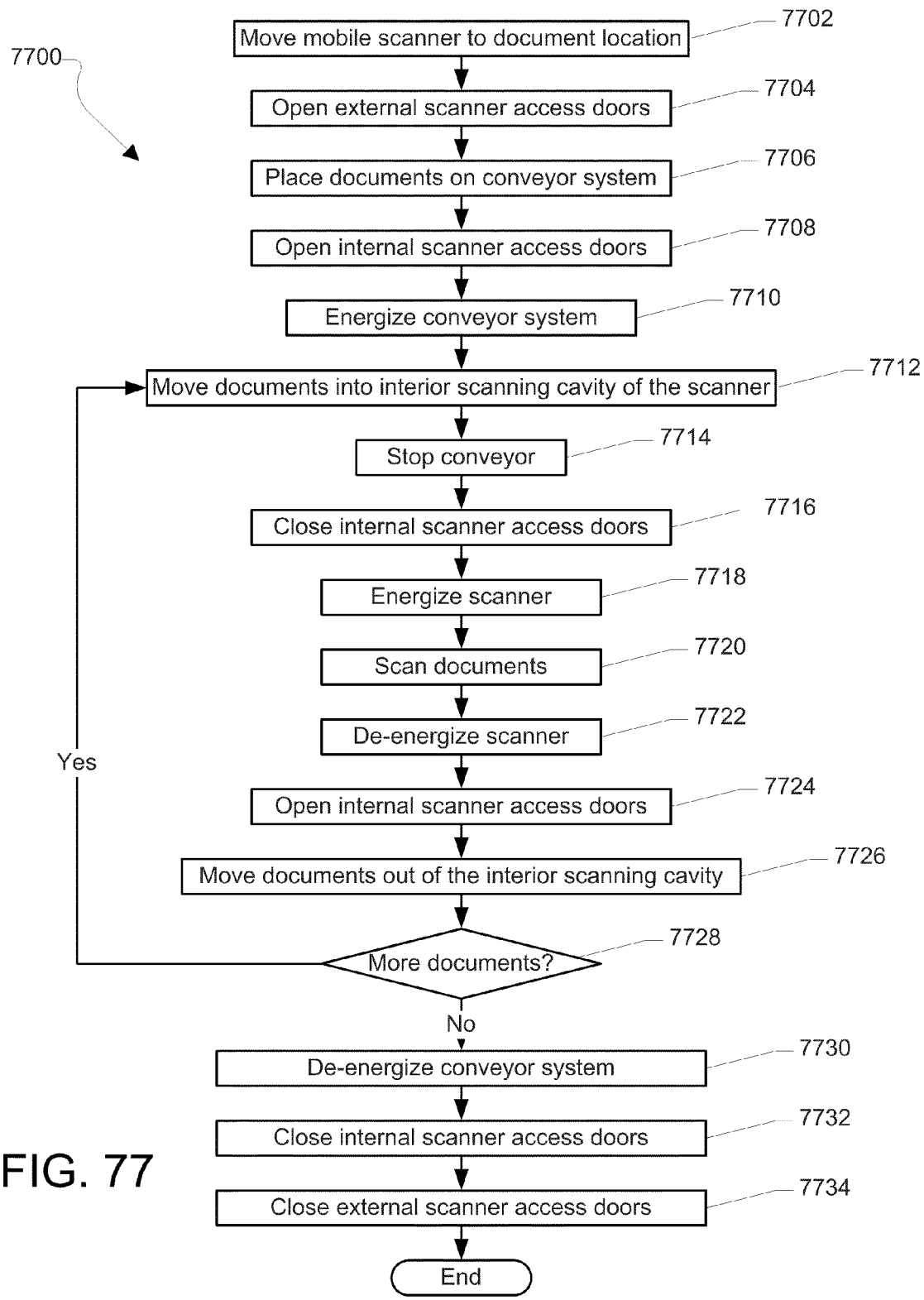
FIG. 77 is a flowchart illustrating a first method of using a mobile scanner.

Referring now to FIG. 77, a first method of using a mobile scanner is shown and is generally designated 7700. Commencing at block 7702, a mobile scanner may be moved to a document location. In this context, document may mean volumes of documents, e.g., documents stored in boxes in a warehouse. At block 7704, external scanner access doors may be opened. Further, at block 7706, documents, e.g., a box of documents, a stack of documents, a sack of documents, or a combination thereof, may be placed on a conveyor system.

Moving to block 7708, internal scanner access doors may be opened. At block 7710, the conveyor system may be energized. Moreover, at block 7712, the documents may be moved into an interior scanning cavity of the scanner using the conveyor. At block 7714, the conveyor may be stopped. Next, at block 7716, the internal scanner access doors may be closed. At block 7718, the scanner may be energized. At block 7720, the documents may be scanned using x-ray CT, MRI, T-ray CT, or a combination thereof in order to create a data set that represents the documents. In a particular aspect, the data set may include ink data, paper data, cardboard data, fastener data, other artifact data, or a combination thereof.

At block 7722, the scanner may be de-energized. Further, at block 7724, the internal scanner access doors may be opened. At block 7726, the documents may be moved out of the scanner cavity using the conveyor and the documents may be removed from the conveyor. Next, at decision 7728, it may be determined whether there are more documents. If so, the method 7700 more documents may be placed on the conveyor and the method 7700 may return to block 7712 and continue as described herein.

Returning to decision 7728, if there are no more documents, the method 7700 may move to block 7730 and the conveyor system may be de-energized. At block 7732, the internal scanner access doors may be closed. Next, at block 7734, the external scanner access doors may be closed. When using x-rays, or similar radiation, to scan the documents, the scanner should not be energized if the internal scanner access doors are open. Accordingly, a safely mechanism may be provided to prevent the scanner from being energized while the internal access doors are opened.

Figure 78:
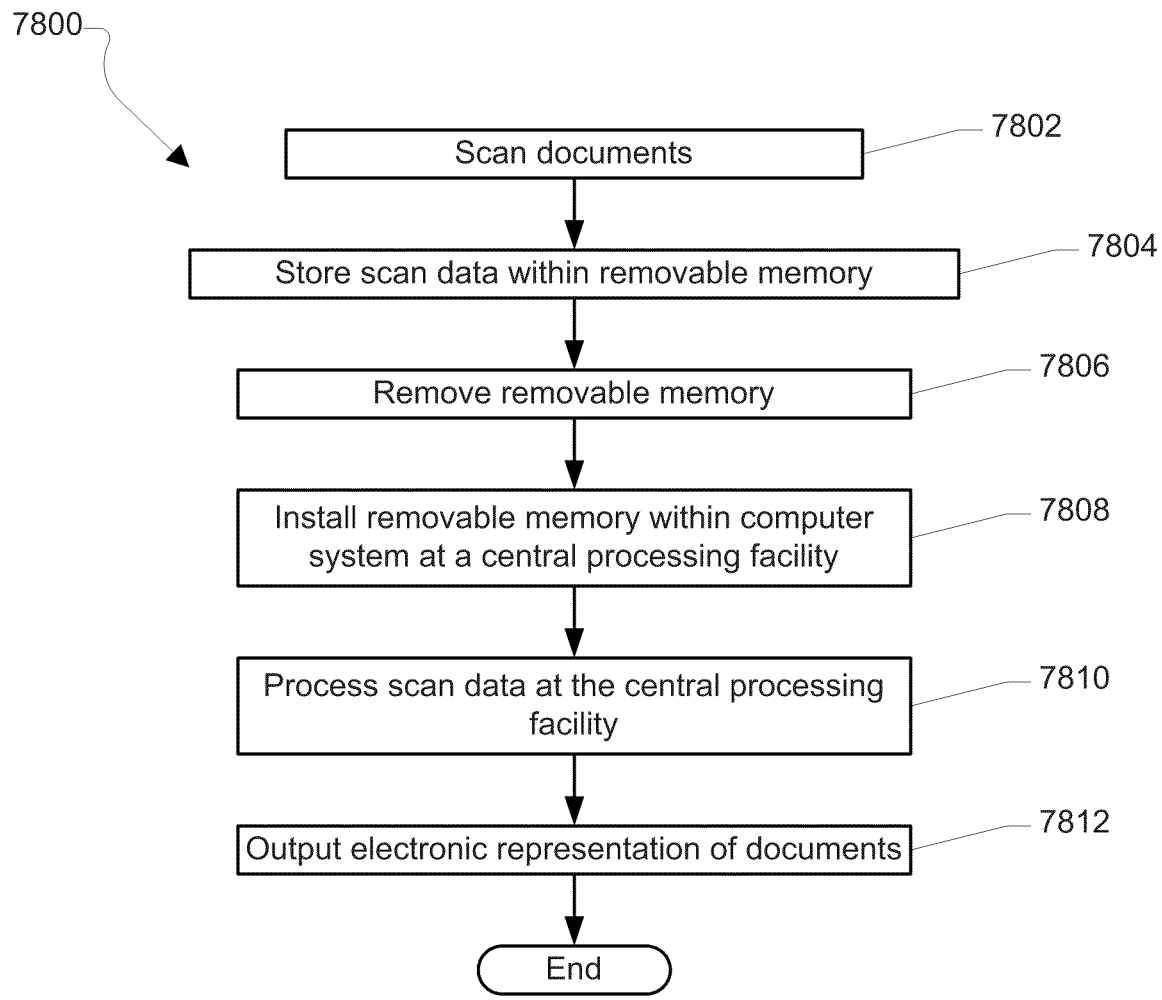
FIG. 78 is a flowchart illustrating a second method of using a mobile scanner.

FIG. 78 illustrates a second method of using a mobile scanner. The method is generally designated 7800 and may begin at 7802. At block 7802, the documents may be scanned using a mobile document scanner that employs MRI, x-ray CT, T-ray CT, or a combination thereof to scan the documents. At block 7804, the scan data may be stored within a removable memory. Next, at block 7806 the removable memory may be removed from the mobile document scanner.

At block 7808, the removable memory may be installed within a computer system at a central processing facility. Then, at block 7810, the scan data may be processed at the central processing facility using one or more of the methods described herein in order to create an electronic representation of the documents. At block 7812, an electronic representation of the documents may be output, e.g., to a memory that may be returned to the owner of the documents. Thereafter, the method 7800 may end.

Figure 79:
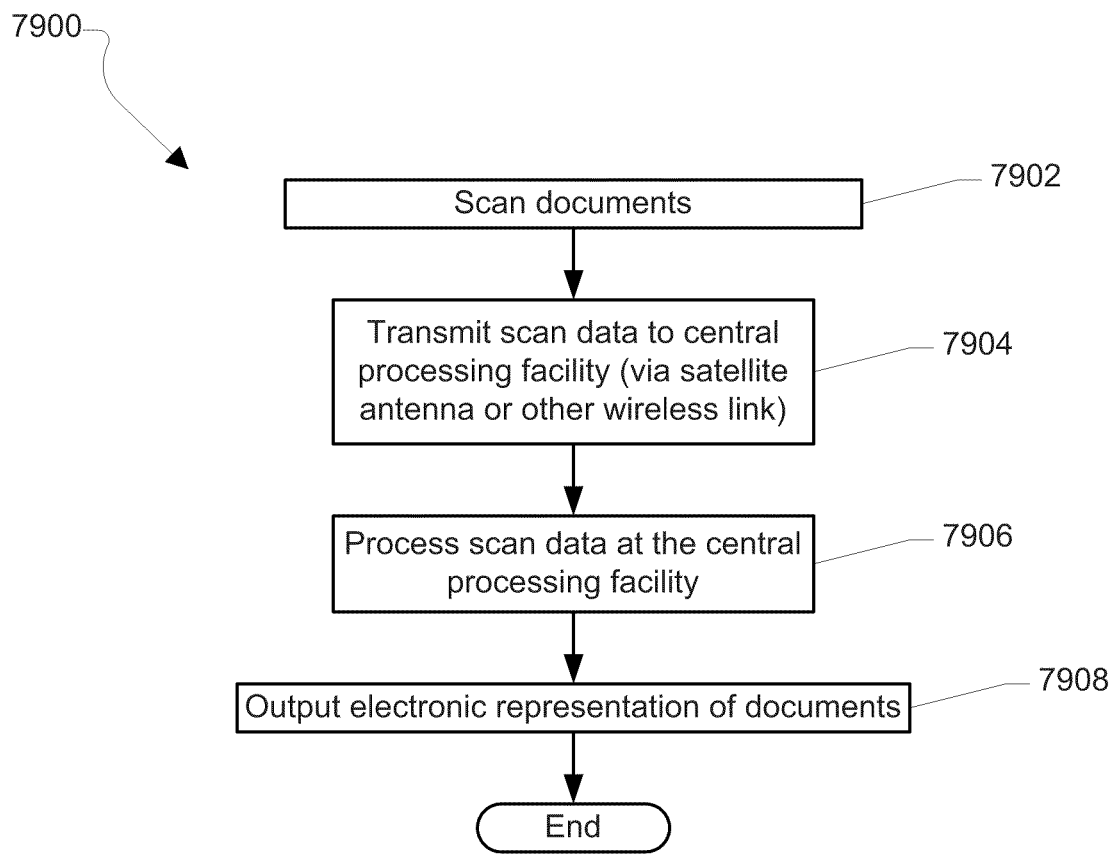
FIG. 79 is a flowchart illustrating a third method of using a mobile scanner.

Referring to FIG. 79, a third method of using a mobile scanner is shown and is generally designated 7900. Beginning at block 7902, the documents may be scanned using a mobile scanner that employs MRI, x-ray CT, T-ray CT, or a combination thereof to scan the documents. At block 7904, the scan data may be transmitted to a central processing facility via a satellite antenna or other wireless link.

Moving to block 7906, the scan data may be processed at the central processing facility using one or more of the methods described herein in order to create an electronic representation of the documents. At block 7908, an electronic representation of the documents may be output, e.g., to a memory that may be returned to the owner of the documents. Thereafter, the method 7900 may end.

Figure 80:
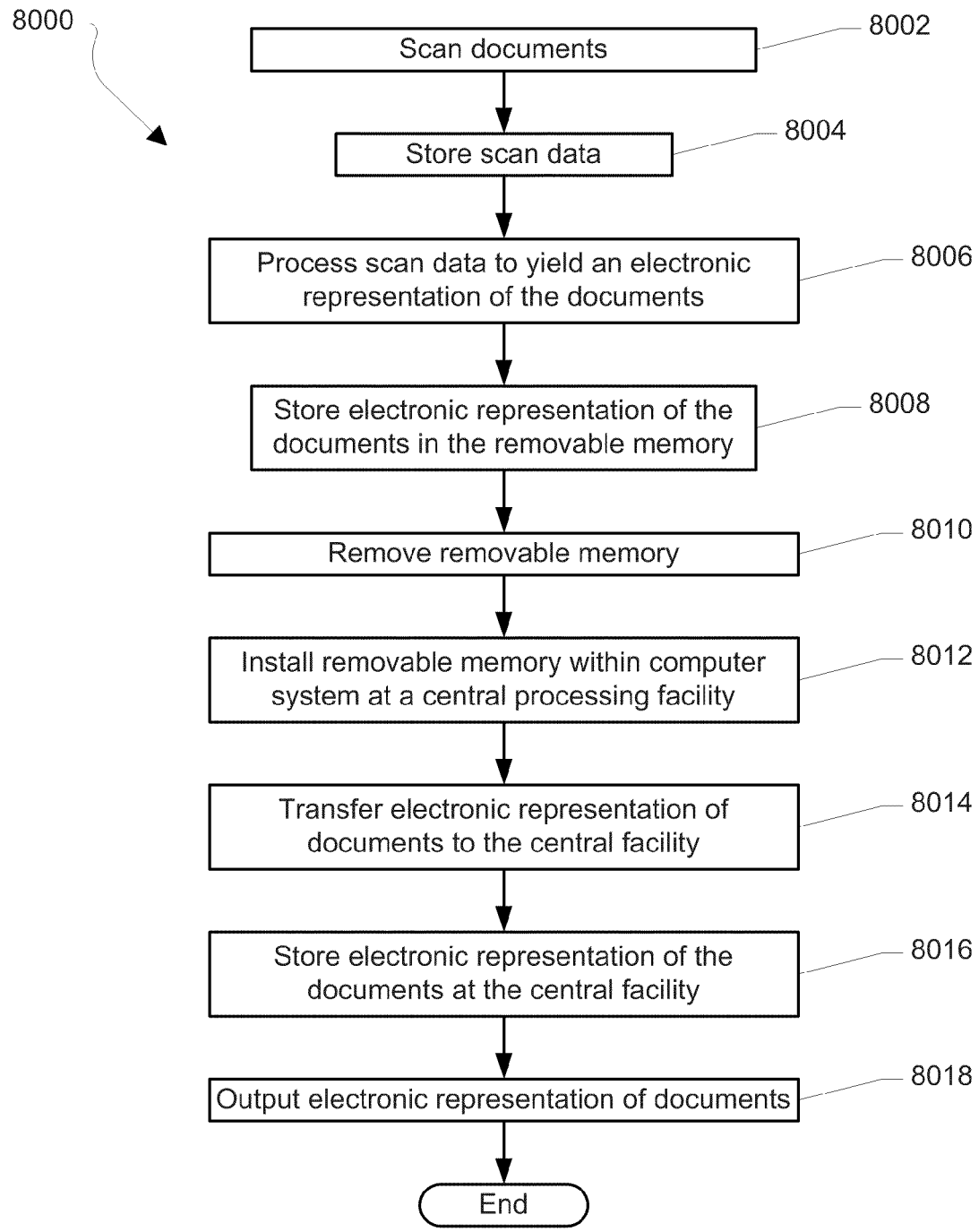
FIG. 80 is a flowchart illustrating a fourth method of using a mobile scanner.

FIG. 80 depicts a fourth method of using a mobile scanner, generally designated 8000. At block 8002, the documents may be scanned using a mobile document scanner that employs MRI, x-ray CT, T-ray CT, or a combination thereof to scan the documents. At block 8004, the scan data may be stored within a memory in the mobile document scanner. At block 8006, the scan data may be processed at the mobile scanner using one or more of the methods described herein in order to create an electronic representation of the documents. Next, at block 8008, the electronic representation of the documents may be stored within a removable memory.

Moving to block 8010, the removable memory may be removed from the mobile document scanner. Further, at block 8012, the removable memory may be installed within a computer system at a central processing facility. At block 8014, the electronic representation of the documents may be transferred to the central facility. At block 8016, the electronic representation of the documents maybe stored at the central facility and the owner of documents may access them through a secure network connection. At block 8018, all or a portion of the electronic representation of the documents may be output. Thereafter, the method 8000 may end.

Figure 81:
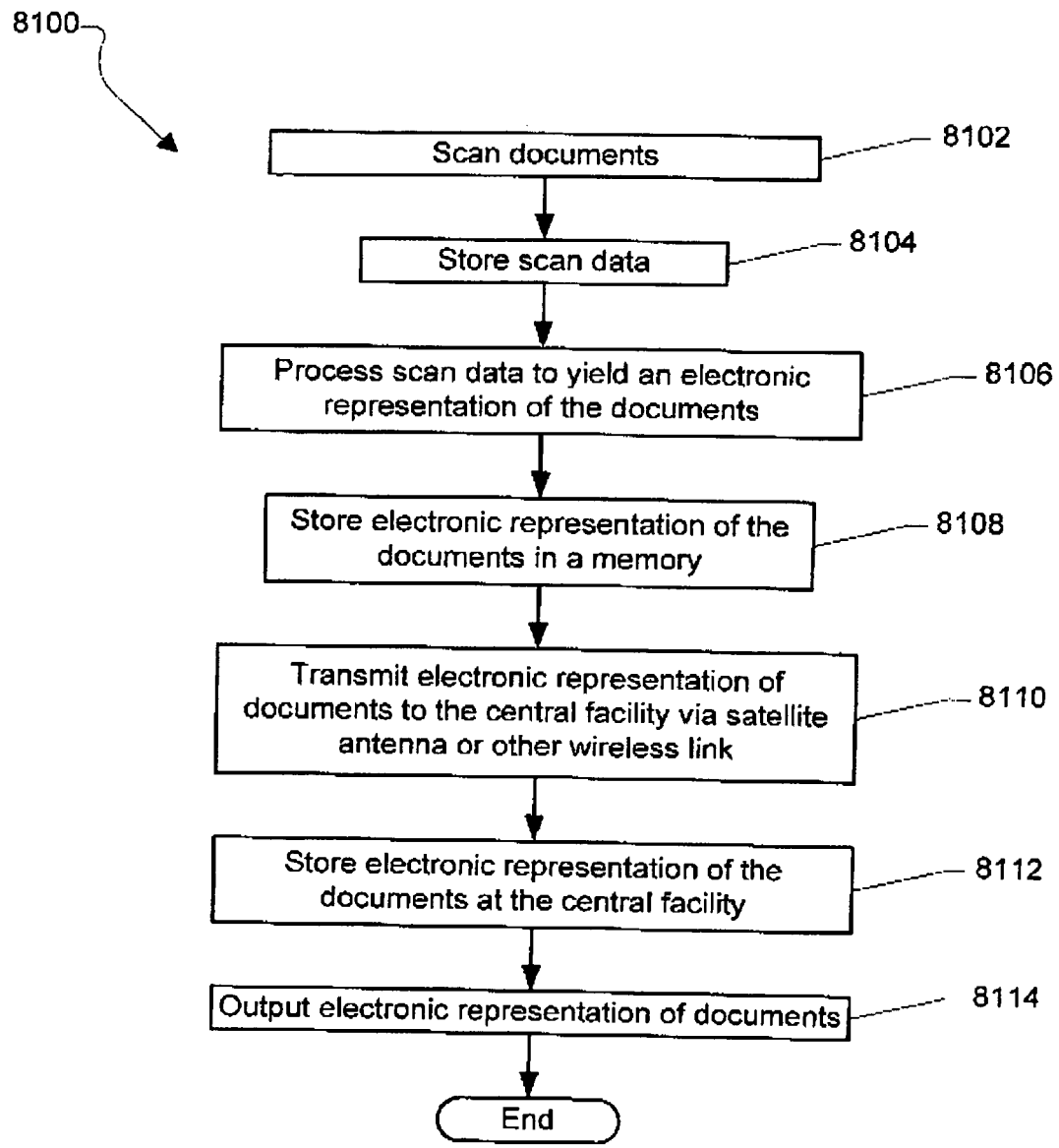
FIG. 81 is a flowchart illustrating a fifth method of using a mobile scanner.

FIG. 81 depicts a fourth method of using a mobile scanner, generally designated 8100. At block 8102, the documents may be scanned using a mobile document scanner that employs MRI, x-ray CT, T-ray CT, or a combination thereof to scan the documents. At block 8104, the scan data may be stored within a memory in the mobile document scanner. At block 8106, the scan data may be processed at the mobile scanner using one or more of the methods described herein in order to create an electronic representation of the documents. Next, at block 8108, the electronic representation of the documents may be stored within a memory at the mobile document scanner.

Moving to block 8110, the electronic representation of the documents may be transmitted to a central facility via a satellite antenna or other wireless link. At block 8112, the electronic representation of the documents maybe stored at the central facility and the owner of documents may access them through a secure network connection. At block 8114, all or a portion of the electronic representation of the documents may be output. Thereafter, the method 8100 may end.

It is to be understood that the method steps described herein need not necessarily be performed in the order as described. Further, words such as "thereafter," "then," "next," etc. are not intended to limit the order of the steps. These words are simply used to guide the reader through the description of the method steps.

Using one or more aspects of the above-described logic, printed media, e.g., loose documents, books, magazines, etc., which is placed in a non-invasive scanner may be scanned using non-invasive scanning means, e.g., NMR, TeraHertz Rays, X-rays, other means, or a combination thereof.

In the case of NMR, the carbon-13 in the paper and the carbon-13 in the ink react to the NMR and data representing the paper and the ink is output to a microprocessor. In the case of TeraHertz Rays, the paper and the ink cause the TeraHertz Rays to react differently as the TeraHertz Rays pass through the paper and the ink. The difference provides a dataset that may be processed as described herein in order to yield an electronic representation of the writing within printed media. Further, in the case of x-ray, the paper and ink may also cause the x-rays to react differently as the x-rays pass through the printed media. Again, this difference results in a dataset that may be processed as described herein to create an electronic representation of the writing within the printed media.

In a particular aspect, the data representing the ink may be separated or filtered from the total data and used to create an electronic representation of the printing on the paper media. Accordingly, relatively high volumes of stacked printed media may be relatively quickly scanned into an electronic database. This database may then be searched using keywords, Boolean searches, semantic searches, or any other search means known in the art.

Another potential application of volumetrically scanning paper media is abstracting, indexing and/or summarizing the contents of the volumetrically scanned paper media so as to enable a user to only output a condensed or summarized version of the scanned sample or only output relevant portions or business critical terms or phrases. Accordingly, in addition to the foregoing, it is an object of this specification to disclose a system and method for abstracting and/or indexing data derived from volumetric scans. The system and method for abstracting and/or indexing data derived from volumetric scans described hereafter relates to an information retrieval system for abstracting, indexing, searching, and/or classifying documents in such environments as the Internet, enterprise content management systems, databases, libraries, hospitals, financial institutes, insurance companies, real estate companies or any entity with a need for abstracting, summarizing, and/or indexing information.

Abstracting (or summarizing) is the process of sorting through large amounts of data and picking out relevant information. It is the process of condensing a source text into a shorter version while still preserving the essence of its information content. Information overload is becoming a problem for an increasingly large number of people, and a key step in reducing the problem is to use an abridgement tool. A summary document tailored to the interests of the end user provides a convenient and efficient way to review the contents of a document or across multiple documents.

Automatic abstracting and/or summarization may target a single source text and/or target multiple texts. When analyzing a single source text, abstracting is carried out over the whole document, either by extracting important sentences or by rephrasing and shortening the original text. When targeting single source texts, key passages or topic sentences are extracted via the abstract means, and may also include rephrasing various portions of the target document. When creating an abstract of a single document, the resultant abstract may be sentence(s), paragraph(s), or even page(s), but the length of the resultant abstract is usually (but not always) smaller in size that the source document. By way of a non-limiting example, abstracting a scientific research article would be an example of single source abstracting.

When analyzing multiple source texts, abstracting is carried out across multiple documents, with the resultant abstract encapsulating, condensing and aggregating the essential information conveyed by the multiple documents and outputting the abstract as sentence(s), paragraph(s), or even page(s), with the length of the resultant abstract usually (but not always) smaller in size that the source documents. When abstracting across multiple documents, even if the individual subject matter and content of the multiple documents fail to relate to each other, it is still possible and advantageous to utilize a means for abstracting. By abstracting and/or summarizing across multiple documents, the retrieved information is adapted to smaller, more manageable reports that end users may integrate into their business flow and use to guide organizational decision making. By way of a non-limiting example, volumetrically scanning multiple scientific research articles simultaneously and outputting a single abstract encapsulating the combined essence of all the documents is an example of abstracting across multiple documents.

Indexing is a particular subset of abstracting, wherein targeted information serves to guide, point out, or otherwise facilitate reference, especially in the context of: an alphabetized list of names, places, and subjects treated in a printed work, giving the page or pages on which each item is mentioned; a thumb index; a table, file, or catalog; a list of keywords associated with a record or document, used especially as an aid in searching for information.

Accordingly, there is a need for an indexing and/or abstracting system and methodology that may comprehensively locate, retrieve, and identify relevant words, phrases, sentences, and/or paragraphs in a large scale; index all of the foregoing; search and rank documents in accordance with their weighted words and phrases; and provide additional clustering and descriptive information about the documents to enable search across multiple documents and across multiple platforms.

It is appreciated and understood by those skilled in the art that a system and method for abstracting and/or indexing data derived from volumetric scans would prove useful in any number of professions. By way of a non-limiting example, certain mortgage applications and contracts may be over one-hundred pages long, but for purposes of the reviewing mortgage analyst, there may only be 10 important pages of variable data and 90 pages of boilerplate common to all mortgage applications. Likewise, a medical chart may be comprised of multiple pages, but only a few truly relevant codes and/or diagnostic notes. By only identifying and abstracting the critical information in these examples, an organization may streamline its business process intake. Additionally, abstracting may enable books to be outputted as single pages or be reduced further, into snippets of a page. These snippets in turn may be remixed into reordered books and virtual bookshelves. Just as the music audience now juggles and reorders songs into new albums (or "playlists," as they are called in iTunes), the universal library will encourage the creation of virtual "bookshelves"—a collection of texts, some as short as a paragraph, others as long as entire books, that form a library shelf's worth of specialized information.

It is appreciated and understood that the abstracting/indexing step set forth herein may be carried out using any one of the means described herein, either alone or in combination, as well as any other means for automatically abstracting and indexing source document(s) known in the art. The foregoing are just some of the features of an information retrieval system and methodology based on phrases. Those of skill in the art of information retrieval will appreciate the flexibility of generality of the phrase information allows for a large variety of uses and applications in indexing, abstracting, document annotation, searching, ranking, and other areas of document analysis and processing. By way of a non-limiting example, it is understood that paper media may be volumetrically scanned, abstracted, translated, tagged with metadata, and have the numerical data outputted simultaneously via the methods and systems set forth herein.

Another potential application of volumetric scanning is the ability and means for recognizing and manipulating the format of the volumetrically scanned printed media. By recognizing and manipulating the format of the volumetrically scanned printed media, an end user will be able to output the resultant three-dimensional dataset to any desired format. Accordingly, in addition to the foregoing, it is an object of this specification to disclose a system and method for recognizing and manipulating the format of data derived from volumetric scans.

As used herein, the term "format" generally refers to the way in which data is presented visually and/or the means by which data is processed, recognized, and stored by a computer and any computer programs. As used herein, "format" or "formatting" specifically includes, without limitation, the type of text font, the size of text font, the shape of text, the color of text font, the physical appearance of text, the layout of any text and/or images on a given page and/or pages, the file format of the text and/or images, and/or any other means known in the art which affect the way in which text and/or images are displayed, recognized by a computer, and/or stored via a storage means. It is appreciated by those in the art that data is usually stored in some format with the expectation that it will be processed by a computer program that is able to recognize, handle, and process that format. Generically, data formats tend to fall into bitmaps (strings of 0s and 1s) that describe images or sound patterns (or both), text formats (in which usually each byte value is mapped to a character), numeric data formats (used by spreadsheet and other database programs).

When recognizing and manipulating the format of "text," one may change the type of font used to depict the text, the size and shape of the text, the color of the text, and/or any other implementation that alters the physical shape and configuration of the text. Text may take on any number or combinations of formats known in the art, such as without limitation: plain text, styled text, and rich text; and may have any shape, color, style (boldface, italic, capitalized, underlined, by way of non-limiting example), size and may include special features, such as hyperlinks.

A non limiting example of manipulating the format of text would be as follows. "The quick brown fox jumps over the lazy dog," contains text that is formatted using Times New Roman as the type of font (a font type found in most word processing applications), and is formatted using the font size of "12." One may change and manipulate the format of the preceding text as follows: "The quick brown fox jumps over the lazy dog," which now has a different format in that the type of font is now Arial (a font type found in most word processing applications) instead of Times New Roman, the size of the font is now 10 instead of 12, and the text is bolded instead of un-bolded. The meaning conveyed by the text remains the same, but the physical appearance of the text has been manipulated. In essence, when recognizing and manipulating the format of text as described herein, anything that affects the physical appearance, shape, and color of the text is contemplated and included.

In addition to recognizing and manipulating the physical appearance and configuration of text and/or images, formatting as used herein also refers to the means by which text and/or images are oriented and arranged on a particular page or pages. When referring to formatting in the context of text "layout," it is understood that text and/or images may be configured and arranged on a page in any number of ways. The layout of a newspaper, by way of a non-limiting example, with its familiar use of text placed in columns and wrapped around images, differs from the typical layout of a book, wherein text is typically not in columns and is arranged in a linear orientation across each page. The layout of a page may be changed in any one of innumerable means, such as, without limitation, altering the placement of the text and/or images on the page, altering the alignment of the text and/or images on a page, adjusting the dimensions of the margins, adding or subtracting columns, manipulate the kennelling, and adjusting any other properties pertaining to the way in which text and/or images are depicted on a page and/or across multiple pages. A non limiting example of manipulating the format of a document's layout would be to take the content of the aforementioned newspaper, remove the columns and text wrapped on or about the newspaper images, and output a new document wherein the exact same content is arranged in a book template format, without any columns or image wrap around.

In addition to recognizing and manipulating the physical appearance and configuration of text and/or images and in addition to recognizing and manipulating the layout of text and/or images on a given document, formatting as used herein also refers to the means by which text and/or images are stored and recognized as file formats. A file format is a particular way to encode information for storage and for recognition in computer program. Computer storage and execution means usually only store bits, and the computer storage and execution means usually utilize some way of converting information to 0s and 1s and vice-versa. There are different kinds of file formats for different kinds of information. Within any file format type, e.g., word processor documents, there will typically be several different file formats. Some file formats are designed to store very particular types of data: the JPEG file format, for example, is designed only to store static photographic images. Other file formats, however, are designed for storage of several different types of data: the GIF format supports storage of both still images and simple animations, and the QuickTime format may act as a container for many different types of multimedia. A text file format is simply one that stores any text, in a format such as without limitation ASCII or UTF-8, with few if any control characters. Some file formats, such as HTML, or the source code of some particular programming language, are in also text files, but adhere to more specific rules which allow them to be used for specific purposes.

Depending on the desired use, it may be advantageous for end users to recognize and manipulate the file format of a given file, changing the file format of a document from one file format to another file format, as applicable, or designating a file format to a document that did not previously have a digital file format and may have only existed in an analog format. Some non-limiting examples of file formats known in the art include without limitation: html, xhtml, .jad, .wap. ect.

Since files are seen by programs as streams of data, a method could be utilized to determine the format of a particular file within any given system (which may be deemed a type of metadata). Different computer operating systems have utilized different means for identifying and recognizing and identifying different file formats. One such means in use by several operating systems (including Mac OS X, CP/M, DOS, VMS, VM/CMS, and Windows) is to determine the file format of a file based on the section of its name following the final period. This portion of the filename is known in the art as the "filename extension." By way of a non-limiting example, HTML documents are identified by names that end with .html (or .htm), and GIF images by .gif. An alternative means for identifying the file format known in the art, often associated with Unix and its derivatives, is to store a "magic number" inside the file itself. This term was used for a specific set of 2-byte identifiers at the beginning of a file, but since any undecoded binary sequence may be regarded as a number, any feature of a file format which uniquely distinguishes it may be used for identification. GIF images, for instance, always begin with the ASCII representation of either GIF87a or GIF89a, depending upon the standard to which they adhere. Another such means for identifying and/or storing a file format known in the art is to explicitly store information about the format in the file system. Other means for include, without limitation: the Mac OS' Hierarchical File System; Mac OS X Uniform Type Identifiers (UTIs); OS/2 Extended Attributes; POSIX extended attributes, which is primarily used on Unix and Unix-like systems, the ext2, ext3, ReiserFS version 3, XFS, JFS, FFS, and HFS+ filesystems allowing the storage of extended attributes with files; PRONOM Unique Identifiers (PUIDs); MIME, which are used in many Internet-related applications; and File format identifiers (FFIDs).

Some non-limiting examples of file extensions used for font files formats known in the art that may be an output of a volumetric scan include without limitation: .abf (Adobe Binary Screen Font File); .acfm (Adobe Composite Font Metrics File); .afm (Adobe Font Metrics File); .amfm (Adobe Multiple Font Metrics File); .bdf (Glyph Bitmap Distribution Format); .chr (Borland Character Set); .dfont (Mac OS X Data Fork Font); .eot (Embedded OpenType Font); .fnt (Font File); .fon (Generic Font File); .gdr (Symbian OS Font File); .lwfn (Adobe Type 1 Mac Font File); .otf (OpenType Font); .pfa (Printer Font ASCII File); .pfb (Printer Font Binary File); .pfm (Printer Font Metrics File); .pfr (Portable Font Resource File); .suit (Macintosh Font Suitcase); .ttc (TrueType Font Collection); .ttf (TrueType Font); .xfn (Ventura Printer Font); .xft (Chi Writer Printer Font); and/or any other font file format known and used in the art.

Some non-limiting examples of file extensions used for text file formats known in the art that may be the output of a volumetric scan include without limitation: .1st (Readme File); .abw (AbiWord Document); act (FoxPro Documenting Wizard Action Diagram); .aim (AIMMS); ASCII Model File; .ans; ANSI Text File; .asc (ASCII Text File); .asc (Autodesk ASCII Export File); .ascii (ASCII Text File); .ase (Autodesk ASCII Scene Export File); .aty (Association Type Placeholder); .bbs (Bulletin Board System Text); .bean (Bean Rich Text Document); .bib (BibTeX Bibliography Database); .bib (Bibliography Document); .boc (EasyWord Big Document); .charset (Character Set); .chord (Song Chords File); .cyi (Clustify Input File); .dbt (Database Text File); .dct (FoxPro Database Memo); .dgs (Dagesh Pro Document); .diz (Description in Zip File); .dne (Netica Text File); .doc (Microsoft Word Document); .doc (WordPad Document); .docm (Word 2007 Macro-Enabled Document); .docx (Microsoft Word Open XML Document); .dot (Microsoft Word Template); .dotm (Word 2007 Macro-Enabled Document Template); .dotx (Word 2007 Document Template); .dvi (Device Independent Format File); .dx (DEC WPS Plus File); .email (Outlook Express Email Message); .emlx (Mail Message); .epp (EditPad Pro Project); .err (Error Log File); .err (FoxPro Compilation Error); .etf (ENIGMA Transportable File); .etx (Structure Enhanced Text (Setext) File); .euc (Extended Unix Code); .faq (Frequently Asked Questions Document); .fb2 (FictionBook 2.0 File); .fdf (Acrobat Forms Data Format); .fpt (FileMaker Pro Database Memo File); .fpt (FoxPro Table Memo); .frt (FoxPro Report Memo); .fxc (FilePackager Configuration); .gio (Adagio Score); .gio (Nyquist MIDI File); .gpn (GlidePlan Map Document); .gsd (Generic Station Description File); .gv (GraphcViz DOT File); .hht (Help and Support Center HHT File); .hs (Java HelpSet File); .hwp [Hangul (Korean) Text Document]; .hz [Chinese (Hanzi) Text]; .idx (Outlook Express Mailbox Index File); .imapmbox (IMAP Mailbox); .ipf (OS/2 Help File); .jis (Japanese Industry Standard Text); .jp1 [Japanese (Romaji) Text File]; .klg (Log File); .kml (Keyhole Markup -

Language); .knt (KeyNote Note File); .kon (Yahoo! Widget) XML File; .kwd (KWord Document); .latex (LaTeX Document); .lbt (FoxPro Label Memo); .lis (SQR Output File); .lit (eBook File); .lnt (Laego Note Taker File); .log(Log File); .lp2 (iLEAP Word Processing Document); .lrc (Lyrics File); .lst (Data List); .lst (FoxPro Documenting Wizard List); .ltr (Letter File); .luf (Lipikar Uniform Format File); .lwp (Lotus Word Pro Document); .lxfml (LEGO Digital Designer XML File); .lyt (TurboTax Install Log Fil); .lyx (LyX Document); .man (Unix Manual); .map (Image Map); .mbox (E-mail Mailbox File); .mell (Mellel Word Processing File); .mellel (Mellel Word Processing Document); .mnt (FoxPro Menu Memo); .msg (Mail Message); .mw (MacWrite Text Document); .mwp (Lotus Word Pro SmartMaster File); .nfo (Warez Information File); .notes (Memento Notes File); .now (Readme File); .nwctxt (Note-Worthy Composer Text File); .nzb (NewzBin File); .ocr (FAXGrapper Fax Text File; .odm (OpenDocument Master Document); .odt (OpenDocument Text Document); .ofl (Ots File List); .oft (Outlook File Template); .opml (OPML File); .ott (OpenDocument Text Document Template); .p7s (Digitally Signed Message); .pages (Pages Document); .pfx (First Choice Word Processing Document); .pjt (FoxPro Project Memo); .prt (Printer Output File); .psw (Pocket Word Document); .pvm (Photo Video Manifest File); .pwi (Pocket Word Document); .rad (Radar ViewPoint Radar Data); .readme (Readme File); .rng (RELAX NG File); .rpt (Generic Report); .rst (reStructuredText File); .rt (RealText Streaming Text File); .rtd (RagTime Document); .rtf (Rich Text Format File); .rtfd (Rich Text Format Directory File); .rtx (Rich Text Document); .run (Runscanner Scan File); .rzk (File Crypt Password File); .rzn (Red Zion Notes File); .saf (SafeText File); .safetext (SafeText File); .sam (Ami Pro Document); .scc (Scenarist Closed Caption File); .scm (Schema File); .sct (FoxPro Form Memo); .scw (Movie Magic Screenwriter Document); .sdm (StarOffice Mail Message); .sdw (StarOffice Writer Text Document); .sgm (SGML File); .sig (Signature File); .sls (Image Playlist); .sms (Exported SMS Text Message); .ssa (Sub Station Alpha Subtitle File); .strings (Text Strings File); .stw (StarOffice Text Document Template); .sub (Subtitle File); .sxw (StarOffice Writer Text Document); .tab (Guitar Tablature File); .tdf (Guide Text Definition File); .tdf (Xserve Test Definition File); .tex (LaTeX Source Document); .text (Plain Text File); .thp (TurboTax Text String); .tlb; VAX Text Library; .tmx (Translation Memory eXchange File); .tpc (Topic Connection Placeholder); .txt (Text File); .u3i (U3 Application Information File); .unauth (SiteMinder Unauthorized Message File); .unx (Unix Text File); .upd (Program Update Information); .utf8 (Unicode UTF8-Encoded Text); .utxt (Unicode Text File); .vct (Visual Class Library Memo); .vnt (Mobile Phone vNote File); .wbk (Word Document Backup); .wbk (WordPerfect Workbook); .wcf (WebEx Saved Chat Session); .wn (WriteNow Text Document); .wp (WordPerfect Document); .wp4 (WordPerfect 4 Document); .wp5 (WordPerfect 5 Document); .wp6 (WordPerfect 6 Document); .wp7 (WordPerfect 7 Document); .wpa (ACT! Word Processing Document; .wpd (WordPerfect Document); .wpd (ACT! 2 Word Processing Document); .wpl (DEC WPS Plus Text Document); .wps (Microsoft Works Word Processor Document); .wpt (WordPerfect Template); .wri (Windows Write Document); .wsc (Windows'Script Component); .wsh (Windows Script Host Settings); .xdl (XML Schema File); .xdl (Oracle Expert Definition Language File); .xlf (XLIFF Document); .xps (XML Paper Specification File); .xwp (XMLwriter Project); .xwp (Xerox Writer Text Document); .xwp (Crosstalk Session File); .xy (XYWrite Document); .xy3 (XYWrite III Document); .xyp (XYWrite Plus Document); .xyw (XYWrite for Windows Document); .ybk (YanCEyWare Reader eBook); .yml (YAML Document); and/or any other text file formats known and used in the art.

Some non-limiting examples of file extensions used for database file formats known in the art include without limitation: .123 (Lotus 1-2-3 Spreadsheet); .csv (Comma Separated Values File); .dat (Data File); .db (Database File); .dll (Dynamic Link Library); .mdb (Microsoft Access Database); .pps (PowerPoint Slide Show); .ppt (PowerPoint Presentation); .sql (Structured Query Language Data); .wks (Microsoft Works Spreadsheet); .xls (Microsoft Excel Spreadsheet); .xml (XML File); and/or any other data and/or database file formats known and used in the art.

In addition to the foregoing, it is also appreciated and understood that there are a variety of web file formats, mobile phone file formats, Intranet file formats, Grid file formats, Virtual World file formats, database file formats, compression file formats, Iphone file formats, blackberry file formats, and handheld computer file formats known and used in the art, all of which may be the chosen format for the system and method for recognizing and manipulating the format of data derived from volumetric scans as described herein.

It is appreciated and understood that a system and method for recognizing and manipulating the format of data derived from volumetric scans will be useful to any number of professions.

It is appreciated and understood that in a particular non-limiting aspect of the disclosed system and method for recognizing and manipulating the format of data derived from volumetric scans as described herein, an end user can: volumetrically scan printed media as an analog non-digital format; render a digital three-dimensional image of the volumetrically scanned printed media using the methods described herein as well as other methods known in the art for rendering three-dimensional images using non-destructive penetrating scans; orient and align the derived data about a certain axis (as set forth herein); perform the steps for smoothing voxel undulations (as described herein), the steps for identifying double sided pages, the steps for removing noise and other artifacts (as described herein); filter the paper data from the ink data (as described herein); perform volumetric character recognition (as described herein); recognize and accept the data as input in a certain format; processes the data with the methods set forth herein; and render previously analog data as digital output in the same format or another chosen format using the means set forth herein.

It is also appreciated and understood that the disclosed system and method for recognizing and manipulating the format of data derived from volumetric scans may be carried out alone or in combination with any of the other methods and systems set forth in this disclosure. By way of a non-limiting example, it is understood that paper media may be volumetrically scanned, electronically unfolded, have volumetric character recognition applied to it, tagged with meta-data, abstracted, and have the format manipulated before having the scanned data outputted to a display device, a database, and/or an output device.

Another potential application of volumetric scanning is appending metadata to volumetrically scanned paper media. Accordingly, in addition to the foregoing, it is an object of this specification to disclose a system and method for appending metadata to data derived from volumetric scans.

Metadata (metadata, or sometimes metainformation) is "data about data," of any sort in any media. An item of metadata may describe an individual datum, or content item, or a collection of data including multiple content items and hierarchical levels, including by way of a non limiting example, a database schema. Metadata is structured, encoded data that describe characteristics of information-bearing entities to aid in the identification, discovery, assessment, and management of the described entities. Metadata is a set of optional structured descriptions that are publicly available to explicitly assist in locating objects. Metadata may be used to guide a computer process in finding certain objects, entities, and resources, and may also be used to optimize certain compression algorithms known in the art, as well as to execute certain computations pertaining to the data in question. In data processing, metadata definitional data may provide information about or documentation of other data managed within an application or environment. By way of a non-limiting example, metadata documents data about data elements or attributes, (such as name, size, data type, etc) and data about records or data structures (such as length, fields, columns, etc) and data about data (such as where it is located, how it is associated, ownership, etc.). Metadata may also include descriptive information about the context, quality and condition, or characteristics of the data. In essence, metadata provides context for data.

Metadata is used to facilitate the understanding, characteristics, and management usage of data. The metadata required for effective data management varies with the type of data and context of use. In a library for example, the data may be the content of the titles stocked, and metadata about a title would typically include a description of the content, the author, the publication date and the physical location. In the context of an information system, by way of a non-limiting example, where the data is the content of the computer files, metadata about an individual data item would typically include the name of the field and its length. Metadata about a collection of data items, a computer file, might typically include the name of the file, the type of file and the name of the data administrator.

Metadata is used to speed up and enrich searching for resources. In general, search queries using metadata may save users from performing more complex filter operations manually. It is now common for web browsers, P2P applications and media management software to automatically download and locally cache metadata, to improve the speed at which files may be accessed and searched. Metadata may also be associated to files manually. This is often the case with documents which are scanned into a document storage repository such as FileNet or Documentum. Once the documents have been converted into an electronic format a user brings the image up in a viewer application, manually reads the document and keys values into an online application to be stored in a metadata repository.

Metadata provide additional information to users of the data it describes. This information may be descriptive and/or algorithmic, by way of a non-limiting example. Metadata helps to bridge the semantic gap. By telling a computer how data items are related and how these relations may be evaluated automatically, it becomes possible to process even more complex filter and search operations. Metadata is useful in the field of knowledge representation and metadata is of special interest to the semantic web and artificial intelligence. Certain metadata is designed to optimize lossy compression. For example, if a video has metadata that allows a computer to tell foreground from background, the latter may be compressed more aggressively to achieve a higher compression rate. Still other metadata is intended to enable variable content presentation. For example, if a picture has metadata that indicates the most important region—the one where there is a person—an image viewer on a small screen, such as on a mobile phone, may narrow the picture to that region and thus show the user the most interesting details. A similar kind of metadata is intended to allow blind people to access diagrams and pictures, by converting them for special output devices or reading their description using text-to-speech software. Other descriptive metadata may be used to automate workflows. By way of a non-limiting example, if a "smart" software tool knows content and structure of data, it may convert it automatically and pass it to another "smart" tool as input.

Metadata is becoming an increasingly important part of electronic discovery, in the context of the legal profession. Application and file system metadata derived from electronic documents and files may be important evidence. Metadata routinely discoverable as part of civil litigation. Parties to litigation are required to maintain and produce metadata as part of discovery, and spoliation of metadata may lead to sanctions.

Metadata has become important on the World Wide Web because of the need to find useful information from the mass of information available. Manually-created metadata adds value because it ensures consistency. If a web page about a certain topic contains a word or phrase, then all web pages about that topic should contain that same word or phrase. Metadata also ensures variety, so that if a topic goes by two names each will be used. In the context of the web and the work of the W3C in providing markup technologies of HTML, XML and SGML the concept of metadata has specific context. With markup technologies there is metadata, markup and data content, all of which may be classified broadly as "metadata." The metadata describes characteristics about the data, while the markup identifies the specific type of data content and acts as a container for that document instance. In the context of markup the metadata is architected to allow optimization of document instances to contain only a minimum amount of metadata, while the metadata itself is likely referenced externally such as in a schema definition (XSD) instance. Also it should be noted that markup provides specialized mechanisms that handle referential data. The reference and ID mechanisms in metadata markup allow reference links between related data items, and links to data items that may then be repeated about a data item, such as an address or product details. Similarly there are concepts such as classifications, ontologies and associations for which markup mechanisms are provided. A data item may then be linked to such categories via markup and hence providing a clean delineation between what is metadata, and actual data instances. Therefore the concepts and descriptions in a classification would be metadata, but the actual classification entry for a data item is simply another data instance.

It is understood that metadata may be stored either internally, in the same file as the data, or externally, in a separate file. Metadata that are embedded with content is called embedded metadata. A data repository typically stores the metadata detached from the data. Storing metadata in a human-readable format such as XML may be useful because users may understand and edit it without specialized tools. On the other hand, these formats are not optimized for storage capacity; it may be useful to store metadata in a binary, non-human-readable format instead to speed up transfer and save memory.

Metadata may be structural or control metadata and guide other metadata. Structural metadata is used to describe the structure of computer systems such as tables, columns and indexes. Guide metadata is used to help humans find specific items and is usually expressed as a set of keywords in a natural language. Metatadata may also be descriptive, administrative, and/or structural.

Metadata is important in the context of relational databases. Each relational database system has its own mechanisms for storing metadata. Some non limiting examples of relational database metadata include: tables of all tables in a database, their names, sizes and number of rows in each table; tables of columns in each database, what tables they are used in; and the type of data stored in each column. In database terminology, this set of metadata is referred to as the catalog. The SQL standard specifies a uniform means to access the catalog, called the INFORMATION_SCHEMA, but not all databases implement it, even if they implement other aspects of the SQL standard. For an example of database-specific metadata access methods, see Oracle metadata, which is well known in the art.

Metadata is important in the context of data warehouses. Data warehouse metadata systems are sometimes separated into back room metadata that are used for extract, transform, load functions to get OLTP data into a data warehouse and front room metadata that are used to label screens and create reports. Some common types of metadata in a data warehouse include without limitation: source specifications, such as repositories, and source logical schemas; source descriptive information, such as ownership descriptions, update frequencies, legal limitations; access methods process information, such as job schedules and extraction code; data staging metadata; data acquisition information, such as data transmission scheduling and results, and file usage dimension table management, such as definitions of dimensions, and surrogate key assignments; transformation and aggregation, such as data enhancement and mapping, DBMS load scripts, and aggregate definitions; audit, job logs and documentation, such as data lineage records, data transform logs; DBMS metadata, such as: DBMS system table contents and/or processing hints.

Metadata is important in the context of business intelligence. Business Intelligence is the process of analyzing large amounts of corporate data, usually stored in large databases such as a data warehouse, tracking business performance, detecting patterns and trends, and helping enterprise business users make better decisions. Business Intelligence metadata describes how data is queried, filtered, analyzed, and displayed in business intelligence software tools, such as Reporting tools, OLAP tools, Data Mining tools. Some non limiting examples include: OLAP metadata, which may include descriptions and structures of dimensions, cubes, measures (metrics), hierarchies, levels, drill paths; reporting metadata, which may include the descriptions and structures of reports, charts, queries, datasets, filters, variables, expressions and other attributes known and appreciated in the art; and/or data mining metadata, which may include the descriptions and structures of datasets, algorithms, queries, ect. Business Intelligence metadata may be used to understand how corporate financial reports reported to Wall Street are calculated, how the revenue, expense and profit are aggregated from individual sales transactions stored in the data warehouse. A good understanding of Business Intelligence metadata is required to solve complex problems such as compliance with corporate governance standards, such as Sarbanes Oxley (SOX) or Basel II.

Metadata is important in the context of file systems as well. Nearly all file systems keep metadata about files out-of-band. Some systems keep metadata in directory entries; others in specialized structure like inodes or even in the name of a file. Metadata may range from simple timestamps, mode bits, and other special-purpose information used by the implementation itself, to icons and free-text comments, to arbitrary attribute-value pairs. With more complex and open-ended metadata, it becomes useful to search for files based on the metadata contents. The Unix find utility was an early example. Apple Computer's Mac OS X operating system supports cataloguing and searching for file metadata. Microsoft worked in the development of similar functionality with the Instant Search system in Windows Vista, as well as being present in SharePoint Server. Linux implements file metadata using extended file attributes.

Metadata is important in the context of images as well. Some non limiting examples of Examples of image files containing metadata include exchangeable image file format (EXIF) and Tagged Image File Format (TIFF). Having metadata about images embedded in TIFF or EXIF files is one way of acquiring additional data about an image. Tagging pictures with subjects, related emotions, and other descriptive phrases helps Internet users find pictures easily rather than having to search through entire image collections.

Metadata is important in the context of computer programs as well. Metadata is casually used to describe the controlling data used in software architectures that are more abstract or configurable. Most executable file formats include what may be termed "metadata" that specifies certain, usually configurable, behavioral runtime characteristics. In Java, by way of a non-limiting example, the class file format contains metadata used by the Java compiler and the Java virtual machine to dynamically link classes and to support reflection. In MS-DOS, the EXE file and Windows PE formats contain metadata. This metadata may include the company that published the program, the date the program was created, the version number and more. In the Microsoft .NET executable format, extra metadata is included to allow reflection at runtime.

Metadata is important in the context of various documents as well. Most programs that create documents, including Microsoft SharePoint, Microsoft Word and other Microsoft Office products, save metadata with the document files. These metadata may contain the name of the person who created the file (obtained from the operating system), the name of the person who last edited the file, how many times the file has been printed, and even how many revisions have been made on the file. Other saved material, such as deleted text (saved in case of an undelete command), document comments and the like, is also commonly referred to as "metadata."

Document Metadata is particularly important in legal environments where litigation may request this sensitive information (metadata) which may include many elements of private detrimental data. This data has been linked to multiple lawsuits that have got corporations into legal complications. Many legal firms today use "Metadata. Management Software" also known as "Metadata Removal Tools." This software may be used to clean documents before they are sent outside of their firm. This process, known as metadata management, protects law firms from potentially unsafe leaking of sensitive data through electronic discovery.

In the context of digital libraries, There are three categories of metadata that are frequently used to describe objects in a digital library: (i) descriptive—information describing the intellectual content of the object, such as MARC cataloguing records, finding aids or similar schemes (It is typically used for bibliographic purposes and for search and retrieval); (ii) structural—information that ties each object to others to make up logical units (e.g., information that relates individual images of pages from a book to the others that make up the book); and (iii) administrative—information used to manage the object or control access to it. This may include information on how it was scanned, its storage format, copyright and licensing information, and information necessary for the long-term preservation of the digital objects.

Metadata is also important in the context of search engine optimization, wherein the metadata may contain information that enables a document and/or website to instruct and aid search engine crawlers, web scapers, and indexing means.

In addition, the use and tracking of metadata may make it possible to create a copyright notice system, wherein the system keeps track of number of times a particular document is viewed, used, copied, ect; as well as tracking whether any derivative works have been created, wherein copyright holders may receive appropriate licensing and royalty payments.

Accordingly, in one illustrative aspect of disclosed system and method for appending metadata to data derived from volumetric scans, a source document is volumetrically scanned, the ink and print data are recognized and filtered out, VCR is performed, the title, author, publisher, publishing data, page numbers, call-number, ISBN number are all identified automatically, recorded in a database, and automatically converted to a metatag, with said metatag appended to the source text and/or an abstract of that volumetrically scanned source text, appending a hyperlink to the source text, and outputting the volumetrically scanned analog source text as digital format to a database, display device, and/or output device, complete with the newly created metatags. Appending metatags to volumetrically scanned materials will also prove useful in the field of search. As used herein, search includes any means used in the art to identify pertinent information and/or filter out extraneous, non-essential information, and specifically includes without limitation so called keyword searching and conceptual (semantic) search, which relies on relationships between words and word patterns.

It is also appreciated and understood that the disclosed system and method for appending metadata to data derived from volumetric scans may be carried out alone or in combination with any of the other methods and systems set forth in this disclosure. By way of a non-limiting example, it is understood that paper media may be volumetrically scanned, electronically unfolded, have volumetric character recognition applied to it, tagged with metadata, abstracted, and have the format manipulated before having the scanned data outputted to a display device, a database, and/or an output device.

Another potential application of volumetric scanning is identifying and filtering certain numerical data which may be embedded in the text or disposed on or about the scanned paper media. By identifying and filtering numerical data from non-numerical text, it is then possible to carry out certain mathematical calculations, statistical analysis, and graphing of said numerical data. Accordingly, in addition to the foregoing, it is an object of this specification to disclose a system and method for manipulating and calculating numerical data derived from volumetric scans.

Data mining is the process of sorting through large amounts of data and picking out relevant information. It is used by business intelligence organizations, financial analysts, and the research sciences to extract pertinent information from enormous datasets. It involves extracting implicit, previously unknown, and potentially useful information from large datasets or databases, and involves the statistical and logical analysis of large sets of transaction data, identifying patterns that may aid organizational decision making. It is appreciated that the manipulation and filtering of numerical data via volumetric scans will be useful to any number of professions that perform data mining and/or carry out a large amount of statistical analysis and mathematical analysis.

By way of a non limiting example, actuaries often have a need to analyze large amounts of numerical data from multiple and sometimes unrelated sources. Sometimes the needed numerical information may be embedded with other non-numeric information, and the actuary may only require the numeric information and not the non-numeric information. Instead of having to manually identify and input numerical data from multiple data sources before performing calculations and analysis (a time consuming and inefficient process), an actuary or the like may utilize volumetric scans (as described herein) to simultaneously scan multiple documents from multiple sources and only identify, filter, and output the desired numerical data for calculation and analysis. In addition, the means for performing mathematical calculations and/or statistical analysis may be performed via any one or more of the microprocessors 202, 204, 214 of FIG. 6, for example, so that when conducting the volumetric scan, a user may output to an output device 212, a database 214 and/or display device 208 only numerical data and/or only output the result of the desired calculation and/or statistical analysis of the numerical data recognized, identified and filtered from multiple or single document(s). This function would prove useful in any number of industries, like, polling, by way of a non-limiting example, wherein polling agents may volumetrically scan a stack of individual poll responses and only output the aggregate poll numerical data to a display or output device.

In addition, another use of the method and system for manipulating and calculating numerical data derived from volumetric scans is that various microprocessors 202, 204, 214 may be used to perform calculations and/or statistical analysis of aggregate numerical data and output the results in a visual format, such as a chart, graph, or any other visual means used by those skilled in the art to depict numerical relationships and/or calculations and analysis. This may be accomplished even if there was not a chart and a graph in the scanned paper media in the first place and is a result of analyzing the numbers transposed on the volumetrically scanned media. Businesses may also find it advantageous to append various business rules and/or user rules to the derived numerical data obtained via a volumetric scan. By way of a non limiting example, insurance companies may scan multiple stacks of insurance claims, filter and output only the highest numerical claim amounts, abstract and append the claimants' contact information to the derived numerical data, output the results to a database or enterprise content management system, append various business rules pertaining to various letter templates, and automatically generate letters to be sent to the claimants.

It is appreciated and understood by those skilled in the art that the foregoing system and method may apply any mathematical calculation method and analysis known in the art, as well as any statistical method and analysis known in the art, including by way of a non limiting example, analysis of variance, regression of analysis, correlation, time series analysis, factor analysis, or any other statistical methods known in the art. It is also appreciated and understood that when describing the manipulation and calculation of numerical data, applicants are also including the recognition and manipulation of any mathematical symbols and annotations known in the art. It is also appreciated and understood that the disclosed method for manipulating and calculating numerical data derived from volumetric scans described herein may be carried out alone or in combination with any of the other methods and systems set forth in this disclosure. By way of a non-limiting example, it is understood that paper media may be volumetrically scanned, abstracted, translated, tagged with metadata, and have the numerical data outputted simultaneously via the methods and systems set forth herein.

Another potential application of volumetric scanning is using volumetric scanning as a tool for the legal profession during the document discovery and review portion of civil and criminal litigation. Accordingly, it is an object of this specification to set forth a system and method of conducting discovery and legal research using volumetric scans.

During civil and criminal litigation, all relevant documents in possession by both sides must be exchanged so as to enable the other side to identify relevant evidence to be used during trail. Before exchanging documents with the other side, a given side must first conduct a privilege review, pulling out and withholding any documents that may be legally withheld for reasons of state or federal recognized privilege (i.e. a document contains privileged communication between attorney-client and/or a document is attorney work product). Conducting a privilege review usually entails manually reviewing boxes and boxes of documents, individually identifying and pulling out documents that are privileged, and recording the privileged document in a privilege log. After conducting a privilege review, a party to litigation must then make multiple sets of copies of the non-privilege documents, stamp them with certain numbers for tracking (usually referred to as Bates Stamping), and ship them to the other side. This process is generally known as document production.

After producing documents and sending them to the other party to the litigation, the next phase of discovery usually entails document review, i.e. reviewing the non-privileged materials produced by the other party to litigation. Usually, the other side may produce hundreds and hundreds of boxes of documents, with a typical box containing 2000 documents. During document review, attorneys will usually manually review each and every document, pulling out those individual documents that may assist in building their case. Documents may contain information regarding damages, elements proving or disproving the cause of action, as well as information that will be used when deposing or examining potential witnesses before and during trial. This process is typically referred to as document review.

Because document production and document review typically involve documents that only exist in an analog and non-digital form, many such documents are not digital and cannot be stored, searched, or organized via any digital means. Because attorneys spend inordinate amounts of time manually searching and reading the analog paper documents produced to the other side and in reviewing the other side's document production, the discovery phase of litigation is often very expensive and time consuming. It is not uncommon for document discovery to last multiple years and comprise the largest portion of overall litigation expense.

According there is a need for a system and method of conducting discovery and legal research using volumetric scans. In one aspect of the system and method of conducting discovery and legal research using volumetric scans, the following steps may be employed via the means set forth herein, in no particular order: (i) perform a volumetric scan of the documents via any of the modalities set forth and described fully in this specification; (ii) scan the documents without taking the documents out of the box, removing staples, paper clips, ect; (iii) orient the pages along a determined axis as set forth herein; (iv) perform any processing steps such as removing noise and artifacts without limitation; (v) differentiate ink data from paper data in the three-dimensional data voxel set; (vi) perform volumetric character analysis as set forth previously in this disclosure; (vii) attach and append any metadata (as described previously in this spec) according to user inputs, said metadata to contain date data scanned, and any other attributes that will assist and create search functionality; (viii) apply the selected output format as set forth by end user; (ix) search for and remove any duplicate documents, recording which documents were removed for being duplicates; (x) apply any user business rules, i.e., automatically flagging certain documents with metadata that contain certain names, places, phrases, privilege items, sending these documents to separate folders for manual review; (xi) appending a numbering system to the scanned documents, i.e., Bates Stamping the documents in a predetermined locale; (xii) outputting the scanned documents to a display device, database, and/or output device; (xiii) allowing end users to conduct certain search functionalities within the source documents, i.e., searching for certain names, phrases, dates, ect; (xiiii) allowing end users to apply certain filters to documents, i.e. arranging documents by dates, organizing documents by name, phrase, location; (xv) automatically gathering certain documents and outputting them to predetermined folders, i.e., every document that contains the name "Smith" is copied and deposited in the folder pertaining to "Smith,"; (xvi) allow user to redact and/or black out certain privileged phrases and names; (xvii) automatically remove any privileged metadata; (xviii) output to the volumetrically scanned and manipulated data to certain databases (concordance, summation, ect) and/or display devices.

It is also appreciated and understood that the disclosed system and method of conducting discovery and legal research using volumetric scans may be carried out alone or in combination with any of the other methods and systems set forth in this disclosure.

The scope of the present disclosure fully encompasses other aspects which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural and functional equivalents to the elements of the above-described preferred aspect that are known or later come to be known to those of ordinary skill in the art are expressly incorporated herein by reference and are intended to be encompassed by the present claims. Moreover, it is not necessary for a device or method to address each and every problem sought to be solved by the present disclosure, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

In one or more exemplary aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although selected aspects have been illustrated and described in detail, it will be understood that various substitutions and alterations may be made therein without departing from the spirit and scope of the present disclosure, as defined by the following claims.

The invention claimed is:

1. A mobile scanner, comprising:
   a frame;
   a front axle attached to the frame, wherein the front axle includes a first tire/wheel assembly mounted thereon and a second tire/wheel assembly mounted thereon;
   a rear axle attached to the frame, wherein the rear axle includes a first tire/wheel assembly mounted thereon and a second tire/wheel assembly mounted thereon;
   a cab mounted on the frame;
   a body mounted on the frame adjacent to the cab;
   a volumetric document scanner disposed within the body, wherein the volumetric document scanner is configured to use x-ray computed tomography in order to scan documents and create a three-dimensional data set representing the documents and wherein the volumetric document scanner includes an interior scanning cavity configured to receive documents; and
   a first external access door on a first side of the body of the mobile scanner;
   a second external access door on a second side of the body of the mobile scanner, wherein the first external access door and the second external access door provide access to the interior scanning cavity of the volumetric document scanner;
   a first conveyor belt portion within the first external access door;
   a second conveyor belt portion within the second external access door; and
   a third conveyor belt portion disposed between the first conveyor belt portion and the second conveyor belt portion.

2. The mobile scanner of claim 1, wherein the body comprises:
   a first portion; and
   a second portion separated from the first portion, wherein the volumetric document scanner is installed within the second portion of the body.

3. The mobile scanner of claim 2, wherein the second portion of the body is shielded to prevent radiation from the volumetric document scanner from passing through the second portion of the body.

4. The mobile scanner of claim 1, wherein the first external access door and the second external access door are movable between an open position, in which access is provided to the scanner, and a closed position, in which access is not provided to the scanner.

5. The mobile scanner of claim 4, wherein the first conveyor portion, the second conveyor portion, and the third conveyor portion establish a conveyor system through the volumetric document scanner when the first external access door and the second external access doors are in the open position.

6. A method of scanning documents, the method comprising:
   moving a mobile scanner to a location associated with one or more documents;
   opening a first access door and a second access door, wherein the first access door and the second access door provide access to an interior scanning cavity within the mobile scanner;
   placing the one or more documents on a conveyor system that extends between the first access door and the second access through the interior scanning cavity of the mobile scanner;
   moving the one or more documents along the conveyor system and into the interior scanning cavity of the mobile scanner;
   scanning the one or more documents in the mobile scanner using x-ray computed tomography in order to create scan data associated with the one or more documents.

7. The method of claim 6, further comprising:
   storing the scan data in a removable memory within the mobile scanner.

8. The method of claim 7, further comprising:
   removing the removable memory from the mobile scanner.

9. The method of claim 8, further comprising:
   installing the removable memory in a computer at a central processing facility.

10. The method of claim 9, further comprising:
    processing the scan data at the central processing facility to create an electronic representation of the one or more documents.

11. The method of claim 10, further comprising:
    outputting the electronic representation of the one or more documents.

12. The method of claim 6, further comprising:
    transmitting the scan data to a central processing facility via a wireless link;
    processing the scan data at the central processing facility to create an electronic representation of the one or more documents; and
    outputting the electronic representation of the one or more documents.

13. A method of scanning documents, the method comprising:
    moving a mobile scanner to a location associated with one or more documents;
    opening a first access door and a second access door, wherein the first access door and the second access door provide access to an interior scanning cavity within the mobile scanner;
    moving the one or more documents through the first access door or the second access door into the interior scanning cavity along a conveyor system that extends between the first access door and the second access through the interior scanning cavity;
    scanning the one or more documents in the mobile scanner using x-ray computed tomography in order to create scan data associated with the one or more documents; and
    processing the scan data at the location to create an electronic representation of the one or more documents.

14. The method of claim 13, further comprising:
    storing the electronic representation of the one or more documents in a removable memory within the mobile scanner.

15. The method of claim 14, further comprising:
    removing the removable memory from the mobile scanner.

16. The method of claim 15, further comprising:
installing the removable memory in a computer at a central processing facility; and
transferring the electronic representation of the one or more documents to the central processing facility.

17. The method of claim 16, further comprising:
storing the electronic representation of the one or more documents at the central facility.

18. The method of claim 13, further comprising:
transmitting the electronic representation of the one or more documents to a central processing facility via a wireless link; and
storing the electronic representation of the one or more documents at the central processing facility.

* * * * *